United States Patent
Blass et al.

(10) Patent No.: US 9,725,436 B2
(45) Date of Patent: Aug. 8, 2017

(54) CYTOCHROME P450 INHIBITORS AND THEIR METHOD OF USE

(71) Applicant: CORTENDO AB (PUBL), Trevose, PA (US)

(72) Inventors: Benjamin Eric Blass, Eagleville, PA (US); Magid A Abou-Gharbia, Exton, PA (US); Wayne E. Childers, New Hope, PA (US); Pravin Iyer, Bangaluru (IN); Joshodeep Boruwa, Mallapur (IN)

(73) Assignee: CORTENDO AB (PUBL), Trevose, PA (US)

( * ) Notice: Subject to any disclaimer, the term of this patent is extended or adjusted under 35 U.S.C. 154(b) by 0 days.

(21) Appl. No.: 15/021,532

(22) PCT Filed: Sep. 15, 2014

(86) PCT No.: PCT/US2014/055677
§ 371 (c)(1),
(2) Date: Mar. 11, 2016

(87) PCT Pub. No.: WO2015/039036
PCT Pub. Date: Mar. 19, 2015

(65) Prior Publication Data
US 2016/0221990 A1 Aug. 4, 2016

Related U.S. Application Data

(60) Provisional application No. 61/877,924, filed on Sep. 13, 2013.

(51) Int. Cl.
| | | |
|---|---|---|
| *C07D 401/10* | (2006.01) | |
| *C07D 213/26* | (2006.01) | |
| *A61K 31/4418* | (2006.01) | |
| *C07D 401/12* | (2006.01) | |
| *C07D 213/71* | (2006.01) | |
| *C07D 233/60* | (2006.01) | |
| *C07D 233/61* | (2006.01) | |
| *C07D 233/84* | (2006.01) | |
| *C07D 405/12* | (2006.01) | |
| *C07D 409/12* | (2006.01) | |
| *C07D 413/12* | (2006.01) | |
| *C07D 213/30* | (2006.01) | |
| *C07D 213/38* | (2006.01) | |
| *C07D 213/65* | (2006.01) | |
| *C07D 213/56* | (2006.01) | |

(52) U.S. Cl.
CPC ........ *C07D 401/12* (2013.01); *A61K 31/4418* (2013.01); *C07D 213/26* (2013.01); *C07D 213/30* (2013.01); *C07D 213/38* (2013.01); *C07D 213/56* (2013.01); *C07D 213/65* (2013.01); *C07D 213/71* (2013.01); *C07D 233/60* (2013.01); *C07D 233/61* (2013.01); *C07D 233/84* (2013.01); *C07D 401/10* (2013.01); *C07D 405/12* (2013.01); *C07D 409/12* (2013.01); *C07D 413/12* (2013.01)

(58) Field of Classification Search
CPC .. C07D 401/10; C07D 401/12; C07D 401/14; C07D 213/26; C07D 213/30; C07D 213/38; C07D 213/56; C07D 233/60; C07D 233/61; A61K 31/4418
USPC ...... 544/360, 364; 546/255, 346; 548/343.1; 514/253.01, 253.1, 254.05, 277, 332, 396
See application file for complete search history.

(56) References Cited

U.S. PATENT DOCUMENTS

2008/0287505 A1   11/2008   McElroy et al.
2012/0178765 A1   7/2012    Yi et al.

FOREIGN PATENT DOCUMENTS

| WO | 9117163 A1 | 11/1991 |
| WO | 03018013 A1 | 3/2003 |
| WO | 2012083112 A2 | 6/2012 |
| WO | 2012177668 A1 | 12/2012 |

OTHER PUBLICATIONS

Bundgaard, Design of Prodrugs, p. 1, 1985.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. I: Principles and Practice, pp. 975-977, 1995.*
Gura et al., Systems for identifying new drugs are often faulty, Science, 278:1041-1042, (1997).*
Johnson et al., Relationships between drug activity in NCI preclinical in vitro and in vivo models and early clinical trials, British Journal of Cancer, 84(10):1424-1431, (2001).*
Simone, Oncology: Introduction, Cecil Textbook of Medicine, 20th Edition, vol. 1, pp. 1004-101 O, (1996).*
Branden et al., Structure-based ligand design to overcome CYP inhibition in drug discovery projects, Drug Discovery Today, vol. 19, No. 7, pp. 905-911 (Jul. 2014).*
Baudrand et al., Cortisol dysregulation in obesity-related metabolic disorders, Curr. Opin. Endocrinol Diabetes Obes. 22(3):143-149, pp. 1-12 (2016).*
PubChem. Compound Summary for CID 56599413. Create Date: Feb. 13, 2012. [retrieved on Mar. 3, 2015]. Retrieved from the Internet. <URL: https://pubchem.ncbi.nlm.nih.gov/compound/56599413. entire document.
PubChem. Compound Summary for CID 46191177. Create Date: Jul. 6, 2010. [retrieved on Mar. 3, 2015]. Retrieved from the Internet. <URL: https://pubchem.ncbi.nlm.nih.gov/compound/46191177. entire document.

* cited by examiner

*Primary Examiner* — Deepak Rao
(74) *Attorney, Agent, or Firm* — Reed Smith LLP; Matthew S. Gibson

(57) ABSTRACT

Embodiments of the present invention relate to novel cytochrome P450 inhibitors and pharmaceutical compositions thereof having a disease-modifying action in the treatment of diseases associated with the production of cortisol that include metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, cancer, stroke or incidentalomas.

13 Claims, 2 Drawing Sheets

Product Profile
Target Activity

| | |
|---|---|
| Cyp17 | < 100 nM* |
| Cyp21 | < 100 nM* |
| Cyp11B1 | < 100 nM* |

Off Target Counter Screens

| | |
|---|---|
| Cyp19 | 50x Cyp 17 |
| Bile Acid (Cyp7A surrogate) | 100 x Cyp 17 |
| Cyp450 3A4 > 50% @ 1 mM | $IC_{50}$ (nM) |
| Cyp450 2D6 > 50% @ 1 mM | > 50% @ 1 µM |
| Cyp450 2C9 > 50% @ 1 mM | > 50% @ 1 µM |

Pharmaceutical Profiling/ADME

| | |
|---|---|
| Solubility >5 uMolar | uMolar |
| Molecular Weight | < 500 AMU |
| ClogP | < 5 |
| TPSA | < 140 |
| Cytoxicity in HerG2 | > 10% @ 1 µM |
| Caco-2 permeability (A-B, B-A) | > 20 ($10^{-6}$ cm/sec) |
| Guinea Pig liver microsomal stability | > 30 min. |
| Human liver microsomal stability | > 30 min. |
| Plasma stability | > 30min. |
| Plasma protein binding | < 95% |
| Guinea Pig Bioavailability | > 25% |
| Guinea Pig $T_{1/2}$ | < 4 h |

FIGURE 1

| COR | MW | TPSA | LogP | Cyp17 | Cyp21 | Cyp11 | Cyp19 | Cyp3A4 | Bile Acid Secretion |
|---|---|---|---|---|---|---|---|---|---|
| | | | | IC50(nM) | | | | | |
| 510032 | 401 | 36 | 4.1 | 5 | 430 | 1200 | 10000 | 695 | >10000 |
| 510064 | 464 | 54 | 4.3 | 5 | 393 | 140 | 10000 | 636.0 | >10000 |
| 510024 | 603 | 68 | 7.0 | 17 | 520 | 4 | 10000 | 873 | 1370 |
| 510065 | 452 | 54 | 4.1 | 5 | 520 | 200 | 10000 | 243.0 | N/T |
| 510068 | 492 | 54 | 5.7 | 6 | 316 | 1500 | 1000 | 9360.0 | >10000 |
| 510026 | 522 | 88 | 3.8 | 4 | 250 | 73 | N/D | 1670 | >10000 |

CYTOCHROME P450 INHIBITORS AND THEIR METHOD OF USE

This application is the United States national stage of International Application No. PCT/US2014/055677, filed Sep. 15, 2014, which claims benefit of U.S. Provisional Application No. 61/877,924, filed Sep. 13, 2013, both of which are herein incorporated by reference in their entirety.

BRIEF SUMMARY

Embodiments of the present invention are directed toward novel compounds of the formula (I),

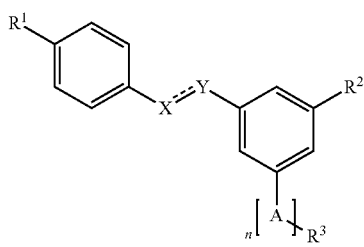
(I)

and hydrates, solvates, enantiomers, diastereomers, pharmaceutically acceptable salts, prodrugs and complexes thereof, wherein:

X and Y are each independently CH and connected by a double bond;

X and Y are each independently $CH_2$ and connected by a single bond;

$R^1$ is selected from a group consisting of Br,

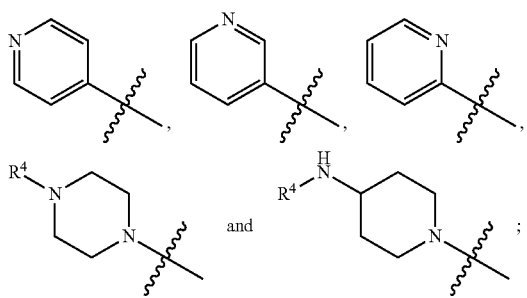

$R^2$ is selected from a group consisting of hydrogen, hydroxyl, fluorine, and chlorine;

$R^3$ is selected from a group consisting of optionally substituted 2-pyridyl, optionally substituted 3-pyridyl, optionally substituted 4-pyridyl, optionally substituted 1-imidazoyl, optionally substituted 2-imidazoyl, optionally substituted 4-imidazoyl, and $CH_2OHetAr$;

$R^4$ is selected from a group consisting of optionally substituted $C_{1-6}$ alkyl, optionally substituted $C_{1-6}$ branched alkyl, optionally substituted $C_{3-7}$ cycloalkyl, optionally substituted phenyl, optionally substituted benzyl, $COR^5$, $C(O)OR^6$, $C(O)NR^{7a}R^{7b}$, $SO_2R^8$,

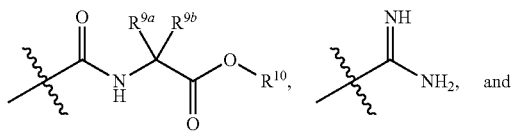

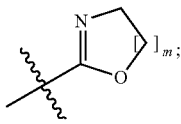

A is selected from a group consisting of $CH_2$,

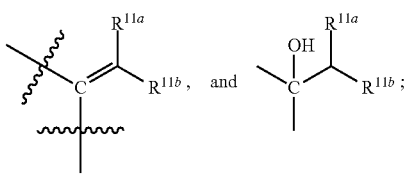

n is 0 or 1;

m is 1 or 2;

$R^5$ is selected from the group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted heteroaryl;

$R^6$ is selected from the group consisting of optionally substituted $C_{1-6}$ linear alkyl, optionally substituted $C_{1-6}$ branchedalkyl, and optionally substituted $C_{3-7}$ cycloalkyl;

$R^{7a}$ and $R^{7b}$ are each independently selected from a group consisting of hydrogen, optionally substituted $C_{1-6}$ linear alkyl, optionally substituted $C_{1-6}$ branched alkyl, and optionally substituted $C_{3-7}$ cycloalkyl;

$R^8$ is selected from the group consisting of optionally substituted $C_{1-6}$ linear alkyl, optionally substituted $C_{1-6}$ branched alkyl, optionally substituted $C_{3-7}$ cycloalkyl, optionally substituted $C_{1-6}$ haloalkyl, optionally substituted aryl, optionally substituted $C_{3-7}$ heterocyclyl, and optionally substituted heteroaryl;

$R^{9a}$ and $R^{9b}$ are each independently selected from a group consisting of hydrogen, optionally substituted $C_{1-6}$ linear alkyl, optionally substituted $C_{1-6}$ branched alkyl, optionally substituted aryl, optionally substituted benzyl, $-CH_2OR^6$, $-CH_2SR^6$, and $CH_2Heteroaryl$;

$R^{10}$ is selected from the group consisting of optionally substituted $C_{1-6}$ linear alkyl, optionally substituted $C_{1-6}$ branched alkyl, and optionally substituted $C_{3-7}$ cycloalkyl; and $R^{11a}$ and $R^{11b}$ are each independently selected from a group consisting of hydrogen and optionally substituted $C_{1-6}$ linear alkyl.

Some embodiments relate to a method for treating, delaying, slowing, or inhibiting the progression of diseases that involve production of cortisol, including, for example, metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke and incidentalomas, said method comprising administering to a subject in need thereof an effective amount of a compound or composition according to embodiments, wherein the disease that involves production of cortisol is treated, delayed, slowed, or inhibited. In some embodiments, the diseases that involve production of cortisol comprise diseases that involve an overproduction of cortisol.

Some embodiments are directed to a method of treating, delaying, slowing, or inhibiting the progression of diseases selected from metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke, or incidentalomas, the method comprising administering to a subject in need thereof an effective amount of a compound or composition according to embodiments described herein, wherein the compound or composition modulates cortisol, and wherein the disease is treated, delayed, slowed, or inhibited. In some embodiments, the compound or composition lowers cortisol levels in the subject.

Some embodiments relate to a method of modulating cortisol activity, the method comprising administering to a subject in need thereof an effective amount of a compound or composition according to embodiments described herein, wherein the compound or composition modulates cortisol. In some embodiments, the compound or composition lowers cortisol levels in the subject.

Some embodiments yet further relate to a method for treating, delaying, slowing, or inhibiting the progression of diseases that involve production of cortisol, including, for example, metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke and incidentalomas, wherein said method comprises administering to a subject a composition comprising an effective amount of one or more compounds according to embodiments described herein and an excipient. In some embodiments, the diseases that involve production of cortisol comprise diseases that involve an overproduction of cortisol.

Some embodiments also relate to a method for treating, delaying, slowing, or inhibiting the progression of diseases or conditions associated with metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke and incidentalomas, and diseases that involve production of cortisol. Said methods comprise administering to a subject an effective amount of a compound or composition according to embodiments described herein. In some embodiments, the diseases that involve production of cortisol comprise diseases that involve an overproduction of cortisol.

Some embodiments yet further relate to a method for treating, delaying, slowing, or inhibiting the progression of disease or conditions associated with metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke and incidentalomas and diseases that involve production of cortisol, wherein said method comprises administering to a subject a composition comprising an effective amount of one or more compounds according to embodiments described herein and an excipient. In some embodiments, the diseases that involve production of cortisol comprise diseases that involve an overproduction of cortisol.

Some embodiments also relate to a method for treating, delaying, slowing, or inhibiting the progression of disease or conditions associated with cortisol. Said methods comprise administering to a subject an effective amount of a compound or composition according to embodiments described herein.

Some embodiments yet further relate to a method for treating, delaying, slowing, or inhibiting the progression of disease or conditions associated with cortisol, wherein said method comprises administering to a subject a composition comprising an effective amount of one or more compounds according to embodiments described herein and an excipient.

Some embodiments yet further relate to a method of lowering the concentration of cortisol in the circulatory system. Said methods comprise administering to a subject an effective amount of a compound or composition according to embodiments described herein.

Some embodiments yet further relate to a method of lowering the concentration of cortisol in the circulatory system, wherein said method comprises administering to a subject a composition comprising an effective amount of one or more compounds according to embodiments described herein and an excipient.

Some embodiments also relate to a method for treating, delaying, slowing, or inhibiting the progression of diseases that involve excess Cyp17 activity, including, for example, such as prostate cancer, prostatic hypertrophy (prostatism), androgenic syndrome (masculinization), andromorphous baldness, breast cancer, mastopathy, uterine cancer, hirsutism, uterine fibroids, PCOS (polycystic ovarian syndrome), endometriosis, and ovarian cancer, said method comprising administering to a subject in need thereof an effective amount of a compound or composition according to embodiments, wherein the disease that involves excess Cyp17 activity is treated, delayed, slowed, or inhibited.

Some embodiments relate to a method for treating, delaying, slowing, or inhibiting the progression of diseases that involve excess Cyp17 activity, wherein said method comprises administering to a subject a composition comprising an effective amount of one or more compounds according to the embodiments described herein and an excipient.

Some embodiments also relate to a method for treating, delaying, slowing, or inhibiting the progression of diseases associated with Cyp17 activity, including, for example, such as prostate cancer, prostatic hypertrophy (prostatism), androgenic syndrome (masculinization), andromorphous baldness, breast cancer, mastopathy, uterine cancer, hirsutism, uterine fibroids, PCOS (polycystic ovarian syndrome), endometriosis, and ovarian cancer, said method comprising administering to a subject in need thereof an effective amount of a compound or composition according to embodiments, wherein the Cyp17 activity is lowered, and wherein the disease that is associated with Cyp17 activity is treated, delayed, slowed, or inhibited.

Some embodiments relate to a method for treating, delaying, slowing, or inhibiting the progression of diseases associated with Cyp17 activity, said method comprising administering to a subject a composition comprising an effective amount of one or more compounds according to embodiments described herein and an excipient, wherein Cyp17 activity is lowered.

Some embodiments also relate to a method for lowering Cyp17 activity in a subject in need thereof, the method comprising administering to the subject an effective amount of a compound or composition according to embodiments, wherein the Cyp17 activity is lowered. In some embodiments, lowering of Cyp17 activity leads to a lowering of testosterone levels to castrate levels in the subject. In some embodiments, lowering of Cyp17 activity leads to a lowering of estrogen levels to post-menopausal levels in the subject. Some embodiments are directed to a method of treating cancer in a subject, the method comprising administering to the subject an effective amount of a compound or composition according to embodiments described herein, wherein Cyp17 activity is lowered. In some embodiments, Cyp17 activity is inhibited almost completely or completely. In some embodiments, lowering of Cyp17 activity leads to a lowering of testosterone levels to castrate levels in the subject. In some embodiments, lowering of Cyp17 activity leads to a lowering of estrogen levels to post-menopausal levels in the subject.

Some embodiments relate to a method of lowering Cyp17 activity, said method comprising administering to a subject a composition comprising an effective amount of one or more compounds according to embodiments described herein and an excipient.

Some embodiments relate to a method of inhibiting Cyp17 activity, said method comprising administering to a subject a composition comprising an effective amount of one or more compounds according to embodiments described herein and an excipient.

Some embodiments relate to a method for treating, delaying, slowing, or inhibiting the progression of diseases that involve excess Cyp11B1 activity, including, for example, prostate cancer, prostatic hypertrophy (prostatism), androgenic syndrome (masculinization), andromorphous baldness, breast cancer, mastopathy, uterine cancer, hirsutism, uterine fibroids, PCOS (polycystic ovarian syndrome), endometriosis, and ovarian cancer, said method comprising administering to a subject in need thereof an effective amount of a compound or composition according to embodiments described herein, wherein the disease that involves excess Cyp11B1 activity is treated, delayed, slowed, or inhibited.

Some embodiments yet further relate to a method for treating, delaying, slowing, or inhibiting the progression of diseases that involve excess Cyp11B1 activity, including, for example, androgenic hormones and estrogens are involved, such as prostate cancer, prostatic hypertrophy (prostatism), androgenic syndrome (masculinization), andromorphous baldness, breast cancer, mastopathy, uterine cancer, hirsutism, uterine fibroids, PCOS (polycystic ovarian syndrome), endometriosis, and ovarian cancer, wherein said method comprises administering to a subject a composition comprising an effective amount of one or more compounds according to embodiments described herein and an excipient.

Some embodiments relate to a method for treating, delaying, slowing, or inhibiting the progression of diseases associated with Cyp11B1 activity, including, for example, prostate cancer, prostatic hypertrophy (prostatism), androgenic syndrome (masculinization), andromorphous baldness, breast cancer, mastopathy, uterine cancer, hirsutism, uterine fibroids, PCOS (polycystic ovarian syndrome), endometriosis, and ovarian cancer, said method comprising administering to a subject in need thereof an effective amount of a compound or composition according to embodiments described herein, wherein the Cyp11B activity is lowered and wherein the disease that involves excess Cyp11B1 activity is treated, delayed, slowed, or inhibited.

Some embodiments yet further relate to a method for treating, delaying, slowing, or inhibiting the progression of diseases associated with Cyp11B1 activity, including, for example, androgenic hormones and estrogens are involved, such as prostate cancer, prostatic hypertrophy (prostatism), androgenic syndrome (masculinization), andromorphous baldness, breast cancer, mastopathy, uterine cancer, hirsutism, uterine fibroids, PCOS (polycystic ovarian syndrome), endometriosis, and ovarian cancer, said method comprising administering to a subject a composition comprising an effective amount of one or more compounds according to embodiments described herein and an excipient, wherein the Cyp11B1 activity is lowered.

Some embodiments also relate to a method for lowering Cyp11B1 activity in a subject in need thereof, the method comprising administering to the subject an effective amount of a compound or composition according to embodiments, wherein the Cyp17 activity is lowered. Some embodiments relate to a method of lowering Cyp11B1 activity, said method comprising administering to a subject a composition comprising an effective amount of one or more compounds according to embodiments described herein and an excipient.

Some embodiments relate to a method of inhibiting Cyp11B1 activity, said method comprising administering to a subject a composition comprising an effective amount of one or more compounds according to embodiments described herein and an excipient.

Some embodiments also relate to a method for treating, delaying, slowing, or inhibiting the progression of diseases that involve excess Cyp21 activity, including, for example, androgenic hormones and estrogens are involved, such as prostate cancer, prostatic hypertrophy (prostatism), androgenic syndrome (masculinization), andromorphous baldness, breast cancer, mastopathy, uterine cancer, hirsutism, uterine fibroids, PCOS (polycystic ovarian syndrome), endometriosis, and ovarian cancer, said method comprising administering to a subject in need thereof an effective amount of a compound or composition according to embodiments described herein, wherein the disease that involves excess Cyp21 activity is treated, delayed, slowed, or inhibited.

Some embodiments yet further relate to a method for treating, delaying, slowing, or inhibiting the progression of diseases that involve excess Cyp21 activity, including, for example, androgenic hormones and estrogens are involved, such as prostate cancer, prostatic hypertrophy (prostatism), androgenic syndrome (masculinization), andromorphous baldness, breast cancer, mastopathy, uterine cancer, hirsutism, uterine fibroids, PCOS (polycystic ovarian syndrome), endometriosis, and ovarian cancer, wherein said method comprises administering to a subject a composition comprising an effective amount of one or more compounds according to embodiments described herein and an excipient.

Some embodiments also relate to a method for treating, delaying, slowing, or inhibiting the progression of diseases associated with Cyp21 activity, including, for example, androgenic hormones and estrogens are involved, such as prostate cancer, prostatic hypertrophy (prostatism), androgenic syndrome (masculinization), andromorphous baldness, breast cancer, mastopathy, uterine cancer, hirsutism, uterine fibroids, PCOS (polycystic ovarian syndrome), endometriosis, and ovarian cancer, said method comprising administering to a subject in need thereof an effective amount of a compound or composition according to embodiments described herein, wherein Cyp21 activity is lowered, and wherein the disease that is associated with Cyp21 activity is treated, delayed, slowed, or inhibited.

Some embodiments yet further relate to a method for treating, delaying, slowing, or inhibiting the progression of diseases associated with Cyp21 activity, including, for example, androgenic hormones and estrogens are involved, such as prostate cancer, prostatic hypertrophy (prostatism), androgenic syndrome (masculinization), andromorphous baldness, breast cancer, mastopathy, uterine cancer, hirsutism, uterine fibroids, PCOS (polycystic ovarian syndrome), endometriosis, and ovarian cancer, said method comprising administering to a subject a composition comprising an effective amount of one or more compounds according to embodiments described herein and an excipient, wherein the Cyp21 activity is lowered.

Some embodiments also relate to a method for lowering Cyp21 activity in a subject in need thereof, the method comprising administering to the subject an effective amount of a compound or composition according to embodiments, wherein the Cyp17 activity is lowered. Some embodiments relate to a method of lowering Cyp21 activity, said method comprising administering to a subject a composition comprising an effective amount of one or more compounds according to embodiments described herein and an excipient.

Some embodiments relate to a method of inhibiting Cyp21 activity, said method comprising administering to a subject a composition comprising an effective amount of one or more compounds according to embodiments described herein and an excipient.

Some embodiments also relate to a method for lowering at least two of the following: Cyp17 activity, Cyp11B1 activity, and Cyp21 activity in a subject in need thereof, the method comprising administering to the subject an effective amount of a compound or composition according to embodiments described herein. In some embodiments, the method further modulates cortisol. Some embodiments relate to a method of treating, delaying, slowing, or inhibiting the progression of a disease selected from metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke, incidentalomas, related conditions, or a combination thereof, the method comprising administering to a subject in need thereof an effective amount of a compound or composition according to embodiments described herein, wherein the compound or composition lowers at least two of the following: Cyp17 activity, Cyp11B1 activity, and Cyp21 activity in the subject. In some embodiments, the compound or composition modulates cortisol. In some embodiments, the compound or composition lowers Cyp17 activity, Cyp11B1 activity, and Cyp21 activity in the subject.

Some embodiments further relate to a process for preparing the compounds of embodiments described herein.

BRIEF DESCRIPTION OF THE DRAWINGS

FIG. 1 represents various in vivo and in vitro testing indices and the target levels thereof used to screen compounds of the present disclosure.

Figure 2:
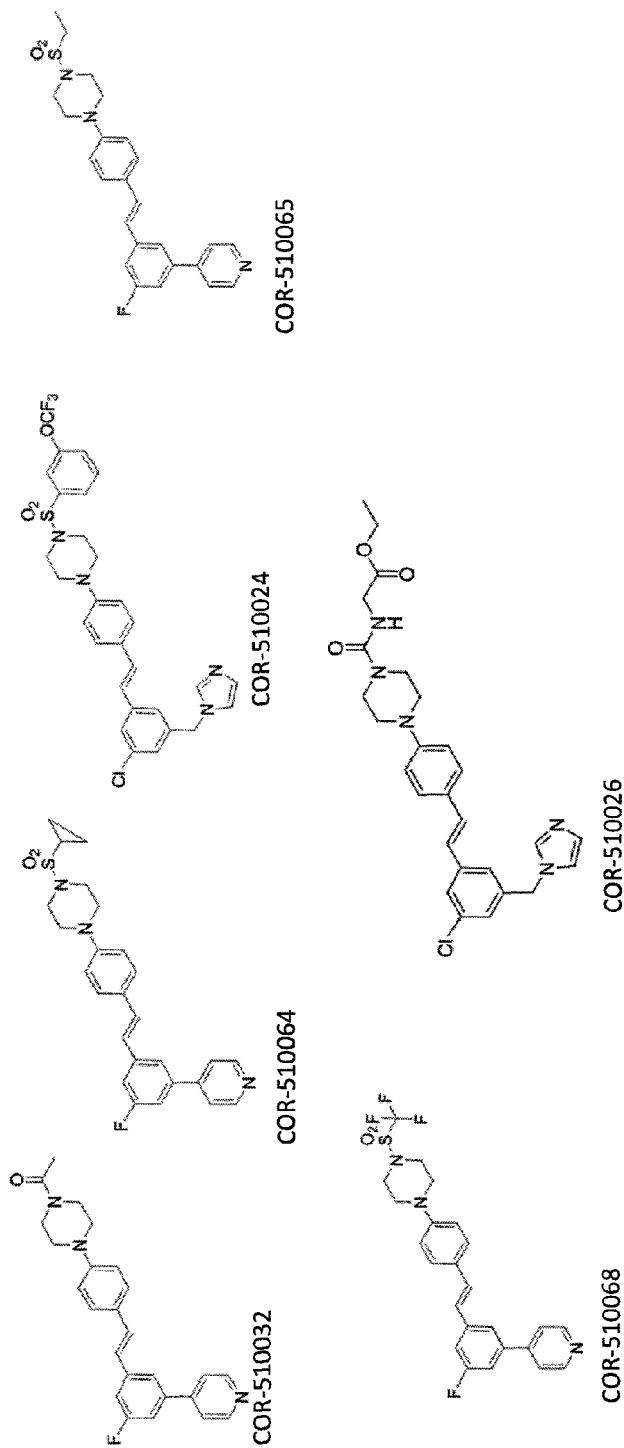
FIG. 2 represents the extraction of over 200 compounds which realized the in vitro and in vivo target levels set forth in FIG. 1.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to embodiments described herein.

DETAILED DESCRIPTION OF THE INVENTION

Embodiments of the present invention describe novel compounds useful for the treatment of diseases associated with the production of cortisol, such as metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke, incidentalomas, and related conditions. In some embodiments, the diseases that involve production of cortisol comprise diseases that involve an overproduction of cortisol. In some embodiments, diabetes mellitus includes diabetes mellitus type I, diabetes mellitus type II, prediabetes, latent autoimmune diabetes of adults (LADA), congenital diabetes, cystic fibrosis-related diabetes, steroid diabetes, monogenic diabetes, gestational diabetes, or a combination thereof Cortisol is a principal human glucocorticoid exhibiting many important physiological functions. It is involved in the regulation of the metabolism of proteins, carbohydrates, and fats; it counteracts insulin, maintains blood pressure and cardiovascular function, and suppresses the immune system's inflammatory response. However, pathological changes in adrenal and the upstream regulating switches can cause an overproduction of cortisol. One disease associated with overproduction of cortisol is metabolic syndrome. Over the course of the last three decades, a growing body of knowledge has been developed to describe metabolic syndrome, also referred to as "Syndrome X" or "Insulin Resistance Syndrome" (Reaven, G. M. Role of insulin resistance in human disease, *Diabetes*, 1988, 37, 1595-1607). Metabolic syndrome is defined as a cluster of abnormalities that occur in concert, including high blood pressure (BP), hyperglycemia, reduced high density lipoprotein cholesterol (HDL-C) levels, elevated triglycerides (TG) and abdominal obesity. The most widely accepted definition of this condition is based on the National Cholesterol Education Program (NCEP) Adult Treatment Panel-III (ATP-III), which provides for the diagnosis of metabolic syndrome in patients that meet at least three of parameters identified in table 1. Current estimates indicate that nearly 25% of the world's adult population suffers from metabolic syndrome, and the incidence is rising, largely as a result of increased obesity rates (Anagnostis, P.; Athyros, V. G.; Tziomalos, K.; Karagiannis, A.; Dimitri P. Mikhailidis, D. P. The Pathogenetic role of cortisol in the Metabolic Syndrome: A hypothesis, *J. Clin. Endocrinol. Metab.* 2009 94, 8, 2692-2701.).

TABLE 1

| Metabolic Syndrome diagnostic parameters | | |
|---|---|---|
| Parameter | Men | Women |
| Waist size | >102 cm | >88 cm |
| HDL-C | <40 mg/dL | <50 mg/dL |
| TG | >150 mg/dL | >150 mg/dL |
| BP | >130/85 | >130/85 |
| Fasting Glucose | >110 mg/dL | >110 mg/dL |

Cortisol production is regulated by several factors, including the enzymatic activity of the 11β-hydroxylase (Cyp11B1), 17α-hydroxylase-C17,20-lyase (Cyp17), and 21-hydroxylase (Cyp21). All three are members of the cytochrome P450 superfamily of enzymes. The 17α-hydroxylase/$C_{17-20}$ lyase enzyme complex is essential for the biosynthesis of androgens. CYP17 is a bifunctional enzyme which possesses both a $C_{17-20}$-lyase activity and a C17-hydroxylase activity. These two alternative enzymatic activities of CYP17 result in the formation of critically different intermediates in steroid biosynthesis and each activity appear to be differentially and developmentally regulated.

Cyp11B1 catalyzes the final step of cortisol synthesis, hydroxylation of the C-11 position of deoxycortisol. Cyp17 has multiple functions in corticosteroid synthesis. The C-17 and C-20 positions of the steroid framework can be modified by this enzyme. Pregnenolone and progesterone are hydroxylated by Cyp17 at C-17 (hydroxylase activity), while the C-20/C-17 bond is cleaved by the same enzyme in 17-hydroxyprogesterone and 17-hydroxypregnenolone (lyase activity). Finally, Cyp21 catalyzes the hydroxylation of C-21 in steroids such as progesterone and 17α-hydroxy progesterone.

Compounds that inhibit the enzymatic activity of Cyp17, Cyp21, or Cyp11B1 will lead to a decrease in the synthesis of cortisol, which would treat, delay, slow, or inhibit the progression of diseases associated with the production of cortisol such as metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke and incidentalomas. Further, compounds that are dual inhibitors of Cyp17 and Cyp21 will lead to a decrease in the synthesis of cortisol, which would treat, delay, slow, or inhibit the progression of diseases associated with the production of cortisol such as metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke and incidentalomas. In addition, compounds that are dual inhibitors of Cyp17 and Cyp11B1 will lead to a decrease in the synthesis of cortisol, which would treat, delay, slow, or inhibit the progression of diseases associated with the production of cortisol such as metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke and incidentalomas. Further, compounds that are dual inhibitors of Cyp11B1 and Cyp21 will lead to a decrease in the synthesis of cortisol, which would treat, delay, slow, or inhibit the progression of diseases associated with the production of cortisol such as metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke and incidentalomas. In some embodiments, the diseases that involve production of cortisol comprise diseases that involve an overproduction of cortisol.

There is a long felt need for new treatments for diseases and symptoms associated with the production of cortisol such as metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke and incidentalomas , that are both disease-modifying and effective in treating patients. Embodiments of the present invention address the need to identify effective treatment for diseases and symptoms associated with the production of cortisol, such as metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke and incidentalomas. In some embodiments, the diseases that involve production of cortisol comprise diseases that involve an overproduction of cortisol.

The cortisol lowering agents of embodiments described herein are capable of treating, delaying, slowing, or inhibiting the progression of diseases associated with the overproduction of cortisol such as, for example, metabolic syndrome. It has been discovered that cortisol is a principal human glucocorticoid exhibiting many important physiological functions. It is involved in the regulation of the metabolism of proteins, carbohydrates, and fats; it counteracts insulin, maintains blood pressure and cardiovascular function, and suppresses the immune system's inflammatory response. However, pathological changes in adrenal gland or other tissues capable of secreting cortisol and the upstream regulating switches can cause an overproduction of cortisol. One disease associated with overproduction of cortisol is metabolic syndrome. In addition, the overproduction of cortisol is associated with hypertension, diabetes mellitus, obesity, headache, depression, hypertension, diabetes mellitus, Cushing's syndrome, pseudo-Cushing syndrome, cognitive impairment, dementia, heart failure, renal failure, psoriasis, glaucoma, cardiovascular disease, stroke and incidentalomas. Without wishing to be limited by theory, it is believed that cortisol lowering agents of embodiments described in this disclosure ameliorate, abate, otherwise cause to be controlled, diseases associated with the overproduction of cortisol, for example metabolic syndrome, obesity, headache, depression, hypertension, diabetes mellitus, Cushing's Syndrome, pseudo-Cushing syndrome, cognitive impairment, dementia, heart failure, renal failure, psoriasis, glaucoma, cardiovascular disease, stroke and incidentalomas.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

As used herein, the term "consists of" or "consisting of" means that the method, use of formulation includes only the elements, steps, or ingredients specifically recited in the particular claimed embodiment or claim.

As used herein, the term "consisting essentially of" or "consists essentially of" means that the only active pharmaceutical ingredient in the formulation or method that treats the specified condition (e.g. Cushing's syndrome) is the specifically recited active pharmaceutical ingredient for treating the specified condition in the particular embodiment or claim; that is, the scope of the claim or embodiment is limited to the specified elements or steps and those that do not materially affect the basic and novel characteristic(s) of the particular embodiment or claimed invention.

In the application, where an element or component is said to be included in and/or selected from a list of recited elements or components, it should be understood that the element or component can be any one of the recited elements or components or a combination thereof, and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" means plus or minus 10% of the numerical value of the number with which it is being used. Therefore, about 50% means in the range of 45%-55%.

It should be understood that the order of steps or order for performing certain actions is immaterial so long as the present teachings remain operable. Moreover, two or more steps or actions can be conducted simultaneously.

As used herein, the term "excess" refers to an amount or quantity surpassing what is considered normal or sufficient. For example, excess Cyp17 activity may refer to an above normal level of the C17-hydroxylase activity of CYP17 which promotes the overproduction of glucocorticoids or an above normal level of the C17,20-lyase activity of Cyp17 which promotes the overproduction of sex hormones. In some embodiments, excess Cyp17 activity may lead to overproduction of cortisol or an overproduction of androgenic or estrogenic hormones.

In some embodiments, the compounds of embodiments herein lower the production of cortisol. In some embodiments, the compounds of emboidments herein lower a level of a hormone selected from CYP17, CYP11B1 and CYP21. For example, in prostate cancer, the compounds of embodiments herein may be administered to lower CYP17 levels to bring down the level of testosterone (which may be at a normal range to begin with) to an almost castrate level to ameliorate the cancer. In another example, the compounds of embodiments herein may be used to lower CYP17 levels in women with ovarian cancer where administration of the compounds of embodiments herein would bring estrogen levels to post-menopausal levels to ameliorate the ovarian cancer. Additionally, in diabetes, where it is believed that cortisol levels are circadian in nature (going to nadir in some times of the day), administration of the compounds of embodiments herein would reduce hormone levels to mid-normal ranges.

As used herein, the term "halogen" includes chlorine, bromine, fluorine, iodine, or a combination thereof.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) refers independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tent-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$ amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Non-limiting examples of alkenyl groups include ethenyl, 3-propenyl, 1-propenyl (also 2-methylethenyl), isopropenyl (also 2-methylethen-2-yl), buten-4-yl, and the like. Non-limiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Non-limiting examples of alkynyl groups include ethynyl, prop-2-ynyl (also propargyl), propyn-1-yl, and 2-methyl-hex-4-yn-1-yl. Non-limiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. In some embodiments, cycloalkyl groups may be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. In some embodiments, cycloalkyl rings may be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[12.1.11]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, the term "haloalkyl" may include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

As used herein, the term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

As used herein, the term "arylalkyl" or "aralkyl" refers to the group -alkyl-aryl, where the alkyl and aryl groups are as defined herein. Aralkyl groups of embodiments described herein are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d] thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposes of embodiments described herein fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

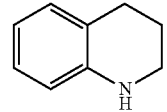

is, for the purposes of embodiments described herein, considered a heterocyclic unit. 6,7-Dihydro-5H-cyclopentapyrimidine having the formula:

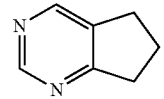

is, for the purposes of embodiments described herein, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

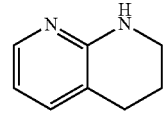

is, for the purposes of embodiments described herein, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —$NO_2$, oxo (=O), —$OR^{12}$, —$SR^{12}$, —$N(R^{12})_2$, —$NR^{12}C(O)R^{12}$, —$SO_2R^{12}$, —$SO_2OR^{12}$, —$SO_2N(R^{12})_2$, —$C(O)R^{12}$, —$C(O)OR^{12}$, —$C(O)N(R^{12})_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —$NO_2$, oxo, and $R^{12}$; wherein $R^{12}$, at each occurrence, independently is hydrogen, —$OR^{13}$, —$SR^{13}$, —$C(O)R^{13}$, —$C(O)OR^{13}$, —C(O)N $(R^{13})_2$, —$SO_2R^{13}$, —$S(O)_2OR^{13}$, —$N(R^{13})_2$, —$NR^{13}C(O)$ $R^{13}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{12}$ units taken together with the atom(s) to which they are bound form an optionally substituted carbocycle or heterocycle wherein said carbocycle or heterocycle has 3 to 7 ring atoms; wherein $R^{13}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{13}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —$OR^{14}$; for example, —OH, —$OCH_3$, —$OCH_2CH_3$, —$OCH_2CH_2CH_3$;
ii) —$C(O)R^{14}$; for example, —$COCH_3$, —$COCH_2CH_3$, —$COCH_2CH_2CH_3$;
iii) —$C(O)OR^{14}$; for example, —$CO_2CH_3$, —$CO_2CH_2CH_3$, —$CO_2CH_2CH_2CH_3$;
iv) —$C(O)N(R^{14})_2$; for example, —$CONH_2$, —$CONHCH_3$, —$CON(CH_3)_2$;
v) —$N(R^{14})_2$; for example, —$NH_2$, —$NHCH_3$, —$N(CH_3)_2$, —$NH(CH_2CH_3)$;
vi) halogen: —F, —Cl, —Br, and —I;
vii) —$CH_eX_g$; wherein X is halogen, m is from 0 to 2, e+g=3; for example, —$CH_2F$, —$CHF_2$, —$CF_3$, —$CCl_3$, or —$CBr_3$;
viii) —$SO_2R^{14}$; for example, —$SO_2H$; —$SO_2CH_3$; —$SO_2C_6H_5$;
ix) $C_1$-$C_6$ linear, branched, or cyclic alkyl;
x) Cyano
xi) Nitro;
xii) $N(R^{14})C(O)R^{14}$;
xiii) Oxo (=O);
xiv) Heterocycle; and
xv) Heteroaryl wherein each $R^{14}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two $R^{14}$ units can be taken together to form a ring comprising 3-7 ring atoms. In certain aspects, each $R^{14}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of embodiments described herein the terms "compound," "analog," and "composition of matter" stand equally well for the cortisol lowering agent described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^{13})_2$, each $R^{13}$ may be the same or different than the other). Combinations of substituents and/or variables are permissible only if such combinations result in stable compounds The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

A "therapeutically effective amount" or "effective amount" of a composition is a predetermined amount calculated to achieve the desired effect, i.e. treat, delay, slow, or inhibit the progression of diseases that involve production of cortisol. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of embodiments described herein.

Embodiments described herein is directed toward novel compounds of the formula (I),

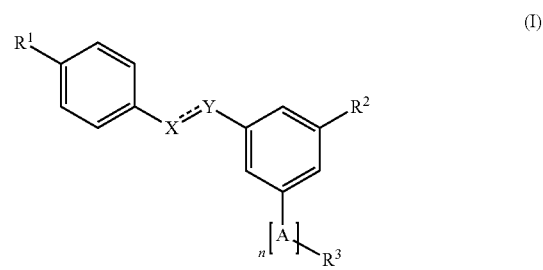

(I)

Including hydrates, solvates, enantiomers, diastereomers, pharmaceutically acceptable salts, prodrugs and complexes thereof, wherein:

X and Y are each independently CH and connected by a double bond;

X and Y are each independently $CH_2$ and connected by a single bond;

$R^1$ is selected from a group consisting of

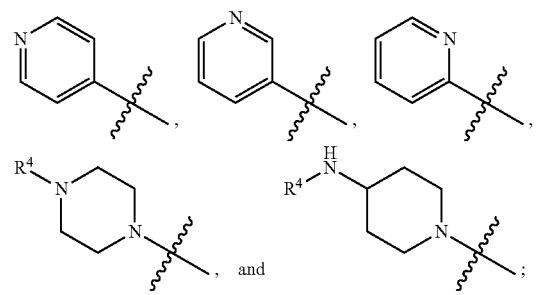

$R^2$ is selected from a group consisting of hydrogen, hydroxyl, fluorine, and chlorine;

$R^3$ is selected from a group consisting of optionally substituted 2-pyridyl, optionally substituted 3-pyridyl, optionally substituted 4-pyridyl, optionally substituted 1-imidazoyl, optionally substituted 2-imidazoyl, optionally substituted 4-imidazoyl, and $CH_2OHetAr$;

$R^4$ is selected from a group consisting of optionally substituted $C_{1-6}$ alkyl, optionally substituted $C_{1-6}$ branched alkyl, optionally substituted $C_{3-7}$ cycloalkyl, optionally substituted phenyl, optionally substituted benzyl, $COR^5$, $C(O)OR^6$, $C(O)NR^{7a}R^{7b}$, $SO_2R^8$,

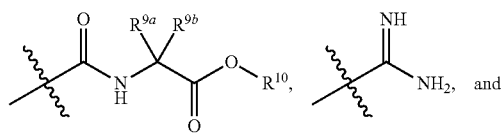

-continued

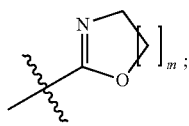

A is selected from a group consisting of CH$_2$, CH$_2$OHetAr,

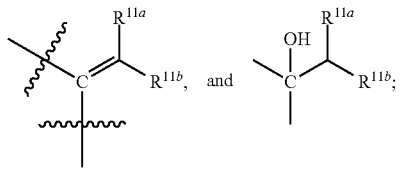

n is 0 or 1;
m is 1 or 2;
$R^5$ is selected from the group consisting of optionally substituted C$_{1-6}$ linear alkyl, optionally substituted C$_{1-6}$ branched alkyl, optionally substituted C$_{3-7}$ cycloalkyl, optionally substituted aryl, and optionally substituted heteroaryl;
$R^6$ is selected from the group consisting of optionally substituted C$_{1-6}$ linear alkyl, optionally substituted C$_{1-6}$ branched alkyl, and optionally substituted C$_{3-7}$ cycloalkyl;
$R^{7a}$ and $R^{7b}$ are each independently selected from a group consisting of hydrogen, optionally substituted C$_{1-6}$ linear alkyl, optionally substituted C$_{1-6}$ branched alkyl, and optionally substituted C$_{3-7}$ cycloalkyl;
$R^8$ is selected from the group consisting of optionally substituted C$_{1-6}$ linear alkyl, optionally substituted C$_{1-6}$ branched alkyl, optionally substituted C$_{3-7}$ cycloalkyl, optionally substituted C$_{1-6}$haloalkyl, optionally substituted aryl, optionally substituted C$_{3-7}$ heterocyclyl, and optionally substituted heteroaryl;
$R^{9a}$ and $R^{9b}$ are each independently selected from a group consisting of hydrogen, optionally substituted C$_{1-6}$ linear alkyl, optionally substituted C$_{1-6}$ branched alkyl, optionally substituted aryl, optionally substituted benzyl, —CH$_2$OR$^6$, —CH$_2$SR$^6$, and CH$_2$Heteroaryl;
$R^{10}$ is selected from the group consisting of optionally substituted C$_{1-6}$ linear alkyl, optionally substituted C$_{1-6}$ branched alkyl, and optionally substituted C$_{3-7}$ cycloalkyl;
$R^{11a}$ and $R^{11b}$ are each independently selected from a group consisting of hydrogen and optionally substituted C$_{1-6}$ linear alkyl.

Some embodiments include compounds having formula (II):

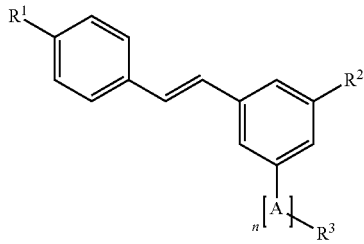

including hydrates, solvates, enantiomers, diastereomers, pharmaceutically acceptable salts, and complexes thereof.

Some embodiments include compounds having formula (III):

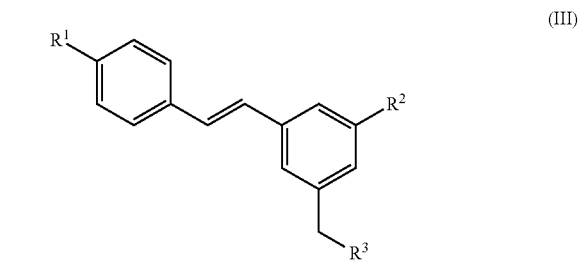

including hydrates, solvates, enantiomers, diastereomers pharmaceutically acceptable salts, and complexes thereof.

Some embodiments include compounds having formula (IV):

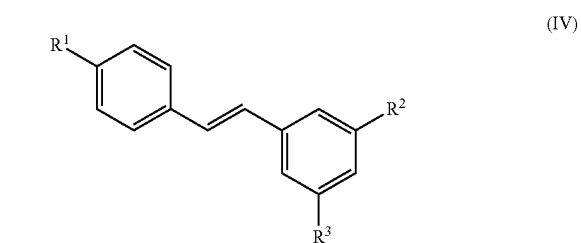

including hydrates, solvates, enantiomers, diastereomers pharmaceutically acceptable salts, and complexes thereof.

Some embodiments include compounds having formula (V):

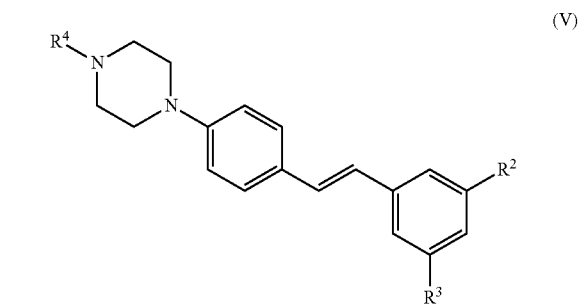

including hydrates, solvates, enantiomers, diastereomers pharmaceutically acceptable salts, and complexes thereof.

Some embodiments include compounds having formula (IIa):

(IIa)

including hydrates, solvates, enantiomers, diastereomers, pharmaceutically acceptable salts, and complexes thereof Some embodiments include compounds having formula (IIIa):

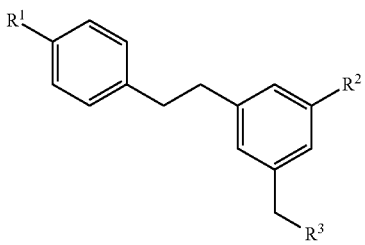

(IIIa)

including hydrates, solvates, enantiomers, diastereomers pharmaceutically acceptable salts, and complexes thereof.

Some embodiments include compounds having formula (IVa):

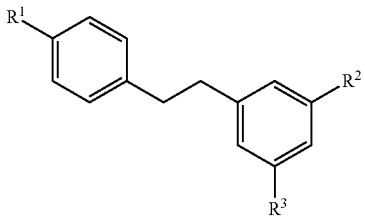

(IVa)

including hydrates, solvates, enantiomers, diastereomers pharmaceutically acceptable salts, and complexes thereof.

Some embodiments include compounds having formula (Va):

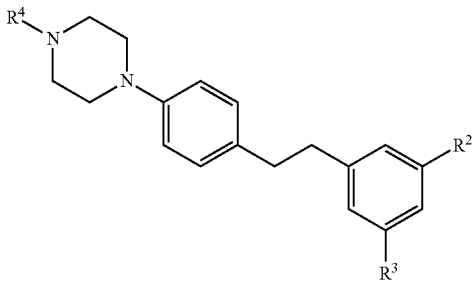

(Va)

including hydrates, solvates, enantiomers, diastereomers pharmaceutically acceptable salts, and complexes thereof.

In some embodiments X and Y are each independently CH and connected by a double bond.

In some embodiments X and Y are each independently $CH_2$ and connected by a single bond [0121] In some embodiments.

In some embodiments $R^1$ is selected from a group consisting of

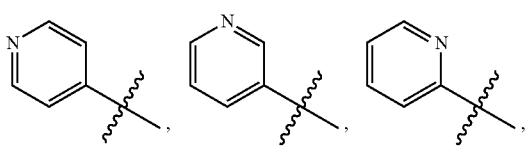

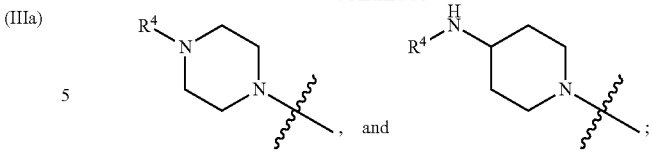

, and ;

In some embodiments $R^2$ is selected from a group consisting of hydrogen, hydroxyl, fluorine, and chlorine;

In some embodiments $R^3$ is selected from a group consisting of optionally substituted 2-pyridyl, optionally substituted 3-pyridyl, optionally substituted 4-pyridyl, optionally substituted 1-imidazoyl, optionally substituted 2-imidazoyl, optionally substituted 4-imidazoyl, and $CH_2OHetAr$.

In some embodiments $R^4$ is selected from a group consisting of optionally substituted $C_{1-6}$ alkyl, optionally substituted $C_{1-6}$ branched alkyl, optionally substituted $C_{3-7}$ cycloalkyl, optionally substituted phenyl, optionally substituted benzyl, $COR^5$, $C(O)OR^6$, $C(O)NR^{7a}R^{7b}$, $SO_2R^8$,

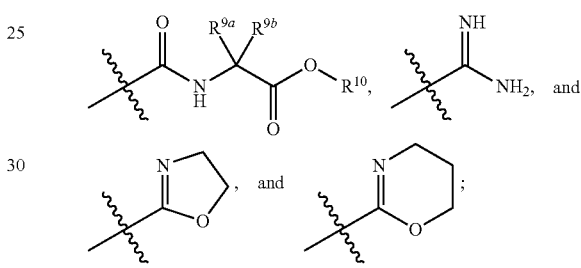

, and

In some embodiments A is selected from a group consisting of $CH_2$,

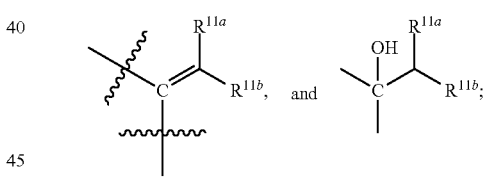

, and ;

In some embodiments n is 0 or 1;

In some embodiments $R^5$ is selected from the group consisting of optionally substituted $C_{1-6}$ linear alkyl, optionally substituted $C_{1-6}$ branched alkyl, optionally substituted $C_{3-7}$ cycloalkyl, optionally substituted aryl, and optionally substituted heteroaryl;

In some embodiments $R^6$ is selected from the group consisting of optionally substituted $C_{1-6}$ linear alkyl, optionally substituted $C_{1-6}$ branched alkyl, and optionally substituted $C_{3-7}$ cycloalkyl;

In some embodiments $R^{7a}$ and $R^{7b}$ are each independently selected from a group consisting of hydrogen, optionally substituted $C_{1-6}$ linear alkyl, optionally substituted $C_{1-6}$ branched alkyl, and optionally substituted $C_{3-7}$ cycloalkyl;

In some embodiments $R^8$ is selected from the group consisting of optionally substituted $C_{1-6}$ linear alkyl, optionally substituted $C_{1-6}$ branched alkyl, optionally substituted $C_{3-7}$ cycloalkyl, optionally substituted $C_{1-6}$ haloalkyl, optionally substituted aryl, optionally substituted $C_{3-7}$ heterocyclyl, and optionally substituted heteroaryl;

In some embodiments $R^{9a}$ and $R^{9b}$ are each independently selected from a group consisting of hydrogen, optionally substituted $C_{1-6}$ linear alkyl, optionally substituted $C_{1-6}$ branched alkyl, optionally substituted aryl, optionally substituted benzyl, —$CH_2OR^6$, —$CH_2SR^6$, and $CH_2$Heteroaryl;

In some embodiments $R^{10}$ is selected from the group consisting of optionally substituted $C_{1-6}$ linear alkyl, optionally substituted $C_{1-6}$ branched alkyl, and optionally substituted $C_{3-7}$ cycloalkyl;

In some embodiments $R^{11a}$ and $R^{11b}$ are each independently selected from a group consisting of hydrogen and optionally substituted $C_{1-6}$ linear alkyl.

Exemplary embodiments include compounds having the formula (VI) or a pharmaceutically acceptable salt form thereof:

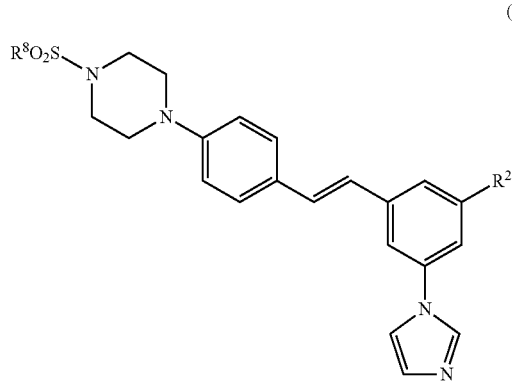

(VI)

wherein non-limiting examples of $R^2$ and $R^8$ are defined herein below in Table 2.

TABLE 2

| Entry | $R^2$ | $R^8$ |
|---|---|---|
| 1 | F | $CH_3$ |
| 2 | F | $CH_2CH_3$ |
| 3 | F | $CH(CH_3)_2$ |
| 4 | F | cyclopropyl |
| 5 | F | $CH_2CH_2CH_2Cl$ |
| 6 | F | $CH_2CF_3$ |
| 7 | F | $CF_3$ |
| 8 | F | $(CH_2)_2CH_3$ |
| 9 | F | $CH_2CH(CH_3)_2$ |
| 10 | F | 3-cynanophenyl |
| 11 | F | 3-(trifluoromethoxy)phenyl |
| 12 | F | 4-Chloro-3-nitrophenyl |
| 13 | F | 4-nitrophenyl |
| 14 | F | 3-pyridyl |
| 15 | F | 2-thiophene |
| 16 | F | 1-methylimidazol-2-yl |
| 17 | F | 1H-imidazol-4-yl |
| 18 | F | $CH_2SO_2CH_3$ |
| 19 | F | $(CH_2)_2CF_3$ |
| 20 | F | $CF_2H$ |
| 21 | F | $CH_2CF_2H$ |
| 22 | F | $CH_2CN$ |
| 23 | F | $(CH_2)_2OCH_3$ |
| 24 | F | tetrahydropyran-4-yl |
| 25 | OH | $CH_3$ |
| 26 | OH | $CH_2CH_3$ |
| 27 | OH | $CH(CH_3)_2$ |
| 28 | OH | cyclopropyl |
| 29 | OH | $CH_2CH_2CH_2Cl$ |
| 30 | OH | $CH_2CF_3$ |
| 31 | OH | $CF_3$ |
| 32 | OH | $(CH_2)_2CH_3$ |
| 33 | OH | $CH_2CH(CH_3)_2$ |
| 34 | OH | 3-cynanophenyl |
| 35 | OH | 3-(trifluoromethoxy)phenyl |
| 36 | OH | 4-Chloro-3-nitrophenyl |
| 37 | OH | 4-nitrophenyl |
| 38 | OH | 3-pyridyl |
| 39 | OH | 2-thiophene |
| 40 | OH | 1-methylimidazol-2-yl |
| 41 | OH | 1H-imidazol-4-yl |
| 42 | OH | $CH_2SO_2CH_3$ |
| 43 | OH | $(CH_2)_2CF_3$ |
| 44 | OH | $CF_2H$ |
| 45 | OH | $CH_2CF_2H$ |
| 46 | OH | $CH_2CN$ |
| 47 | OH | $(CH_2)_2OCH_3$ |
| 48 | OH | tetrahydropyran-4-yl |
| 49 | Cl | $CH_3$ |
| 50 | Cl | $CH_2CH_3$ |
| 51 | Cl | $CH(CH_3)_2$ |
| 52 | Cl | cyclopropyl |
| 53 | Cl | $CH_2CH_2CH_2Cl$ |
| 54 | Cl | $CH_2CF_3$ |
| 55 | Cl | $CF_3$ |
| 56 | Cl | $(CH_2)_2CH_3$ |
| 57 | Cl | $CH_2CH(CH_3)_2$ |
| 58 | Cl | 3-cynanophenyl |
| 59 | Cl | 3-(trifluoromethoxy)phenyl |
| 60 | Cl | 4-Chloro-3-nitrophenyl |
| 61 | Cl | 4-nitrophenyl |
| 62 | Cl | 3-pyridyl |
| 63 | Cl | 2-thiophene |
| 64 | Cl | 1-methylimidazol-2-yl |
| 65 | Cl | 1H-imidazol-4-yl |
| 66 | Cl | $CH_2SO_2CH_3$ |
| 67 | Cl | $(CH_2)_2CF_3$ |
| 68 | Cl | $CF_2H$ |
| 69 | Cl | $CH_2CF_2H$ |
| 70 | Cl | $CH_2CN$ |
| 71 | Cl | $(CH_2)_2OCH_3$ |
| 72 | Cl | tetrahydropyran-4-yl |
| 73 | H | $CH_3$ |
| 74 | H | $CH_2CH_3$ |
| 75 | H | $CH(CH_3)_2$ |
| 76 | H | cyclopropyl |
| 77 | H | $CH_2CH_2CH_2Cl$ |
| 78 | H | $CH_2CF_3$ |
| 79 | H | $CF_3$ |
| 80 | H | $(CH_2)_2CH_3$ |
| 81 | H | $CH_2CH(CH_3)_2$ |
| 82 | H | 3-cynanophenyl |
| 83 | H | 3-(trifluoromethoxy)phenyl |
| 84 | H | 4-Chloro-3-nitrophenyl |
| 85 | H | 4-nitrophenyl |
| 86 | H | 3-pyridyl |
| 87 | H | 2-thiophene |
| 88 | H | 1-methylimidazol-2-yl |
| 89 | H | 1H-imidazol-4-yl |
| 90 | H | $CH_2SO_2CH_3$ |
| 91 | H | $(CH_2)_2CF_3$ |
| 92 | H | $CF_2H$ |
| 93 | H | $CH_2CF_2H$ |

TABLE 2-continued

| Entry | R² | R⁸ |
|---|---|---|
| 94 | H | CH₂CN |
| 95 | H | (CH₂)₂OCH₃ |
| 96 | H |  |

Exemplary embodiments include compounds having the formula (VII) or a pharmaceutically acceptable salt form thereof:

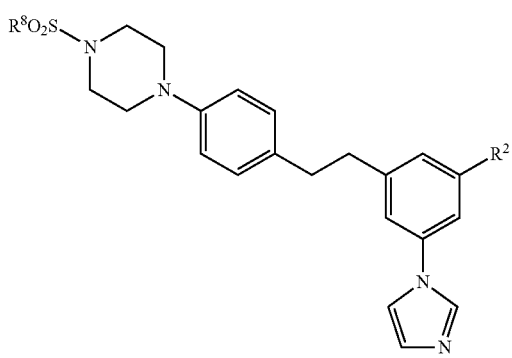

(VII)

wherein non-limiting examples of R² and R⁸ are defined herein below in Table 3.

TABLE 3

| Entry | R² | R⁸ |
|---|---|---|
| 1 | F | CH₃ |
| 2 | F | CH₂CH₃ |
| 3 | F | CH(CH₃)₂ |
| 4 | F | cyclopropyl |
| 5 | F | CH₂CH₂CH₂Cl |
| 6 | F | CH₂CF₃ |
| 7 | F | CF₃ |
| 8 | F | (CH₂)₂CH₃ |
| 9 | F | CH₂CH(CH₃)₂ |
| 10 | F | 3-cynanophenyl |
| 11 | F | 3-(trifluoromethoxy)phenyl |
| 12 | F | 4-Chloro-3-nitrophenyl |
| 13 | F | 4-nitrophenyl |
| 14 | F | 3-pyridyl |
| 15 | F | 2-thiophene |
| 16 | F | 1-methylimidazol-2-yl |
| 17 | F | 1H-imidazol-4-yl |
| 18 | F | CH₂SO₂CH₃ |
| 19 | F | (CH₂)₂CF₃ |
| 20 | F | CF₂H |
| 21 | F | CH₂CF₂H |
| 22 | F | CH₂CN |
| 23 | F | (CH₂)₂OCH₃ |
| 24 | F |  |
| 25 | OH | CH₃ |
| 26 | OH | CH₂CH₃ |
| 27 | OH | CH(CH₃)₂ |
| 28 | OH | cyclopropyl |
| 29 | OH | CH₂CH₂CH₂Cl |
| 30 | OH | CH₂CF₃ |
| 31 | OH | CF₃ |
| 32 | OH | (CH₂)₂CH₃ |
| 33 | OH | CH₂CH(CH₃)₂ |
| 34 | OH | 3-cynanophenyl |
| 35 | OH | 3-(trifluoromethoxy)phenyl |
| 36 | OH | 4-Chloro-3-nitrophenyl |
| 37 | OH | 4-nitrophenyl |
| 38 | OH | 3-pyridyl |
| 39 | OH | 2-thiophene |
| 40 | OH | 1-methylimidazol-2-yl |
| 41 | OH | 1H-imidazol-4-yl |
| 42 | OH | CH₂SO₂CH₃ |
| 43 | OH | (CH₂)₂CF₃ |
| 44 | OH | CF₂H |
| 45 | OH | CH₂CF₂H |
| 46 | OH | CH₂CN |
| 47 | OH | (CH₂)₂OCH₃ |
| 48 | OH |  |
| 49 | Cl | CH₃ |
| 50 | Cl | CH₂CH₃ |
| 51 | Cl | CH(CH₃)₂ |
| 52 | Cl | cyclopropyl |
| 53 | Cl | CH₂CH₂CH₂Cl |
| 54 | Cl | CH₂CF₃ |
| 55 | Cl | CF₃ |
| 56 | Cl | (CH₂)₂CH₃ |
| 57 | Cl | CH₂CH(CH₃)₂ |
| 58 | Cl | 3-cynanophenyl |
| 59 | Cl | 3-(trifluoromethoxy)phenyl |
| 60 | Cl | 4-Chloro-3-nitrophenyl |
| 61 | Cl | 4-nitrophenyl |
| 62 | Cl | 3-pyridyl |
| 63 | Cl | 2-thiophene |
| 64 | Cl | 1-methylimidazol-2-yl |
| 65 | Cl | 1H-imidazol-4-yl |
| 66 | Cl | CH₂SO₂CH₃ |
| 67 | Cl | (CH₂)₂CF₃ |
| 68 | Cl | CF₂H |
| 69 | Cl | CH₂CF₂H |
| 70 | Cl | CH₂CN |
| 71 | Cl | (CH₂)₂OCH₃ |
| 72 | Cl |  |
| 73 | H | CH₃ |
| 74 | H | CH₂CH₃ |
| 75 | H | CH(CH₃)₂ |
| 76 | H | cyclopropyl |
| 77 | H | CH₂CH₂CH₂Cl |
| 78 | H | CH₂CF₃ |
| 79 | H | CF₃ |
| 80 | H | (CH₂)₂CH₃ |
| 81 | H | CH₂CH(CH₃)₂ |
| 82 | H | 3-cynanophenyl |
| 83 | H | 3-(trifluoromethoxy)phenyl |
| 84 | H | 4-Chloro-3-nitrophenyl |
| 85 | H | 4-nitrophenyl |
| 86 | H | 3-pyridyl |
| 87 | H | 2-thiophene |
| 88 | H | 1-methylimidazol-2-yl |
| 89 | H | 1H-imidazol-4-yl |
| 90 | H | CH₂SO₂CH₃ |
| 91 | H | (CH₂)₂CF₃ |
| 92 | H | CF₂H |
| 93 | H | CH₂CF₂H |
| 94 | H | CH₂CN |
| 95 | H | (CH₂)₂OCH₃ |

TABLE 3-continued

| Entry | R² | R⁸ |
|---|---|---|
| 96 | H | 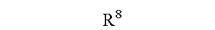 |

Exemplary embodiments include compounds having the formula (VIII) or a pharmaceutically acceptable salt form thereof:

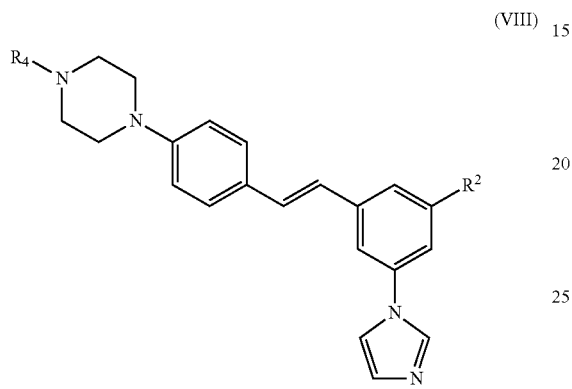

(VIII)

wherein non-limiting examples of R² and R⁸ are defined herein below in Table 4.

TABLE 4

| Entry | R² | R⁴ |
|---|---|---|
| 1 | F | Acetyl |
| 2 | F | tert-butyl ester group |
| 3 | F | ethyl glycinate amide group |
| 4 | F | pyridin-3-yl ketone |
| 5 | F | 3-nitrophenyl ketone |
| 6 | F | 3-cyanophenyl ketone |
| 7 | F | cyclopropylmethyl |
| 8 | F | cyclopropyl ketone |
| 9 | F | 3-cyanobenzyl |
| 10 | OH | Acetyl |
| 11 | OH | tert-butyl ester group |
| 12 | OH | ethyl glycinate amide group |
| 13 | OH | pyridin-3-yl ketone |
| 14 | OH | 3-nitrophenyl ketone |
| 15 | OH | 3-cyanophenyl ketone |
| 16 | OH | cyclopropylmethyl |
| 17 | OH | cyclopropyl ketone |
| 18 | OH | 3-cyanobenzyl |
| 19 | Cl | Acetyl |

TABLE 4-continued

| Entry | R² | R⁴ |
|---|---|---|
| 20 | Cl | (tert-butyl ester group) |
| 21 | Cl | (ethyl glycinate amide group) |
| 22 | Cl | (pyridin-3-yl ketone) |
| 23 | Cl | (3-nitrophenyl ketone) |
| 24 | Cl | (3-cyanophenyl ketone) |
| 25 | Cl | (cyclopropylmethyl) |
| 26 | Cl | (cyclopropyl ketone) |
| 27 | Cl | (3-cyanobenzyl) |
| 28 | H | Acetyl |
| 29 | H | (tert-butyl ester group) |
| 30 | H | (ethyl glycinate amide group) |
| 31 | H | (pyridin-3-yl ketone) |
| 32 | H | (3-nitrophenyl ketone) |
| 33 | H | (3-cyanophenyl ketone) |
| 34 | H | (cyclopropylmethyl) |
| 35 | H | (cyclopropyl ketone) |
| 36 | H | (3-cyanobenzyl) |

Exemplary embodiments include compounds having the formula (IX) or a pharmaceutically acceptable salt form thereof:

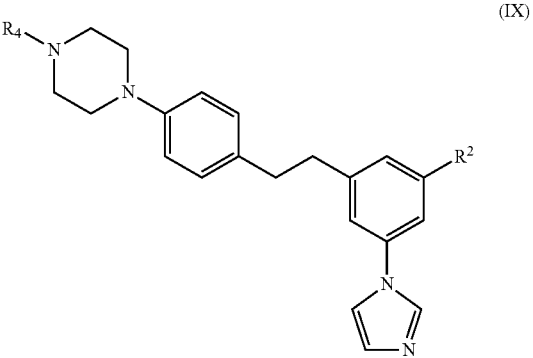

(IX)

wherein non-limiting examples of R² and R⁸ are defined herein below in Table 5.

TABLE 5
| Entry | R² | R⁴ |
|---|---|---|
| 1 | F | Acetyl |
| 2 | F | 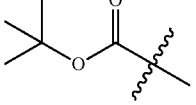 |
| 3 | F | 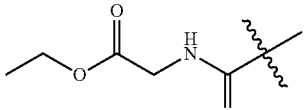 |
| 4 | F | 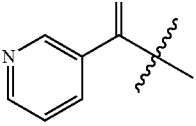 |
| 5 | F | 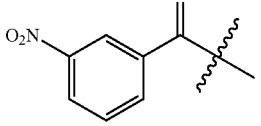 |
| 6 | F | 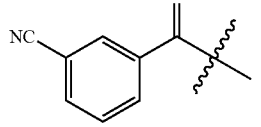 |
| 7 | F |  |
| 8 | F | 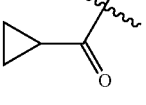 |
| 9 | F | 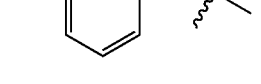 |
| 10 | OH | Acetyl |
| 11 | OH | 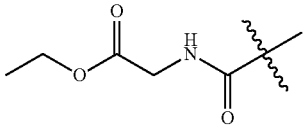 [SMILES: *C(=O)NCC(=O)OCC] |
| 12 | OH | 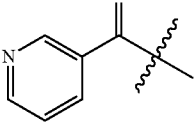 |
| 13 | OH | 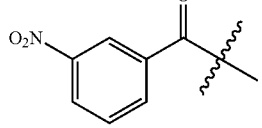 |
| 14 | OH | 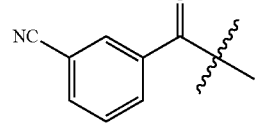 |
| 15 | OH | 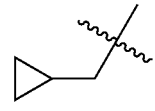 |
| 16 | OH | 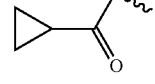 |
| 17 | OH | 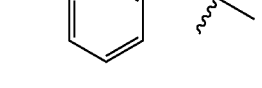 |
| | Cl | Acetyl |
| | Cl | 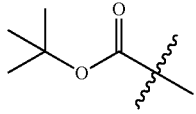 [SMILES: *C(=O)OC(C)(C)C] |
| | Cl | 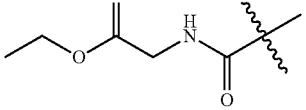 |
| | Cl | 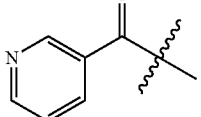 |
| | Cl | 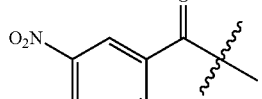 |
| | Cl | 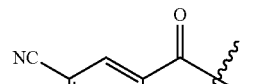 |
| | Cl |  |

TABLE 5-continued

| Entry | R² | R⁴ |
|---|---|---|
|  | Cl | cyclopropyl ketone |
|  | Cl | 3-cyanobenzyl |
|  | H | Acetyl |
|  | H | ethyl N-acyl glycinate |
|  | H | 3-pyridyl ketone |
|  | H | 3-nitrophenyl ketone |
|  | H | 3-cyanophenyl ketone |
|  | H | cyclopropylmethyl |
|  | H | cyclopropyl ketone |
|  | H | 3-cyanobenzyl |

Exemplary embodiments include compounds having the formula (X) or a pharmaceutically acceptable salt form thereof:

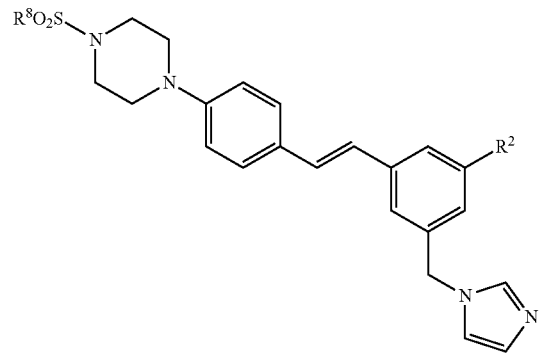

(X)

wherein non-limiting examples of $R^2$ and $R^8$ are defined herein below in Table 6.

TABLE 6

| Entry | R² | R⁸ |
|---|---|---|
| 1 | F | $CH_3$ |
| 2 | F | $CH_2CH_3$ |
| 3 | F | $CH(CH_3)_2$ |
| 4 | F | cyclopropyl |
| 5 | F | $CH_2CH_2CH_2Cl$ |
| 6 | F | $CH_2CF_3$ |
| 7 | F | $CF_3$ |
| 8 | F | $(CH_2)_2CH_3$ |
| 9 | F | $CH_2CH(CH_3)_2$ |
| 10 | F | 3-cynanophenyl |
| 11 | F | 3-(trifluoromethoxy)phenyl |
| 12 | F | 4-Chloro-3-nitrophenyl |
| 13 | F | 4-nitrophenyl |
| 14 | F | 3-pyridyl |
| 15 | F | 2-thiophene |
| 16 | F | 1-methylimidazol-2-yl |
| 17 | F | 1H-imidazol-4-yl |
| 18 | F | $CH_2SO_2CH_3$ |
| 19 | F | $(CH_2)_2CF_3$ |
| 20 | F | $CF_2H$ |
| 21 | F | $CH_2CF_2H$ |
| 22 | F | $CH_2CN$ |
| 23 | F | $(CH_2)_2OCH_3$ |
| 24 | F | tetrahydropyran-4-yl |
| 25 | OH | $CH_3$ |
| 26 | OH | $CH_2CH_3$ |
| 27 | OH | $CH(CH_3)_2$ |
| 28 | OH | cyclopropyl |
| 29 | OH | $CH_2CH_2CH_2Cl$ |
| 30 | OH | $CH_2CF_3$ |
| 31 | OH | $CF_3$ |
| 32 | OH | $(CH_2)_2CH_3$ |
| 33 | OH | $CH_2CH(CH_3)_2$ |
| 34 | OH | 3-cynanophenyl |
| 35 | OH | 3-(trifluoromethoxy)phenyl |
| 36 | OH | 4-Chloro-3-nitrophenyl |
| 37 | OH | 4-nitrophenyl |
| 38 | OH | 3-pyridyl |
| 39 | OH | 2-thiophene |
| 40 | OH | 1-methylimidazol-2-yl |
| 41 | OH | 1H-imidazol-4-yl |
| 42 | OH | $CH_2SO_2CH_3$ |
| 43 | OH | $(CH_2)_2CF_3$ |
| 44 | OH | $CF_2H$ |
| 45 | OH | $CH_2CF_2H$ |
| 46 | OH | $CH_2CN$ |
| 47 | OH | $(CH_2)_2OCH_3$ |

TABLE 6-continued

| Entry | R² | R⁸ |
|---|---|---|
| 48 | OH | 4-tetrahydropyranyl |
| 49 | Cl | CH₃ |
| 50 | Cl | CH₂CH₃ |
| 51 | Cl | CH(CH₃)₂ |
| 52 | Cl | cyclopropyl |
| 53 | Cl | CH₂CH₂CH₂Cl |
| 54 | Cl | CH₂CF₃ |
| 55 | Cl | CF₃ |
| 56 | Cl | (CH₂)₂CH₃ |
| 57 | Cl | CH₂CH(CH₃)₂ |
| 58 | Cl | 3-cynanophenyl |
| 59 | Cl | 3-(trifluoromethoxy)phenyl |
| 60 | Cl | 4-Chloro-3-nitrophenyl |
| 61 | Cl | 4-nitrophenyl |
| 62 | Cl | 3-pyridyl |
| 63 | Cl | 2-thiophene |
| 64 | Cl | 1-methylimidazol-2-yl |
| 65 | Cl | 1H-imidazol-4-yl |
| 66 | Cl | CH₂SO₂CH₃ |
| 67 | Cl | (CH₂)₂CF₃ |
| 68 | Cl | CF₂H |
| 69 | Cl | CH₂CF₂H |
| 70 | Cl | CH₂CN |
| 71 | Cl | (CH₂)₂OCH₃ |
| 72 | Cl | 4-tetrahydropyranyl |
| 73 | H | CH₃ |
| 74 | H | CH₂CH₃ |
| 75 | H | CH(CH₃)₂ |
| 76 | H | cyclopropyl |
| 77 | H | CH₂CH₂CH₂Cl |
| 78 | H | CH₂CF₃ |
| 79 | H | CF₃ |
| 80 | H | (CH₂)₂CH₃ |
| 81 | H | CH₂CH(CH₃)₂ |
| 82 | H | 3-cynanophenyl |
| 83 | H | 3-(trifluoromethoxy)phenyl |
| 84 | H | 4-Chloro-3-nitrophenyl |
| 85 | H | 4-nitrophenyl |
| 86 | H | 3-pyridyl |
| 87 | H | 2-thiophene |
| 88 | H | 1-methylimidazol-2-yl |
| 89 | H | 1H-imidazol-4-yl |
| 90 | H | CH₂SO₂CH₃ |
| 91 | H | (CH₂)₂CF₃ |
| 92 | H | CF₂H |
| 93 | H | CH₂CF₂H |
| 94 | H | CH₂CN |
| 95 | H | (CH₂)₂OCH₃ |
| 96 | H | 4-tetrahydropyranyl |

Exemplary embodiments include compounds having the formula (XI) or a pharmaceutically acceptable salt form thereof:

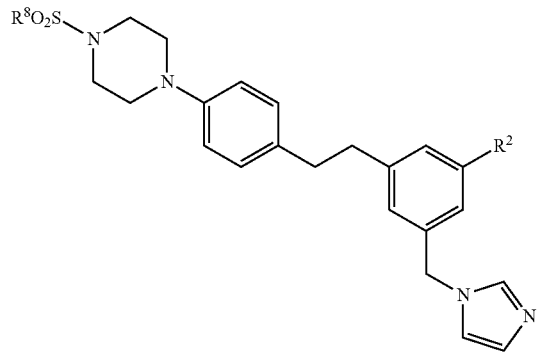

(XI)

wherein non-limiting examples of $R^2$ and $R^8$ are defined herein below in Table 7.

TABLE 7

| Entry | R² | R⁸ |
|---|---|---|
| 1 | F | CH₃ |
| 2 | F | CH₂CH₃ |
| 3 | F | CH(CH₃)₂ |
| 4 | F | cyclopropyl |
| 5 | F | CH₂CH₂CH₂Cl |
| 6 | F | CH₂CF₃ |
| 7 | F | CF₃ |
| 8 | F | (CH₂)₂CH₃ |
| 9 | F | CH₂CH(CH₃)₂ |
| 10 | F | 3-cynanophenyl |
| 11 | F | 3-(trifluoromethoxy)phenyl |
| 12 | F | 4-Chloro-3-nitrophenyl |
| 13 | F | 4-nitrophenyl |
| 14 | F | 3-pyridyl |
| 15 | F | 2-thiophene |
| 16 | F | 1-methylimidazol-2-yl |
| 17 | F | 1H-imidazol-4-yl |
| 18 | F | CH₂SO₂CH₃ |
| 19 | F | (CH₂)₂CF₃ |
| 20 | F | CF₂H |
| 21 | F | CH₂CF₂H |
| 22 | F | CH₂CN |
| 23 | F | (CH₂)₂OCH₃ |
| 24 | F | 4-tetrahydropyranyl |
| 25 | OH | CH₃ |
| 26 | OH | CH₂CH₃ |
| 27 | OH | CH(CH₃)₂ |
| 28 | OH | cyclopropyl |
| 29 | OH | CH₂CH₂CH₂Cl |
| 30 | OH | CH₂CF₃ |
| 31 | OH | CF₃ |
| 32 | OH | (CH₂)₂CH₃ |
| 33 | OH | CH₂CH(CH₃)₂ |
| 34 | OH | 3-cynanophenyl |
| 35 | OH | 3-(trifluoromethoxy)phenyl |
| 36 | OH | 4-Chloro-3-nitrophenyl |
| 37 | OH | 4-nitrophenyl |
| 38 | OH | 3-pyridyl |
| 39 | OH | 2-thiophene |
| 40 | OH | 1-methylimidazol-2-yl |
| 41 | OH | 1H-imidazol-4-yl |
| 42 | OH | CH₂SO₂CH₃ |
| 43 | OH | (CH₂)₂CF₃ |
| 44 | OH | CF₂H |
| 45 | OH | CH₂CF₂H |
| 46 | OH | CH₂CN |
| 47 | OH | (CH₂)₂OCH₃ |

TABLE 7-continued

| Entry | R² | R⁸ |
|---|---|---|
| 48 | OH | 4-tetrahydropyranyl |
| 49 | Cl | CH₃ |
| 50 | Cl | CH₂CH₃ |
| 51 | Cl | CH(CH₃)₂ |
| 52 | Cl | cyclopropyl |
| 53 | Cl | CH₂CH₂CH₂Cl |
| 54 | Cl | CH₂CF₃ |
| 55 | Cl | CF₃ |
| 56 | Cl | (CH₂)₂CH₃ |
| 57 | Cl | CH₂CH(CH₃)₂ |
| 58 | Cl | 3-cynanophenyl |
| 59 | Cl | 3-(trifluoromethoxy)phenyl |
| 60 | Cl | 4-Chloro-3-nitrophenyl |
| 61 | Cl | 4-nitrophenyl |
| 62 | Cl | 3-pyridyl |
| 63 | Cl | 2-thiophene |
| 64 | Cl | 1-methylimidazol-2-yl |
| 65 | Cl | 1H-imidazol-4-yl |
| 66 | Cl | CH₂SO₂CH₃ |
| 67 | Cl | (CH₂)₂CF₃ |
| 68 | Cl | CF₂H |
| 69 | Cl | CH₂CF₂H |
| 70 | Cl | CH₂CN |
| 71 | Cl | (CH₂)₂OCH₃ |
| 72 | Cl | 4-tetrahydropyranyl |
| 73 | H | CH₃ |
| 74 | H | CH₂CH₃ |
| 75 | H | CH(CH₃)₂ |
| 76 | H | cyclopropyl |
| 77 | H | CH₂CH₂CH₂Cl |
| 78 | H | CH₂CF₃ |
| 79 | H | CF₃ |
| 80 | H | (CH₂)₂CH₃ |
| 81 | H | CH₂CH(CH₃)₂ |
| 82 | H | 3-cynanophenyl |
| 83 | H | 3-(trifluoromethoxy)phenyl |
| 84 | H | 4-Chloro-3-nitrophenyl |
| 85 | H | 4-nitrophenyl |
| 86 | H | 3-pyridyl |
| 87 | H | 2-thiophene |
| 88 | H | 1-methylimidazol-2-yl |
| 89 | H | 1H-imidazol-4-yl |
| 90 | H | CH₂SO₂CH₃ |
| 91 | H | (CH₂)₂CF₃ |
| 92 | H | CF₂H |
| 93 | H | CH₂CF₂H |
| 94 | H | CH₂CN |
| 95 | H | (CH₂)₂OCH₃ |
| 96 | H | 4-tetrahydropyranyl |

Exemplary embodiments include compounds having the formula (XII) or a pharmaceutically acceptable salt form thereof:

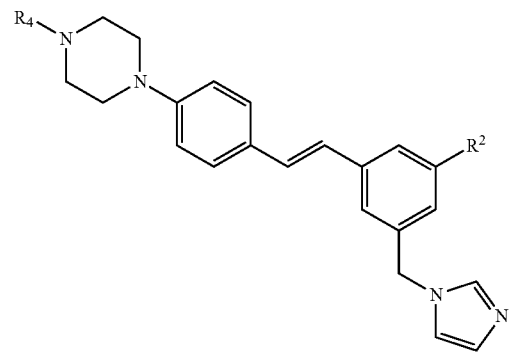

(XII)

wherein non-limiting examples of R² and R⁸ are defined herein below in Table 8.

TABLE 8

| Entry | R² | R⁴ |
|---|---|---|
| 1 | F | Acetyl |
| 2 | F | tert-butyl 2-methylpropanoate |
| 3 | F | ethyl N-acyl glycinate |
| 4 | F | 3-pyridyl ketone |
| 5 | F | 3-nitrophenyl ketone |
| 6 | F | 3-cyanophenyl ketone |
| 7 | F | cyclopropylmethyl |
| 8 | F | cyclopropyl ketone |

TABLE 8-continued
| Entry | R² | R⁴ |
|---|---|---|
| 9 | F | 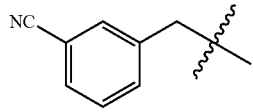 [SMILES: *Cc1cccc(C#N)c1] |
| 10 | OH | Acetyl |
| 11 | OH | 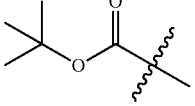 |
| 12 | OH | 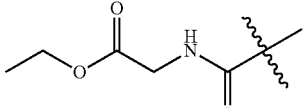 |
| 13 | OH | 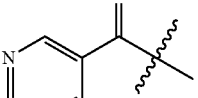 |
| 14 | OH | 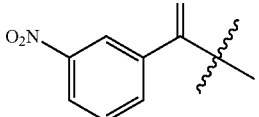 |
| 15 | OH | 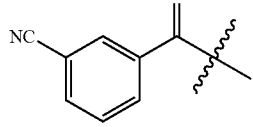 |
| 16 | OH | 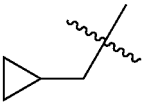 [SMILES: *CC1CC1] |
| 17 | OH | 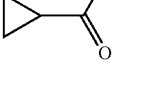 |
| 18 | OH | 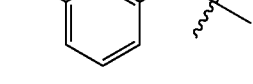 |
| | Cl | Acetyl |
| | Cl | 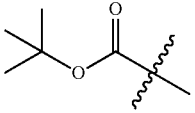 [SMILES: *C(=O)OC(C)(C)C] |
| | Cl | 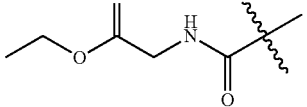 |
TABLE 8-continued
| Entry | R² | R⁴ |
|---|---|---|
| | Cl | 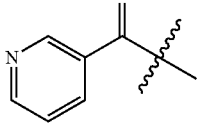 |
| | Cl | 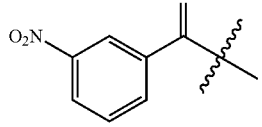 |
| | Cl | 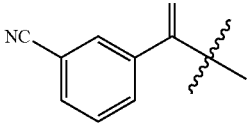 |
| | Cl |  |
| | Cl | 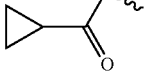 |
| | Cl | 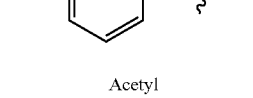 |
| | H | Acetyl |
| | H | 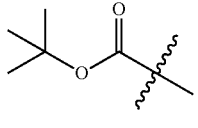 [SMILES: *C(=O)OC(C)(C)C] |
| | H |  |
| | H | 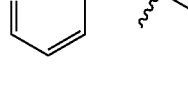 |
| | H | 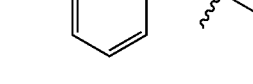 |

TABLE 8-continued

| Entry | R² | R⁴ |
|---|---|---|
|  | H | 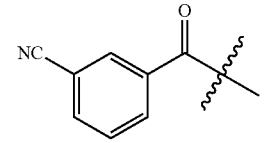 [SMILES: *C(=O)c1cccc(C#N)c1] |
|  | H | 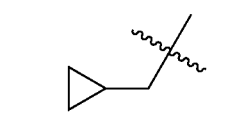 [SMILES: *CC1CC1] |
|  | H | 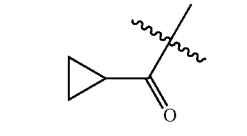 [SMILES: *C(=O)C1CC1] |
|  | H | 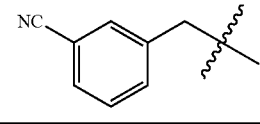 |

Exemplary embodiments include compounds having the formula (XIII) or a pharmaceutically acceptable salt form thereof:

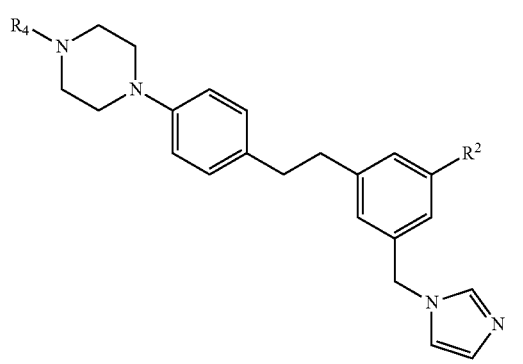

(XIII)

wherein non-limiting examples of R² and R⁸ are defined herein below in Table 9.

TABLE 9

| Entry | R² | R⁴ |
|---|---|---|
| 1 | F | Acetyl |
| 2 | F |  |
| 3 | F | 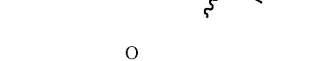 |

TABLE 9-continued

| Entry | R² | R⁴ |
|---|---|---|
| 4 | F | pyridine-C(O)- |
| 5 | F | 3-O₂N-C₆H₄-C(O)- |
| 6 | F | 3-NC-C₆H₄-C(O)- |
| 7 | F | cyclopropylmethyl |
| 8 | F | cyclopropyl-C(O)- |
| 9 | F | 3-NC-C₆H₄-CH₂- |
| 10 | OH | Acetyl |
| 11 | OH | tBuO-C(O)- |
| 12 | OH | EtO-C(O)-CH₂-NH-C(O)- |
| 13 | OH | pyridine-C(O)- |
| 14 | OH | 3-O₂N-C₆H₄-C(O)- |

US 9,725,436 B2
TABLE 9-continued
| Entry | R² | R⁴ |
|---|---|---|
| 15 | OH | 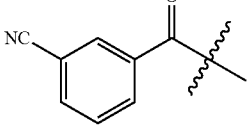 |
| 16 | OH | 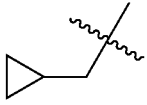 [SMILES: *CC1CC1] |
| 17 | OH | 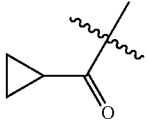 [SMILES: *C(=O)C1CC1] |
| 18 | OH | 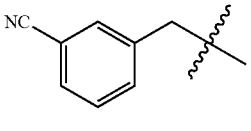 [SMILES: *Cc1cccc(C#N)c1] |
|  | Cl | Acetyl |
|  | Cl | 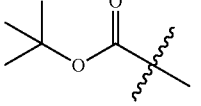 |
|  | Cl | 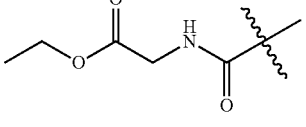 |
|  | Cl | 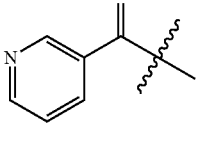 |
|  | Cl | 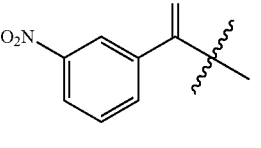 |
|  | Cl | 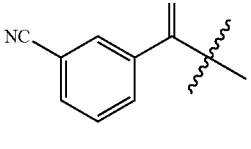 |
|  | Cl |  |
|  | Cl | 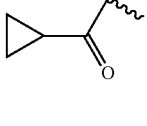 |
TABLE 9-continued
| Entry | R² | R⁴ |
|---|---|---|
|  | Cl | 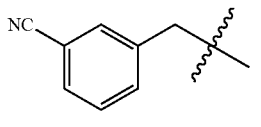 [SMILES: *Cc1cccc(C#N)c1] |
|  | H | Acetyl |
|  | H | 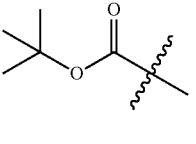 [SMILES: *C(=O)OC(C)(C)C] |
|  | H | 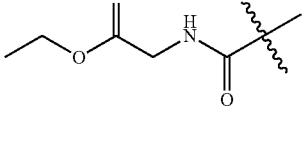 |
|  | H | 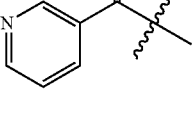 |
|  | H | 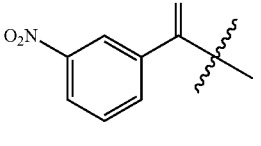 |
|  | H | 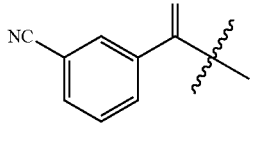 |
|  | H |  |
|  | H | 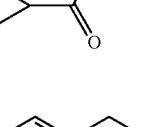 |
|  | H | 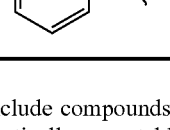 |
|  | H | 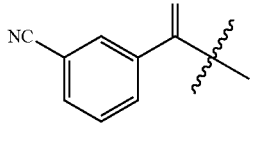 |
Exemplary embodiments include compounds having the formula (XIV) or a pharmaceutically acceptable salt form thereof:

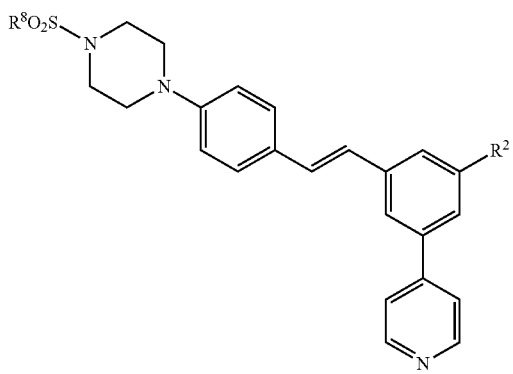

(XIV)

wherein non-limiting examples of R² and R⁸ are defined herein below in Table 10.

TABLE 10

| Entry | R² | R⁸ |
|---|---|---|
| 1 | F | $CH_3$ |
| 2 | F | $CH_2CH_3$ |
| 3 | F | $CH(CH_3)_2$ |
| 4 | F | cyclopropyl |
| 5 | F | $CH_2CH_2CH_2Cl$ |
| 6 | F | $CH_2CF_3$ |
| 7 | F | $CF_3$ |
| 8 | F | $(CH_2)_2CH_3$ |
| 9 | F | $CH_2CH(CH_3)_2$ |
| 10 | F | 3-cynanophenyl |
| 11 | F | 3-(trifluoromethoxy)phenyl |
| 12 | F | 4-Chloro-3-nitrophenyl |
| 13 | F | 4-nitrophenyl |
| 14 | F | 3-pyridyl |
| 15 | F | 2-thiophene |
| 16 | F | 1-methylimidazol-2-yl |
| 17 | F | 1H-imidazol-4-yl |
| 18 | F | $CH_2SO_2CH_3$ |
| 19 | F | $(CH_2)_2CF_3$ |
| 20 | F | $CF_2H$ |
| 21 | F | $CH_2CF_2H$ |
| 22 | F | $CH_2CN$ |
| 23 | F | $(CH_2)_2OCH_3$ |
| 24 | F | tetrahydropyran-4-yl |
| 25 | OH | $CH_3$ |
| 26 | OH | $CH_2CH_3$ |
| 27 | OH | $CH(CH_3)_2$ |
| 28 | OH | cyclopropyl |
| 29 | OH | $CH_2CH_2CH_2Cl$ |
| 30 | OH | $CH_2CF_3$ |
| 31 | OH | $CF_3$ |
| 32 | OH | $(CH_2)_2CH_3$ |
| 33 | OH | $CH_2CH(CH_3)_2$ |
| 34 | OH | 3-cynanophenyl |
| 35 | OH | 3-(trifluoromethoxy)phenyl |
| 36 | OH | 4-Chloro-3-nitrophenyl |
| 37 | OH | 4-nitrophenyl |
| 38 | OH | 3-pyridyl |
| 39 | OH | 2-thiophene |
| 40 | OH | 1-methylimidazol-2-yl |
| 41 | OH | 1H-imidazol-4-yl |
| 42 | OH | $CH_2SO_2CH_3$ |
| 43 | OH | $(CH_2)_2CF_3$ |
| 44 | OH | $CF_2H$ |
| 45 | OH | $CH_2CF_2H$ |
| 46 | OH | $CH_2CN$ |
| 47 | OH | $(CH_2)_2OCH_3$ |
| 48 | OH | tetrahydropyran-4-yl |
| 49 | Cl | $CH_3$ |
| 50 | Cl | $CH_2CH_3$ |
| 51 | Cl | $CH(CH_3)_2$ |
| 52 | Cl | cyclopropyl |
| 53 | Cl | $CH_2CH_2CH_2Cl$ |
| 54 | Cl | $CH_2CF_3$ |
| 55 | Cl | $CF_3$ |
| 56 | Cl | $(CH_2)_2CH_3$ |
| 57 | Cl | $CH_2CH(CH_3)_2$ |
| 58 | Cl | 3-cynanophenyl |
| 59 | Cl | 3-(trifluoromethoxy)phenyl |
| 60 | Cl | 4-Chloro-3-nitrophenyl |
| 61 | Cl | 4-nitrophenyl |
| 62 | Cl | 3-pyridyl |
| 63 | Cl | 2-thiophene |
| 64 | Cl | 1-methylimidazol-2-yl |
| 65 | Cl | 1H-imidazol-4-yl |
| 66 | Cl | $CH_2SO_2CH_3$ |
| 67 | Cl | $(CH_2)_2CF_3$ |
| 68 | Cl | $CF_2H$ |
| 69 | Cl | $CH_2CF_2H$ |
| 70 | Cl | $CH_2CN$ |
| 71 | Cl | $(CH_2)_2OCH_3$ |
| 72 | Cl | tetrahydropyran-4-yl |
| 73 | H | $CH_3$ |
| 74 | H | $CH_2CH_3$ |
| 75 | H | $CH(CH_3)_2$ |
| 76 | H | cyclopropyl |
| 77 | H | $CH_2CH_2CH_2Cl$ |
| 78 | H | $CH_2CF_3$ |
| 79 | H | $CF_3$ |
| 80 | H | $(CH_2)_2CH_3$ |
| 81 | H | $CH_2CH(CH_3)_2$ |
| 82 | H | 3-cynanophenyl |
| 83 | H | 3-(trifluoromethoxy)phenyl |
| 84 | H | 4-Chloro-3-nitrophenyl |
| 85 | H | 4-nitrophenyl |
| 86 | H | 3-pyridyl |
| 87 | H | 2-thiophene |
| 88 | H | 1-methylimidazol-2-yl |
| 89 | H | 1H-imidazol-4-yl |
| 90 | H | $CH_2SO_2CH_3$ |
| 91 | H | $(CH_2)_2CF_3$ |
| 92 | H | $CF_2H$ |
| 93 | H | $CH_2CF_2H$ |
| 94 | H | $CH_2CN$ |
| 95 | H | $(CH_2)_2OCH_3$ |
| 96 | H | tetrahydropyran-4-yl |

Exemplary embodiments include compounds having the formula (XV) or a pharmaceutically acceptable salt form thereof:

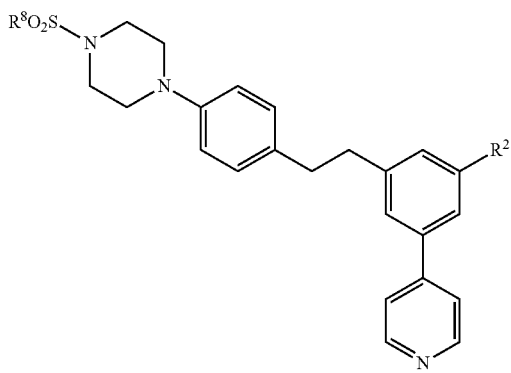

(XV)

wherein non-limiting examples of $R^2$ and $R^8$ are defined herein below in Table 11.

TABLE 11

| Entry | $R^2$ | $R^8$ |
|---|---|---|
| 1 | F | $CH_3$ |
| 2 | F | $CH_2CH_3$ |
| 3 | F | $CH(CH_3)_2$ |
| 4 | F | cyclopropyl |
| 5 | F | $CH_2CH_2CH_2Cl$ |
| 6 | F | $CH_2CF_3$ |
| 7 | F | $CF_3$ |
| 8 | F | $(CH_2)_2CH_3$ |
| 9 | F | $CH_2CH(CH_3)_2$ |
| 10 | F | 3-cynanophenyl |
| 11 | F | 3-(trifluoromethoxy)phenyl |
| 12 | F | 4-Chloro-3-nitrophenyl |
| 13 | F | 4-nitrophenyl |
| 14 | F | 3-pyridyl |
| 15 | F | 2-thiophene |
| 16 | F | 1-methylimidazol-2-yl |
| 17 | F | 1H-imidazol-4-yl |
| 18 | F | $CH_2SO_2CH_3$ |
| 19 | F | $(CH_2)_2CF_3$ |
| 20 | F | $CF_2H$ |
| 21 | F | $CH_2CF_2H$ |
| 22 | F | $CH_2CN$ |
| 23 | F | $(CH_2)_2OCH_3$ |
| 24 | F | tetrahydropyran-4-yl |
| 25 | OH | $CH_3$ |
| 26 | OH | $CH_2CH_3$ |
| 27 | OH | $CH(CH_3)_2$ |
| 28 | OH | cyclopropyl |
| 29 | OH | $CH_2CH_2CH_2Cl$ |
| 30 | OH | $CH_2CF_3$ |
| 31 | OH | $CF_3$ |
| 32 | OH | $(CH_2)_2CH_3$ |
| 33 | OH | $CH_2CH(CH_3)_2$ |
| 34 | OH | 3-cynanophenyl |
| 35 | OH | 3-(trifluoromethoxy)phenyl |
| 36 | OH | 4-Chloro-3-nitrophenyl |
| 37 | OH | 4-nitrophenyl |
| 38 | OH | 3-pyridyl |
| 39 | OH | 2-thiophene |
| 40 | OH | 1-methylimidazol-2-yl |
| 41 | OH | 1H-imidazol-4-yl |
| 42 | OH | $CH_2SO_2CH_3$ |
| 43 | OH | $(CH_2)_2CF_3$ |
| 44 | OH | $CF_2H$ |
| 45 | OH | $CH_2CF_2H$ |
| 46 | OH | $CH_2CN$ |
| 47 | OH | $(CH_2)_2OCH_3$ |
| 48 | OH | tetrahydropyran-4-yl |
| 49 | Cl | $CH_3$ |
| 50 | Cl | $CH_2CH_3$ |
| 51 | Cl | $CH(CH_3)_2$ |
| 52 | Cl | cyclopropyl |
| 53 | Cl | $CH_2CH_2CH_2Cl$ |
| 54 | Cl | $CH_2CF_3$ |
| 55 | Cl | $CF_3$ |
| 56 | Cl | $(CH_2)_2CH_3$ |
| 57 | Cl | $CH_2CH(CH_3)_2$ |
| 58 | Cl | 3-cynanophenyl |
| 59 | Cl | 3-(trifluoromethoxy)phenyl |
| 60 | Cl | 4-Chloro-3-nitrophenyl |
| 61 | Cl | 4-nitrophenyl |
| 62 | Cl | 3-pyridyl |
| 63 | Cl | 2-thiophene |
| 64 | Cl | 1-methylimidazol-2-yl |
| 65 | Cl | 1H-imidazol-4-yl |
| 66 | Cl | $CH_2SO_2CH_3$ |
| 67 | Cl | $(CH_2)_2CF_3$ |
| 68 | Cl | $CF_2H$ |
| 69 | Cl | $CH_2CF_2H$ |
| 70 | Cl | $CH_2CN$ |
| 71 | Cl | $(CH_2)_2OCH_3$ |
| 72 | Cl | tetrahydropyran-4-yl |
| 73 | H | $CH_3$ |
| 74 | H | $CH_2CH_3$ |
| 75 | H | $CH(CH_3)_2$ |
| 76 | H | cyclopropyl |
| 77 | H | $CH_2CH_2CH_2Cl$ |
| 78 | H | $CH_2CF_3$ |
| 79 | H | $CF_3$ |
| 80 | H | $(CH_2)_2CH_3$ |
| 81 | H | $CH_2CH(CH_3)_2$ |
| 82 | H | 3-cynanophenyl |
| 83 | H | 3-(trifluoromethoxy)phenyl |
| 84 | H | 4-Chloro-3-nitrophenyl |
| 85 | H | 4-nitrophenyl |
| 86 | H | 3-pyridyl |
| 87 | H | 2-thiophene |
| 88 | H | 1-methylimidazol-2-yl |
| 89 | H | 1H-imidazol-4-yl |
| 90 | H | $CH_2SO_2CH_3$ |
| 91 | H | $(CH_2)_2CF_3$ |
| 92 | H | $CF_2H$ |
| 93 | H | $CH_2CF_2H$ |
| 94 | H | $CH_2CN$ |
| 95 | H | $(CH_2)_2OCH_3$ |
| 96 | H | tetrahydropyran-4-yl |

Exemplary embodiments include compounds having the formula (XVI) or a pharmaceutically acceptable salt form thereof:

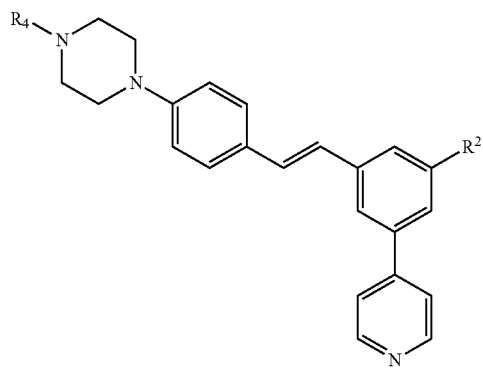

(XVI)

wherein non-limiting examples of $R^2$ and $R^8$ are defined herein below in Table 12.

TABLE 12

| Entry | $R^2$ | $R^4$ |
|---|---|---|
| 1 | F | Acetyl |
| 2 | F | *tert*-butyl ester group |
| 3 | F | ethyl glycinate amide group |
| 4 | F | 3-pyridyl ketone group |
| 5 | F | 3-nitrophenyl ketone group |
| 6 | F | 3-cyanophenyl ketone group |
| 7 | F | cyclopropylmethyl group |
| 8 | F | cyclopropyl ketone group |
| 9 | F | 3-cyanobenzyl group |
| 10 | OH | Acetyl |
| 11 | OH | *tert*-butyl ester group |
| 12 | OH | ethyl glycinate amide group |
| 13 | OH | 3-pyridyl ketone group |
| 14 | OH | 3-nitrophenyl ketone group |
| 15 | OH | 3-cyanophenyl ketone group |
| 16 | OH | cyclopropylmethyl group |
| 17 | OH | cyclopropyl ketone group |
| 18 | OH | 3-cyanobenzyl group |
|  | Cl | Acetyl |
|  | Cl | *tert*-butyl ester group |

TABLE 12-continued

| Entry | R² | R⁴ |
|---|---|---|
| | Cl | ethyl glycinate amide |
| | Cl | nicotinoyl |
| | Cl | 3-nitrobenzoyl |
| | Cl | 3-cyanobenzoyl |
| | Cl | cyclopropylmethyl |
| | Cl | cyclopropyl ketone |
| | Cl | 3-cyanobenzyl |
| | H | Acetyl |
| | H | tert-butyl ester |
| | H | ethyl glycinate amide |
| | H | nicotinoyl |
| 5 | H | 3-nitrobenzoyl |
| 10 | H | 3-cyanobenzoyl |
| 15 | H | cyclopropylmethyl |
| 20 | H | cyclopropyl ketone |
| 25 | H | 3-cyanobenzyl |

Exemplary embodiments include compounds having the formula (XVII) or a pharmaceutically acceptable salt form thereof:

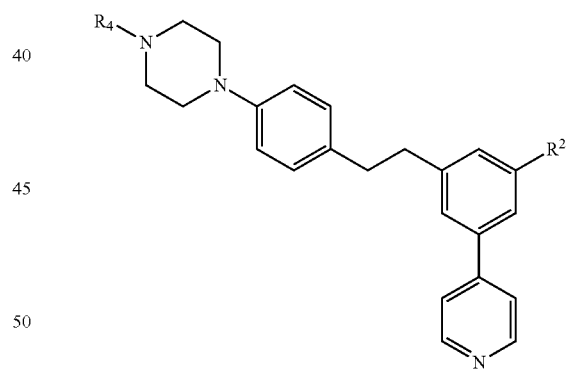

(XVII)

wherein non-limiting examples of R² and R⁸ are defined herein below in Table 13.

TABLE 13

| Entry | R² | R⁴ |
|---|---|---|
| 1 | F | Acetyl |
| 2 | F | tert-butyl ester |

TABLE 13-continued

| Entry | R² | R⁴ |
|---|---|---|
| 3 | F | ethyl glycinate amide |
| 4 | F | pyridin-3-yl ketone |
| 5 | F | 3-nitrophenyl ketone |
| 6 | F | 3-cyanophenyl ketone |
| 7 | F | cyclopropylmethyl |
| 8 | F | cyclopropyl ketone |
| 9 | F | 3-cyanobenzyl |
| 10 | OH | Acetyl |
| 11 | OH | tert-butyl ester |
| 12 | OH | ethyl glycinate amide |
| 13 | OH | pyridin-3-yl ketone |
| 14 | OH | 3-nitrophenyl ketone |
| 15 | OH | 3-cyanophenyl ketone |
| 16 | OH | cyclopropylmethyl |
| 17 | OH | cyclopropyl ketone |
| 18 | OH | 3-cyanobenzyl |
|  | Cl | Acetyl |
|  | Cl | tert-butyl ester |
|  | Cl | ethyl glycinate amide |
|  | Cl | pyridin-3-yl ketone |
|  | Cl | 3-nitrophenyl ketone |
|  | Cl | 3-cyanophenyl ketone |
|  | Cl | cyclopropylmethyl |
|  | Cl | cyclopropyl ketone |

TABLE 13-continued

| Entry | R² | R⁴ |
|---|---|---|
|  | Cl | 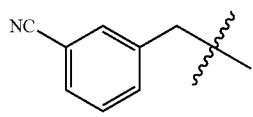 [SMILES: *Cc1cccc(C#N)c1] 3-cyanobenzyl |
|  | H | Acetyl |
|  | H | 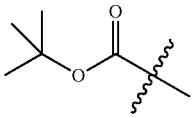 [SMILES: *C(=O)OC(C)(C)C] tert-butyl 2-methylpropanoate |
|  | H | 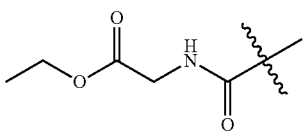 [SMILES: *C(=O)NCC(=O)OCC] ethyl glycinamide derivative |
|  | H | 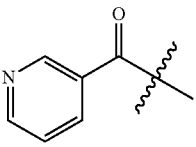 pyridin-3-yl ketone |
|  | H | 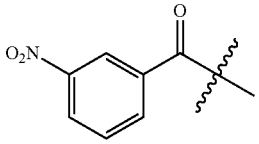 [SMILES: *C(=O)c1cccc([N+](=O)[O-])c1] 3-nitrophenyl ketone |
|  | H | 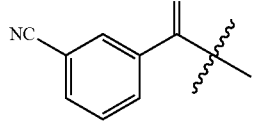 3-cyanophenyl ketone |
|  | H | 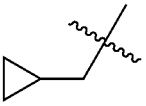 [SMILES: *CC1CC1] cyclopropylmethyl |
|  | H | 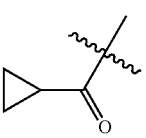 [SMILES: *C(=O)C1CC1] cyclopropyl ketone |
|  | H | 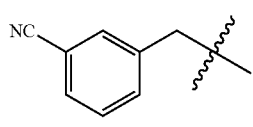 [SMILES: *Cc1cccc(C#N)c1] 3-cyanobenzyl |

Exemplary embodiments include compounds having the formula (XVIII) or a pharmaceutically acceptable salt form thereof:

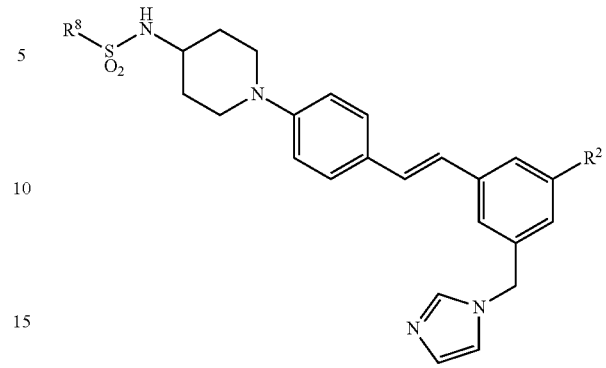

(XVIII)

wherein non-limiting examples of R² and R⁸ are defined herein below in Table 14.

TABLE 14

| Entry | R² | R⁸ |
|---|---|---|
| 1 | F | $CH_3$ |
| 2 | F | $CH_2CH_3$ |
| 3 | F | $CH(CH_3)_2$ |
| 4 | F | cyclopropyl |
| 5 | F | $CH_2CH_2CH_2Cl$ |
| 6 | F | $CH_2CF_3$ |
| 7 | F | $CF_3$ |
| 8 | F | $(CH_2)_2CH_3$ |
| 9 | F | $CH_2CH(CH_3)_2$ |
| 10 | F | 3-cyanophenyl |
| 11 | F | 3-(trifluoromethoxy)phenyl |
| 12 | F | 4-Chloro-3-nitrophenyl |
| 13 | F | 4-nitrophenyl |
| 14 | F | 3-pyridyl |
| 15 | F | 2-thiophene |
| 16 | F | 1-methylimidazol-2-yl |
| 17 | F | 1H-imidazol-4-yl |
| 18 | F | $CH_2SO_2CH_3$ |
| 19 | F | $(CH_2)_2CF_3$ |
| 20 | F | $CF_2H$ |
| 21 | F | $CH_2CF_2H$ |
| 22 | F | $CH_2CN$ |
| 23 | F | $(CH_2)_2OCH_3$ |
| 24 | F | 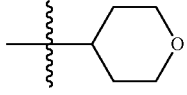 tetrahydropyran-4-yl |
| 25 | OH | $CH_3$ |
| 26 | OH | $CH_2CH_3$ |
| 27 | OH | $CH(CH_3)_2$ |
| 28 | OH | cyclopropyl |
| 29 | OH | $CH_2CH_2CH_2Cl$ |
| 30 | OH | $CH_2CF_3$ |
| 31 | OH | $CF_3$ |
| 32 | OH | $(CH_2)_2CH_3$ |
| 33 | OH | $CH_2CH(CH_3)_2$ |
| 34 | OH | 3-cyanophenyl |
| 35 | OH | 3-(trifluoromethoxy)phenyl |
| 36 | OH | 4-Chloro-3-nitrophenyl |
| 37 | OH | 4-nitrophenyl |
| 38 | OH | 3-pyridyl |
| 39 | OH | 2-thiophene |
| 40 | OH | 1-methylimidazol-2-yl |
| 41 | OH | 1H-imidazol-4-yl |
| 42 | OH | $CH_2SO_2CH_3$ |
| 43 | OH | $(CH_2)_2CF_3$ |
| 44 | OH | $CF_2H$ |
| 45 | OH | $CH_2CF_2H$ |

TABLE 14-continued

| Entry | R² | R⁸ |
|---|---|---|
| 46 | OH | CH₂CN |
| 47 | OH | (CH₂)₂OCH₃ |
| 48 | OH | 4-tetrahydropyranyl |
| 49 | Cl | CH₃ |
| 50 | Cl | CH₂CH₃ |
| 51 | Cl | CH(CH₃)₂ |
| 52 | Cl | cyclopropyl |
| 53 | Cl | CH₂CH₂CH₂Cl |
| 54 | Cl | CH₂CF₃ |
| 55 | Cl | CF₃ |
| 56 | Cl | (CH₂)₂CH₃ |
| 57 | Cl | CH₂CH(CH₃)₂ |
| 58 | Cl | 3-cynanophenyl |
| 59 | Cl | 3-(trifluoromethoxy)phenyl |
| 60 | Cl | 4-Chloro-3-nitrophenyl |
| 61 | Cl | 4-nitrophenyl |
| 62 | Cl | 3-pyridyl |
| 63 | Cl | 2-thiophene |
| 64 | Cl | 1-methylimidazol-2-yl |
| 65 | Cl | 1H-imidazol-4-yl |
| 66 | Cl | CH₂SO₂CH₃ |
| 67 | Cl | (CH₂)₂CF₃ |
| 68 | Cl | CF₂H |
| 69 | Cl | CH₂CF₂H |
| 70 | Cl | CH₂CN |
| 71 | Cl | (CH₂)₂OCH₃ |
| 72 | Cl | 4-tetrahydropyranyl |
| 73 | H | CH₃ |
| 74 | H | CH₂CH₃ |
| 75 | H | CH(CH₃)₂ |
| 76 | H | cyclopropyl |
| 77 | H | CH₂CH₂CH₂Cl |
| 78 | H | CH₂CF₃ |
| 79 | H | CF₃ |
| 80 | H | (CH₂)₂CH₃ |
| 81 | H | CH₂CH(CH₃)₂ |
| 82 | H | 3-cynanophenyl |
| 83 | H | 3-(trifluoromethoxy)phenyl |
| 84 | H | 4-Chloro-3-nitrophenyl |
| 85 | H | 4-nitrophenyl |
| 86 | H | 3-pyridyl |
| 87 | H | 2-thiophene |
| 88 | H | 1-methylimidazol-2-yl |
| 89 | H | 1H-imidazol-4-yl |
| 90 | H | CH₂SO₂CH₃ |
| 91 | H | (CH₂)₂CF₃ |
| 92 | H | CF₂H |
| 93 | H | CH₂CF₂H |
| 94 | H | CH₂CN |
| 95 | H | (CH₂)₂OCH₃ |
| 96 | H | 4-tetrahydropyranyl |

Exemplary embodiments include compounds having the formula (XIX) or a pharmaceutically acceptable salt form thereof:

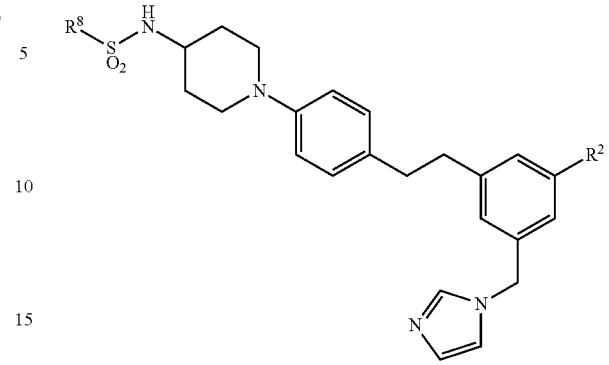

(XIX)

wherein non-limiting examples of R² and R⁸ are defined herein below in Table 15.

TABLE 15

| Entry | R² | R⁸ |
|---|---|---|
| 1 | F | CH₃ |
| 2 | F | CH₂CH₃ |
| 3 | F | CH(CH₃)₂ |
| 4 | F | cyclopropyl |
| 5 | F | CH₂CH₂CH₂Cl |
| 6 | F | CH₂CF₃ |
| 7 | F | CF₃ |
| 8 | F | (CH₂)₂CH₃ |
| 9 | F | CH₂CH(CH₃)₂ |
| 10 | F | 3-cynanophenyl |
| 11 | F | 3-(trifluoromethoxy)phenyl |
| 12 | F | 4-Chloro-3-nitrophenyl |
| 13 | F | 4-nitrophenyl |
| 14 | F | 3-pyridyl |
| 15 | F | 2-thiophene |
| 16 | F | 1-methylimidazol-2-yl |
| 17 | F | 1H-imidazol-4-yl |
| 18 | F | CH₂SO₂CH₃ |
| 19 | F | (CH₂)₂CF₃ |
| 20 | F | CF₂H |
| 21 | F | CH₂CF₂H |
| 22 | F | CH₂CN |
| 23 | F | (CH₂)₂OCH₃ |
| 24 | F | 4-tetrahydropyranyl |
| 25 | OH | CH₃ |
| 26 | OH | CH₂CH₃ |
| 27 | OH | CH(CH₃)₂ |
| 28 | OH | cyclopropyl |
| 29 | OH | CH₂CH₂CH₂Cl |
| 30 | OH | CH₂CF₃ |
| 31 | OH | CF₃ |
| 32 | OH | (CH₂)₂CH₃ |
| 33 | OH | CH₂CH(CH₃)₂ |
| 34 | OH | 3-cynanophenyl |
| 35 | OH | 3-(trifluoromethoxy)phenyl |
| 36 | OH | 4-Chloro-3-nitrophenyl |
| 37 | OH | 4-nitrophenyl |
| 38 | OH | 3-pyridyl |
| 39 | OH | 2-thiophene |
| 40 | OH | 1-methylimidazol-2-yl |
| 41 | OH | 1H-imidazol-4-yl |
| 42 | OH | CH₂SO₂CH₃ |
| 43 | OH | (CH₂)₂CF₃ |
| 44 | OH | CF₂H |
| 45 | OH | CH₂CF₂H |

TABLE 15-continued

| Entry | R² | R⁸ |
|---|---|---|
| 46 | OH | CH₂CN |
| 47 | OH | (CH₂)₂OCH₃ |
| 48 | OH | 4-tetrahydropyranyl |
| 49 | Cl | CH₃ |
| 50 | Cl | CH₂CH₃ |
| 51 | Cl | CH(CH₃)₂ |
| 52 | Cl | cyclopropyl |
| 53 | Cl | CH₂CH₂CH₂Cl |
| 54 | Cl | CH₂CF₃ |
| 55 | Cl | CF₃ |
| 56 | Cl | (CH₂)₂CH₃ |
| 57 | Cl | CH₂CH(CH₃)₂ |
| 58 | Cl | 3-cyanophenyl |
| 59 | Cl | 3-(trifluoromethoxy)phenyl |
| 60 | Cl | 4-Chloro-3-nitrophenyl |
| 61 | Cl | 4-nitrophenyl |
| 62 | Cl | 3-pyridyl |
| 63 | Cl | 2-thiophene |
| 64 | Cl | 1-methylimidazol-2-yl |
| 65 | Cl | 1H-imidazol-4-yl |
| 66 | Cl | CH₂SO₂CH₃ |
| 67 | Cl | (CH₂)₂CF₃ |
| 68 | Cl | CF₂H |
| 69 | Cl | CH₂CF₂H |
| 70 | Cl | CH₂CN |
| 71 | Cl | (CH₂)₂OCH₃ |
| 72 | Cl | 4-tetrahydropyranyl |
| 73 | H | CH₃ |
| 74 | H | CH₂CH₃ |
| 75 | H | CH(CH₃)₂ |
| 76 | H | cyclopropyl |
| 77 | H | CH₂CH₂CH₂Cl |
| 78 | H | CH₂CF₃ |
| 79 | H | CF₃ |
| 80 | H | (CH₂)₂CH₃ |
| 81 | H | CH₂CH(CH₃)₂ |
| 82 | H | 3-cyanophenyl |
| 83 | H | 3-(trifluoromethoxy)phenyl |
| 84 | H | 4-Chloro-3-nitrophenyl |
| 85 | H | 4-nitrophenyl |
| 86 | H | 3-pyridyl |
| 87 | H | 2-thiophene |
| 88 | H | 1-methylimidazol-2-yl |
| 89 | H | 1H-imidazol-4-yl |
| 90 | H | CH₂SO₂CH₃ |
| 91 | H | (CH₂)₂CF₃ |
| 92 | H | CF₂H |
| 93 | H | CH₂CF₂H |
| 94 | H | CH₂CN |
| 95 | H | (CH₂)₂OCH₃ |
| 96 | H | 4-tetrahydropyranyl |

Exemplary embodiments include compounds having the formula (XX) or a pharmaceutically acceptable salt form thereof:

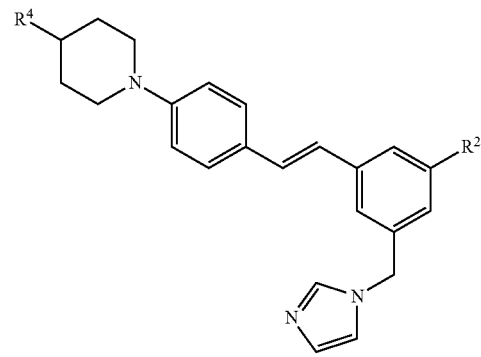

(XX)

wherein non-limiting examples of R² and R⁸ are defined herein below in Table 16.

TABLE 16

| Entry | R² | R⁴ |
|---|---|---|
| 1 | F | Acetyl |
| 2 | F | tert-butyl ester of 2-methylpropanoate |
| 3 | F | ethyl glycinate amide |
| 4 | F | 3-pyridyl ketone |
| 5 | F | 3-nitrophenyl ketone |
| 6 | F | 3-cyanophenyl ketone |
| 7 | F | cyclopropylmethyl |
| 8 | F | cyclopropyl ketone |

TABLE 16-continued
| Entry | R² | R⁴ |
|---|---|---|
| 9 | F | 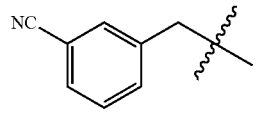 [SMILES: *Cc1cccc(C#N)c1] |
| 10 | OH | Acetyl |
| 11 | OH | 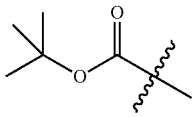 [SMILES: *C(=O)OC(C)(C)C] |
| 12 | OH | 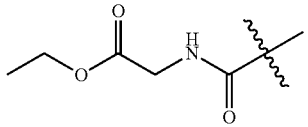 [SMILES: *C(=O)NCC(=O)OCC] |
| 13 | OH | 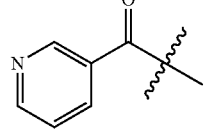 |
| 14 | OH | 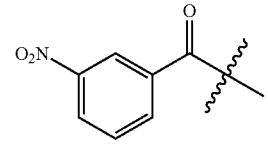 [SMILES: *C(=O)c1cccc([N+](=O)[O-])c1] |
| 15 | OH | 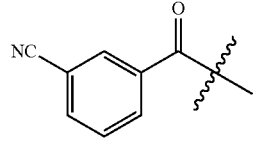 |
| 16 | OH | 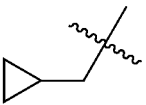 [SMILES: *CC1CC1] |
| 17 | OH | 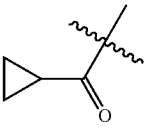 [SMILES: *C(=O)C1CC1] |
| 18 | OH | 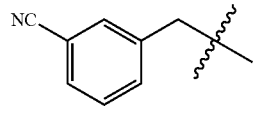 [SMILES: *Cc1cccc(C#N)c1] |
| 19 | Cl | Acetyl |
| 20 | Cl | 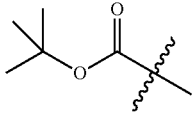 [SMILES: *C(=O)OC(C)(C)C] |
TABLE 16-continued
| Entry | R² | R⁴ |
|---|---|---|
| 21 | Cl | 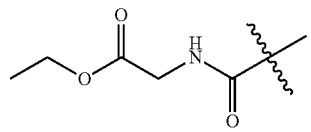 [SMILES: *C(=O)NCC(=O)OCC] |
| 22 | Cl | 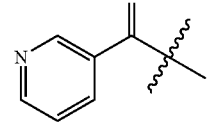 |
| 23 | Cl | 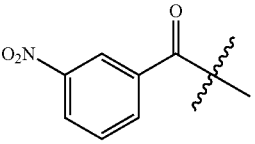 [SMILES: *C(=O)c1cccc([N+](=O)[O-])c1] |
| 24 | Cl | 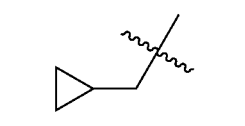 [SMILES: *CC1CC1] |
| 25 | Cl | 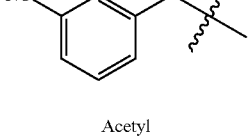 |
| 26 | Cl | 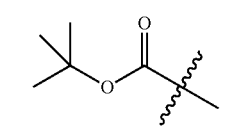 |
| 27 | Cl | 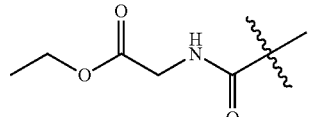 |
| 28 | H | Acetyl |
| 29 | H | 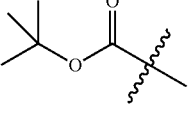 |
| 30 | H | 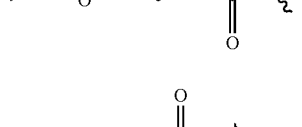 |
| 31 | H |  |

TABLE 16-continued

| Entry | R² | R⁴ |
|---|---|---|
| 32 | H | 3-nitrobenzoyl (O₂N-C₆H₄-C(O)-) |
| 33 | H | 3-cyanobenzoyl (NC-C₆H₄-C(O)-) |
| 34 | H | cyclopropylmethyl |
| 35 | H | cyclopropylcarbonyl |
| 36 | H | 3-cyanobenzyl |

Exemplary embodiments include compounds having the formula (XXI) or a pharmaceutically acceptable salt form thereof:

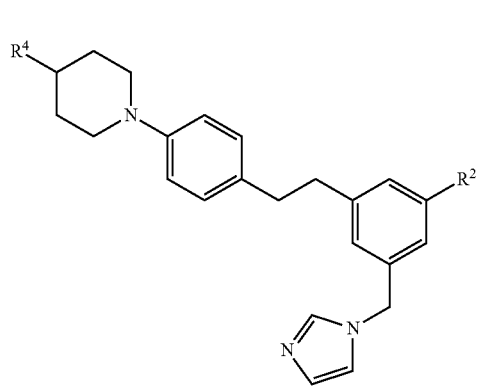

(XXI)

wherein non-limiting examples of R² and R⁸ are defined herein below in Table 17.

TABLE 17

| Entry | R² | R⁴ |
|---|---|---|
| 1 | F | Acetyl |
| 2 | F | tert-butoxycarbonyl-type group |

TABLE 17-continued

| Entry | R² | R⁴ |
|---|---|---|
| 3 | F | ethoxycarbonylmethyl-NH-C(O)- |
| 4 | F | pyridin-3-ylcarbonyl |
| 5 | F | 3-nitrobenzoyl |
| 6 | F | 3-cyanobenzoyl |
| 7 | F | cyclopropylmethyl |
| 8 | F | cyclopropylcarbonyl |
| 9 | F | 3-cyanobenzyl |
| 10 | OH | Acetyl |
| 11 | OH | tert-butoxycarbonyl-type group |
| 12 | OH | ethoxycarbonylmethyl-NH-C(O)- |
| 13 | OH | pyridin-3-ylcarbonyl |

TABLE 17-continued
| Entry | R² | R⁴ |
|---|---|---|
| 14 | OH | 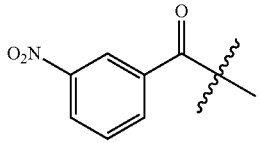 [SMILES: *C(=O)c1cccc([N+](=O)[O-])c1] |
| 15 | OH | 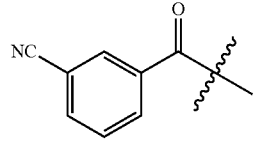 [SMILES: *C(=O)c1cccc(C#N)c1] |
| 16 | OH |  |
| 17 | OH | 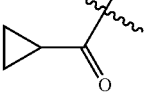 |
| 18 | OH | 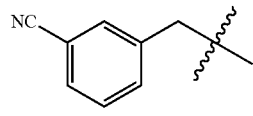 [SMILES: *Cc1cccc(C#N)c1] |
| 19 | Cl | Acetyl |
| 20 | Cl | 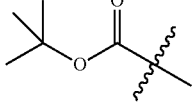 |
| 21 | Cl | 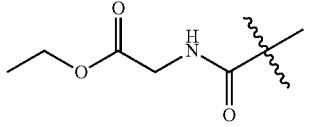 [SMILES: *C(=O)NCC(=O)OCC] |
| 22 | Cl | 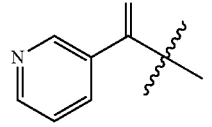 |
| 23 | Cl | 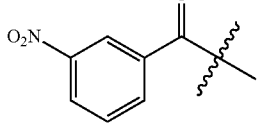 |
| 24 | Cl | 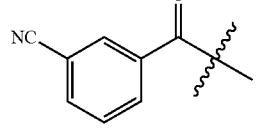 |
| 25 | Cl | 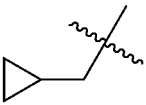 [SMILES: *CC1CC1] |
| 26 | Cl | 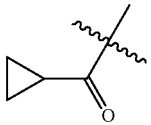 [SMILES: *C(=O)C1CC1] |
| 27 | Cl | 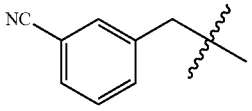 [SMILES: *Cc1cccc(C#N)c1] |
| 28 | H | Acetyl |
| 29 | H | 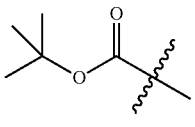 [SMILES: *C(=O)OC(C)(C)C] |
| 30 | H | 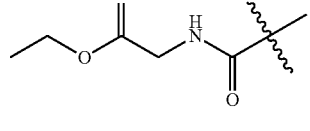 |
| 31 | H | 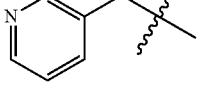 |
| 32 | H | 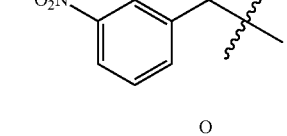 |
| 33 | H | 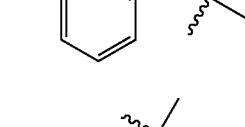 |
| 34 | H |  |
| 35 | H | 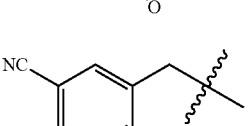 |
| 36 | H | 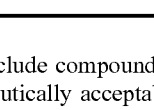 |
Exemplary embodiments include compounds having the formula (XXII) or a pharmaceutically acceptable salt form thereof:

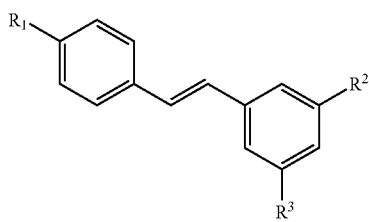

(XXII)

wherein non-limiting examples of $R^2$ and $R^8$ are defined herein below in Table 18.

TABLE 18

| Entry | $R^1$ | $R^2$ | $R^3$ |
|---|---|---|---|
| 1 | Br | OH | imidazol-1-yl |
| 2 | Br | F | imidazol-1-yl |
| 3 | Br | Cl | imidazol-1-yl |
| 4 | Br | OH | 4-pyridyl |
| 5 | Br | F | 4-pyridyl |
| 6 | Br | Cl | 4-pyridyl |
| 7 | 4-Pyridyl | OH | 3-pyridyl |
| 8 | 4-Pyridyl | F | 3-pyridyl |
| 9 | 4-Pyridyl | Cl | 3-pyridyl |
| 10 | 4-acetylpiperazin-1-yl | OH | 3-pyridyl |
| 11 | 4-acetylpiperazin-1-yl | F | 3-pyridyl |
| 12 | 4-acetylpiperazin-1-yl | Cl | 3-pyridyl |
| 13 | 4-acetylpiperazin-1-yl | OH | (pyridin-3-yloxy)methyl |
| 14 | 4-acetylpiperazin-1-yl | F | (pyridin-3-yloxy)methyl |
| 15 | 4-acetylpiperazin-1-yl | Cl | (pyridin-3-yloxy)methyl |
| 16 | 4-acetylpiperazin-1-yl | OH | (pyridin-3-yl)methyl |
| 17 | 4-acetylpiperazin-1-yl | F | (pyridin-3-yl)methyl |
| 18 | 4-acetylpiperazin-1-yl | Cl | (pyridin-3-yl)methyl |

TABLE 18-continued

| Entry | R¹ | R² | R³ |
|---|---|---|---|
| 19 | acetyl-piperazine | OH | isopropyl-C(OH)-3-pyridyl |
| 20 | acetyl-piperazine | F | isopropyl-C(OH)-3-pyridyl |
| 21 | acetyl-piperazine | Cl | isopropyl-C(OH)-3-pyridyl |
| 22 | acetyl-piperazine | OH | C(=C(CH₃))-3-pyridyl |
| 23 | acetyl-piperazine | F | C(=C(CH₃))-3-pyridyl |
| 24 | acetyl-piperazine | Cl | C(=C(CH₃))-3-pyridyl |
| 25 | 4-Pyridyl | OH | C(=C(CH₃))-3-pyridyl |
| 26 | 4-Pyridyl | F | C(=C(CH₃))-3-pyridyl |
| 27 | 4-Pyridyl | Cl | C(=C(CH₃))-3-pyridyl |

Exemplary embodiments include compounds having the formula (XXIII) or a pharmaceutically acceptable salt form thereof:

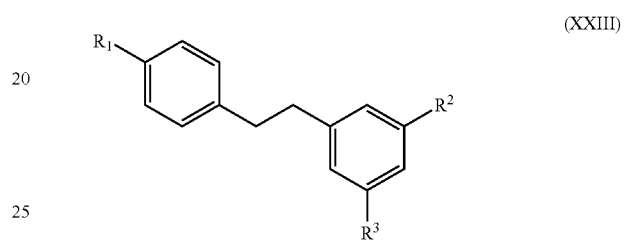

(XXIII)

wherein non-limiting examples of R² and R⁸ are defined herein below in Table 19

TABLE 19

| Entry | R¹ | R² | R³ |
|---|---|---|---|
| 1 | Br | OH | N-imidazolyl |
| 2 | Br | F | N-imidazolyl |
| 3 | Br | Cl | N-imidazolyl |
| 4 | Br | OH | 4-pyridyl |
| 5 | Br | F | 4-pyridyl |
| 6 | Br | Cl | 4-pyridyl |
| 7 | 4-Pyridyl | OH | 3-pyridyl |

TABLE 19-continued
| Entry | R¹ | R² | R³ |
|---|---|---|---|
| 8 | 4-Pyridyl | F | 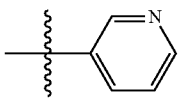 [SMILES: *c1cccnc1] |
| 9 | 4-Pyridyl | Cl | 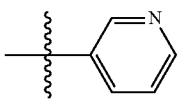 [SMILES: *c1cccnc1] |
| 10 | 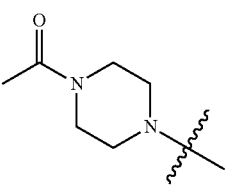 [SMILES: *N1CCN(C(C)=O)CC1] | OH | 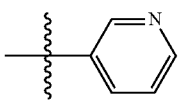 |
| 11 | 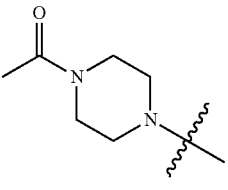 [SMILES: *N1CCN(C(C)=O)CC1] | F | 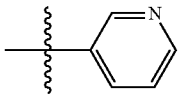 |
| 12 | 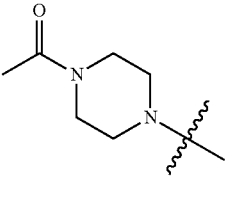 [SMILES: *N1CCN(C(C)=O)CC1] | Cl | 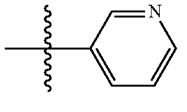 [SMILES: *c1cccnc1] |
| 13 | 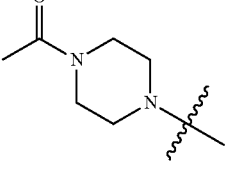 | OH | 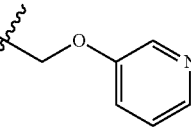 |
| 14 | 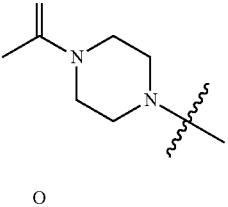 | F | 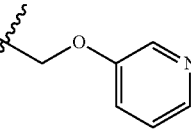 |
| 15 | 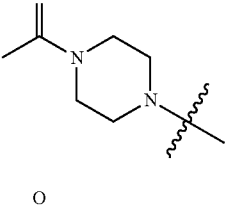 | Cl | 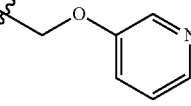 |
| 16 | 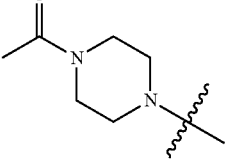 | OH | 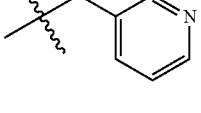 |
TABLE 19-continued
| Entry | R¹ | R² | R³ |
|---|---|---|---|
| 17 | 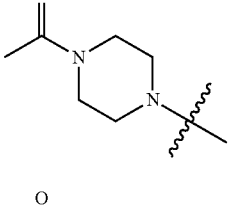 | F | 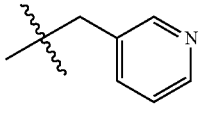 [SMILES: *Cc1cccnc1] |
| 18 | 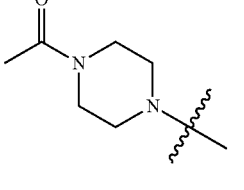 | Cl | 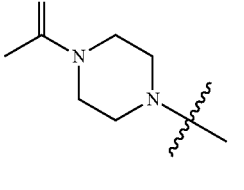 |
| 19 | 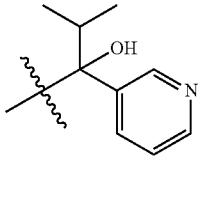 [SMILES: *C(O)(c1cccnc1)C(C)C] | OH | 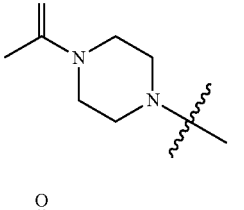 |
| 20 | 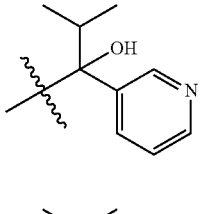 | F | 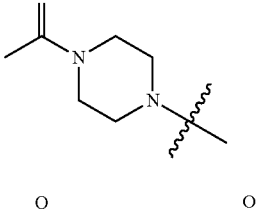 |
| 21 | 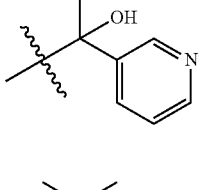 | Cl | 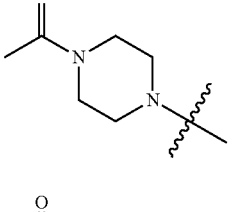 |
| 22 | 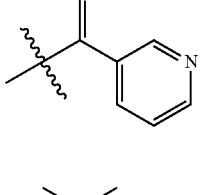 | OH | 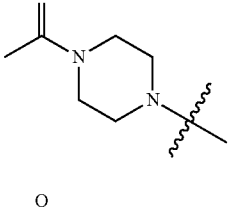 |
| 23 | 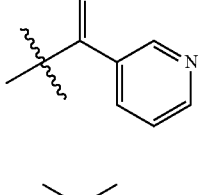 | F | 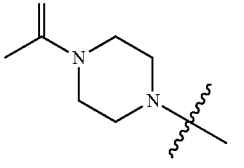 |
| 24 | 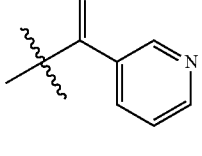 | Cl | |

TABLE 19-continued

| Entry | R¹ | R² | R³ |
|---|---|---|---|
| 25 | 4-Pyridyl | OH | 3-pyridyl isopropenyl |
| 26 | 4-Pyridyl | F | 3-pyridyl isopropenyl |
| 27 | 4-Pyridyl | Cl | 3-pyridyl isopropenyl |

Exemplary embodiments include compounds having the formula (XXIV) or a pharmaceutically acceptable salt form thereof:

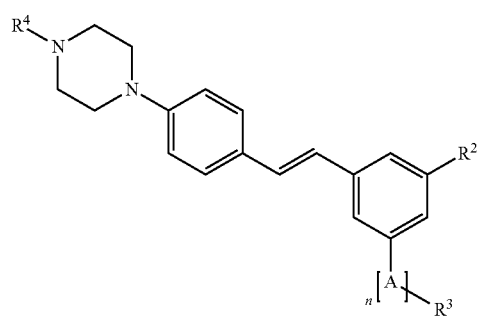

(XXIV)

wherein non-limiting examples of R² and R⁸ are defined herein below in Table 20.

TABLE 20

| Entry | R² | R³ | A | n | R⁴ |
|---|---|---|---|---|---|
| 1 | OH | imidazol-1-yl | CH₂ | 1 | amidine (NH, NH₂) |
| 2 | F | imidazol-1-yl | CH₂ | 1 | amidine (NH, NH₂) |
| 3 | Cl | imidazol-1-yl | CH₂ | 1 | amidine (NH, NH₂) |
| 4 | OH | imidazol-1-yl | CH₂ | 1 | oxazoline |
| 5 | F | imidazol-1-yl | CH₂ | 1 | oxazoline |
| 6 | Cl | imidazol-1-yl | CH₂ | 1 | oxazoline |
| 7 | OH | imidazol-1-yl | CH₂ | 1 | 1,3-oxazine |
| 8 | F | imidazol-1-yl | CH₂ | 1 | 1,3-oxazine |
| 9 | Cl | imidazol-1-yl | CH₂ | 1 | 1,3-oxazine |
| 10 | OH | 4-pyridyl | — | 0 | amidine (NH, NH₂) |
| 11 | F | 4-pyridyl | — | 0 | amidine (NH, NH₂) |
| 12 | Cl | 4-pyridyl | — | 0 | amidine (NH, NH₂) |
| 13 | OH | 4-pyridyl | — | 0 | oxazoline |
| 14 | F | 4-pyridyl | — | 0 | oxazoline |

TABLE 20-continued
| Entry | R² | R³ | A | n | R⁴ |
|---|---|---|---|---|---|
| 15 | Cl | 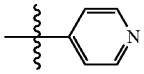 | — | 0 | 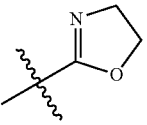 [SMILES: *C1=NCCO1] |
| 16 | OH | 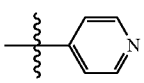 | — | 0 | 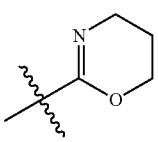 |
| 17 | F | 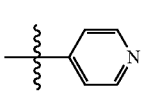 | — | 0 | 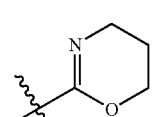 |
| 18 | Cl | 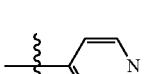 | — | 0 | 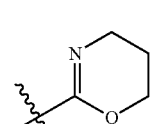 |
| 19 | OH | 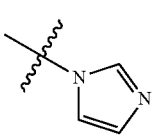 [SMILES: *n1ccnc1] | — | 0 | 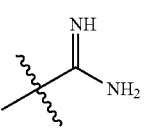 |
| 20 | F | 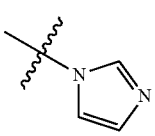 | — | 0 | 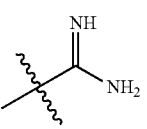 [SMILES: *C(=N)N] |
| 21 | Cl | 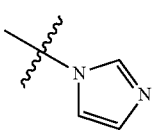 [SMILES: *n1ccnc1] | — | 0 | 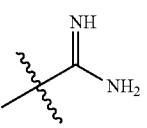 [SMILES: *C(=N)N] |
| 22 | OH | 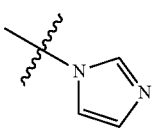 | — | 0 | 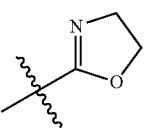 [SMILES: *C1=NCCO1] |
| 23 | F | 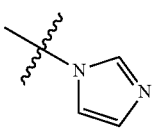 [SMILES: *n1ccnc1] | — | 0 | 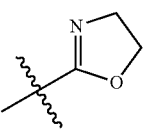 [SMILES: *C1=NCCO1] |
| 24 | Cl | 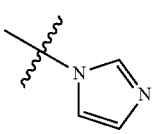 | — | 0 | 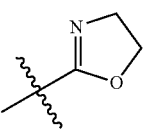 |
| 25 | OH | 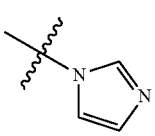 [SMILES: *n1ccnc1] | — | 0 | 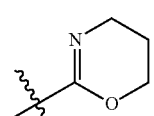 |
| 26 | F | 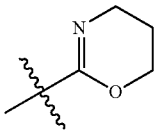 [SMILES: *C1=NCCCO1] | — | 0 | 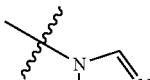 |
| 27 | Cl | 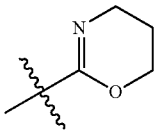 [SMILES: *C1=NCCCO1] | — | 0 |  |
| 28 | OH | 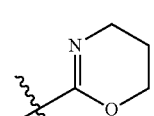 | 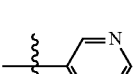 | 1 | 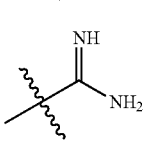 |
| 29 | F | 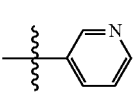 [SMILES: *c1cccnc1] | 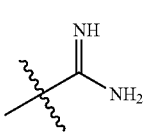 | 1 | 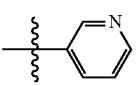 |
| 30 | Cl | 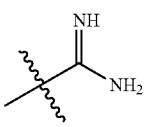 | 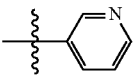 | 1 | 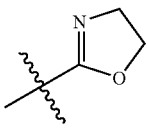 [SMILES: *C1=NCCO1] |
| 31 | OH | 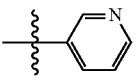 | 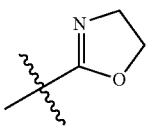 | 1 | 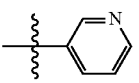 [SMILES: *c1cccnc1] |
| 32 | F | 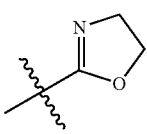 [SMILES: *C1=NCCO1] | 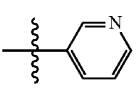 | 1 | 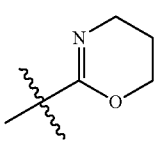 [SMILES: *C1=NCCCO1] |
| 33 | Cl | 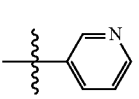 | 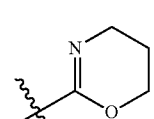 | 1 | 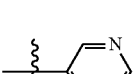 |
| 34 | OH | 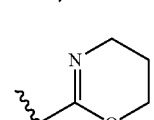 | | 1 | |
| 35 | F | | | 1 | |
| 36 | Cl | | | 1 | |

Exemplary embodiments include compounds having the formula (XXV) or a pharmaceutically acceptable salt form thereof:

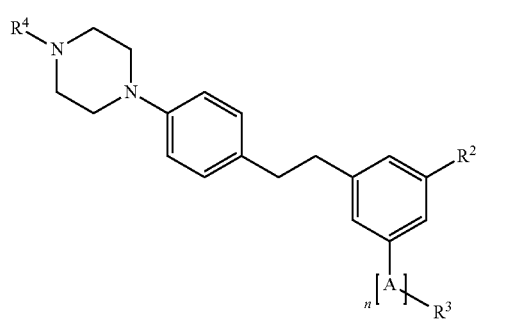

(XXV)

wherein non-limiting examples of $R^2$ and $R^8$ are defined herein below in Table 22.

TABLE 21

| Entry | $R^2$ | $R^3$ | A | n | $R^4$ |
|---|---|---|---|---|---|
| 1 | OH | imidazole | $CH_2$ | 1 | amidine |
| 2 | F | imidazole | $CH_2$ | 1 | amidine |
| 3 | Cl | imidazole | $CH_2$ | 1 | amidine |
| 4 | OH | imidazole | $CH_2$ | 1 | oxazoline |
| 5 | F | imidazole | $CH_2$ | 1 | oxazoline |
| 6 | Cl | imidazole | $CH_2$ | 1 | oxazoline |
| 7 | OH | imidazole | $CH_2$ | 1 | oxazine |
| 8 | F | imidazole | $CH_2$ | 1 | oxazine |
| 9 | Cl | imidazole | $CH_2$ | 1 | oxazine |
| 10 | OH | pyridine | — | 0 | amidine |
| 11 | F | pyridine | — | 0 | amidine |
| 12 | Cl | pyridine | — | 0 | amidine |
| 13 | OH | pyridine | — | 0 | oxazoline |
| 14 | F | pyridine | — | 0 | oxazoline |
| 15 | Cl | pyridine | — | 0 | oxazoline |
| 16 | OH | pyridine | — | 0 | oxazine |
| 17 | F | pyridine | — | 0 | oxazine |
| 18 | Cl | pyridine | — | 0 | oxazine |
| 19 | OH | imidazole | — | 0 | amidine |
| 20 | F | imidazole | — | 0 | amidine |

TABLE 21-continued

| Entry | R² | R³ | A | n | R⁴ |
|---|---|---|---|---|---|
| 21 | Cl | imidazolyl | — | 0 | C(=NH)NH₂ |
| 22 | OH | imidazolyl | — | 0 | oxazoline |
| 23 | F | imidazolyl | — | 0 | oxazoline |
| 24 | Cl | imidazolyl | — | 0 | oxazoline |
| 25 | OH | imidazolyl | — | 0 | oxazine |
| 26 | F | imidazolyl | — | 0 | oxazine |
| 27 | Cl | imidazolyl | — | 0 | oxazine |
| 28 | OH | pyridyl | C=C(CH₃) | 1 | C(=NH)NH₂ |
| 29 | F | pyridyl | C=C(CH₃) | 1 | C(=NH)NH₂ |
| 30 | Cl | pyridyl | C=C(CH₃) | 1 | C(=NH)NH₂ |
| 31 | OH | pyridyl | C=C(CH₃) | 1 | oxazoline |
| 32 | F | pyridyl | C=C(CH₃) | 1 | oxazoline |
| 33 | Cl | pyridyl | C=C(CH₃) | 1 | oxazoline |
| 34 | OH | pyridyl | C=C(CH₃) | 1 | oxazine |
| 35 | F | pyridyl | C=C(CH₃) | 1 | oxazine |
| 36 | Cl | pyridyl | C=C(CH₃) | 1 | oxazine |

For the purposes of demonstrating the manner in which the compounds of the present invention are named and referred to herein, the compound having the formula (XXVI):

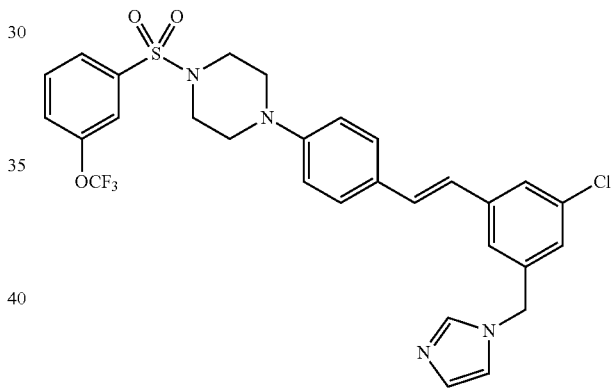

(XXVI)

has the chemical name (E)-1-(4-(3-((1H-imidazol-1-yl)methyl)-5-chlorostyryl)phenyl)-4-(3-(trifluoromethoxy)phenylsulfonyl)piperazine.

For the purposes of demonstrating the manner in which the compounds of the present invention are named and referred to herein, the compound having the formula (XXVII):

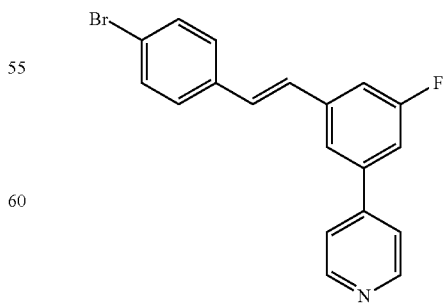

has the chemical name (E)-4-(3-(4-bromostyryl)-5-fluorophenyl)pyridine.

For the purposes of demonstrating the manner in which the compounds of the present invention are named and referred to herein, the compound having the formula (XXVIII):

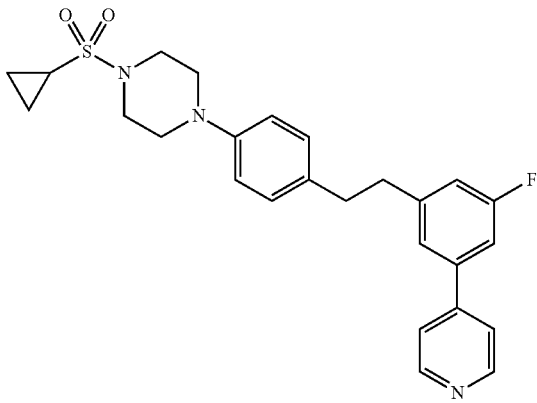 [SMILES: O=S(=O)(C1CC1)N1CCN(c2ccc(CCc3cc(F)cc(-c4ccncc4)c3)cc2)CC1]

has the chemical name (E)-1-(cyclopropylsulfonyl)-4-(4-(3-fluoro-5-(pyridin-4-yl)styryl)phenyl)piperazine.

For the purposes of the present invention, a compound depicted by the racemic formula will stand equally well for either of the two enantiomers or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Process

Some embodiments of the present invention further relate to a process for preparing the cortisol lowering agents of embodiments described herein.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of embodiments described herein can be prepared according to the method illustrated in the General Synthetic Schemes.

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of the disclosure may be prepared according to the processes outlined in schemes 1-x

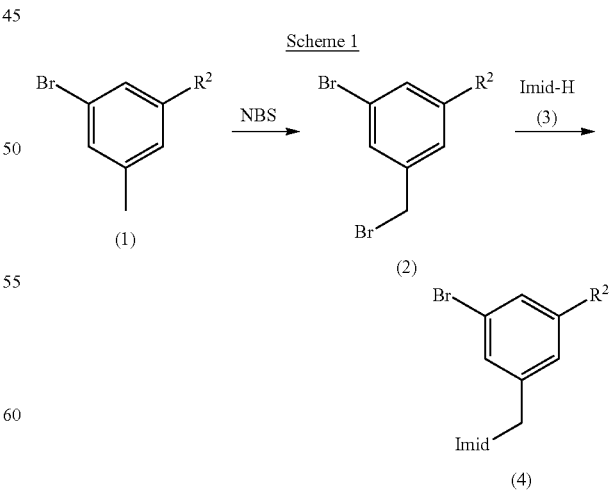

In embodiments, a suitably substituted compound of formula (1), a known compound or compound prepared by known methods, is reacted with N-bromosuccinimide (NBS)

in an organic solvent such as methylene chloride, dichloromethane, carbontetrachloride, 1,2-dichloroethane, acetonitrile, tetrahydrofuan, 1,4-dioxane, and the like, optionally with heating, optionally with microwave irradiation to provide a compound of the formula (2). A compound of the formula (2) is then reacted with a compound of the formula (3), a known compound or compound prepared by known methods wherein "Imid-H" is an optionally substituted imidazole, in an organic solvent such as tetrahydrofuran, 1,4-dioxane, acetonitrile, N,N-diemthylformamide, N,N-dimethylacetamide, dimethylsulfoxide, and the like, optionally with heating, optionally with microwave irradiation to provide a compound of the formula (4).

presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, in the presence of a phosphine reagent such as triphenylphosphine, tri-(o-tolyl)phosphine, and the like, in the presence of a base such as triethylamine, diisopropylethylamine, pyridine, 2,6-dimethylpyridine, N-methylmorpholine, potassium carbonate, sodium carbonate, lithium carbonate, cesium carbonate, sodium hydroxide, lithium hydroxide, potassium hydroxide, and the like in a solvent such as toluene, benzene, p-xylene, 1,4-dioxane, tetrahydrofuran, acetonitrile, and the like, optionally in the presence of water, optionally with heating, optionally with microwave irradiation, to provide a compound of the formula (8).

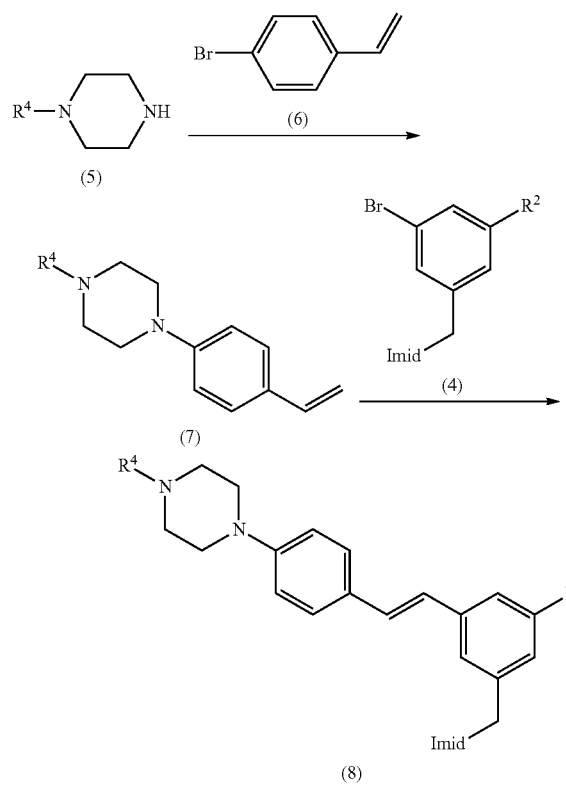

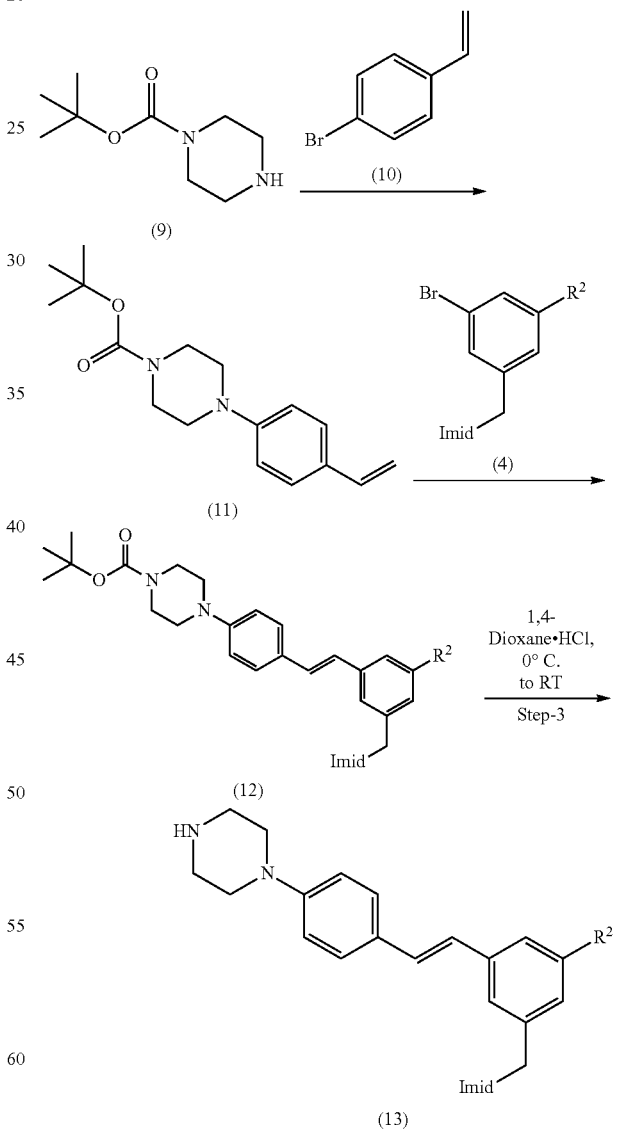

A suitably substituted compound of formula (5), a known compound or compound prepared by known methods, is reacted with a compound of the formula (6), a known compound or compound prepared by known methods, in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, optionally in the presence of 2-Dicyclohexylphosphino-2',4',6'-triisopropylbiphenyl (X-phos), in the presence of a base such as potassium carbonate, sodium carbonate, lithium carbonate, cesium carbonate, sodium hydroxide, lithium hydroxide, potassium hydroxide, and the like in a solvent such as toluene, benzene, p-xylene, 1,4-dioxane, tetrahydrofuran, acetonitrile, and the like, optionally in the presence of water, optionally with heating, optionally with microwave irradiation, to provide a compound of the formula (7). A compound of the formula (7) is then reacted with a compound of the formula (4) in the A suitably substituted compound of formula (9 known compound or compound prepared by known methods, is reacted with a compound of the formula (10), a known compound or compound prepared by known methods, in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, optionally in the presence of 2-Dicyclohexylphosphino-2',4',6'-triisopropylbiphenyl (X-phos), in the presence of a base such as potassium carbonate, sodium carbonate, lithium carbonate, cesium carbonate, sodium hydroxide, lithium hydroxide, potassium hydroxide, and the like in a solvent such as toluene, benzene, p-xylene, 1,4-dioxane, tetrahydrofuran, acetonitrile, and the like, optionally in the presence of water, optionally with heating, optionally with microwave irradiation, to provide a compound of the formula (11). A compound of the formula (11) is then reacted with a compound of the formula (4) in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, in the presence of a phosphine reagent such as triphenylphosphine, tri-(o-tolyl)phosphine, and the like, in the presence of a base such as potassium carbonate, sodium carbonate, lithium carbonate, cesium carbonate, sodium hydroxide, lithium hydroxide, potassium hydroxide, triethylamine, diisopropylethylamine, pyridine, 2,6-lutidine, and the like in a solvent such as toluene, benzene, p-xylene, 1,4-dioxane, tetrahydrofuran, acetonitrile, and the like, optionally in the presence of water, optionally with heating, optionally with microwave irradiation, to provide a compound of the formula (12). A compound of the formula (12) is then reacted with an acid such as hydrochloric acid, sulfuric acid, trifluoroacetic acid, and the like, in an organic solvent such as tetrahydrofuran, 1,4-dioxane, methanol, ethanol, methylene chloride, and the like to provide a compound of the formula (13).

Scheme 4

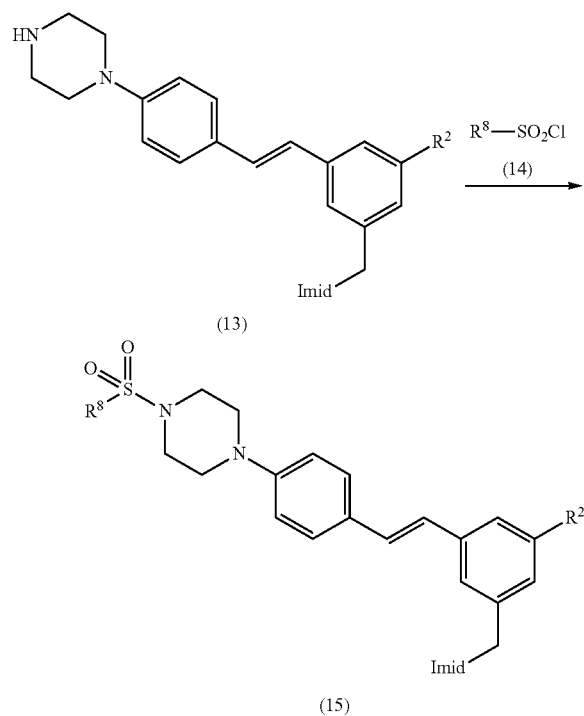

A suitably substituted compound of formula (13), a known compound or compound prepared by known methods, is reacted with a compound of the formula (14), a known compound or compound prepared by known methods, in the presence of a bases such as such as triethylamine, diisopropylethylamine, pyridine, 2,6-dimethylpyridine, N-methylmorpholine, and the like, in an organic solvent such as methylene chloride, 1,2-dichloroethane, tetrahydrofuran, 1,4-dioxane, acetonitrile, N,N-dimethylformamide, and the like to provide a compound of the formula (15).

Scheme 5

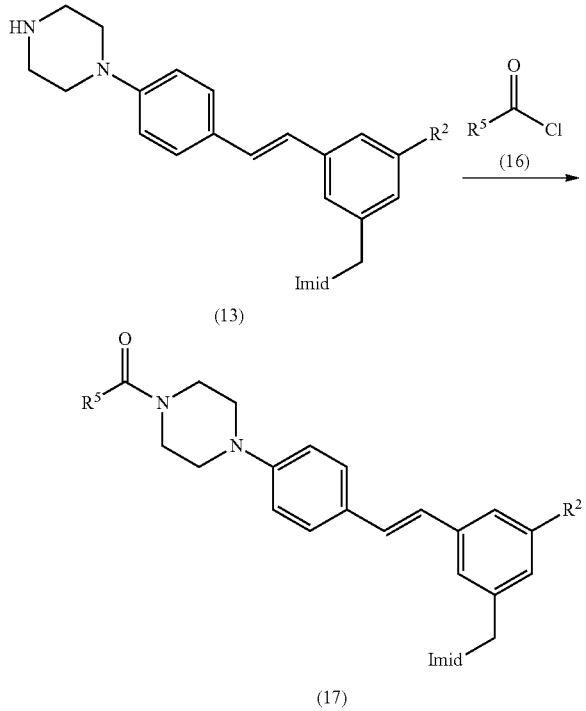

A suitably substituted compound of formula (13), a known compound or compound prepared by known methods, is reacted with a compound of the formula (16), a known compound or compound prepared by known methods, in the presence of a bases such as such as triethylamine, diisopropylethylamine, pyridine, 2,6-dimethylpyridine, N-methylmorpholine, and the like, in an organic solvent such as methylene chloride, 1,2-dichloroethane, tetrahydrofuran, 1,4-dioxane, acetonitrile, N,N-dimethylformamide, and the like to provide a compound of the formula (17).

Scheme 6

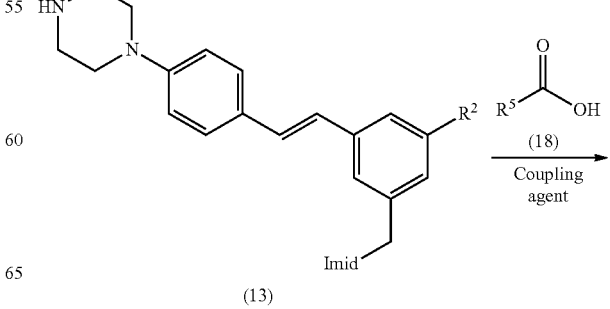

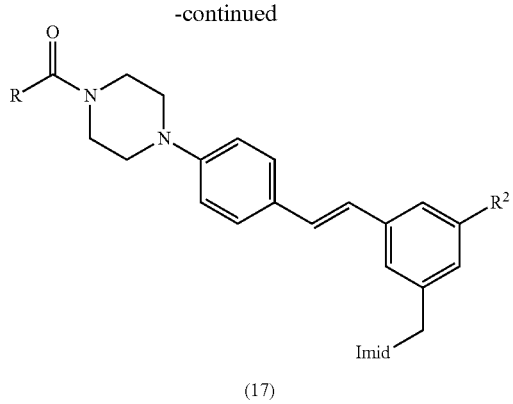

(17)

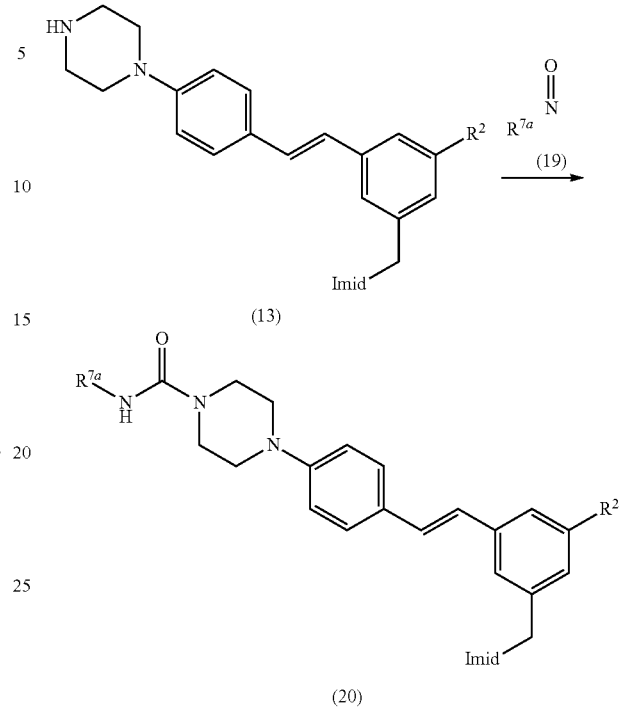

Scheme 7

Alternatively, a compound of the formula (13) is reacted with a compound of the formula (18), a known compound or compound prepared by known methods, in the presence of a coupling agent such as 1-ethyl-3-(3-dimethylaminopropyl)carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyl-uronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydronfuran, 1,4-dioxane, dimethylformamide, methylene chloride, 1,2-dichloroethane, methanol, ethanol, acetonitrile, and the like, optionally in the presence of a base such as triethylamine, diisopropylethylamine, pyridine, 2,6-lutidine, and the like, optionally in the presence of 4-N,N-dimethylaminopyridine, to provide a compound of the formula (17).

A compound of formula (13) is reacted with a compound of the formula (19), a known compound or compound prepared by known methods in an organic solvent such as methylene chloride, 1,2-dichloroethane, tetrahydrofuran, 1,4-dioxane, acetonitrile, N,N-dimethylformamide, and the like to provide a compound of the formula (20).

Scheme 8

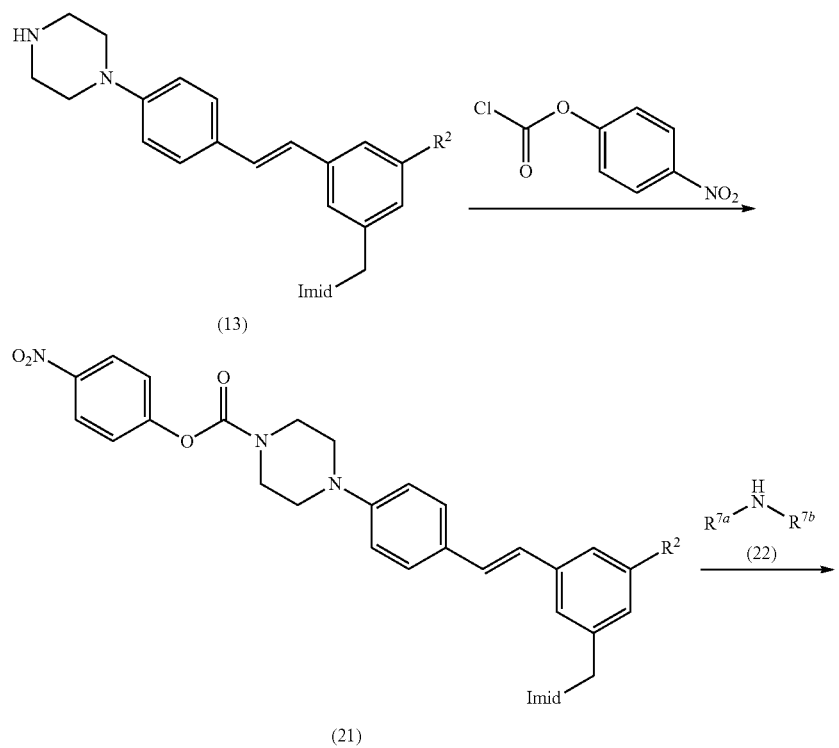

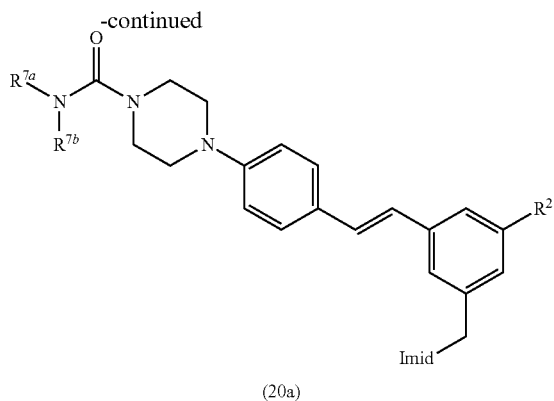

(20a)

Alternatively, a compound of formula (13) is reacted with a p-nitrophenylchloroformate in the presence of a bases such as such as triethylamine, diisopropylethylamine, pyridine, 2,6-dimethylpyridine, N-methylmorpholine, and the like, in an organic solvent such as methylene chloride, 1,2-dichloroethane, acetonitrile, tetrahydrofuran, 1,4-dioxane, N,N-dimethylformamide, and the like to provide a compound of the formula (21). A compound of formula (21) is then reacted with a compound of the formula (22), a known compound or compound prepared by known methods, in the presence of a bases such as such as triethylamine, diisopropylethylamine, pyridine, 2,6-dimethylpyridine, N-methylmorpholine, and the like, in an organic solvent such as methylene chloride, 1,2-dichloroethane, tetrahydrofuran, 1,4-dioxane, acetonitrile, N,N-dimethylformamide, and the like to provide a compound of the formula (20a).

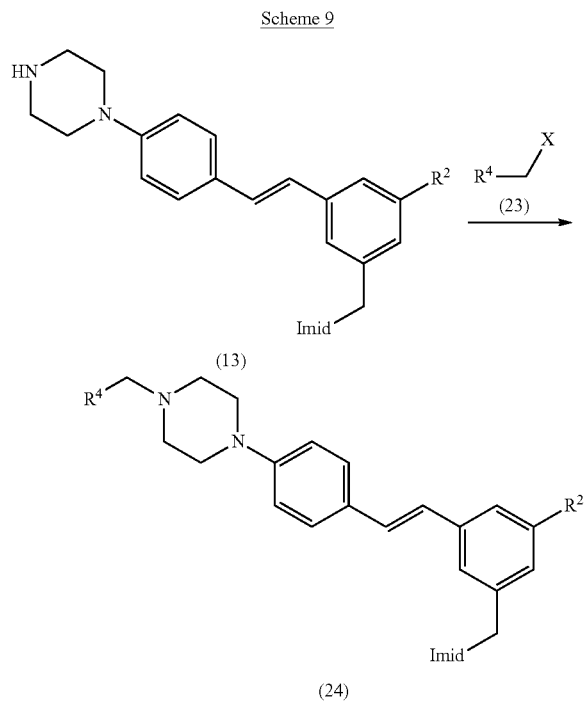

Scheme 9

(13)

(24)

A compound of formula (13) is reacted with a compound of the formula (23), a known compound or compound prepared by known methods, wherein X is a leaving group such as bromine, chlorine, iodine, methanesulfonate, toluenesulfonate, and the like, in the presence of a base such as potassium carbonate, sodium carbonate, lithium carbonate, cesium carbonate, triethylamine, diisopropylethylamine, pyridine, 2,6-lutidine, and the like in an organic solvent such as methylene chloride, 1,2-dichloroethane, tetrahydrofuran, 1,4-dioxane, acetonitrile, N,N-dimethylformamide, N,N-dimethylacetamide, and the like, optionally with heating, optionally with microwave irradiation to provide a compound of the formula (24).

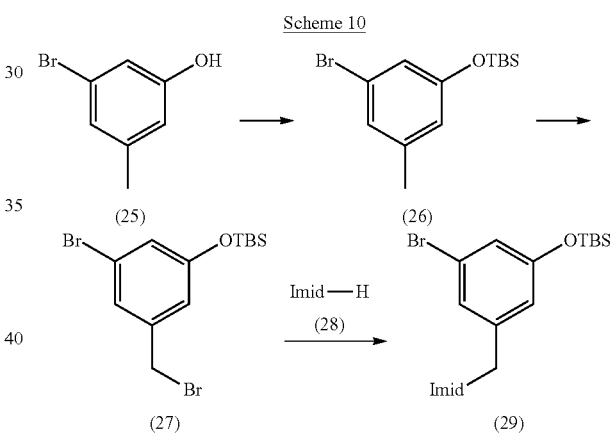

Scheme 10

(25) (26)

(27) (29)

A compound of formula (25), a known compound or compound prepared by known methods, is reacted with tert-butyldimethylsilyl chloride in the presence of imidazole in an organic solvent such as as methylene chloride, 1,2-dichloroethane, tetrahydrofuran, 1,4-dioxane, acetonitrile, N,N-dimethylformamide, N,N-dimethylacetamide, and the like, optionally with heating, optionally with microwave irradiation to provide a compound of the formula (26). A compound of the formula (26) is then reacted with N-bromosuccinimide (NBS) in an organic solvent such as methylene chloride, dichloromethane, carbontetrachloride, 1,2-dichloroethane tetrahydrofuan, 1,4-dioxane, and the like, optionally with heating, optionally with microwave irradiation to provide a compound of the formula (27). A compound of the formula (27) is then reacted with a compound of the formula (28), a known compound or compound prepared by known methods wherein "Imid-H" is an optionally substituted imidazole, in an organic solvent such as tetrahydrofuran, 1,4-dioxane, acetonitrile, N,N-diemthylformamide, N,N-dimethylacetamide, dimethylsulfoxide, and the like, optionally with heating, optionally with microwave irradiation to provide a compound of the formula (29).

Scheme 11

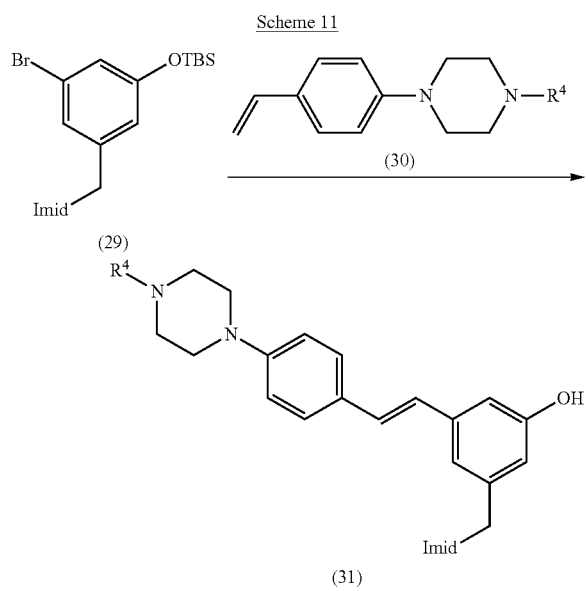

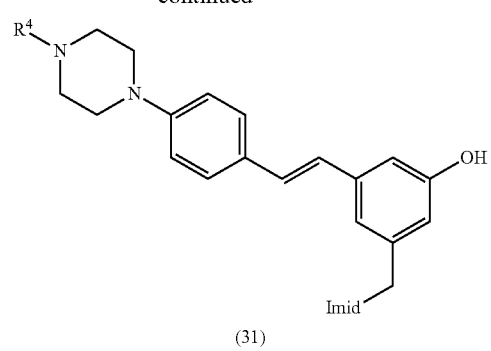

A compound of formula (29) is then reacted with a compound of the formula (30) in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, in the presence of a phosphine reagent such as triphenylphosphine, tri-(o-tolyl)phosphine, and the like, in the presence of a base such as triethylamine, diisopropylethylamine, pyridine, 2,6-dimethylpyridine, N-methylmorpholine, potassium carbonate, sodium carbonate, lithium carbonate, cesium carbonate, sodium hydroxide, lithium hydroxide, potassium hydroxide, and the like in a solvent such as toluene, benzene, p-xylene, 1,4-dioxane, tetrahydrofuran, acetonitrile, and the like, optionally in the presence of water, optionally with heating, optionally with microwave irradiation, to provide a compound of the formula (31).

Alternatively, a compound of formula (29) is then reacted with a compound of the formula (30) in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, in the presence of a phosphine reagent such as triphenylphosphine, tri-(o-tolyl)phosphine, and the like, in the presence of a base such as triethylamine, diisopropylethylamine, pyridine, 2,6-dimethylpyridine, N-methylmorpholine, potassium carbonate, sodium carbonate, lithium carbonate, cesium carbonate, sodium hydroxide, lithium hydroxide, potassium hydroxide, and the like in a solvent such as toluene, benzene, p-xylene, 1,4-dioxane, tetrahydrofuran, acetonitrile, and the like, optionally in the presence of water, optionally with heating, optionally with microwave irradiation, to provide a compound of the formula (32). A compound of the formula (32) is then reacted with an acid such as hydrochloric acid, sulfuric acid, trifluoroacetic acid, and the like, in an organic solvent such as 1,4-dioxane, tetrahydrofuran, acetonitrile, methylene chloride, methanol, ethanol, and the like to provide a compound of the formula (31).

Scheme 12

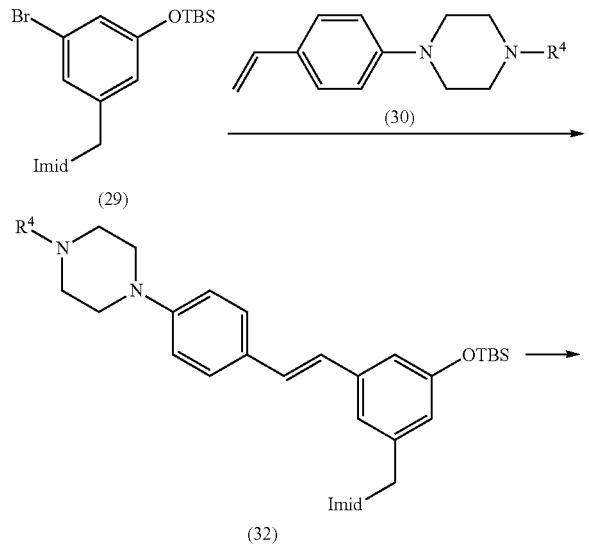

Scheme 13

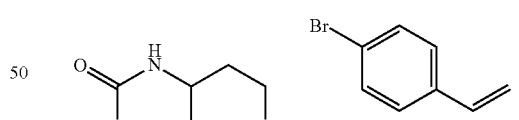

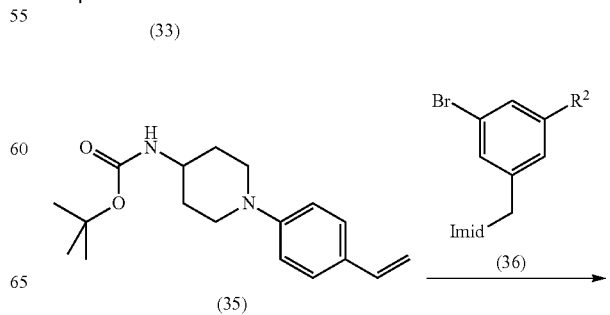

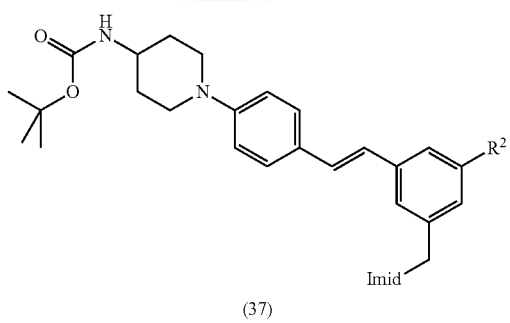

(37)

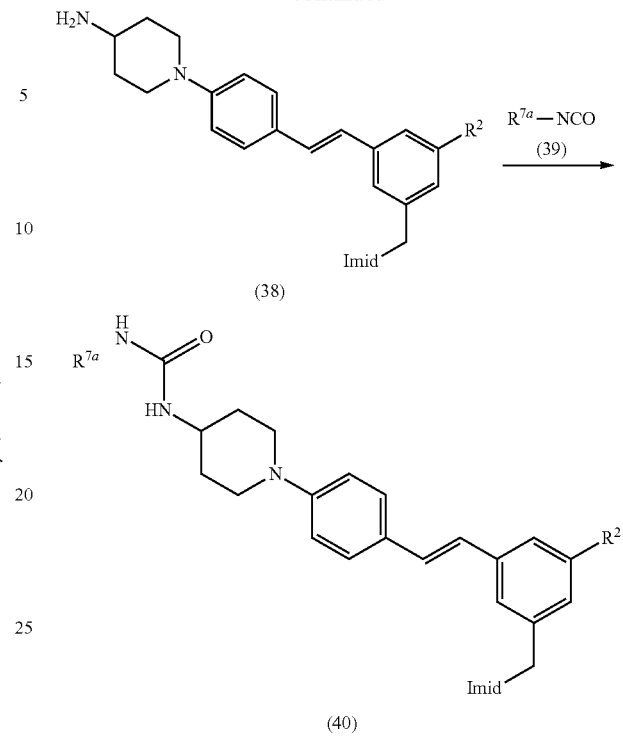

(38)

(40)

A compound of formula (33), a known compound or compound prepared by known methods, is reacted with a compound of the formula (34), a known compound or compound prepared by known methods, in the presence of a palladium catalyst such as palladium acetate, palladium bis(triphenylphosphine) dichloride, palladium tetrakis(triphenylphospine), bis(acetonitrile) dichloropalladium [1,1'-Bis (diphenylphosphino) ferrocene]dichloropalladium, and the like, optionally in the presence of 2-Dicyclohexylphosphino-2',4',6'-triisopropylbiphenyl (X-phos), in the presence of a base such as potassium carbonate, sodium carbonate, lithium carbonate, cesium carbonate, sodium hydroxide, lithium hydroxide, potassium hydroxide, and the like in a solvent such as toluene, benzene, p-xylene, 1,4-dioxane, tetrahydrofuran, acetonitrile, and the like, optionally in the presence of water, optionally with heating, optionally with microwave irradiation, to provide a compound of the formula (35). A compound of the formula (35) is then reacted with a compound of the formula (36) in the presence of a palladium catalyst such as palladium acetate, palladium bis(triphenylphosphine) dichloride, palladium tetrakis(triphenylphospine), bis(acetonitrile) dichloropalladium [1,1'-Bis (diphenylphosphino) ferrocene]dichloropalladium, and the like, in the presence of a phosphine reagent such as triphenylphosphine, tri-(o-tolyl)phosphine, and the like, in the presence of a base such as potassium carbonate, sodium carbonate, lithium carbonate, cesium carbonate, sodium hydroxide, lithium hydroxide, potassium hydroxide, and the like in a solvent such as toluene, benzene, p-xylene, 1,4-dioxane, tetrahydrofuran, acetonitrile, and the like, optionally in the presence of water, optionally with heating, optionally with microwave irradiation, to provide a compound of the formula (37).

A compound of formula (37) is then reacted with an acid such as hydrochloric acid, sulfuric acid, trifluoroacetic acid, and the like, in an organic solvent such as 1,4-dioxane, tetrahydrofuran, acetonitrile, methanol, ethanol, and the like to provide a compound of the formula (38). A compound of the formula (38) is then reacted with a compound of the formula (39), a known compound or compound prepared by known methods, optionally in the presence of a bases such as such as triethylamine, diisopropylethylamine, pyridine, 2,6-dimethylpyridine, N-methylmorpholine, and the like, in an organic solvent such as methylene chloride, 1,2-dichloroethane, tetrahydrofuran, 1,4-dioxane, acetonitrile, N,N-dimethylformamide, and the like to provide a compound of the formula (40).

Scheme 14

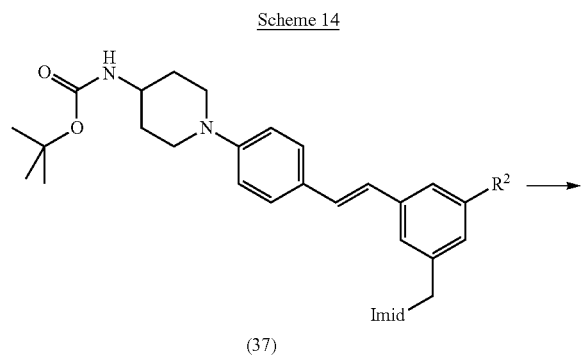

(37)

Scheme 15

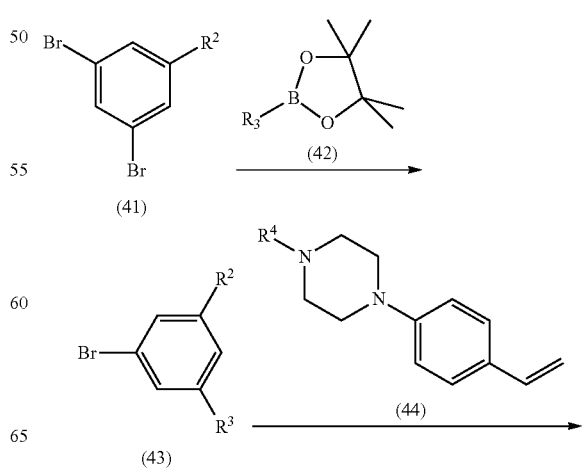

-continued

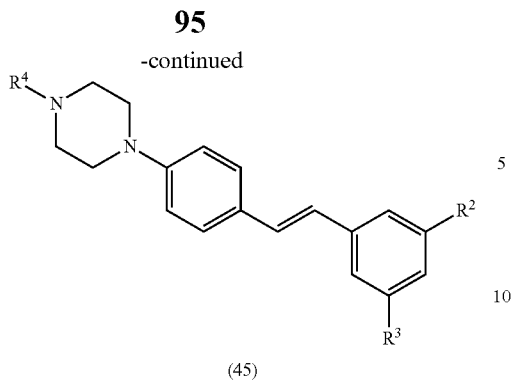

(45)

A compound of formula (41), a known compound or compound prepared by known methods, is reacted with a compound of the formula (42), a known compound or compound prepared by known methods wherein Hetaryl is an optionally substituted heteroaryl ring, in the presence of a palladium catalyst such as palladium acetate, palladium bis(triphenylphosphine) dichloride, palladium tetrakis(triphenylphospine), bis(acetonitrile) dichloropalladium [1,1'-Bis (diphenylphosphino) ferrocene]dichloropalladium, and the like, in the presence of a base such as potassium carbonate, sodium carbonate, lithium carbonate, cesium carbonate, sodium hydroxide, lithium hydroxide, potassium hydroxide, and the like in a solvent such as tetrahydrofuran, 1,4-dioxane, acetonitrile, toluene, N,N-dimethylformamide, and the like to, optionally with heating, optionally with microwave irradiation, to provide a compound of the formula (43). A compound of the formula (43) is then reacted with a compound of the formula (44) in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, in the presence of a phosphine reagent such as triphenylphosphine, tri-(o-tolyl)phosphine, and the like, in the presence of a base such as triethylamine, diisopropylethylamine, pyridine, 2,6-dimethylpyridine, N-methylmorpholine, potassium carbonate, sodium carbonate, lithium carbonate, cesium carbonate, sodium hydroxide, lithium hydroxide, potassium hydroxide, and the like in a solvent such as toluene, benzene, p-xylene, 1,4-dioxane, tetrahydrofuran, acetonitrile, and the like, optionally in the presence of water, optionally with heating, optionally with microwave irradiation. to provide a compound of the formula (45).

A compound of formula (41), a known compound or compound prepared by known methods, is reacted with a compound of the formula (46), a known compound or compound prepared by known methods wherein Hetaryl is an optionally substituted heteroaryl ring, in the presence of a palladium catalyst such as palladium acetate, palladium bis(triphenylphosphine) dichloride, palladium tetrakis(triphenylphospine), bis(acetonitrile) dichloropalladium [1,1'-Bis (diphenylphosphino) ferrocene]dichloropalladium, and the like, in the presence of a base such as potassium carbonate, sodium carbonate, lithium carbonate, cesium carbonate, sodium hydroxide, lithium hydroxide, potassium hydroxide, and the like in a solvent such as tetrahydrofuran, 1,4-dioxane, acetonitrile, toluene, N,N-dimethylformamide, and the like to, optionally with heating, optionally with microwave irradiation, to provide a compound of the formula (43). A compound of the formula (43) is then reacted with a compound of the formula (44) in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, in the presence of a phosphine reagent such as triphenylphosphine, tri-(o-tolyl)phosphine, and the like, in the presence of a base such as triethylamine, diisopropylethylamine, pyridine, 2,6-dimethylpyridine, N-methylmorpholine, potassium carbonate, sodium carbonate, lithium carbonate, cesium carbonate, sodium hydroxide, lithium hydroxide, potassium hydroxide, and the like in a solvent such as toluene, benzene, p-xylene, 1,4-dioxane, tetrahydrofuran, acetonitrile, and the like, optionally in the presence of water, optionally with heating, optionally with microwave irradiation, to provide a compound of the formula (45).

Scheme 16

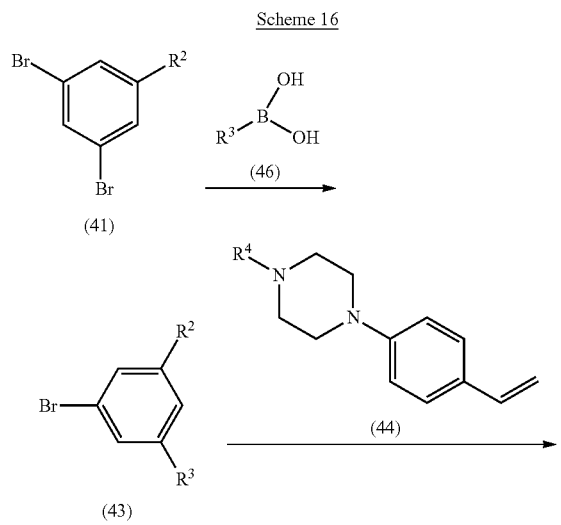

Scheme 17

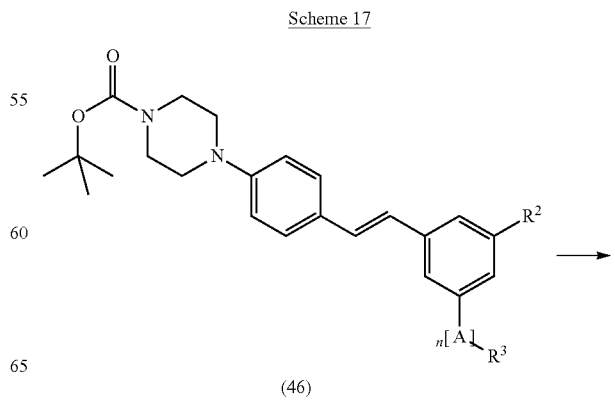

-continued

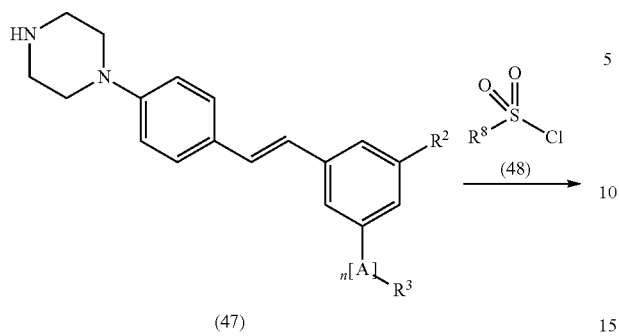

(47)

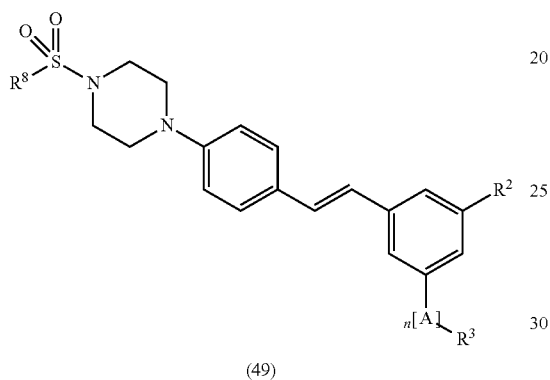

(49)

A compound of the formula (46) is reacted with an acid such as hydrochloric acid, sulfuric acid, trifluoroacetic acid, and the like, in an organic solvent such as 1,4-dioxane, tetrahydrofuran, methylene chloride, methanol, ethanol, and the like to provide a compound of the formula (47). A compound of the formula (47) is then reacted with a compound of the formula (48), a known compound or compound prepared by known methods, in the presence of a base such as triethylamine, diisopropylethylamine, pyridine, 2,6-dimethylpyridine, N-methylmorpholine, and the like, in a solvent such as methylene chloride, 1,2-dichloroethane, tetrahydrofuran, 1,4-dioxane, acetonitrile, N,N-dimethylformamide, and the like to provide a compound of the formula (49).

Scheme 18

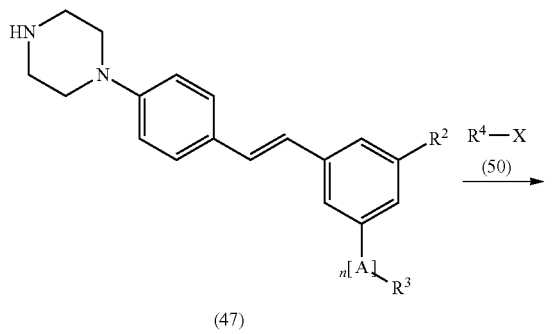

(47)

-continued

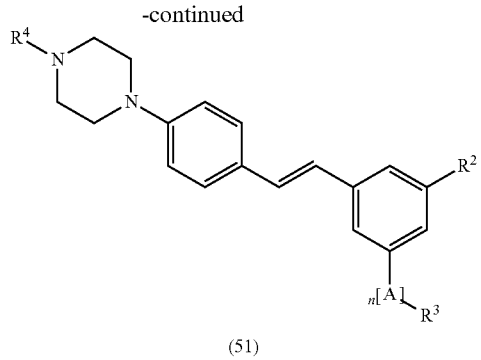

(51)

A compound of formula (47) is reacted with a compound of the formula (50), a known compound or compound prepared by known methods, wherein X is a leaving group such as bromine, chlorine, iodine, methanesulfonate, toluenesulfonate, and the like, in the presence of a base such as potassium carbonate, sodium carbonate, lithium carbonate, cesium carbonate, triethylamine, diisopropylethylamine, pyridine, 2,6-lutidine, and the like in an organic solvent such as methylene chloride, 1,2-dichloroethane, tetrahydrofuran, 1,4-dioxane, acetonitrile, N,N-dimethylformamide, N,N-dimethylacetamide, and the like, optionally with heating, optionally with microwave irradiation to provide a compound of the formula (51).

Scheme 19

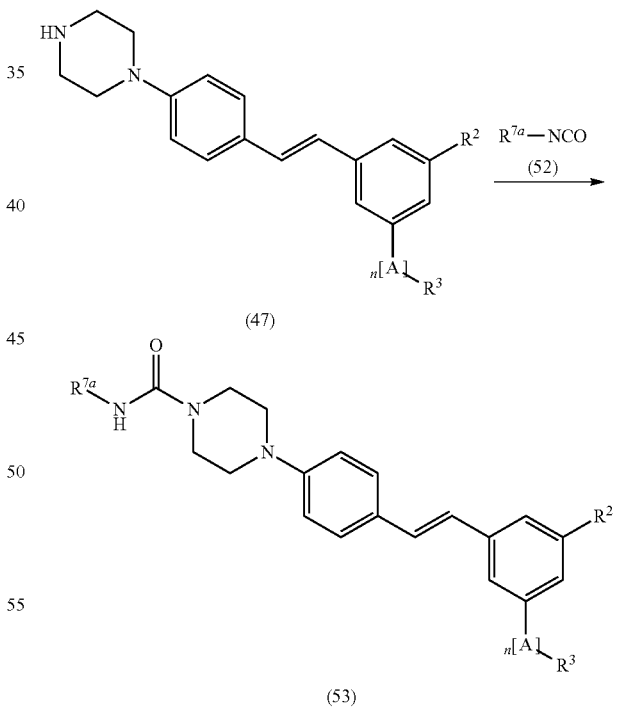

A compound of formula (47) is reacted with a compound of the formula (52), a known compound or compound prepared by known methods, optionally in the presence of a bases such as such as triethylamine, diisopropylethylamine, pyridine, 2,6-dimethylpyridine, N-methylmorpholine, and the like, in an organic solvent such as methylene chloride, 1,2-dichloroethane, tetrahydrofuran, 1,4-dioxane, acetonitrile, N,N-dimethylformamide, and the like to provide a compound of the formula (53).

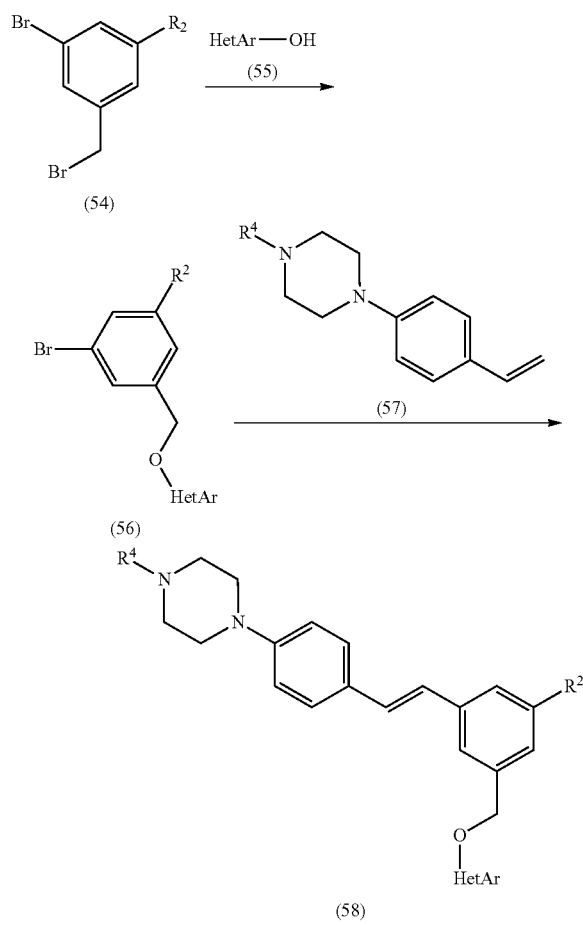

hydroxide, potassium hydroxide, and the like in a solvent such as toluene, benzene, p-xylene, 1,4-dioxane, tetrahydrofuran, acetonitrile and the like, optionally with heating, optionally with microwave irradiation, to provide a compound of the formula (58).

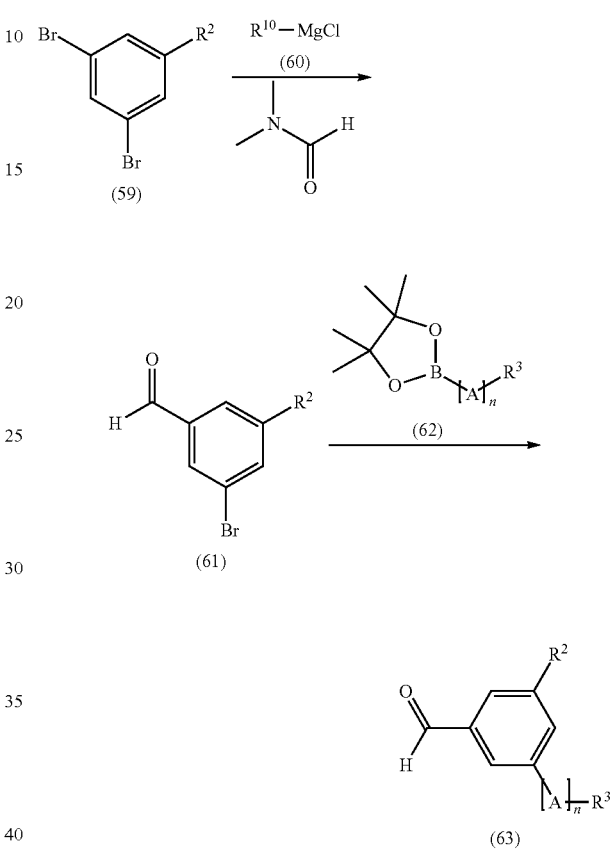

A compound of formula (54), a known compound or compound prepared by known methods, is reacted with a compound of the formula (55), a known compound or compound prepared by known methods wherein Hetaryl is an optionally substituted heteroaryl ring, in the presence of a base such as sodium hydride, lithium hydride, n-butyl lithium, lithium diisopropyl amide, sodium diisopropyl amide, potassium tert-butoxide, and the like, in an organic solvent such as methylene chloride, 1,2-dichloroethane, tetrahydrofuran, 1,4-dioxane, acetonitrile, N,N-dimethylformamide, and the like to provide a compound of the formula (56). A compound of the formula (56) is then reacted with a compound of the formula (57) in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, in the presence of a phosphine reagent such as triphenylphosphine, tri-(o-tolyl)phosphine, and the like, in the presence of a base such as triethylamine, diisopropylethylamine, pyridine, 2,6-dimethylpyridine, N-methylmorpholine, potassium carbonate, sodium carbonate, lithium carbonate, cesium carbonate, sodium hydroxide, lithium A compound of formula (59), a known compound or compound prepared by known methods, is reacted with a compound of the formula (60), a known compound or compound prepared by known methods, in the presence of dimethylformamide, in an organic solvent such as methylene chloride, 1,2-dichloroethane, tetrahydrofuran, 1,4-dioxane, acetonitrile, and the like to provide a compound of the formula (61). A compound of the formula (61) is then reacted with a compound of the formula (62), a known compound or compound prepared by known methods wherein Hetaryl is an optionally substituted heteroaryl ring, in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino)ferrocene]dichloropalladium, and the like, in the presence of a base such as potassium carbonate, sodium carbonate, lithium carbonate, cesium carbonate, sodium hydroxide, lithium hydroxide, potassium hydroxide, and the like in a solvent such as tetrahydrofuran, 1,4-dioxane, acetonitrile, toluene, N,N-dimethylformamide, and the like to, optionally with heating, optionally with microwave irradiation, to provide a compound of the formula (63).

Scheme 22

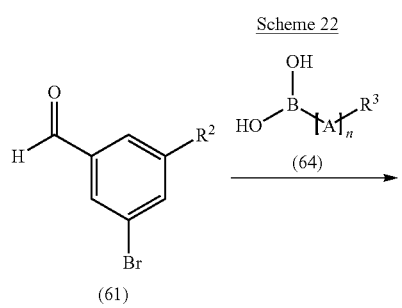

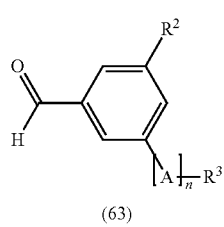

Alternatively, a compound of the formula (61) is then reacted with a compound of the formula (64), a known compound or compound prepared by known methods wherein Hetaryl is an optionally substituted heteroaryl ring, in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, in the presence of a base such as potassium carbonate, sodium carbonate, lithium carbonate, cesium carbonate, sodium hydroxide, lithium hydroxide, potassium hydroxide, and the like in a solvent such as tetrahydrofuran, 1,4-dioxane, acetonitrile, toluene, N,N-dimethylformamide, and the like to, optionally with heating, optionally with microwave irradiation, to provide a compound of the formula (63).

Scheme 23

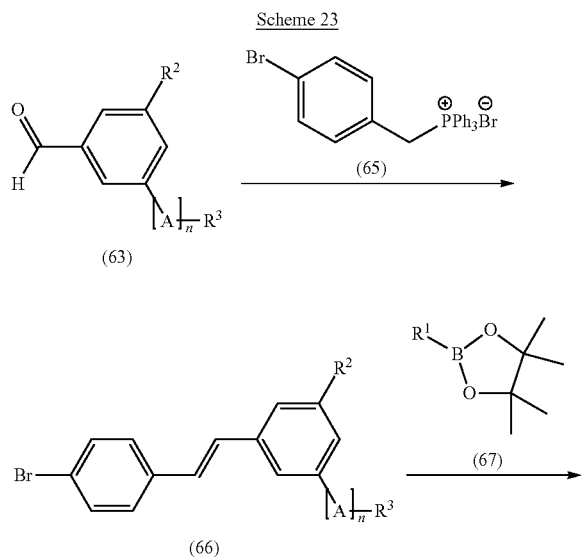

A compound of formula (63) is reacted with a compound of the formula (65), a known compound or compound prepared by known methods, in the presence of a base such as sodium hydride, lithium hydride, n-butyl lithium, lithium diisopropyl amide, sodium diisopropyl amide, potassium tert-butoxide, and the like, in an organic solvent such as methylene chloride, 1,2-dichloroethane, tetrahydrofuran, 1,4-dioxane, acetonitrile, N,N-dimethylformamide, and the like to provide a compound of the formula (66). A compound of the formula (66) is then reacted with a compound of the formula (67), a known compound or compound prepared by known methods wherein Hetaryl is an optionally substituted heteroaryl ring, in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, in the presence of a base such as potassium carbonate, sodium carbonate, lithium carbonate, cesium carbonate, sodium hydroxide, lithium hydroxide, potassium hydroxide, and the like in a solvent such as tetrahydrofuran, 1,4-dioxane, acetonitrile, toluene, N,N-dimethylformamide, and the like to, optionally with heating, optionally with microwave irradiation, to provide a compound of the formula (68).

Scheme 24

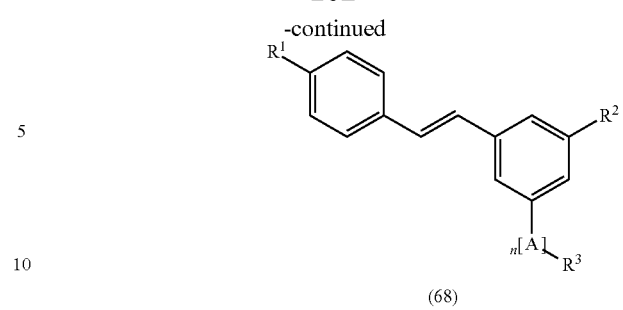

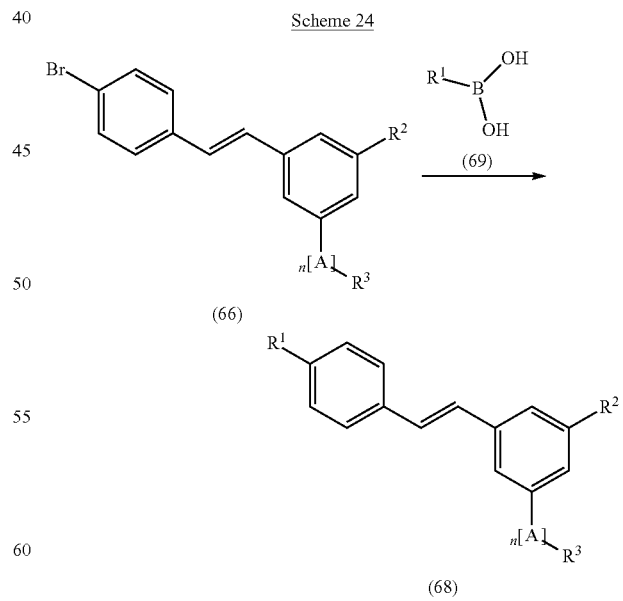

Alternatively, a compound of the formula (66) is reacted with a compound of the formula (69), a known compound or compound prepared by known methods wherein Hetaryl is an optionally substituted heteroaryl ring, in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, in the presence of a base such as potassium carbonate, sodium carbonate, lithium carbonate, cesium carbonate, sodium hydroxide, lithium hydroxide, potassium hydroxide, and the like in a solvent such as tetrahydrofuran, 1,4-dioxane, acetonitrile, toluene, N,N-dimethylformamide, and the like to, optionally with heating, optionally with microwave irradiation, to provide a compound of the formula (68).

hydroxide, lithium hydroxide, potassium hydroxide, and the like in a solvent such as ethylene glycol and the like, optionally with heating, optionally with microwave irradiation, to provide a compound of the formula (73). A compound of the formula (73) is then reacted with a compound of the formula (74) in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, and the like, in the presence of a phosphine reagent such as triphenylphosphine, tri-(o-tolyl)phosphine, and the like, in the presence of a base such as potassium carbonate, sodium carbonate, lithium carbonate, cesium carbonate, sodium hydroxide, lithium hydroxide, potassium hydroxide, and the like in an organic solvent such as tetrahydrofuran, 1,4-dioxane, acetonitrile, toluene, N,N-dimethylformamide, and the like to, optionally with heating, optionally with microwave irradiation, to provide a compound of the formula (75).

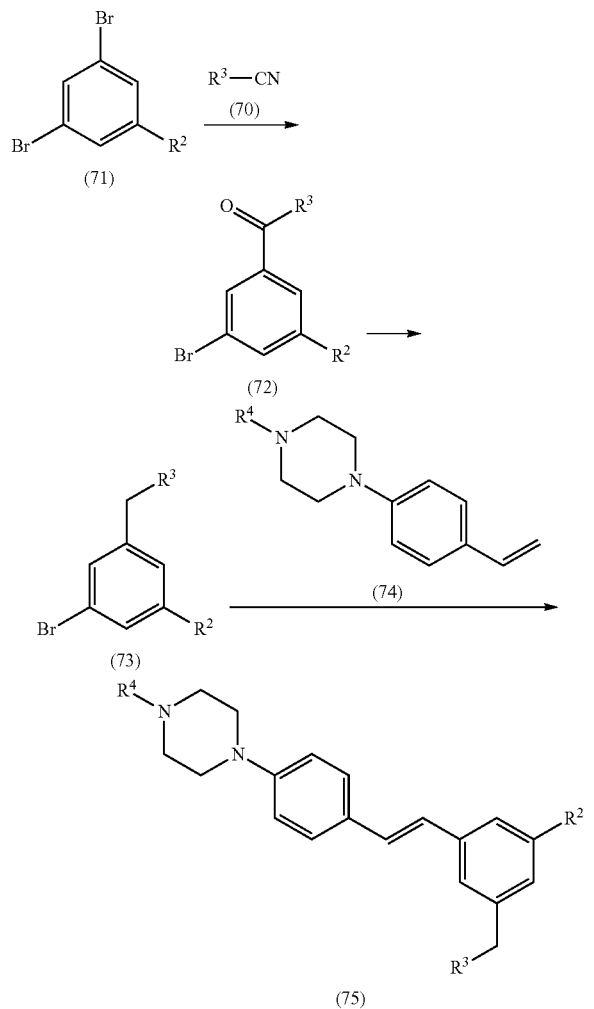

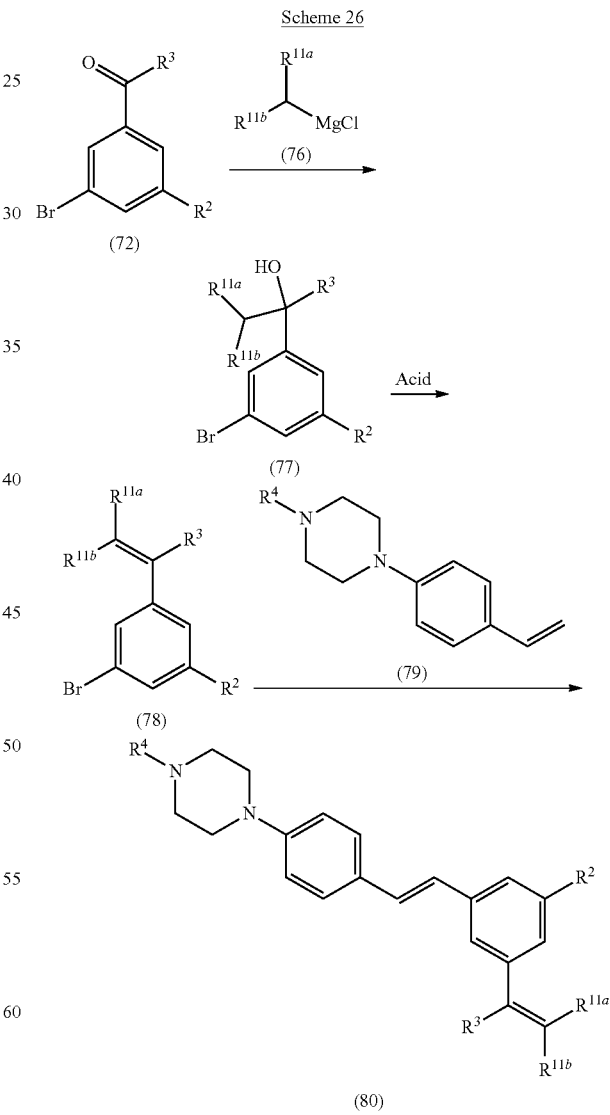

A compound of formula (70) is reacted with a compound of the formula (71), a known compound or compound prepared by known methods wherein Hetaryl is an optionally substituted heteroaryl ring, in the presence of a base such as sodium hydride, lithium hydride, n-butyl lithium, lithium diisopropyl amide, sodium diisopropyl amide, potassium tert-butoxide, and the like, in an organic solvent such as methylene chloride, 1,2-dichloroethane, tetrahydrofuran, 1,4-dioxane, acetonitrile, N,N-dimethylformamide, and the like to provide a compound of the formula (72). A compound of the formula (72) is then reacted with hydrazine in the presence of a base such as potassium carbonate, sodium carbonate, lithium carbonate, cesium carbonate, sodium Alternatively, a compound of the formula (72) is reacted with a compound of the formula (76) in an organic solvent such as methylene chloride, 1,2-dichloroethane, tetrahydrofuran, 1,4-dioxane, acetonitrile, N,N-dimethylformamide, and the like to provide a compound of the formula (77). A compound of the formula (77) is then reacted with an acid such as hydrochloric acid, hydrobromic acid, sulfuric acid and the like, in the presence of acetic acid, optionally in the presence of a solvent such as tetrahydrofuran, 1,4-dioxane, acetonitrile, N,N-dimethylformamide, and the like, optionally with heating, optionally with microwave irradiation to provide a compound of the formula (78). A compound of the formula (78) is then reacted with a compound of the formula (79) in the presence of a palladium catalyst such as palladium acetate, palladium bis(triphenylphosphine)dichloride, palladium tetrakis(triphenylphospine), bis(acetonitrile) dichloropalladium [1,1'-Bis(diphenylphosphino) ferrocene] dichloropalladium, and the like, in the presence of a phosphine reagent such as triphenylphosphine, tri-(o-tolyl)phosphine, and the like, in the presence of a base such as potassium carbonate, sodium carbonate, lithium carbonate, cesium carbonate, sodium hydroxide, lithium hydroxide, potassium hydroxide, and the like in an organic solvent such as tetrahydrofuran, 1,4-dioxane, acetonitrile, toluene, N,N-dimethylformamide, and the like to, optionally with heating, optionally with microwave irradiation, to provide a compound of the formula (80).

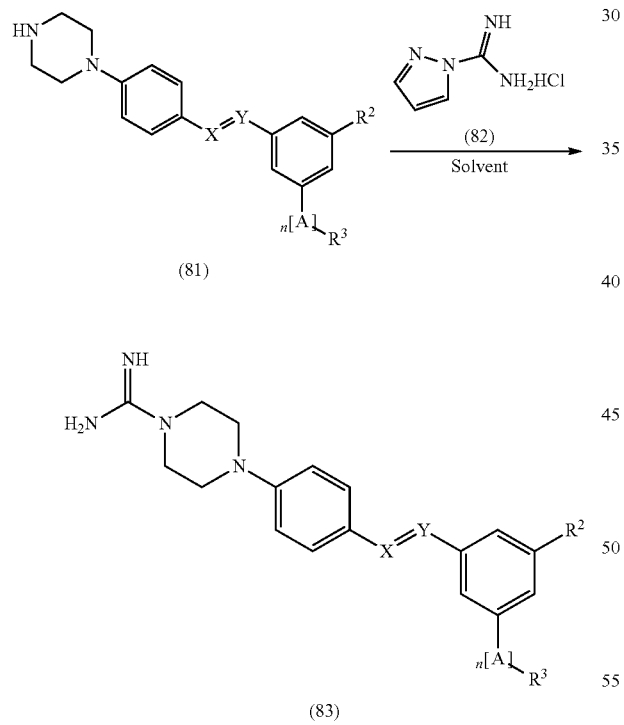

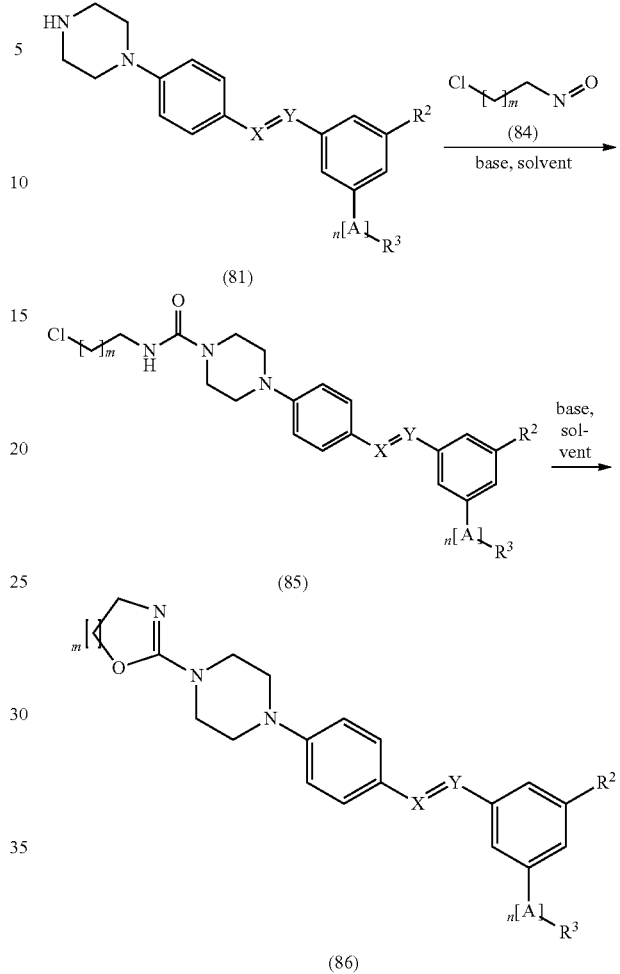

A suitably substituted compound of formula (81) is reacted with a compound of the formula (82), in the presence of a bases such as such as triethylamine, diisopropylethylamine, pyridine, 2,6-dimethylpyridine, N-methylmorpholine, and the like, in an organic solvent such as methylene chloride, dichloroethane, tetrahydrofuran, 1,4-dioxane, N,N-dimethylformamide, and the like to provide a compound of the formula (83).

A suitably substituted compound of formula (81) is reacted with a compound of the formula (84), a known compound or compound prepared by known methods wherein n is 1 or 2, in an organic solvent such as methylene chloride, dichloroethane, tetrahydrofuran, 1,4-dioxane, N,N-dimethylformamide, and the like to provide a compound of the formula (85). A compound of formula (85) is then reacted with a bases such as such as triethylamine, diisopropylethylamine, pyridine, 2,6-dimethylpyridine, N-methylmorpholine, potassium carbonate, sodium carbonate, lithium carbonate, and the like, in an organic solvent such as methylene chloride, dichloroethane, tetrahydrofuran, 1,4-dioxane, N,N-dimethylformamide, and the like to provide a compound of the formula (86).

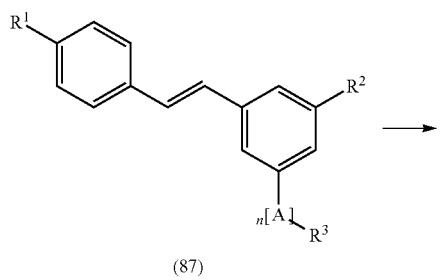

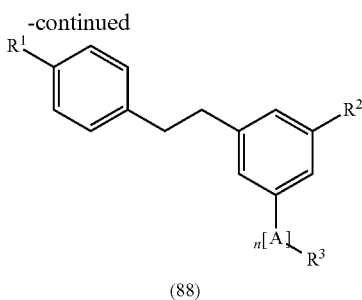

(88)

A suitably substituted compound of formula (87) is reacted with hydrogen gas in the presence of a palladium catalyst such as palladium on carbon, palladium acetate, palladium bis(triphenylphosphine) dichloride, palladium tetrakis(triphenylphospine), bis(acetonitrile), and the like, in an organic solvent such as methanol, ethanol, isopropanol, ethyl acetate, tetrahydrofuran, 1,4-dioxane, and the like to provide a compound of the formula (88).

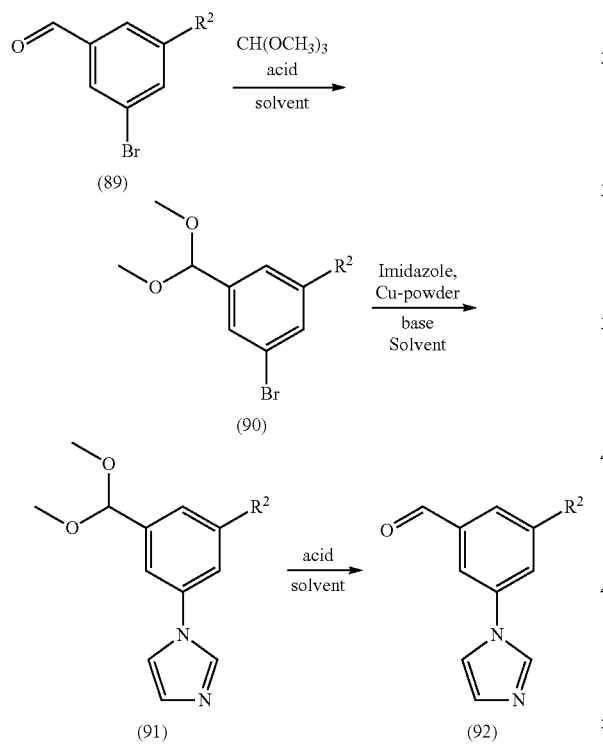

A suitably substituted compound of formula (89) is reacted with trimethylorthoformate in the presence of an acid such p-toluenesulfonic acid, benzenesulfonic acid, hydrochloric acid, sulfuric acid, and the like, in an organic solvent such as methanol, ethanol, tetrahydrofuran, 1,4-dioxane, N,N-dimethylformamide, and the like, optionally with heating, optionally with microwave irradiation to provide a compound of the formula (90). A compound of the formula (90) is then reacted with imidazole in the presence of copper, in the presence of a base such as sodium hydride, n-butyl lithium, lithium diisopropyl amide, lithium bis(trimethylsilyl)amide, potassium bis(trimethylsilyl)amide, and the like, in an organic solvent such as tetrahydrofuran, 1,4-dioxane, N,N-dimethylformamide, dimethylsulfoxide, and the like, optionally with heating, optionally with microwave irradiation, to provide a compound of the formula (91). A compound of the formula (91) is then reacted with an acid such as p-toluenesulfonic acid, benzenesulfonic acid, hydrochloric acid, sulfuric acid, and the like, in an organic solvent such as methanol, ethanol, tetrahydrofuran, 1,4-dioxane, N,N-dimethylformamide, and the like, optionally in the presence of water, optionally with heating, optionally with microwave irradiation to provide a compound of the formula (92).

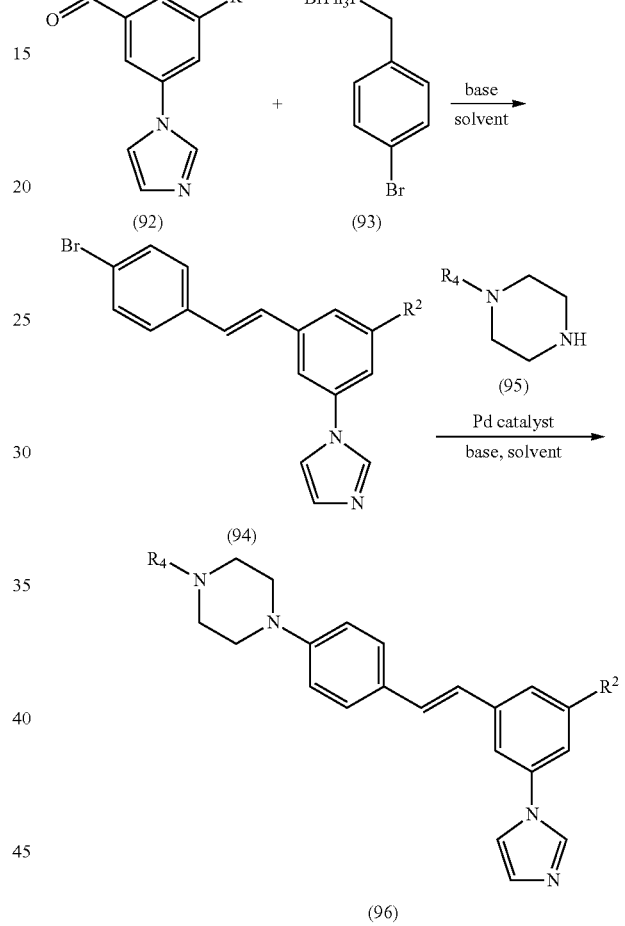

A suitably substituted compound of formula (92) is reacted with a compound of the formula (93) in the presence of a base such as sodium hydride, n-butyl lithium, lithium diisopropyl amide, lithium bis(trimethylsilyl)amide, potassium bis(trimethylsilyl)amide, and the like, in an organic solvent such as tetrahydrofuran, 1,4-dioxane, N,N-dimethylformamide, toluene, benzene, and the like to provide a compound of the formula (94). A compound of the formula (94) is then reacted with a compound of the formula (95), a known compound or compound prepared by known methods, in the presence of a palladium catalyst such as Pd($\eta^3$—$C_3H_5$)Cl]$_2$ tris(dibenzylideneacetone)dipalladium(0), tetrakis(triphenylphosphine)palladium(0), bis(triphenylphosphine)palladium(II) dichloride, palladium(II) acetate, palladium(II) acetylacetonate, palladium on carbon, platinum(II) chloride, platinum(II) acetylacetonate, bis(triphenylphosphine)palladium(II)dichloride, and the like, in the presence of 2-dicyclohexylphosphino-2',4',6'-triisopropylbiphenyl, 2-dicyclohexylphosphino-2',6'-dimethoxybiphenyl, 2-dicyclohexylphosphino-2'-(N,N-dimethylamino)biphenyl, and the like, in the presence of a base such as sodium carbonate, potassium carbonate, lithium carbonate, cesium carbonate, and the like, in an organic solvent such as tetrahydrofuran, 1,4-dioxane, N,N-dimethylformamide, toluene, benzene, and the like, optionally with heating, optionally with microwave irradiation to provide a compound of the formula (95).

The Examples provided below provide representative methods for preparing exemplary compounds of embodiments described herein. The skilled practitioner will know how to substitute the appropriate reagents, starting materials and purification methods known to those skilled in the art, in order to prepare the compounds of embodiments described herein.

The examples provide methods for preparing representative compounds of the disclosure The skilled practitioner will know how to substitute the appropriate reagents, starting materials and purification methods known to those skilled in the art, in order to prepare additional compounds of embodiments described herein.

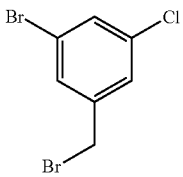

EXAMPLE 1

Synthesis of 1-Bromo-3-(bromomethyl)-5-chlorobenzene: Azobisisobutyronitrile (AIBN, 1.0 g, 6.05 mmol) was added to a stirred solution of 1-bromo-3-chloro-5-methylbenzene (25 g, 121 mmol) in $CCl_4$ (250 mL). The reaction mixture was then cooled to 0° C. and N-Bromosuccinimide (21.65 gm, 121 mmol) was added and the reaction mixture was refluxed for 3 hours. The reaction mixture was cooled to room temperature and the solid was removed by filtration. The filtrate was concentrated to give the title compound as brown liquid (25 g), which was taken to the next step without further purification. $^1$H NMR: (400 MHz, $CDCl_3$) δ 7.45-7.42 (m, 2H), 7.32 (s, 1H), 4.36 (s, 2H).

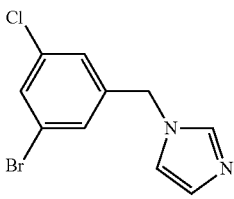 [SMILES: Clc1cc(Br)cc(Cn2ccnc2)c1]

EXAMPLE 2

Synthesis of 1-(3-bromo-5-chlorobenzyl)-1H-imidazole: Imidazole (29.9 g, 440.0 mmol) was added to a stirred solution of 1-bromo-3-(bromomethyl)-5-chlorobenzene (25.0 g, 88.0 mmol) in N,N-dimethylformamide (250 mL) at room temperature, and the reaction mixture was then refluxed for 6 hours. The reaction was then poured into ice water and extracted with ethyl acetate. The organic layer was washed with water followed by brain, dried ($Na_2SO_4$), filtered, and concentrated. The residue was purified by column chromatography on silica (100-200 mesh) eluting with ethyl acetate to afford the title compound as brown solid (9.0 g, 39%). $^1$H NMR: (300 MHz, $CDCl_3$) δ 7.71 (s, 1H), 7.48 (s, 1H), 7.18 (d, J=8.7 Hz, 2H), 7.07 (s, 1H), 6.91 (s, 1H), 5.11 (s, 2H); ESIMS: m/z=272.9 [(M+2H)$^+$].

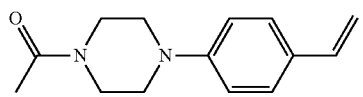

EXAMPLE 3

Synthesis of 1-(4-(4-vinylphenyl)piperazin-1-yl)ethanone: Cesium carbonate (3.5 g, 10.9 mmol) was added to a solution of 1-bromo-4-vinylbenzene (1.0 g, 5.4 mmol) and 1-(piperazin-1-yl)ethanone (830 mg, 6.5 mmol) in toluene (10 mL) and the mixture was degassed with argon. $Pd(OAc)_2$ (120 mg, 0.54 mmol) and 2-dicyclohexylphosphino-2',4',6'-triisopropylbiphenyl (X-Phos, 386 mg, 0.81 mmol) were then added and the reaction was degassed with argon. The resulting mixture was refluxed for 16 hours under argon. The reaction mixture was filtered through celite pad, filtrate was concentrated and the residue was purified by column chromatography on silica (100-200 mesh) eluting with 80% ethyl acetate in petroleum ether to afford the title compound as yellow solid (650 mg, 55%). $^1$H NMR: (300 MHz, $CDCl_3$) δ 7.35 (d, J=8.7 Hz, 2H), 6.89 (d, J=8.7 Hz, 2H), 6.69 (dd, J=17.7, 10.8 Hz, 1H), 5.64 (d, J=17.7 Hz, 1H), 5.13 (d, J=11.1 Hz, 1H), 3.77 (t, J=4.8 Hz, 2H), 3.62 (t, J=5.4 Hz, 4H), 3.21-3.15 (m, 4H), 2.17 (s, 3H); ESIMS: m/z=231.1 [(M+H)$^+$].

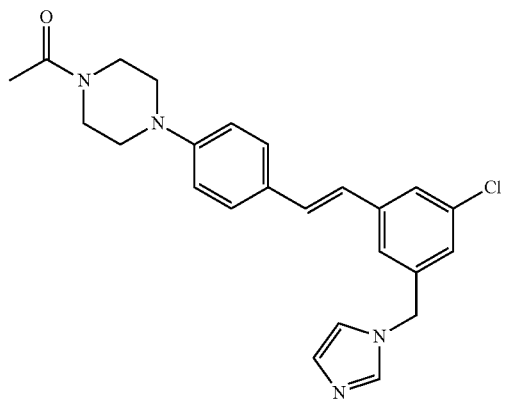 [SMILES: CC(=O)N1CCN(c2ccc(/C=C/c3cc(Cl)cc(Cn4ccnc4)c3)cc2)CC1]

EXAMPLE 4

Synthesis of (E)-1-(4-(4-(3-((1H-imidazol-1-yl)methyl)-5-chlorostyryl)phenyl)piperazin-1-yl)ethanone: To a solution of 1-(3-bromo-5-chlorobenzyl)-1H-imidazole (2.0 g, 7.4 mmol) and 1-(4-(4-vinylphenyl)piperazin-1-yl)ethanone (2.0 g, 8.8 mmol) in tetrahydrofuran (250 mL), triethylamine (3.0 mL, 22 mmol) was added and the mixture was degassed with argon. $Pd(OAc)_2$ (330 mg, 1.48 mmol) and $P(o-Tolyl)_3$ (2.7 g, 8.8 mmol) were then added and the mixture was degassed with argon. The resulting mixture was refluxed under argon for 48 hours. The reaction mixture was filtered through celite; the filtrate was concentrated and the residue was purified by column chromatography on silica (100-200 mesh) eluting with 5% methanol in dichloromethane to afford the title compound as pale yellow solid (1.2 g, 38%). $^1$H NMR: (300 MHz, CDCl$_3$) δ 7.59 (s, 1H), 7.43-7.40 (m, 3H), 7.13-7.04 (m, 3H), 6.98-6.80 (m, 5H), 5.11 (s, 2H), 3.78 (t, J=5.1 Hz, 2H), 3.63 (t, J=5.4 Hz, 2H), 3.26-3.19 (m, 4H), 2.14 (s, 3H); mp: 209-213° C.; ESIMS: m/z=421.02 [(M+H)$^+$]; IR (thin film): 3104, 2931, 1625, 1384, 749 cm$^{-1}$.

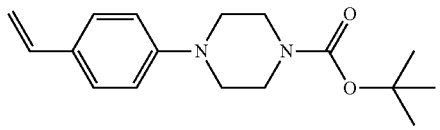

EXAMPLE 5

Synthesis of tert-butyl 4-(4-vinylphenyl)piperazine-1-carboxylate: Cesium carbonate (5.31 g, 16.2 mmol) was added to a solution of 1-bromo-4-vinylbenzene (1.0 g, 5.4 mmol) and tert-butyl piperazine-1-carboxylate (1.3 g, 6.4 mmol) in toluene (15 mL) at room temperature, and the mixture was degassed with argon. Pd(OAc)$_2$ (120 mg, 0.5 mmol) and 2-dicyclohexylphosphino-2',4',6'-triisopropylbiphenyl (X-Phos, 500 mg, 1.1 mmol) were then added to reaction mixture and again degassed with argon. The resulting mixture was refluxed under argon for 16 hours. Reaction mixture was filtered through celite pad, filtrate was concentrated and the residue was purified by column chromatography on silica (100-200 mesh) eluting with 30% ethyl acetate in petroleum ether to afford the title compound as off-white solid (300 mg, 22%). $^1$H NMR: (400 MHz, CDCl$_3$) δ 7.33 (d, J=8.0 Hz, 2H), 6.88 (d, J=8.8 Hz, 2H), 6.67 (dd, J=18.0, 10.8 Hz, 1H), 5.62 (d, J=17.6 Hz, 1H), 5.11 (d, J=10.8 Hz, 1H), 3.57 (t, J=5.2 Hz, 4H), 3.14 (t, J=4.8 Hz, 4H), 1.48 (s, 9H); ESIMS: m/z=289.1 [(M+H)$^+$].

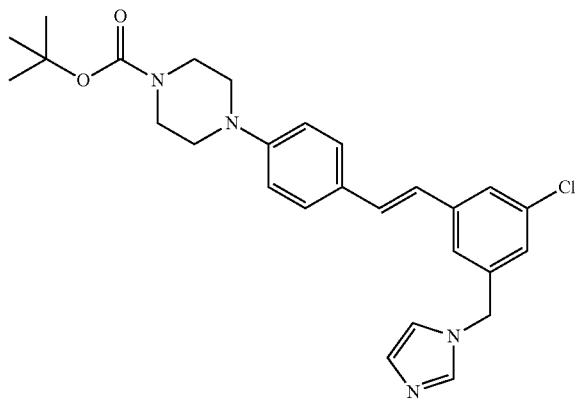 [SMILES: CC(C)(C)OC(=O)N1CCN(c2ccc(/C=C/c3cc(Cl)cc(Cn4ccnc4)c3)cc2)CC1]

EXAMPLE 6

Synthesis of (E)-tert-butyl-4-(4-(3-((1H-imidazol-1-yl)methyl)-5-chlorostyryl)phenyl)piperazine-1-carboxylate: Triethylamine (1.5 mL, 11.0 mmol) was added to a stirred solution of 1-(3-bromo-5-chlorobenzyl)-1H-imidazole (1.0 g, 3.70 mmol) and tent-butyl-4-(4-vinylphenyl)piperazine-1-carboxylate (1.28 g, 4.40 mmol) in tetrahydrofuran (10 mL) and the mixture was degassed with argon. Pd(OAc)$_2$ (165 mg, 0.74 mmol) and P(o-Tolyl)$_3$ (1.35 g, 4.40 mmol) were then added to reaction mixture and again degassed with argon. The resulting mixture was refluxed under argon for 48 hours. Reaction mixture was filtered through celite pad, filtrate was concentrated and the residue was purified by column chromatography on silica (100-200 mesh) eluting with 80% ethyl acetate in petroleum ether to afford the title compound as pale yellow solid (600 mg, 35%). $^1$H NMR: (400 MHz, CDCl$_3$) δ 7.59 (s, 1H), 7.47-7.39 (m, 3H), 7.35-7.30 (m, 1H), 7.23-6.97 (m, 4H), 6.92-6.88 (m, 2H), 6.84-6.80 (d, J=16.4 Hz, 1H), 5.10 (s, 2H), 3.58 (t, J=5.2 Hz, 4H), 3.19 (t, J=4.8 Hz, 4H), 1.48 (s, 9H); ESIMS: m/z=479.1 [(M+H)$^+$].

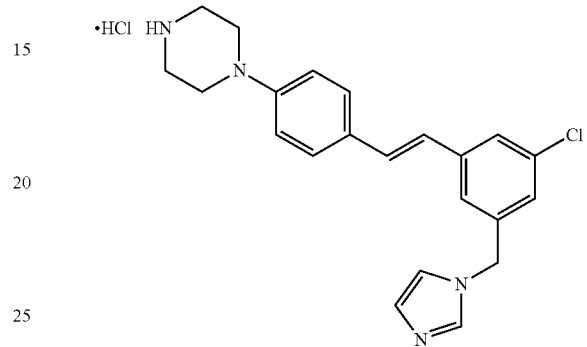

EXAMPLE 7

Synthesis of (E)-1-(4-(3-((1H-imidazol-1-yl) methyl)-5-chlorostyryl)phenyl) piperazine HCl: HCl in 1,4-dioxane (5 mL) was added dropwise to a solution of (E)-tert-butyl-4-(4-(3-((1H-imidazol-1-yl)methyl)-5-chlorostyryl)phenyl) piperazine-1-carboxylate (600 mg, 1.25 mmol) in 1,4-dioxane (10 mL) 0° C. and the reaction mixture was then stirred at room temperature for 4 hours. The volatiles were evaporated and the residue was washed with pentane to afford the title compound as pale yellow solid (300 mg, 63%). $^1$H NMR: (400 MHz, DMSO-d$_6$) δ 9.40 (bs, 2H), 7.86 (s, 1H), 7.72 (s, 1H), 7.65 (s, 1H), 7.60 (s, 21H), 7.51 (d, J=8.8 Hz, 2H), 7.38 (s, 1H), 7.32 (d, J=16.8 Hz, 1H), 7.08-7.00 (m, 3H), 5.45 (s, 2H), 3.45-3.43 (m, 4H), 3.20-3.16 (m, 4H); ESIMS: m/z=379.0 [(M+H)$^+$].

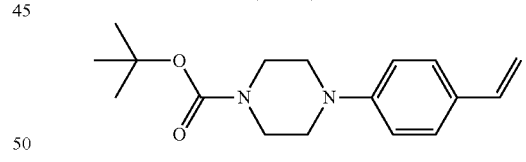

EXAMPLE 8

Synthesis of tert-butyl 4-(4-vinylphenyl)piperazine-1-carboxylate: Cesium carbonate (5.31 g, 16.2 mmol) was added to a solution of 1-bromo-4-vinylbenzene (1.0 g, 5.4 mmol) and tert-butyl piperazine-1-carboxylate (1.3 g, 6.4 mmol) in toluene (15 mL) at room temperature, and the mixture was degassed with argon. Pd(OAc)$_2$ (120 mg, 0.5 mmol) and 2-dicyclohexylphosphino-2',4',6'-triisopropylbiphenyl (X-Phos, 500 mg, 1.1 mmol) were then added to reaction mixture and again degassed with argon. The resulting mixture was refluxed under argon for 16 hours. Reaction mixture was filtered through celite pad, filtrate was concentrated and the residue was purified by column chromatography on silica (100-200 mesh) eluting with 30% ethyl acetate in petroleum ether to afford the title compound as off-white solid (300 mg, 22%). ¹H NMR: (400 MHz, CDCl₃) δ 7.33 (d, J=8.0 Hz, 2H), 6.88 (d, J=8.8 Hz, 2H), 6.67 (dd, J=18.0, 10.8 Hz, 1H), 5.62 (d, J=17.6 Hz, 1H), 5.11 (d, J=10.8 Hz, 1H), 3.57 (t, J=5.2 Hz, 4H), 3.14 (t, J=4.8 Hz, 4H), 1.48 (s, 9H); ESIMS: m/z=289.1 [(M+H)⁺].

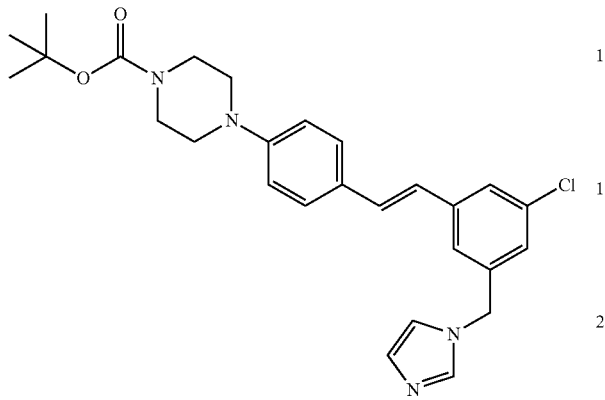

EXAMPLE 9

Synthesis of (E)-tert-butyl-4-(4-(3-((1H-imidazol-1-yl)methyl)-5-chlorostyryl)phenyl)piperazine-1-carboxylate: Triethylamine (1.5 mL, 11.0 mmol) was added to a stirred solution of 1-(3-bromo-5-chlorobenzyl)-1H-imidazole (1.0 g, 3.70 mmol) and tent-butyl-4-(4-vinylphenyl)piperazine-1-carboxylate (1.28 g, 4.40 mmol) in tetrahydrofuran (10 mL) and the mixture was degassed with argon. Pd(OAc)₂ (165 mg, 0.74 mmol) and P(o-Tol)₃ (1.35 g, 4.40 mmol) were then added to reaction mixture and again degassed with argon. The resulting mixture was refluxed under argon for 48 hours. Reaction mixture was filtered through celite pad, filtrate was concentrated and the residue was purified by column chromatography on silica (100-200 mesh) eluting with 80% ethyl acetate in petroleum ether to afford the title compound as pale yellow solid (600 mg, 35%). ¹H NMR: (400 MHz, CDCl₃) δ 7.59 (s, 1H), 7.47-7.39 (m, 3H), 7.35-7.30 (m, 1H), 7.23-6.97 (m, 4H), 6.92-6.88 (m, 2H), 6.84-6.80 (d, J=16.4 Hz, 1H), 5.10 (s, 2H), 3.58 (t, J=5.2 Hz, 4H), 3.19 (t, J=4.8 Hz, 4H), 1.48 (s, 9H); ESIMS: m/z=479.1 [(M+H)⁺].

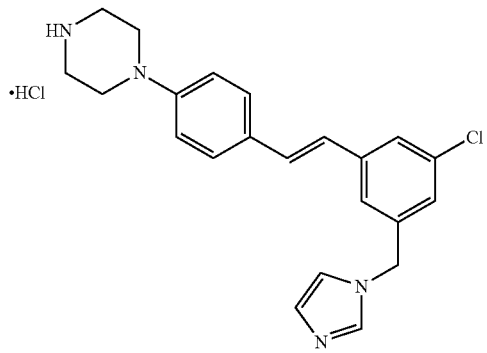 [SMILES: Cl ; Clc1cc(/C=C/c2ccc(N3CCNCC3)cc2)cc(Cn2ccnc2)c1]

EXAMPLE 10

Synthesis of (E)-1-(4-(3-((1H-imidazol-1-yl) methyl)-5-chlorostyryl) phenyl) piperazine. HCl: HCl in 1,4-dioxane (5 mL) was added dropwise to a solution of (E)-tert-butyl-4-(4-(3-((1H-imidazol-1-yl)methyl)-5-chlorostyryl)phenyl) piperazine-1-carboxylate (600 mg, 1.25 mmol) in 1,4-dioxane (10 mL) 0° C. and the reaction mixture was then stirred at room temperature for 4 hours. The volatiles were evaporated and the residue was washed with pentane to afford the title compound as pale yellow solid (300 mg, 63%).

¹H NMR: (400 MHz, DMSO-d₆) δ 9.40 (bs, 2H), 7.86 (s, 1H), 7.72 (s, 1H), 7.65 (s, 1H), 7.60 (s, 21H), 7.51 (d, J=8.8 Hz, 2H), 7.38 (s, 1H), 7.32 (d, J=16.8 Hz, 1H), 7.08-7.00 (m, 3H), 5.45 (s, 2H), 3.45-3.43 (m, 4H), 3.20-3.16 (m, 4H); ESIMS: m/z=379.0 [(M+H)⁺].

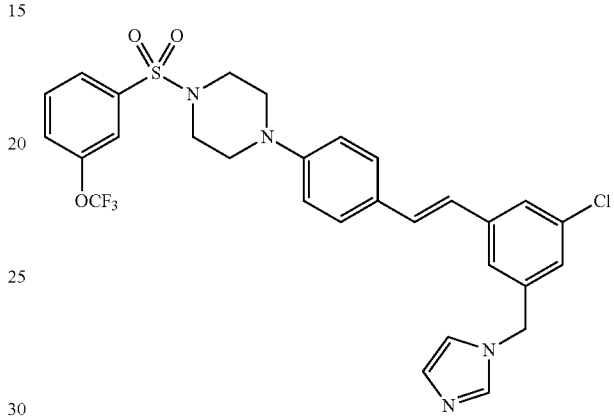

EXAMPLE 11

Synthesis of (E)-1-(4-(3-((1H-imidazol-1-yl)methyl)-5-chlorostyryl)phenyl)-4-(3-(trifluoromethoxy)phenylsulfonyl)piperazine: Triethylamine (0.1 mL, 0.79 mmol) was added to a stirred solution of (E)-1-(4-(3-((1H-imidazol-1-yl)methyl)-5-chlorostyryl)phenyl)piperazine HCl (100 mg, 0.26 mmol) in dichloromethane (5 mL) at room temperature. The reaction mixture was cooled to 0° C. and 3-(trifluoromethoxy)benzene-1-sulfonyl chloride (82 mg, 0.31 mmol) was added and the reaction mixture was stirred at room temperature for 4 hours. Reaction mixture was diluted with dichloromethane and washed with water followed by saturated NaHCO₃ solution and brain solution. The organic layer was dried (Na₂SO₄), filtered, concentrated and the residue was purified by prep TLC to afford the compound (20 mg, 15%) as off white solid. ¹H NMR: (400 MHz, CDCl₃) δ 7.74-7.72 (m, 1H), 7.65-7.60 (m, 3H), 7.49-7.47 (m, 1H), 7.41-7.37 (m, 3H), 7.13 (s, 1H), 7.04 (s, 1H), 6.98 (d, J=4.8 Hz, 1H), 6.92 (s, 1H), 6.86-6.84 (m, 3H), 6.79 (s, 1H), 5.09 (s, 2H), 3.31 (t, J=3.6 Hz, 4H), 3.20 (t, J=4.4 Hz, 4H). ESIMS: m/z=603.0 [(M+H)⁺]; IR (thin film): 3029, 2923, 1596, 1109, 745 cm⁻¹.

The following compounds can be prepared by the procedure of (E)-1-(4-(3-((1H-imidazol-1-yl)methyl)-5-chlorostyryl)phenyl)-4-(3-(trifluoromethoxy)phenylsulfonyl) piperazine. The skilled practitioner will know how to substitute the appropriate reagents, starting materials and purification methods known to those skilled in the art, in order to prepare the compounds provided herein.

115

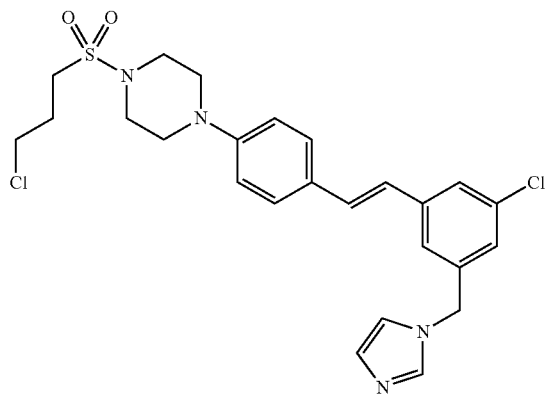 [SMILES: O=S(=O)(CCCCl)N1CCN(c2ccc(/C=C/c3cc(Cl)cc(Cn4ccnc4)c3)cc2)CC1]

EXAMPLE 12

Synthesis of (E)-1-(4-(3-((1H-imidazol-1-yl)methyl)-5-chlorostyryl)phenyl)-4-(3-chloropropylsulfonyl)piperazine: The title compounds were prepared according to the procedure for (E)-1-(4-(3-((1H-imidazol-1-yl)methyl)-5-chlorostyryl)phenyl)-4-(3-(trifluoromethoxy)phenyl sulfonyl)piperazine, except 3-chloropropane-1-sulfonyl chloride was substituted for 3-(trifluoromethoxy)benzene-1-sulfonyl chloride. $^1$H NMR: (300 MHz, CDCl$_3$) δ 7.58 (s, 1H), 7.43-7.40 (m, 3H), 7.13-7.04 (m, 2H), 6.98-6.89 (m, 5H), 6.86-6.81 (d, J=16.8 Hz, 1H), 5.10 (s, 2H), 3.71 (t, J=6.0 Hz, 2H), 3.48-3.44 (m, 4H), 3.34-3.30 (m, 4H), 3.13 (t, J=7.2 Hz, 2H), 2.35-2.31 (m, 2H); ESIMS: m/z=519.0 [(M+H)$^+$].

EXAMPLE 13

Synthesis of (E)-3-(4-(4-(3-((1H-imidazol-1-yl)methyl)-5-chlorostyryl)phenyl)piperazin-1-ylsulfonyl)benzonitrile: The title compounds were prepared according to the procedure for (E)-1-(4-(3-((1H-imidazol-1-yl)methyl)-5-chlorostyryl)phenyl)-4-(3-(trifluoromethoxy)phenylsulfonyl)piperazine, except 3-cyanobenzene-1-sulfonyl chloride was substituted for 3-(trifluoromethoxy)benzene-1-sulfonyl chloride. $^1$H NMR: (300 MHz, CDCl$_3$) δ 8.08 (s, 1H), 8.03-8.00 (m, 1H), 7.92-7.89 (m, 1H), 7.74-7.71 (m, 1H), 7.57 (s, 1H), 7.41-7.37 (m, 3H), 7.12 (s, 1H), 7.04-7.01 (m, 1H), 6.98-6.92 (m, 3H), 6.86-6.79 (m, 3H), 5.09 (s, 2H), 3.32 (t, J=4.5 Hz, 4H), 3.21 (t, J=5.1 Hz, 4H); ESIMS: m/z=544.0 [(M+H)$^+$].

116

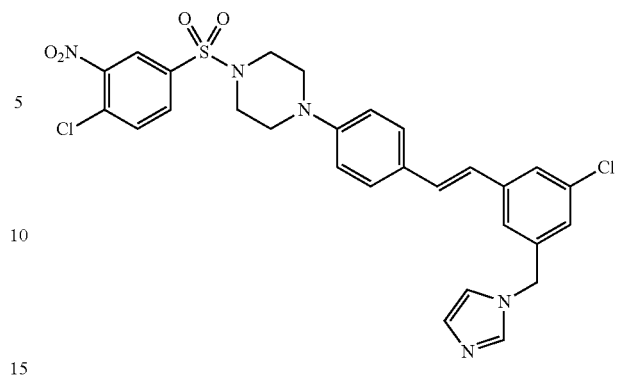

EXAMPLE 14

Synthesis of (E)-1-(4-(3-((1H-imidazol-1-yl)methyl)-5-chlorostyryl)phenyl)-4-(4-chloro-3-nitrophenylsulfonyl)piperazine: The title compounds were prepared according to the procedure for (E)-1-(4-(3-((1H-imidazol-1-yl)methyl)-5-chlorostyryl)phenyl)-4-(3-(trifluoromethoxy) phenylsulfonyl)piperazine, except 3-cyanobenzene-1-sulfonyl chloride was substituted for 3-(trifluoromethoxy)benzene-1-sulfonyl chloride. $^1$H NMR: (300 MHz, DMSO-d$_6$) δ 8.43 (s, 1H), 8.06 (d, J=1.2 Hz, 2H), 7.83 (s, 1H), 7.56 (s, 1H), 7.46-7.41 (m, 3H), 7.25-7.19 (m, 2H), 7.13-7.10 (m, 1H), 7.02-6.97 (m, 1H), 6.94-6.91 (m, 3H), 5.19 (s, 2H), 3.39-3.31 (m, 4H), 3.17-3.14 (m, 4H); ESIMS: m/z=598.1 [(M+H)$^+$].

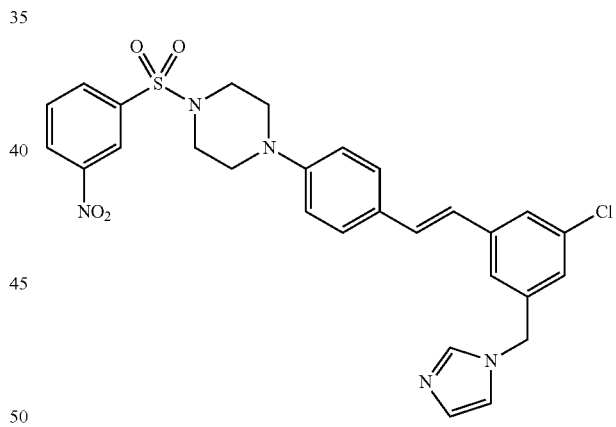

EXAMPLE 15

Synthesis of (E)-1-(4-(3-((1H-imidazol-1-yl)methyl)-5-chlorostyryl)phenyl)-4-(3-nitrophenylsulfonyl)piperazine: The title compounds were prepared according to the procedure for (E)-1-(4-(3-((1H-imidazol-1-yl)methyl)-5-chlorostyryl)phenyl)-4-(3-(trifluoromethoxy)phenyl sulfonyl)piperazine, except 3-nitrobenzene-1-sulfonyl chloride was substituted for 3-(trifluoromethoxy)benzene-1-sulfonyl chloride. $^1$H NMR: (300 MHz, CDCl$_3$) δ 8.63-8.62 (m, 1H), 8.49-8.46 (m, 1H), 8.13 (d, J=7.8 Hz, 1H), 7.82-7.76 (m, 1H), 7.58 (s, 1H), 7.40-7.36 (m, 3H), 7.12 (s, 1H), 7.03-6.92 (m, 4H), 6.85-6.78 (m, 3H), 5.09 (s, 2H), 3.34-3.24 (m, 8H); ESIMS: m/z=564.0 [(M+H)$^+$].

2.32-2.27 (m, 1H), 1.24-1.19 (m, 2H), 1.05-0.98 (m, 2H); ESIMS: m/z=483.3 [(M+H)$^+$]; IR (thin film): 3063, 2925, 1711, 1380, 1079, 767 cm$^{-1}$.

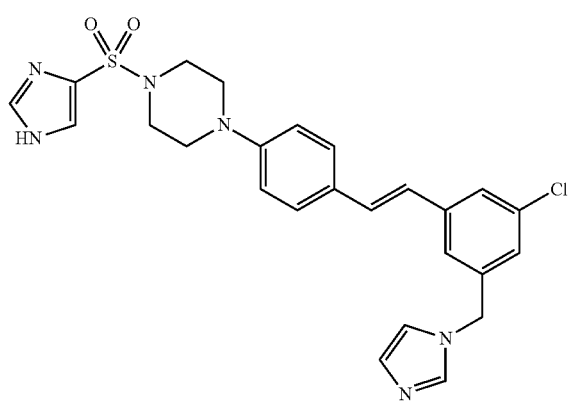 [SMILES: O=S(=O)(c1c[nH]cn1)N1CCN(c2ccc(/C=C/c3cc(Cl)cc(Cn4ccnc4)c3)cc2)CC1]

EXAMPLE 16

Synthesis of (E)-1-(4-(3-((1H-imidazol-1-yl)methyl)-5-chlorostyryl)phenyl)-4-(1H-imidazol-4-ylsulfonyl)piperazine: The title compounds were prepared according to the procedure for (E)-1-(4-(3-((1H-imidazol-1-yl)methyl)-5-chlorostyryl)phenyl)-4-(3-(trifluoromethoxy)phenyl sulfonyl)piperazine, except 1H-imidazole-5-sulfonyl chloride was substituted for 3-(trifluoromethoxy)benzene-1-sulfonyl chloride. $^1$H NMR: (300 MHz, DMSO-d$_6$) δ 12.90 (s, 1H), 8.09 (s, 1H), 7.86 (s, 1H), 7.81 (s, 1H), 7.55 (s, 1H), 7.43-7.40 (m, 3H), 7.35 (s, 1H), 7.24-7.23 (m, 1H), 7.18 (d, J=8.4 Hz, 1H), 7.07-7.00 (m, 1H), 6.95-6.89 (m, 3H), 5.22 (s, 2H), 3.35-3.30 (m, 4H), 3.18-3.00 (m, 4H); ESIMS: m/z=509.1 [(M+H)$^+$]; IR (thin film): 3491, 3141, 2823, 1596, 1355, 1079, 746 cm$^{-1}$.

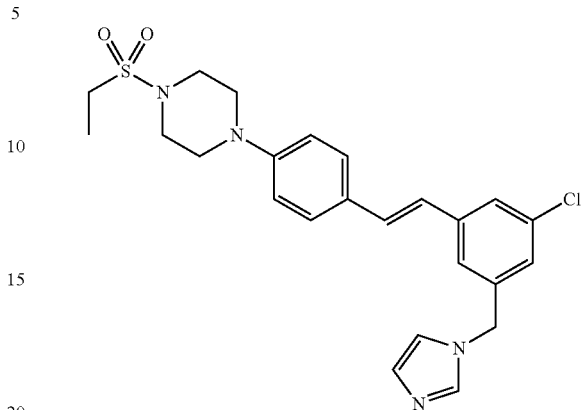

EXAMPLE 18

Synthesis of (E)-1-(4-(3-((1H-imidazol-1-yl)methyl)-5-chlorostyryl)phenyl)-4-(ethylsulfonyl)piperazine: The title compounds were prepared according to the procedure for (E)-1-(4-(3-((1H-imidazol-1-yl)methyl)-5-chlorostyryl)phenyl)-4-(3-(trifluoromethoxy)phenylsulfonyl)piperazine, except ethylsulfonyl chloride was substituted for 3-(trifluoromethoxy)benzene-1-sulfonyl chloride. $^1$H NMR: (400 MHz, DMSO-d$_6$) δ 7.83 (s, 1H), 7.57 (s, 1H), 7.49 (d, J=8.8 Hz, 2H), 7.42 (s, 1H), 7.26 (s, 1H), 7.22-7.04 (m, 3H), 6.99-6.94 (m, 3H), 5.20 (s, 2H), 3.31-3.29 (m, 8H), 3.12 (q, J=8.0 Hz, 2H), 1.23 (t, J=7.6 Hz, 3H); ESIMS: m/z=471.0 [(M+H)$^+$]; IR (thin film): 3109, 2923, 1596, 1336, 1153, 755 cm$^{-1}$.

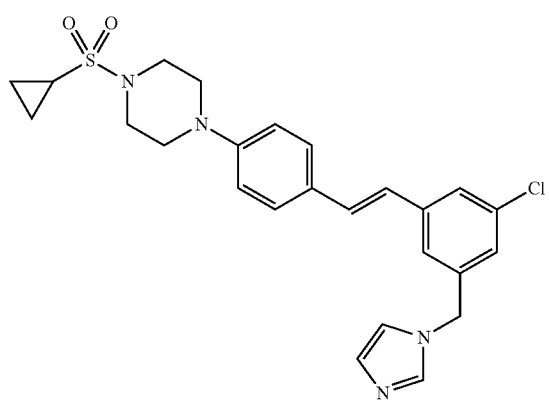 [SMILES: O=S(=O)(C1CC1)N1CCN(c2ccc(/C=C/c3cc(Cl)cc(Cn4ccnc4)c3)cc2)CC1]

EXAMPLE 17

Synthesis of (E)-1-(4-(3-((1H-imidazol-1-yl)methyl)-5-chlorostyryl)phenyl)-4-(cyclopropylsulfonyl)piperazine. The title compounds were prepared according to the procedure for (E)-1-(4-(3-((1H-imidazol-1-yl)methyl)-5-chlorostyryl)phenyl)-4-(3-(trifluoromethoxy)phenyl sulfonyl)piperazine, except cyclopropylsulfonyl chloride was substituted for 3-(trifluoromethoxy)benzene-1-sulfonyl chloride. $^1$H NMR: (300 MHz, CDCl$_3$) δ 7.65 (s, 1H), 7.43-7.40 (m, 3H), 7.33 (s, 1H), 7.15 (s, 1H), 7.06 (d, J=6.0 Hz, 1H), 6.99 (s, 1H), 6.94 (d, J=9.0 Hz, 3H), 6.86 (d, J=15.2 Hz, 1H), 5.11 (s, 2H), 3.48-3.44 (m, 4H), 3.34-3.31 (m, 4H),

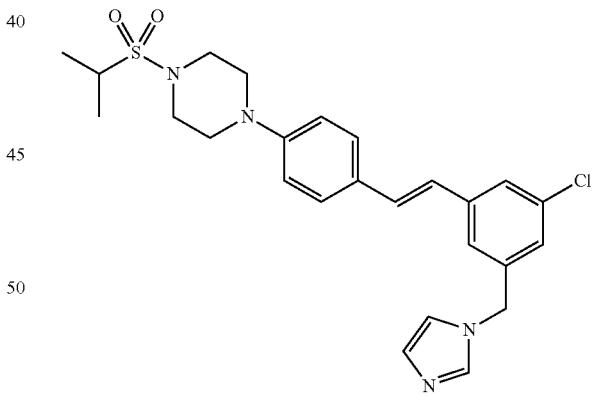

EXAMPLE 19

Synthesis of (E)-1-(4-(3-((1H-imidazol-1-yl)methyl)-5-chlorostyryl)phenyl)-4-(isopropylsulfonyl)piperazine: The title compounds were prepared according to the procedure for (E)-1-(4-(3-((1H-imidazol-1-yl)methyl)-5-chlorostyryl)phenyl)-4-(3-(trifluoromethoxy)phenylsulfonyl) piperazine, except isopropylsulfonyl chloride was substituted for 3-(trifluoromethoxy)benzene-1-sulfonyl chloride. $^1$H NMR: (300 MHz, DMSO-d$_6$) δ 8.12 (s, 1H), 7.58 (s, 1H), 7.46-7.38 (m, 4H), 7.27-7.18 (m, 2H), 7.10-6.99 (m, 4H), 5.25 (s, 2H), 3.37-3.31 (m, 8H), 3.10-3.00 (m, 1H), 1.25-1.17 (m, 6H); ESIMS: m/z=485.2 [(M+H)⁺]; IR (thin film): 3109, 2923, 1596, 1336, 1153, 755 cm⁻¹.

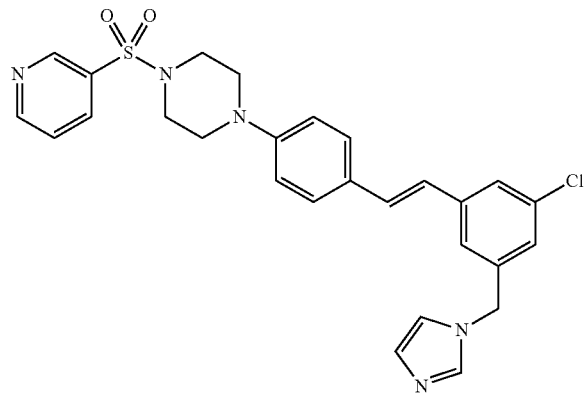 [SMILES: O=S(=O)(c1cccnc1)N1CCN(c2ccc(/C=C/c3cc(Cl)cc(Cn4ccnc4)c3)cc2)CC1]

EXAMPLE 20

Synthesis of (E)-1-(4-(3-((1H-imidazol-1-yl)methyl)-5-chlorostyryl)phenyl)-4-(pyridin-3-ylsulfonyl)piperazine: The title compounds were prepared according to the procedure for (E)-1-(4-(3-((1H-imidazol-1-yl)methyl)-5-chlorostyryl)phenyl)-4-(3-(trifluoromethoxy)phenyl sulfonyl)piperazine, except pyridine-3-sulfonyl chloride was substituted for 3-(trifluoromethoxy)benzene-1-sulfonyl chloride. ¹H NMR: (400 MHz, CDCl₃) δ 9.03 (d, J=2.0 Hz, 1H), 8.85 (d, J=4.4 Hz, 1H), 8.09 (d, J=7.6 Hz, 1H), 7.71 (s, 1H), 7.53-7.50 (m, 1H), 7.42-7.37 (m, 3H), 7.15 (s, 1H), 7.05 (s, 1H), 7.01-6.94 (m, 3H), 6.86-6.79 (m, 3H), 5.11 (s, 2H), 3.32 (t, J=4.8 Hz, 4H), 3.23 (t, J=4.4 Hz, 4H); mp: 121-125° C.; ESIMS: m/z=520.1 [(M+H)⁺]; IR (thin film): 3031, 2829, 1594, 1349, 1171, 754 cm⁻¹

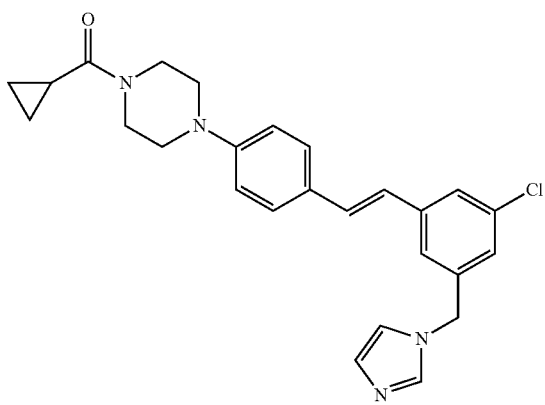 [SMILES: O=C(C1CC1)N1CCN(c2ccc(/C=C/c3cc(Cl)cc(Cn4ccnc4)c3)cc2)CC1]

EXAMPLE 21

Synthesis of (E)-(4-(4-(3-((1H-imidazol-1-yl)methyl)-5-chlorostyryl)phenyl)piperazin-1-yl)(cyclopropyl)methanone: Triethylamine (0.18 mL, 1.31 mmol) was added to a stirred solution of (E)-1-(4-(3-((1H-imidazol-1-yl)methyl)-5-chlorostyryl)phenyl)piperazine HCl (100 mg, 0.26 mmol) in dichloromethane (5 mL) at room temperature. The reaction mixture was cooled to 0° C. and cyclopropanecarbonyl chloride (0.027 mL, 0.31 mmol) was added and the reaction mixture was stirred at room temperature for 4 hours. Reaction mixture was diluted with dichloromethane and washed with water followed by saturated NaHCO₃ solution and brain. The organic layer was dried (Na₂SO₄), filtered, concentrated and the residue was purified by preparative thin layer chromatography to afford the title compound as off white solid (25 mg, 21%); ¹H NMR: (300 MHz, CDCl₃) δ 7.60 (s, 1H), 7.43-7.40 (m, 3H), 7.14 (s, 1H), 7.06-7.04 (m, 2H), 6.99-6.97 (m, 2H), 6.92-6.85 (m, 3H), 5.10 (s, 2H), 3.82-3.74 (m, 4H), 3.25-3.11 (m, 4H), 1.80-1.73 (m, 1H), 1.05-1.00 (m, 2H), 0.90-0.77 (m, 2H); ESIMS: m/z=447.1 [(M+H)⁺]; IR (thin film): 3006, 2922, 1633, 1606, 748 cm⁻¹.

The following compounds can be prepared by the procedure of (E)-(4-(4-(3-((1H-imidazol-1-yl)methyl)-5-chlorostyryl) phenyl)piperazin-1-yl)(cyclopropyl)methanone. The skilled practitioner will know how to substitute the appropriate reagents, starting materials and purification methods known to those skilled in the art, in order to prepare the compounds provided herein.

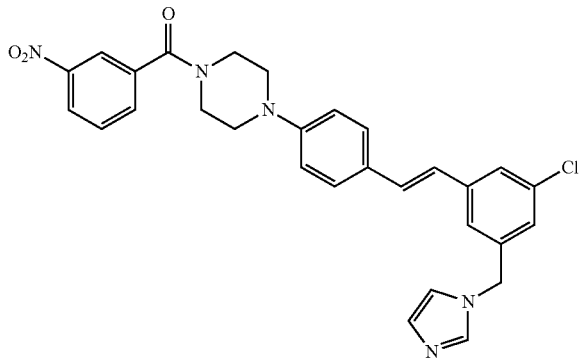 [SMILES: O=C(c1cccc([N+](=O)[O-])c1)N1CCN(c2ccc(/C=C/c3cc(Cl)cc(Cn4ccnc4)c3)cc2)CC1]

EXAMPLE 22

Synthesis of (E)-(4-(4-(3-((1H-imidazol-1-yl)methyl)-5-chlorostyryl)phenyl)piperazin-1-yl)(3-nitrophenyl)methanone: The title compounds were prepared according to the procedure for (E)-(4-(4-(3-((1H-imidazol-1-yl)methyl)-5-chlorostyryl) phenyl)piperazin-1-yl)(cyclopropyl)methanone, except 3-nitrobenzoyl chloride was substituted for cyclopropane carbonyl chloride. ¹H NMR: (300 MHz, CDCl₃) δ 8.33-8.31 (m, 2H), 7.81 (d, J=7.8 Hz, 1H), 7.69-7.62 (m, 2H), 7.44-7.41 (m, 3H), 7.15 (s, 2H), 7.07-7.04 (m, 2H), 6.94-6.81 (m, 4H), 5.11 (s, 2H), 3.85-3.26 (m, 8H); ESIMS: m/z=528.1 [(M+H)⁺]; IR (thin film): 3071, 2919, 1633, 1595, 1348, 720 cm⁻¹.

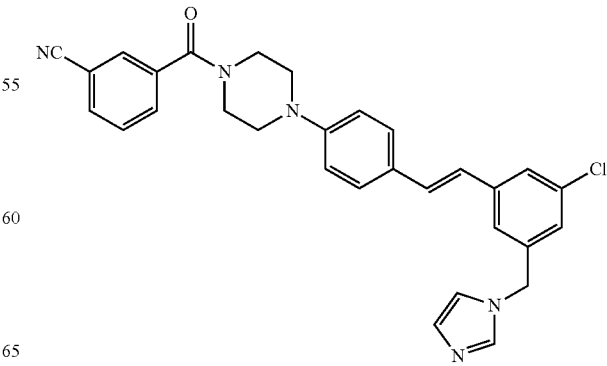

EXAMPLE 23

Synthesis of (E)-3-(4-(4-(3-((1H-imidazol-1-yl)methyl)-5-chlorostyryl)phenyl)piperazine-1-carbonyl)benzonitrile:
The title compounds were prepared according to the procedure for (E)-(4-(4-(3-((1H-imidazol-1-yl)methyl)-5-chlorostyryl)phenyl)piperazin-1-yl)(cyclopropyl)methanone, except 3-cyaniobenzoyl chloride was substituted for cyclopropane carbonyl chloride. $^1$H NMR: (400 MHz, CDCl$_3$) δ 7.76-7.67 (m, 4H), 7.60 (d, J=7.8 Hz, 1H), 7.44-7.41 (m, 3H), 7.16 (s, 1H), 7.07 (s, 1H), 6.99 (s, 2H), 6.92-6.81 (m, 4H), 5.12 (s, 2H), 3.95-3.26 (m, 8H); ESIMS: m/z=508.1 [(M+H)$^+$]; IR (thin film): 3027, 2919, 2229, 1631, 1594, 742 cm$^{-1}$.

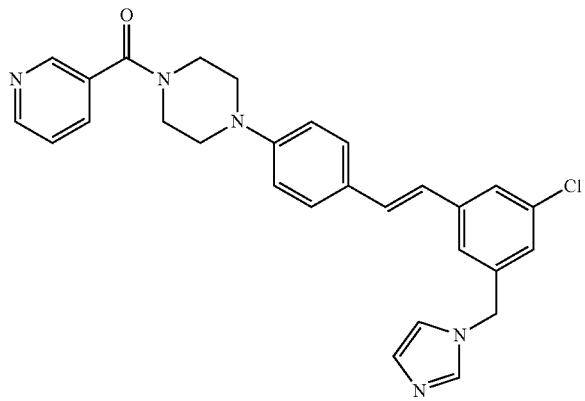 [SMILES: O=C(c1cccnc1)N1CCN(c2ccc(/C=C/c3cc(Cl)cc(Cn4ccnc4)c3)cc2)CC1]

EXAMPLE 24

Synthesis of (E)-(4-(4-(3-((1H-imidazol-1-yl)methyl)-5-chlorostyryl)phenyl)piperazin-1-yl)(pyridin-3-yl)methanone: The title compounds were prepared according to the procedure for (E)-(4-(4-(3-((1H-imidazol-1-yl)methyl)-5-chlorostyryl) phenyl)piperazin-1-yl)(cyclopropyl)methanone, except nicotinoyl chloride was substituted for cyclopropanecarbonyl chloride. $^1$H NMR: (400 MHz, CDCl$_3$) δ 8.69-8.67 (m, 2H), 7.79-7.60 (m, 1H), 7.59 (s, 1H), 7.41-7.35 (m, 4H), 7.12 (s, 1H), 7.04-7.01 (m, 2H), 6.97 (d, J=2.8 Hz, 1H), 6.91-6.87 (m, 3H), 6.83 (d, J=16.8 Hz, 1H), 5.10 (s, 2H), 3.95-3.65 (m, 4H), 3.35-3.15 (m, 4H); ESIMS: m/z=484.1 [(M+H)$^+$].

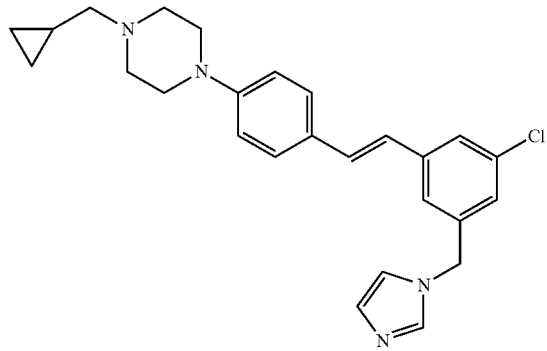 [SMILES: Clc1cc(/C=C/c2ccc(N3CCN(CC4CC4)CC3)cc2)cc(Cn2ccnc2)c1]

EXAMPLE 25

Synthesis of (E)-1-(4-(3-((1H-imidazol-1-yl)methyl)-5-chlorostyryl)phenyl)-4-(cyclopropylmethyl)piperazine:
Potassium carbonate (180 mg, 1.31 mmol) was added to a stirred solution of (E)-1-(4-(3-((1H-imidazol-1-yl)methyl)-5-chlorostyryl)phenyl)piperazine HCl (100 mg, 026 mmol) in N,N-dimethylformamide (5 mL) at room temperature. After stirring for 5 minutes, (bromomethyl)cyclopropane (0.030 mL, 0.31 mmol) was added and the reaction mixture was stirred at 100° C. till complete consumption of the starting material. Reaction mixture was poured into ice-water and extracted with ethyl acetate. The organic layer was washed with water and brain, dried (Na$_2$SO$_4$), filtered, concentrated and the residue was purified by preparative thin layer chromatography to afford the title compound as off white solid (30 mg, 26%); $^1$H NMR: (400 MHz, CDCl$_3$) δ 7.56 (s, 1H), 739-7.36 (m, 3H), 7.11 (s, 1H), 7.04 (s, 1H), 7.00 (d, J=16.0 Hz, 1H), 6.94 (s, 1H), 6.90-6.87 (m, 3H), 6.81 (d, J=16.4 Hz, 1H), 5.07 (s, 2H), 3.40-3.32 (m, 4H), 2.80-2.74 (m, 4H), 2.37 (s, 2H), 0.85-0.83 (m, 1H), 0.57-0.55 (m, 2H); ESIMS: m/z=433.1 [(M+H)$^+$].

The following compounds can be prepared by the procedure of (E)-1-(4-(3-((1H-imidazol-1-yl)methyl)-5-chlorostyryl)phenyl)-4-(cyclopropylmethyl)piperazine. The skilled practitioner will know how to substitute the appropriate reagents, starting materials and purification methods known to those skilled in the art, in order to prepare the compounds provided herein.

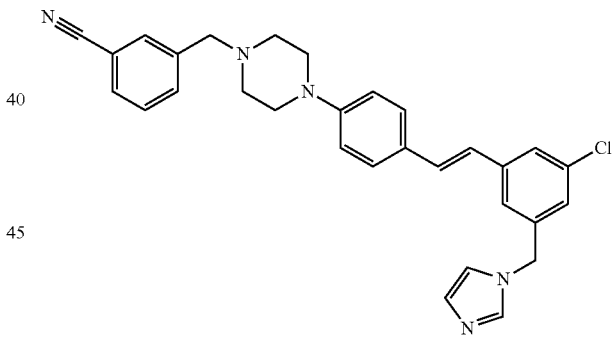

EXAMPLE 26

Synthesis of (E)-3-((4-(4-(3-((1H-imidazol-1-yl)methyl)-5-chlorostyryl)phenyl)piperazin-1-yl)methyl)benzonitrile:
The title compounds were prepared according to the procedure for (E)-1-(4-(3-((1H-imidazol-1-yl)methyl)-5-chlorostyryl)phenyl)-4-(cyclopropylmethyl)piperazine, except 3-(bromomethyl)benzonitrile was substituted for (bromomethyl)cyclopropane. $^1$H NMR: (300 MHz, CDCl$_3$) δ 7.69 (s, 1H), 7.62-7.56 (m, 3H), 7.46-7.38 (m, 4H), 7.14 (s, 1H), 7.06-7.04 (m, 1H), 6.98-6.84 (m, 6H), 5.09 (s, 2H), 3.59 (s, 2H), 3.26 (t, J=5.1 Hz, 4H), 2.61 (t, J=4.8 Hz, 4H); ESIMS: m/z=494.1 [(M+H)$^+$].

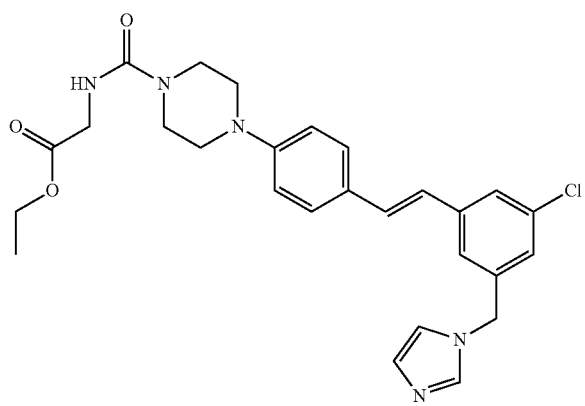 [SMILES: CCOC(=O)CNC(=O)N1CCN(c2ccc(/C=C/c3cc(Cl)cc(Cn4ccnc4)c3)cc2)CC1]

EXAMPLE 27

Synthesis of (E)-ethyl 2-(4-(4-(3-((1H-imidazol-1-yl)methyl)-5-chlorostyryl)phenyl)piperazine-1-carboxamido)acetate: Triethylamine (0.10 mL, 1.0 mmol) was added to a stirred solution of (E)-1-(4-(3-((1H-imidazol-1-yl)methyl)-5-chlorostyryl)phenyl)piperazine HCl (100 mg, 0.26 mmol) in methylene chloride (5 mL) at room temperature. The reaction mixture was cooled to 0° C. and ethyl 2-isocyanatoacetate (49 mg, 0.3 mmol) was added and the reaction mixture was stirred at room temperature for 4 hours. Reaction mixture was diluted with dichloromethane and washed with water followed by saturated NaHCO₃ solution and brain. The organic layer was dried (Na₂SO₄), filtered, concentrated and the residue was purified preparative thin layer chromatography (Solvent system: ethyl acetate) to afford the title compound as off white solid (35 mg, 25%); ¹H NMR: (400 MHz, CDCl₃) δ 7.65 (s, 1H), 7.40-7.37 (m, 3H), 7.12 (s, 1H), 7.05-7.01 (d, J=16.0 Hz, 1H), 6.97-6.91 (m, 3H), 6.88 (d, J=8.0 Hz, 2H), 6.82 (d, J=16.0 Hz, 1H), 5.09 (s, 2H), 5.09-5.00 (m, 1H), 4.23-4.15 (m, 2H), 4.02-3.98 (m, 2H), 3.56 (t, J=5.2 Hz, 4H), 3.24 (t, J=4.8 Hz, 4H), 1.29-1.23 (m, 3H); ESIMS: m/z=508.2 [(M+H)⁺]; IR (thin film): 3349, 3031, 2989, 1750, 1639, 1594, 744 cm⁻¹.

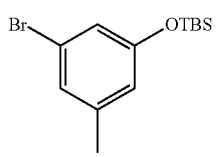 [SMILES: Cc1cc(Br)cc(O[Si](C)(C)C(C)(C)C)c1]

EXAMPLE 28

Synthesis of (3-bromo-5-methylphenoxy)(tert-butyl)dimethylsilane: To a stirred solution of 3-bromo-5-methylphenol (2.0 g, 10.0 mmol) in tetrahydrofuran (30 mL) cooled to 0° C., imidazole (1.70 g, 12.0 mmol) and tert-Butyldimethylsilyl chloride (1.93 g, 12.0 mmol) were added and then reaction mixture was stirred at room temperature for 16 hours. The reaction mixture was poured into ice-water extracted with ethyl acetate. The organic layer was washed with water and brain solution, dried (Na₂SO₄) filtered and concentrated to give the title compound as colorless liquid (3 g) which was taken to the next step without purification. ¹H NMR: (400 MHz, CDCl₃) δ 6.82 (s, 1H), 6.70 (d, J=2.0 Hz, 1H), 6.47 (s, 1H), 2.16 (s, 3H), 0.87 (s, 9H), 0.09 (s, 6H).

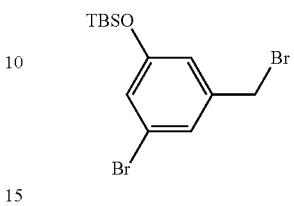

EXAMPLE 29

Synthesis of (3-bromo-5-(bromomethyl)phenoxy)(tert-butyl)dimethylsilane: Azobisisobutyronitrile (AIBN, 109 mg, 0.6 mmol) was added to a stirred solution of (3-bromo-5-methylphenoxy)(tert-butyl)dimethylsilane (4.0 g, 13.3 mmol) in CCl₄ (30 mL) was added at rt. The mixture was cooled to 0° C. then N-bromo succinamide (2.3 g, 13.3 mmol) was added and slowly and the reaction mixture was then refluxed for 6 hours. The reaction mixture was through a celite pad and filtrate was concentrated to afford the title compound as brown liquid (4.5 g), which was taken to the next step without purification. ¹H NMR: (400 MHz, CDCl₃) δ 7.13 (s, 1H), 6.92-6.91 (m, 1H), 6.79-6.78 (m, 1H), 4.33 (s, 2H), 0.97 (s, 9H), 0.21 (s, 6H).

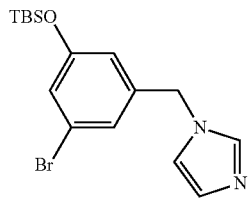 [SMILES: CC(C)(C)[Si](C)(C)Oc1cc(Br)cc(Cn2ccnc2)c1]

EXAMPLE 30

Synthesis of 1-(3-bromo-5-(tert-butyldimethylsilyloxy)benzyl)-1H-imidazole: To a stirred solution of (3-bromo-5-(bromomethyl)phenoxy)(tert-butyl)dimethylsilane (8.0 g, 21 mmol) in N,N-dimethylformamide (50 mL) was added imidazole (14.32 g, 210 mmol) was added at room temperature and the mixture was then stirred at 100° C. for 4 hours. The reaction was poured into ice-water extracted with ethyl acetate. The organic layer was washed with water and brain, dried (Na₂SO₄), filtered concentrated and the residue was purified by column chromatography on silica (100-200 mesh), eluting with 80% ethyl acetate in petroleum ether to afford the title compound as off white solid (1.5 g, 20%). ¹H NMR: (400 MHz, CDCl₃) δ 7.54 (s, 1H), 7.11 (s, 1H), 6.94-6.88 (m, 3H), 6.47 (s, 1H), 5.05 (s, 2H), 0.95 (s, 9H), 0.20 (s, 6H); ESIMS: m/z=368.9 [(M+H)⁺]

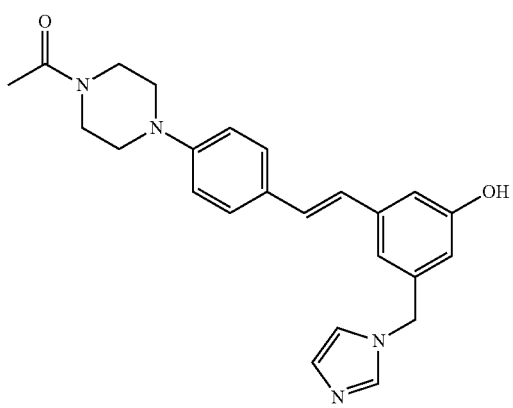 [SMILES: CC(=O)N1CCN(c2ccc(/C=C/c3cc(O)cc(Cn4ccnc4)c3)cc2)CC1]

EXAMPLE 31

Synthesis of (E)-1-(4-(4-(3-((1H-imidazol-1-yl)methyl)-5-hydroxystyryl)phenyl)piperazin-1-yl)ethanone: Triethylamine (1.1 mL, 8.17 mmol) was added to a solution of 1-(3-bromo-5-(tert-butyldimethylsilyloxy)benzyl)-1H-imidazole (1.0 g, 2.70 mmol) and (E)-1-(4-(4-(3-((1H-imidazol-1-yl)methyl)-5-hydroxystyryl)phenyl)piperazin-1-yl)ethanone (620 mg, 2.70 mmol) in tetrahydrofuran (10 mL) and the mixture was degassed with argon. Pd(OAc)$_2$ (120 mg, 0.5 mmol) and P(o-Tolyl)$_3$ (914 mg, 2.9 mmol) were then added and the mixture was again degassed with argon. The resulting mixture was the stirred at 70° C. under argon for 48 hours. The reaction mixture was filtered through a celite pad; the filtrate was concentrated and the residue was purified by column chromatography on silica (100-200 mesh) eluting with 5% methanol in methylene chloride to afford the title compound as off-white solid (100 mg, 9%). $^1$H NMR: (400 MHz, DMSO-d$_6$) δ 9.50 (s, 1H), 7.75 (s, 1H), 7.46 (d, J=8.8 Hz, 2H), 7.18 (s, 1H), 7.07-7.05 (m, 1H), 7.01 (s, 1H), 6.96-6.88 (m, 4H), 6.83 (s, 1H), 6.44 (s, 1H), 5.11 (s, 2H), 3.65-3.55 (m, 4H), 3.22-3.13 (m, 4H), 2.04 (s, 3H); ESIMS: m/z=403.2 [(M+H)$^+$]

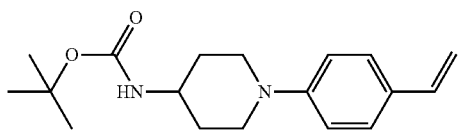

EXAMPLE 32

Synthesis of tert-butyl -1-(4-vinylphenyl)piperidin-4-ylcarbamate: To a stirred solution of 1-bromo-4-vinylbenzene (5.0 g, 27.0 mmol) and tert-butyl piperidin-4-ylcarbamate (6.5 g, 32.0 mmol) in toluene (50 mL) Cs$_2$CO$_3$ (17.7 g, 54.0 mmol) was added and the mixture was degassed with argon for 20 minutes. Pd(OAc)$_2$ (610 mg, 2.7 mmol), 2-dicyclohexylphosphino-2',4',6'-triisopropylbiphenyl (X-Phos, 2.6 g, 5.4 mmol) were added to reaction mixture and degassed with argon for another 20 minutes. The mixture was refluxed under stirring for 16 hours. Filtered through a celite pad, the filtrate was concentrated and the residue was purified by column chromatography on silica (100-200 mesh), eluting with 30% ethyl acetate in petroleum ether to afford the title compound as off-white solid (4.0 g, 75%). $^1$H NMR: (300 MHz, DMSO-d$_6$) δ 7.30 (d, J=9.0 Hz, 2H), 6.89-6.82 (m, 3H), 6.64 (dd, J=17.4, 11.1 Hz, 1H), 5.61 (d, J=18.6 Hz, 1H), 5.03 (d, J=11.7 Hz, 1H), 3.69-3.64 (m, 2H), 3.42-3.35 (m, 1H), 2.77-2.70 (m, 2H), 1.79-1.75 m, 2H), 1.48-1.45 (m, 2H), 1.38 (s, 9H). ESIMS: m/z=303.2 [(M+H)$^+$].

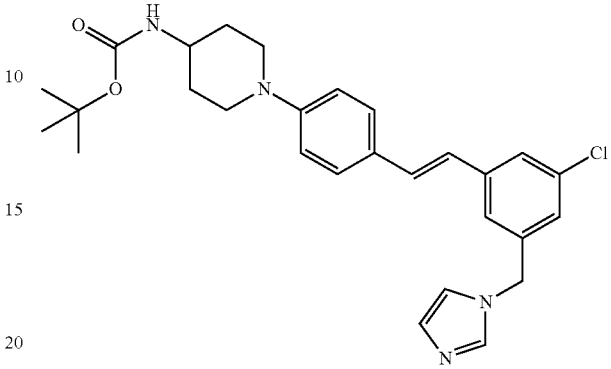

EXAMPLE 33

Synthesis of (E)-tert-butyl 1-(4-(3-((1H-imidazol-1-yl)methyl)-5-chlorostyryl)phenyl)piperidin-4-ylcarbamate: To a stirred solution of 1-(3-bromo-5-chlorobenzyl)-1H-imidazole (2.0 g, 7.36 mmol) and tert-butyl 1-(4-vinylphenyl)piperidin-4-ylcarbamate (2.69 g, 8.83 mmol) in tetrahydrofuran (20 mL) triethylamine (3.08 mL, 22.08 mmol) was added, and the mixture was degassed with argon for 20 min. Pd(OAc)$_2$ (330 mg, 1.47 mmol), P(o-tolyl)$_3$ (2.7 g, 8.83 mmol) were added degassed with argon for another 20 minutes. The reaction mixture was refluxed under stirring for 48 hours. Reaction was cooled to room temperature and filtered through celite pad. The filtrate was concentrated and the residue was purified by column chromatography on silica (100-200 mesh) eluting with 80% ethyl acetate in petroleum ether to afford the title compound as off-white solid (1.0 g, 27%). $^1$11NMR: (400 MHz, CDCl$_3$) δ 7.58 (s, 1H), 7.41 (s, 1H), 7.39 (d, J=8.4 Hz, 2H), 7.12 (s, 1H), 7.05 (s, 1H), 7.02 (d, J=16.0 Hz, 1H), 6.95 (s, 1H), 6.92-6.88 (m, 3H), 6.82 (d, J=16.4 Hz, 1H), 5.09 (s, 2H), 4.48 (bs, 1H), 3.69-3.66 (m, 3H), 2.92-2.86 (m, 2H), 2.06-2.04 (m, 2H), 1.61-1.50 (m, 2H), 1.45 (s, 9H); ESIMS: m/z=493.2 [(M+H)$^+$].

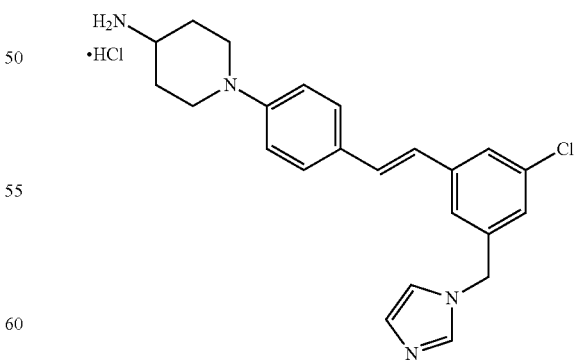

EXAMPLE 34

Synthesis of (E)-1-(4-(3-((1H-imidazol-1-yl)methyl)-5-chlorostyryl)phenyl)piperidin-4-amine.HCl: To a stirred solution of (E)-tert-butyl 1-(4-(3-((1H-imidazol-1-yl)methyl)-5-chlorostyryl)phenyl)piperidin-4-ylcarbamate (800 mg, 1.62 mmol) in 1,4 dioxane (10 mL) HCl in dioxane (5.0 mL) was added at 0° C., and the reaction mixture was stirred at room temperature for 4 hours. The volatiles were evaporated and the residue was washed with diethyl ether to afford the title compound as pale yellow solid (500 mg, 78%). $^1$H NMR: (400 MHz, DMSO-$d_6$) δ 14.95 (bs, 1H), 9.41 (s, 1H), 8.47 (bs, 3H), 7.88-7.87 (m, 1H), 7.73-7.72 (m, 1H), 7.68-7.58 (m, 4H), 7.43-7.33 (m, 3H), 7.17 (d, J=16.8 Hz, 1H), 5.47 (s, 2H), 3.82-3.79 (m, 2H), 3.40-3.35 (m, 1H), 3.25-3.15 (m, 2H), 2.14-2.12 (m, 2H), 1.91-1.85 (m, 2H); ESIMS: m/z=393.0 [(M+H)$^+$].

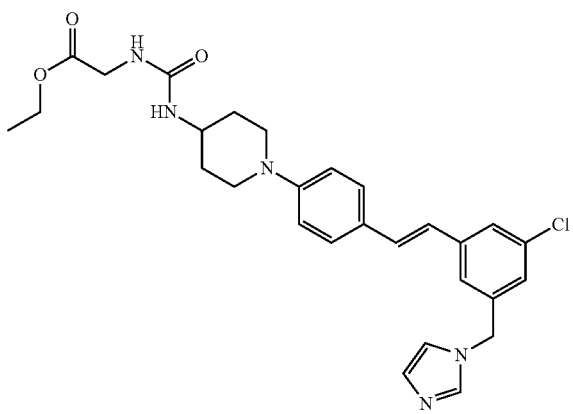 [SMILES: CCOC(=O)CNC(=O)NC1CCN(c2ccc(/C=C/c3cc(Cl)cc(Cn4ccnc4)c3)cc2)CC1]

EXAMPLE 35

Synthesis of (E)-ethyl 2-(3-(1-(4-(3-((1H-imidazol-1-yl)methyl)-5-chlorostyryl)phenyl)piperidin-4-yl)ureido)acetate: Triethylamine (0.1 mL, 0.79 mmol) was added to a stirred solution of (E)-1-(4-(3-((1H-imidazol-1-yl)methyl)-5-chlorostyryl)phenyl)piperidin-4-amine HCl (100 mg, 0.2 mmol) in methylene chloride (5 mL) at room temperature. The reaction mixture was cooled to 0° C. and ethyl 2-isocyanatoacetate (39 mg, 2.8 mmol) was added and then stirred at room temperature for 4 hours. The reaction was diluted with dichloromethane and washed with water, followed by saturated NaHCO$_3$ solution and brain. The organic layer was dried (Na$_2$SO$_4$), filtered, concentrated and the residue was purified by preparative thin layer chromatography (solvent system: 80% ethyl acetate in petroleum ether) to afford the title compound as white solid (40 mg, 30%). $^1$H NMR: (300 MHz, CDCl$_3$) δ 7.74 (s, 1H), 7.42-7.36 (m, 3H), 7.15 (s, 1H), 7.07-7.03 (m, 2H), 6.98-6.88 (m, 4H), 6.83-6.77 (m, 1H), 5.11 (s, 2H), 5.07-5.02 (m, 1H), 4.48-4.00 (m, 1H), 4.00-3.98 (m, 2H), 3.85-3.75 (m, 1H), 3.70-3.66 (m, 2H), 2.95-2.91 (m, 2H), 2.08-2.04 (m, 2H), 1.55-1.47 (m, 4H), 1.31-1.28 (m, 3H); ESIMS: m/z=522.2 [(M+H)$^+$].

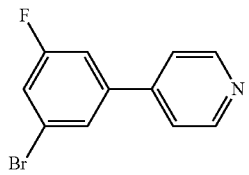 [SMILES: Fc1cc(Br)cc(-c2ccncc2)c1]

EXAMPLE 36

Synthesis of 4-(3-bromo-5-fluorophenyl)pyridine: To a stirred solution of 1,3-dibromo-5-fluorobenzene (300 mg, 1.2 mmol) and 4-(4,4,5,5-tetramethyl-1,3,2-dioxaborolan-2-yl)pyridine (240 mg, 1.2 mmol) in 1,4-dioaxane (10 mL) K$_2$CO$_3$ (480 mg, 3.5 mmol) was added and the mixture was degassed with argon for 20 min. Pd (PPh$_3$)$_4$ (40 mg, 0.035 mmol) was added to reaction mixture and degassed for another 20 minutes. The reaction mixture was refluxed under stirring for 8 hours and then filtered through celite pad. The filtrate was concentrated and the residue was purified by column chromatography on silica (100-200 mesh) eluting with 15% ethyl acetate in petroleum ether to afford the title compound as white solid (150 mg, 51%). $^1$H NMR: (300 MHz, CDCl$_3$) δ 8.70 (dd, J=4.2. 2.4 Hz, 2H), 7.57 (s, 1H), 7.46 (dd, J=4.5, 1.5 Hz, 2H), 7.34-7.25 (m, 2H); ESIMS: m/z=255.0 [(M+2H)$^+$].

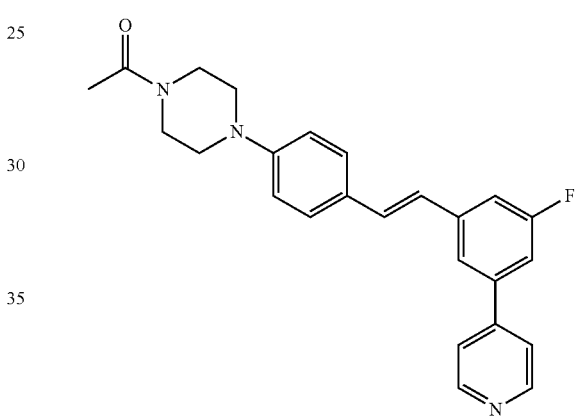

EXAMPLE 37

Synthesis of (E)-1-(4-(4-(3-fluoro-5-(pyridin-4-yl) styryl) phenyl) piperazin-1-yl) ethanone: Triethylamine (0.24 mL, 1.78 mmol) was added to a stirred solution of 4-(3-bromo-5-fluorophenyl) pyridine (150 mg, 0.60 mmol) and 1-(4-(4-vinylphenyl)piperazin-1-yl)ethanone (164 mg, 0.71 mmol) in tetrahydrofuran (10 mL) and the mixture was degassed with argon for 20 min. Pd (OAc)$_2$ (20 mg, 0.12 mmol), P(o-tolyl)$_3$ (217 mg, 0.71 mmol) were added to reaction mixture and degassed for another 20 minutes. The reaction mixture was then refluxed for 48 hours. Filtered through a celite pad, the filtrate was concentrated and the residue was purified by preparative thin layer chromatography (solvent system: ethyl acetate) to afford the title compound as off-white solid (15 mg, 7%). $^1$H NMR: (400 MHz, CDCl$_3$) δ 8.68 (d, J=4.8 Hz, 2H), 7.50-7.47 (m, 5H), 7.24 (s, 1H), 7.17-7.15 9m, 1H), 7.12 (d, J=16.4 Hz, 1H), 6.98-6.94 (d, J=16.8 Hz, 1H), 6.92 (d, J=8.8 Hz, 2H), 3.77 (t, J=5.6 Hz, 2H), 3.62 (t, J=4.8 Hz, 4H), 3.25-3.19 (m, 4H), 2.13 (s, 3H); ESIMS: m/z=402.2 [(M+H)$^+$].

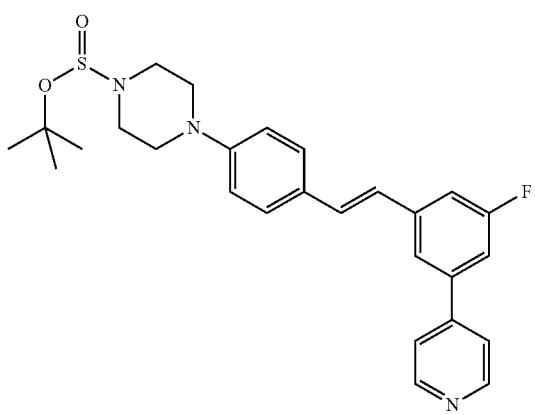 [SMILES: CC(C)(C)OS(=O)N1CCN(c2ccc(/C=C/c3cc(F)cc(-c4ccncc4)c3)cc2)CC1]

EXAMPLE 38

Synthesis of (E)-tert-butyl 2-(4-(4-(3-fluoro-5-(pyridin-4-yl)styryl)phenyl)piperazin-1-yl)-2-oxoacetate: Triethylamine (1.1 mL, 8.17 mmol) was added to a stirred solution of 4-(3-bromo-5-fluorophenyl)pyridine (1.0 g, 2.7 mmol) and tert-butyl 4-(4-vinylphenyl)piperazine-1-carboxylate (620 mg, 2.7 mmol) in N,N-dimethylformamide (10 mL) and the mixture was degassed with argon for 20 minutes. Pd (OAc)$_2$ (120 mg, 0.5 mmol), P(o-tolyl)$_3$ (914 mg, 2.9 mmol) were added to reaction mixture and degassed for another 20 minutes. The reaction mixture was then refluxed for 48 hours. Filtered through a celite pad, the filtrate was concentrated and the residue was purified by column chromatography on silica (100-200 mesh) eluting with 50% ethyl acetate in petroleum ether to afford the title compound as off-white solid (600 mg, 34%). $^1$H NMR: (400 MHz, CDCl$_3$) δ 8.70 (d, J=5.6 Hz, 2H), 7.51-7.44 (m, 5H), 7.26-7.24 (m, 1H), 7.18 (d, J=8.8 Hz, 1H), 7.13 (d, J=16.0 Hz, 1H), 6.99 (d, J=16.0 Hz, 1H), 6.93 (d, J=8.4 Hz, 2H), 3.59 (t, J=5.2 Hz, 4 H), 3.20 (t, J=4.8 Hz, 4H), 1.49 (s, 9H); ESIMS: m/z=460.2 [(M+H)$^+$].

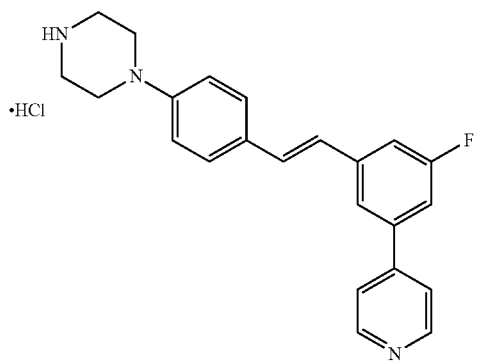 [SMILES: Cl ; Fc1cc(/C=C/c2ccc(N3CCNCC3)cc2)cc(-c2ccncc2)c1]

EXAMPLE 39

Synthesis of (E)-1-(4-(3-fluoro-5-(pyridin-4-yl)styryl)phenyl)piperazine HCl: To a stirred solution of (E)-tert-butyl 2-(4-(4-(3-fluoro-5-(pyridin-4-yl)styryl)phenyl) piperazin-1-yl)-2-oxoacetate (600 mg, 1.25 mmol) in 1,4 dioxane (10 mL) HCl in dioxane (5.0 mL) was added at 0° C., and the reaction mixture was stirred at room temperature for 4 hours. The volatiles were evaporated and the residue was washed with pentane to afford the title compound as pale yellow solid (300 mg, 63%). $^1$H NMR: (300 MHz, DMSO-d$_6$) δ 9.43 (bs, 2H), 9.04 (d, J=6.3 Hz, 2H), 8.51 (d, J=6.3 Hz, 2H), 8.09 (s, 1H), 7.81-7.78 (m, 1H), 7.70-7.67 (m, 1H), 7.55-7.46 (m, 3H), 7.22 (d, J=16.2 Hz, 1H), 7.06 (d, J=8.7 Hz, 2H), 3.47-3.45 (m, 4H), 3.20-3.16 (m, 4H); ESIMS: m/z=360.2 [(M+H)$^+$].

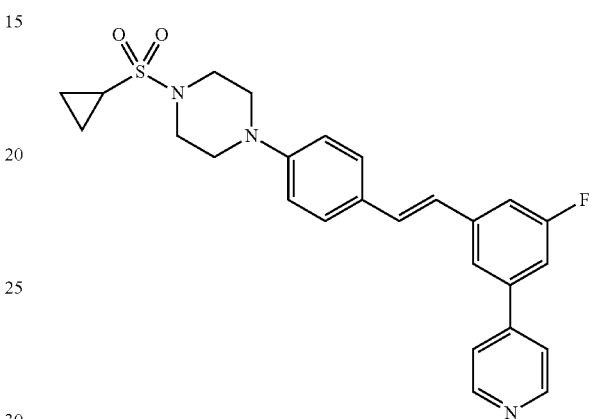

EXAMPLE 40

Synthesis of (E)-1-(cyclopropylsulfonyl)-4-(4-(3-fluoro-5-(pyridin-4-yl)styryl)phenyl)piperazine: Triethylamine (0.19 mL, 1.38 mmol) was added to a stirred solution of (E)-1-(4-(3-fluoro-5-(pyridin-4-yl)styryl)phenyl)piperazine HCl (100 mg, 0.27 mmol) in dichloromethane (5 mL) at room temperature. The reaction mixture was cooled to 0° C. and cyclopropanesulfonyl chloride (0.03 mL, 0.33 mmol) was added and the reaction mixture was stirred at RT for 4 h. Reaction mixture was diluted with dichloromethane and washed with water followed by saturated NaHCO$_3$ solution and brain solution. The organic layer was dried (Na$_2$SO$_4$), filtered, concentrated and the residue was purified using with prep TLC to afford the title compound (20 mg, 15%) as pale yellow solid. $^1$H NMR: (400 MHz, CDCl$_3$) δ 8.70 (d, J=4.4 Hz, 2H), 7.52-7.45 (m, 5H), 7.27-7.26 (m, 1H), 7.19 (d, J=8.8 Hz, 1H), 7.14 (d, J=16.0 Hz, 1H), 7.01 (d, J=16.0 Hz, 1H), 6.94 (d, J=8.0 Hz, 2H), 3.48 (t, J=4.4 Hz, 4H), 3.33 (t, J=5.6 Hz, 4H), 2.32-2.28 (m, 1H), 1.24-1.20 (m, 2H), 1.05-1.01 (m, 2H); ESIMS: m/z=464.2 [(M+H)$^+$].

The following compounds can be prepared by the procedure of (E)-1-(cyclopropylsulfonyl)-4-(4-(3-fluoro-5-(pyridin-4-yl)styryl)phenyl)piperazine. The skilled practitioner will know how to substitute the appropriate reagents, starting materials and purification methods known to those skilled in the art, in order to prepare the compounds provided herein.

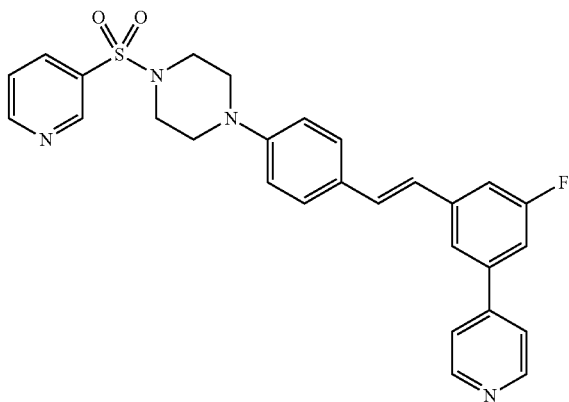 [SMILES: O=S(=O)(c1cccnc1)N1CCN(c2ccc(/C=C/c3cc(F)cc(-c4ccncc4)c3)cc2)CC1]

EXAMPLE 41

Synthesis of (E)-1-(4-(3-fluoro-5-(pyridin-4-yl)styryl)phenyl)-4-(pyridin-3-ylsulfonyl)piperazine: The title compounds were prepared according to the procedure for (E)-1-(cyclopropylsulfonyl)-4-(4-(3-fluoro-5-(pyridin-4-yl)styryl)phenyl)piperazine, except pyridine-3-sulfonyl chloride was substituted for cyclopropanesulfonyl chloride. $^1$H NMR: (400 MHz, CDCl$_3$) δ 9.03 (d, J=1.6 Hz, 1H), 8.86 (d, J=4.8 Hz, 1H), 8.69 (d, J=6.0 Hz, 2H), 8.10 (d, J=7.6 Hz, 1H), 7.53-7.47 (m, 4H), 7.44 (d, J=8.8 Hz, 2H), 7.26-7.23 (m, 1H), 7.19 (d, J=8.8 Hz, 1H), 7.11 (d, J=16.0 Hz, 1H), 6.99 (d, J=16.4 Hz, 1H), 6.88 (d, J=8.8 Hz, 2H), 3.33 (t, J=4.4 Hz, 4H), 3.24 (t, J=5.6 Hz, 4H); ESIMS: m/z=501.2 [(M+H)$^+$].

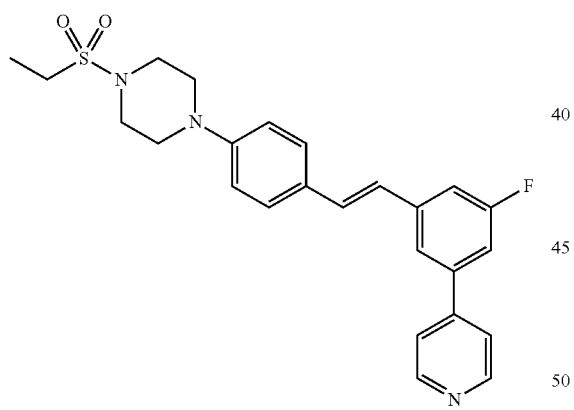

EXAMPLE 42

Synthesis of (E)-1-(ethylsulfonyl)-4-(4-(3-fluoro-5-(pyridin-4-yl)styryl)phenyl)piperazine: The title compounds were prepared according to the procedure for (E)-1-(cyclopropylsulfonyl)-4-(4-(3-fluoro-5-(pyridin-4-yl)styryl)phenyl)piperazine, except ethanesulfonyl chloride was substituted for cyclopropanesulfonyl chloride. $^1$H NMR: (400 MHz, CDCl$_3$) δ 8.72-8.68 (m, 2H), 7.53 (d, J=5.2 Hz, 2H), 7.49-7.45 (m, 3H), 7.27-7.26 (m, 1H), 7.20-7.17 (m, 1H), 7.14 (d, J=16.0 Hz, 1H), 7.01 (d, J=16.4 Hz, 1H), 6.94 (d, J=8.4 Hz, 2H), 3.47 (t, J=4.4 Hz, 4H), 3.32 (t, J=5.2 Hz, 4H), 3.03 (q, J=7.2 Hz, 2H), 1.41 (t, J=7.2 Hz, 3H); ESIMS: m/z=452.2 [(M+H)$^+$].

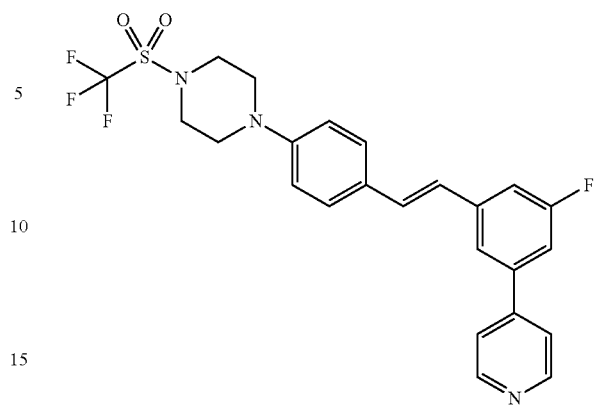

EXAMPLE 43

Synthesis of (E)-1-(4-(3-fluoro-5-(pyridin-4-yl)styryl)phenyl)-4-(trifluoromethylsulfonyl)piperazine: The title compounds were prepared according to the procedure for (E)-1-(cyclopropylsulfonyl)-4-(4-(3-fluoro-5-(pyridin-4-yl)styryl)phenyl)piperazine, except trifluoromethanesulfonyl chloride was substituted for cyclopropanesulfonyl. $^1$H NMR: (400 MHz, CDCl$_3$) δ 8.75-8.65 (m, 2H), 7.52-7.46 (m, 5H), 7.28-7.26 (m, 1H), 7.20-7.18 (m, 1H), 7.14 (d, J=16.4 Hz, 1H), 7.02 (d, J=16.4 Hz, 1H), 6.94 (d, J=8.8 Hz, 2H), 3.80-3.65 (m, 4H), 3.35-3.00 (m, 4H); ESIMS: m/z=492.0 [(M+H)$^+$].

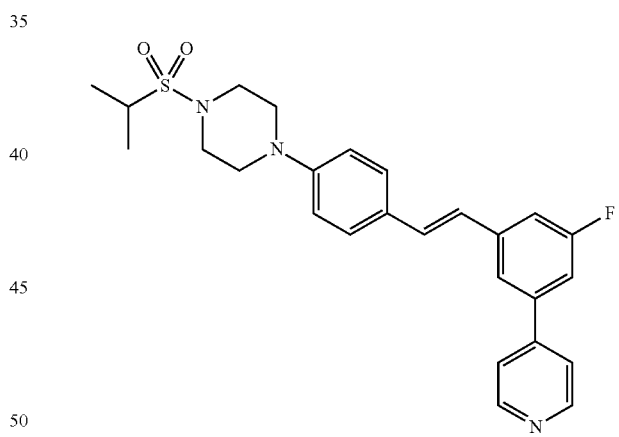

EXAMPLE 44

Synthesis of (E)-1-(4-(3-fluoro-5-(pyridin-4-yl)styryl)phenyl)-4-(isopropylsulfonyl)piperazine: The title compounds were prepared according to the procedure for (E)-1-(cyclopropylsulfonyl)-4-(4-(3-fluoro-5-(pyridin-4-yl)styryl)phenyl)piperazine, except isopropylsulfonyl chloride was substituted for cyclopropanesulfonyl. $^1$H NMR: (400 MHz, CDCl$_3$) δ 8.74-8.68 (m, 2H), 7.52-7.45 (m, 5H), 7.27-7.26 (m, 1H), 7.19-7.17 (m, 1H), 7.13 (d, J=16.4 Hz, 1H), 7.00 (d, J=16.4 Hz, 1H), 6.93 (d, J=8.4 Hz, 2H), 3.53 (t, J=4.4 Hz, 4H), 3.28 (t, J=5.6 Hz, 4H), 3.25-3.20 (m, 1H), 1.39-1.37 (m, 6H); ESIMS: m/z=466.2 [(M+H)$^+$].

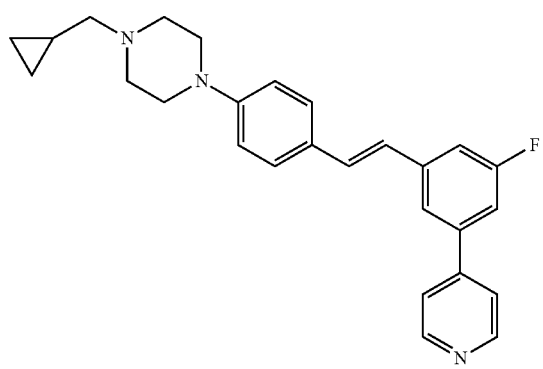 [SMILES: Fc1cc(/C=C/c2ccc(N3CCN(CC4CC4)CC3)cc2)cc(-c2ccncc2)c1]

EXAMPLE 45

Synthesis of (E)-1-(cyclopropylmethyl)-4-(4-(3-fluoro-5-(pyridin-4-yl)styryl)phenyl)piperazine: Potassium carbonate (229 mg, 1.6 mmol) was added to a stirred solution of (E)-1-(4-(3-fluoro-5-(pyridin-4-yl)styryl)phenyl)piperazine HCl (200 mg, 0.5 mmol) in N,N-dimethylformamide (5 mL) at RT. After stirring for 5 minutes (bromomethyl)cyclopropane (89 mg, 0.6 mmol) was added and the reaction mixture was stirred at 100° C. till complete consumption of the starting material. The reaction mixture was poured into ice-water and extracted with ethyl acetate. The organic layer was washed with water and brine, dried (Na$_2$SO$_4$), filtered, concentrated and the residue was purified by preparative thin layer chromatography (solvent system: ethyl acetate) to afford the title compound as brown solid (20 mg, 8%). $^1$H NMR: (400 MHz, CDCl$_3$) δ 8.71-8.67 (m, 2H), 7.52-7.43 (m, 5H), 7.26-7.24 (m,1H), 7.17 (d, J=8.8 Hz, 1H), 7.13 (d, J=16.4 Hz, 1H), 6.98-6.91 (m, 3H), 3.38-3.30 (m, 4H), 2.79-2.72 (m, 4H), 2.38 (d, J=6.0 Hz, 2H), 1.00-0.92 (m, 1H), 0.58-0.57 (m, 2H), 0.18-0.16 (m, 2H); ESIMS: m/z=414.2 [(M+H)$^+$].

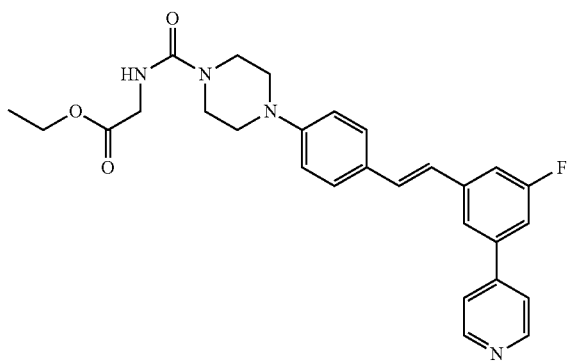 [SMILES: CCOC(=O)CNC(=O)N1CCN(c2ccc(/C=C/c3cc(F)cc(-c4ccncc4)c3)cc2)CC1]

EXAMPLE 46

Synthesis of (E)-ethyl 2-(4-(4-(3-fluoro-5-(pyridin-4-yl)styryl)phenyl)piperazine-1-carboxamido)acetate: Triethylamine (0.15 mL, 1.3 mmol) was added to a stirred solution of (E)-1-(4-(3-fluoro-5-(pyridin-4-yl)styryl)phenyl)piperazine HCl (100 mg, 0.2 mmol) in dichloromethane (5 mL) at room temperature. The reaction mixture was cooled to 0° C. and ethyl 2-isocyanatoacetate (35 mg, 0.2 mmol) was added and the reaction mixture was stirred at room temperature for 4 hours. Reaction mixture was diluted with dichloromethane and washed with water followed by saturated NaHCO$_3$ solution and brine. The organic layer was dried (Na$_2$SO$_4$), filtered, concentrated and the residue was purified by preparative thin layer chromatography (solvent system: ethyl acetate) to afford the title compound as pale yellow solid (20 mg, 15%). $^1$H NMR: (400 MHz, DMSO-d$_6$) δ 8.68 (d, J=6.0 Hz, 2H), 7.84-7.79 (m, 3H), 7.53-7.48 (m, 4H), 7.42 (d, J=16.4 Hz, 1H), 7.16-7.09 (m, 2H), 7.01 (d, J=8.8 Hz, 4.10 (q, J=6.8 Hz, 2H), 3.75 (d, J=6.0 Hz, 2H), 3.47-3.45 (m, 4H), 3.20-3.19 (m, 4H), 1.18 (t, J=7.2 Hz, 3H); ESIMS: m/z=489.3 [(M+H)$^+$].

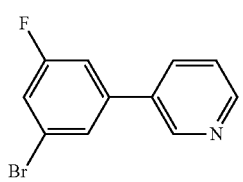 [SMILES: Fc1cc(Br)cc(-c2cccnc2)c1]

EXAMPLE 47

Synthesis of 3-(3-bromo-5-fluorophenyl) pyridine: To a stirred solution of 1,3-dibromo-5-fluorobenzene (600 mg, 2.36 mmol) and 3-(4,4,5,5-tetramethyl-1,3,2-dioxaborolan-2-yl)pyridine (484 mg, 2.36 mmol) in 1,4-dioxaane (15 mL) K$_2$CO$_3$ (979 mg, 7.08 mmol) was added and the mixture was degassed with argon for 20 minutes. Pd (PPh$_3$)$_4$ (81 mg, 0.071 mmol) was added to reaction mixture and degassed for another 20 minutes. The reaction mixture was refluxed under stirring for 8 hours and then filtered through celite pad. The filtrate was concentrated and the residue was purified by column chromatography on silica (100-200 mesh) eluting with 15% ethyl acetate in petroleum ether to afford the title compound as white solid (300 mg, 50%). $^1$H NMR: (400 MHz, CDCl$_3$) δ 8.81 (d, J=2.0 Hz, 1H), 8.65 (dd, J=4.8, 1.2 Hz, 1H), 7.85-7.82 (m, 1H), 7.52 (s, 1H), 7.41-7.37 (m, 1H), 7.31-7.28 (m, 1H), 7.24-7.21 (m, 1H); ESIMS: m/z=255.0 [(M+2H)$^+$].

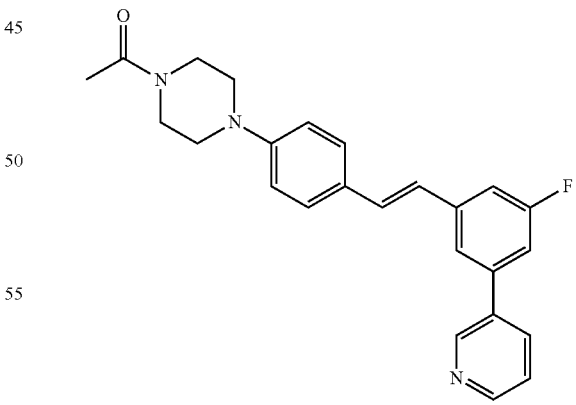

EXAMPLE 48

Synthesis of (E)-1-(4-(4-(3-fluoro-5-(pyridin-3-yl)styryl)phenyl)piperazin-1-yl)ethanone: Triethylamine (0.55 mL, 3.96 mmol) was added to a stirred solution of 3-(3-bromo-5-fluorophenyl) pyridine (200 mg, 0.793 mmol) and 1-(4-

(4-vinylphenyl)piperazin-1-yl)ethanone (220 mg, 0.95 mmol) in acetonitrile (10 mL) and the mixture was degassed with argon for 20 minutes. Pd (OAc)$_2$ (35 mg, 0.15 mmol), PPh$_3$ (104 mg, 0.39 mmol) were added to reaction mixture and degassed for another 20 minutes. The reaction mixture was then refluxed for 48 hours. Filtered through a celite pad, the filtrate was concentrated and the residue was purified by preparative thin layer chromatography (solvent system: ethyl acetate) to afford the title compound as off-white solid (20 mg, 6%). $^1$H NMR: (300 MHz, CDCl$_3$) δ 8.78 (s, 1H), 8.64 (s, 1H), 7.90 (d, J=7.5 Hz, 1H), 7.48-7.43 (m, 4H), 7.21 (s, 1H), 7.14-7.09 (m, 2H), 7.01 (s, 1H), 6.95-6.91 (m, 2H), 3.79 (t, J=5.1 Hz, 2H), 3.64 (t, J=5.1 Hz, 2H), 3.25-3.20 (m, 4H), 2.15 (s, 3H); ESIMS: m/z=402.1 [(M+H)$^+$].

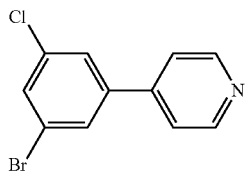

EXAMPLE 49

Synthesis of 4-(3-bromo-5-chlorophenyl)pyridine: To a stirred solution of 1,3-dibromo-5-chlorobenzene (800 mg, 2.96 mmol) and 4-(4,4,5,5-tetramethyl-1,3,2-dioxaborolan-2-yl)pyridine (600 mg, 2.96 mmol) in 1,4-dioaxane (15 mL) K$_2$CO$_3$ (1.2 g, 8.80 mmol) was added and the mixture was degassed with argon for 20 minutes. Pd (PPh$_3$)$_4$ (102 mg, 0.08 mmol) was added to reaction mixture and degassed for another 20 minutes. The reaction mixture was refluxed under stirring for 8 hours and then filtered through celite pad. The filtrate was concentrated and the residue was purified by column chromatography on silica (100-200 mesh) eluting with 15% ethyl acetate in petroleum ether to afford the title compound as white solid (400 mg, 50%). $^1$H NMR: (300 MHz, CDCl$_3$) δ 8.70 (dd, J=4.5, 1.5 Hz, 2H), 7.65-7.64 (m, 1H), 7.59-7.58 (m, 1H), 7.54-7.53 (m, 1H), 7.45 (dd, J=4.2, 1.5 Hz, 2H); ESIMS: m/z=268.0 [(M+H)$^+$].

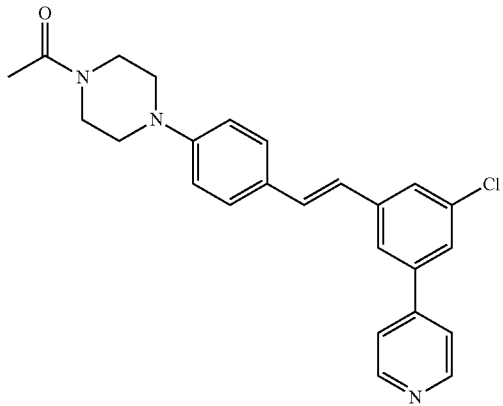 [SMILES: CC(=O)N1CCN(c2ccc(/C=C/c3cc(Cl)cc(-c4ccncc4)c3)cc2)CC1]

EXAMPLE 50

Synthesis of (E)-1-(4-(4-(3-chloro-5-(pyridin-4-yl)styryl) phenyl)piperazin-1-yl)ethanone: Triethylamine (0.38 mL, 3.7 mmol) was added to a stirred solution of 4-(3-bromo-5-chlorophenyl)pyridine (200 mg, 0.74 mmol) and 1-(4-(4-vinylphenyl)piperazin-1-yl)ethanone (205 mg, 0.89 mmol) in acetonitrile (10 mL) and the mixture was degassed with argon for 20 minutes. Pd (OAc)$_2$ (33 mg, 0.10 mmol), PPh$_3$ (234 mg, 0.80 mmol) were added to reaction mixture and degassed for another 20 minutes. The reaction mixture was then refluxed for 48 hours. Filtered through a celite pad, the filtrate was concentrated and the residue was purified by preparative thin layer chromatography (solvent system: ethyl acetate) to afford the title compound as off-white solid (40 mg, 12%). $^1$H NMR: (400 MHz, CDCl$_3$) δ 8.70 (d, J=5.6 Hz, 2H), 7.56-7.54 (m, 2H), 7.51-7.50 (m, 2H), 7.47-7.45 (m, 3H), 7.14 (d, J=16.0 Hz, 1H), 6.97-6.91 (m, 3H), 3.79 (t, J=5.6 Hz, 2H), 3.64 (t, J=4.8 Hz, 2H), 3.27-3.21 (m, 4H), 2.15 (s, 3H); ESIMS: m/z=418.1 [(M+H)$^+$].

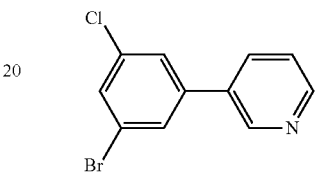

EXAMPLE 51

Synthesis of 3-(3-bromo-5-chlorophenyl) pyridine: To a stirred solution of 1,3-dibromo-5-chlorobenzene (600 mg, 2.20 mmol) and 3-(4,4,5,5-tetramethyl-1,3,2-dioxaborolan-2-yl)pyridine (455 mg, 2.20 mmol) in 1,4-dioaxane (15 mL) K$_2$CO$_3$ (920 mg, 6.60 mmol) was added and the mixture was degassed with argon for 20 minutes. Pd(PPh$_3$)$_4$ (76 mg, 0.06 mmol) was added to reaction mixture and degassed for another 20 minutes. The reaction mixture was refluxed under stirring for 8 hours and then filtered through celite pad. The filtrate was concentrated and the residue was purified by column chromatography on silica (100-200 mesh) eluting with 15% ethyl acetate in petroleum ether to afford the title compound as white solid (300 mg, 50%). $^1$H NMR: (400 MHz, CDCl$_3$) δ 8.80 (d, J=2.8 Hz, 1H), 8.66 (dd, J=5.2, 1.6 Hz, 1H), 7.84-7.81 (m, 1H), 7.61-7.60 (m, 1H), 7.56-7.55 (m, 1H), 7.50-7.49 (m, 1H), 7.41-7.37 (m, 1H); ESIMS: m/z=268.0 [(M+H)$^+$].

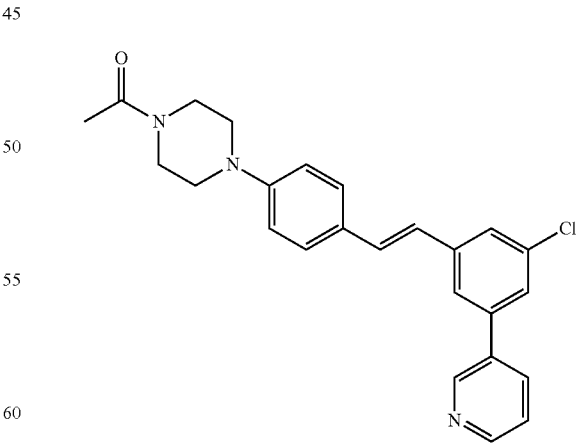

EXAMPLE 52

Synthesis of (E)-1-(4-(4-(3-chloro-5-(pyridin-3-yl)styryl) phenyl)piperazin-1-yl)ethanone: Triethylamine (0.38 mL, 3.7 mmol) was added to a stirred solution of 3-(3-bromo-5-chlorophenyl)pyridine (200 mg, 0.74 mmol) and 1-(4-(4-vinylphenyl)piperazin-1-yl)ethanone (205 mg, 0.89 mmol) in acetonitrile (10 mL) and the mixture was degassed with argon for 20 minutes. Pd(OAc)$_2$ (33 mg, 0.10 mmol), PPh$_3$ (234 mg, 0.80 mmol) were added to reaction mixture and degassed for another 20 minutes. The reaction mixture was then refluxed for 48 hours. Filtered through a celite pad, the filtrate was concentrated and the residue was purified by preparative thin layer chromatography (solvent system: ethyl acetate) to afford the title compound as off-white solid (50 mg, 16%). $^1$H NMR: (400 MHz, CDCl$_3$) δ 8.85 (d, J=1.6 Hz, 1H), 8.64 (d, J=3.2 Hz, 1H), 7.89-7.86 (m, 1H), 7.52-7.51 (m, 2H), 7.47 (d, J=8.8 Hz, 2H), 7.40-7.37 (m, 2H), 7.14 (d, J=16.8 Hz, 1H), 6.97-6.91 (m, 3H), 3.78 (t, J=5.2 Hz, 2H), 3.63 (t, J=5.2 Hz, 2H), 3.27-3.21 (m, 4H), 2.15 (s, 3H); ESIMS: m/z=418.2 [(M+H)$^+$].

mmol) and 1-(4-(4-vinylphenyl)piperazin-1-yl)ethanone (138 mg, 0.60 mmol) in acetonitrile (10 mL) and the mixture was degassed with argon for 20 minutes. Pd(OAc)$_2$ (22 mg, 0.10 mmol), PPh$_3$ (158 mg, 0.60 mmol) were added to reaction mixture and degassed for another 20 minutes. The reaction mixture was then refluxed for 48 hours. Filtered through a celite pad, the filtrate was concentrated and the residue was purified by preparative thin layer chromatography (solvent system: ethyl acetate) to afford the title compound as brown solid (25 mg, 11%). $^1$H NMR: (400 MHz, CDCl$_3$) δ 8.41 (d, J=2.0 Hz, 1H), 8.26 (d, J=2.8 Hz, 1H), 7.44-7.39 (m, 4H), 7.26-7.21 (m, 3H), 7.08 (d, J=16.4 Hz, 1H), 6.92-6.87 (m, 3H), 5.09 (s, 2H), 3.78 (t, J=4.8 Hz, 2H), 3.63 (t, J=5.6 Hz, 2H), 3.26-3.20 (m, 4H), 2.15 (s, 3H) ; ESIMS: m/z=447.9 [(M+H)$^+$].

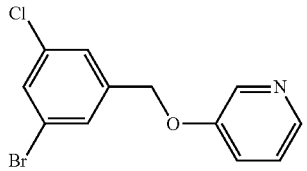

EXAMPLE 53

Synthesis of 3-(3-bromo-5-chlorobenzyloxy)pyridine: Sodium hydride (55% in paraffin, 180 mg, 3.9 mmol) was added to a stirred solution of pyridin-3-ol (1.0 g, 3.54 mmol) in THF (10 mL) at 0° C., after stirring for 15 min 1-bromo-3-(bromomethyl)-5-chlorobenzene (336 mg, 3.54 mmol) was added and the mixture was stirred at room temperature for 12 hours. The reaction mixture was poured into ice-water, extracted with ethyl acetate and washed with water followed by brine. Organic layer was dried (Na$_2$SO$_4$), filtered and concentrated to afford the title compound as brown solid (500 mg, 48%). $^1$H NMR: (300 MHz, CDCl$_3$) δ 8.38 (s, 1H), 8.27 (s, 1H), 7.49-7.48 (m, 2H), 7.37 (s, 1H), 7.24-7.23 (m, 2H), 5.05 (s, 2H); ESIMS: m/z=298.0 [(M+H)$^+$].

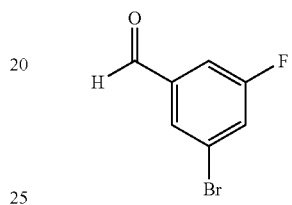

EXAMPLE 55

Synthesis of 3-bromo-5-fluorobenzaldehyde: 1,3-dibromo-5-fluorobenzene (10.0 g, 39.0 mmol) in tetrahydrofuran (10 mL) was added dropwise to a stirred solution of isopropyl magnesium chloride (1.3M in tetrahydrofuran, 36.0 mL, 46.0 mmol) in tetrahydrofuran (100 mL) at 0° C., and the reaction mixture was then stirred at room temperature for 3 hours. The reaction mixture was cooled to 0° C. and N,N-dimethylformamide (9.63 mL, 11.7 mmol) was added dropwise to the reaction mixture and stirred at room temperature for 1 hour. The reaction mixture was poured into ice water and extracted with ethyl acetate. The organic layer was washed with water followed by brine, dried (Na$_2$SO$_4$), filtered, concentrated to afford the title compound as light brown gum (6.0 gm, 75%). The crude material was used for next reaction without purification. $^1$H NMR: (400 MHz, CDCl$_3$) δ 9.93 (s, 1H), 7.82 (s, 1H), 7.53 (dd, J=4.4, 4.2 Hz, 2H).

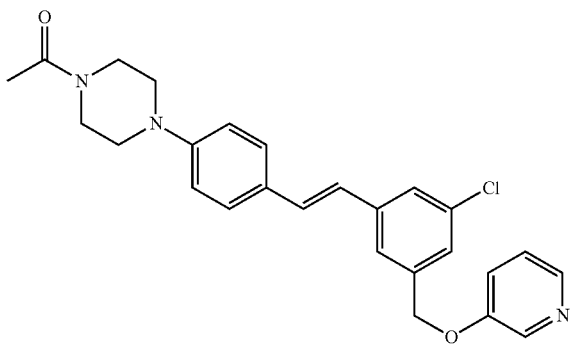 [SMILES: CC(=O)N1CCN(c2ccc(/C=C/c3cc(Cl)cc(COc4cccnc4)c3)cc2)CC1]

EXAMPLE 54

Synthesis of (E)-1-(4-(4-(3-chloro-5-((pyridin-3-yloxy)methyl)styryl)phenyl)piperazin-1-yl)ethanone: Triethylamine (0.21 mL, 1.50 mmol) was added to a stirred solution of 3-(3-bromo-5-chlorobenzyloxy)pyridine (150 mg, 0.50

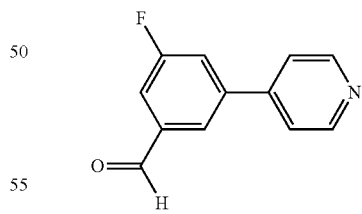

EXAMPLE 56

Synthesis of 3-fluoro-5-(pyridin-4-yl)benzaldehyde: To a stirred solution of 3-bromo-5-fluorobenzaldehyde (2.0 g, 9.7 mmol) and 4-(4,4,5,5-tetramethyl-1,3,2-dioxaborolan-2-yl)pyridine (2.18 g, 10.6 mmol) in 1,4-dioaxane (20 mL) K$_2$CO$_3$ (4.01 g, 43.6 mmol) was added and the mixture was degassed with argon for 20 minutes. Pd (PPh$_3$)$_4$ (560 mg, 0.485 mmol) was added to reaction mixture and was again degassed for 20 minutes, The reaction mixture was the refluxed under argon 8 hours. Filtered through a celite pad, the filtrate was concentrated and the residue was purified by column chromatography on silica (100-200 mesh) eluting 20% ethyl acetate in petroleum ether to afford the title compound as white solid (1.0 g, 52%). $^1$H NMR: (400 MHz, CDCl$_3$) δ 10.07 (s, 1H), 8.75 (d, J=6.0 Hz, 2H), 7.96 (s, 1H), 7.65 (dd, J=13.6, 7.6 Hz, 2H), 7.54 (d, J=1.6 Hz, 2H); ESIMS: m/z=202.0 [(M+H)$^+$].

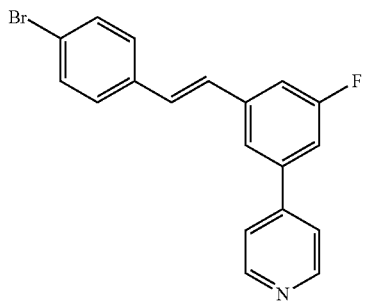 [SMILES: Fc1cc(/C=C/c2ccc(Br)cc2)cc(-c2ccncc2)c1]

EXAMPLE 57

Synthesis of (E)-4-(3-(4-bromostyryl)-5-fluorophenyl) pyridine: Sodium hydride (60% in paraffin, 340 mg, 4.95 mmol) was added to a stirred solution of (4-bromobenzyl) triphenylphosphonium bromide (2.5 g, 4.95 mmol) in dry tetrahydrofuran at 0° C. and stirred for 1 hour. 3-fluoro-5-(pyridin-4-yl) benzaldehyde (1.0 g, 4.95 mmol) in tetrahydrofuran (10 mL) was added to reaction mixture at 0° C. and was stirred for 1 hour. The reaction mixture was poured into water and was extracted with ethyl acetate. The organic layer was washed with water followed by brain, dried (Na$_2$SO$_4$), filtered and concentrated. The residue was purified using column chromatography on silica (100-200 mesh) eluting with 25% ethyl acetate in petroleum ether to afford the title compound as off-white solid (1.0 g , 57%). $^1$H NMR: (400 MHz, CDCl$_3$) δ 8.73 (d, J=5.6 Hz, 2H), 8.67 (d, J=5.6 Hz, 2H), 7.54-7.52 (m, 5H), 7.44-7.41 (m, 4H), 7.34-7.29 (m, 3H), 7.26-7.24 (m, 2H), 7.21-7.13 (m, 5H), 7.02-7.00 (m, 1H), 6.67 (d, J=4.0 Hz, 2H); ESIMS: m/z=356.0 [(M+2H)$^+$].

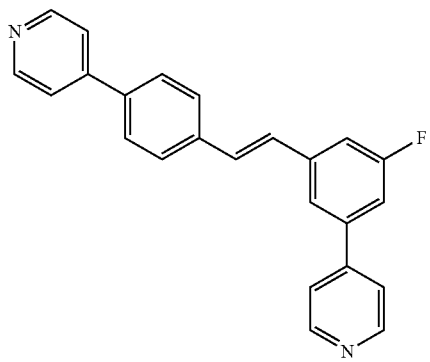 [SMILES: Fc1cc(/C=C/c2ccc(-c3ccncc3)cc2)cc(-c2ccncc2)c1]

EXAMPLE 57

Synthesis of (E)-4-(3-fluoro-5-(4-(pyridin-4-yl)styryl) phenyl)pyridine: To a stirred solution of (E,Z)-4-(3-(4-bromostyryl)-5-fluorophenyl) pyridine (200 mg, 0.56 mmol), 4-(4, 4, 5, 5-tetramethyl-1,3,2-dioxaborolan-2-yl)pyridine (127 mg, 0.62 mmol) in 1,4-dioaxane (10 mL) K$_2$CO$_3$ (233 mg , 1.6 mmol) was added, and the mixture was degassed with argon for 20 minutes. Pd(PPh$_3$)$_4$ (32 mg, 0. 02 mmol) was added to reaction mixture and again degassed for 20 minutes. The reaction mixture was refluxed under argon for 8 hours. and then filtered through a celite pad. The filtrate was concentrated and the residue was purified preparative thin layer chromatography (Solvent system: 90% EtOAc in petroleum ether) to afford the title product. $^1$H NMR: (400 MHz, CDCl$_3$) δ 8.72 (d, J=6.0 Hz, 2H), 8.68 (d, J=6.0 Hz, 2H), 7.70-7.68 (m, 4H), 7.54-7.52 (m, 5H), 7.34-7.31 (m, 2H), 7.23-7.21 (m, 2H); ESIMS: m/z=353.0 [(M+H)$^+$].

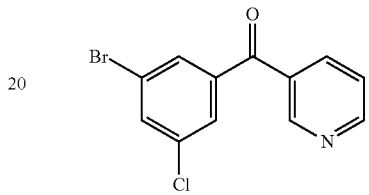

EXAMPLE 58

Synthesis of (3-bromo-5-chlorophenyl) (pyridin-3-yl) methanone: n-BuLi (2.1 M in hexane, 3.4 mL, 7.38 mmol) was added dropwise to a stirred solution of 1,3-dibromo-5-chlorobenzene (2.0 g, 7.38 mmol) in ether (50 mL) at −78° C. and the reaction mixture was stirred for 1 hour. 3-cyano pyridine (767 mg, 7.38 mmol) in ether (10 mL) was added drop wise at −78° C. and was stirred for 1 hour. The temperature was raised to room temperature and 2N HCl was added dropwise and the ether layer was separated. The ether layer was extracted several times with 2N HCl solution. The HCl solution was warmed to 50° C. for 15 minutes then was cooled to 0° C. and basified with 2N KOH solution, the precipitated solid was filtered to afford the title compound as yellow solid (1.3 g, 62%). $^1$H NMR: (400 MHz, DMSO-d$_6$) δ 8.90 (d, J=1.6 Hz, 1H), 8.68 (dd, J=1.2, 1.6 Hz, 1H), 8.15 (d, J=8.0 Hz, 1H), 8.1 (s, 1H), 7.85 (s, 1H), 7.77 (s, 1H), 7.63-7.60 (m, 1H); ESIMS: m/z=296.0 [(M+H)$^+$]

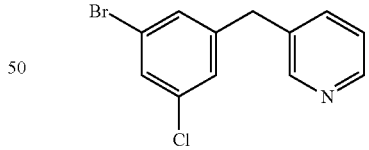

EXAMPLE 59

Synthesis of 3-(3-bromo-5-chlorobenzyl)pyridine: To a stirred solution of (3-bromo-5-chlorophenyl) (pyridin-3-yl) methanone (1.0 g, 3.37 mmol) in ethylene glycol (10 mL) hydrazine hydrate (1.3 mL, 26.97 mmol) was added and the mixture was heated to 180° C. for 30 min. The reaction temperature was brought to 80° C. and KOH (421 mg, 8.42 mmol) was added and was stirred at 180° C. for 30 minutes. Reaction mixture was cooled to room temperature and poured into water, extracted with ethyl acetate. The organic phase was dried (Na$_2$SO$_4$), filtered concentrated and the residue was purified by column chromatography on silica (100-200 mesh) eluting with 30% ethyl acetate in petroleum ether to afford the title compound as yellow liquid (700 mg, 70%). ¹H NMR: (400 MHz, CDCl₃) δ 8.52-8.48 (m, 2H), 7.46-7.43 (m, 1H), 7.39-7.38 (m, 1H), 7.26-7.25 (m, 1H), 7.24-7.21 (m, 1H), 7.10 (d, J=2.0 Hz, 1H), 3.92 (s, 2H); ESIMS: m/z=284.0 [(M+H)⁺].

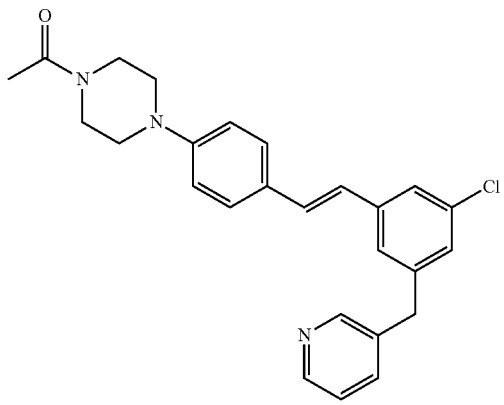 [SMILES: CC(=O)N1CCN(c2ccc(/C=C/c3cc(Cl)cc(Cc4cccnc4)c3)cc2)CC1]

EXAMPLE 60

Synthesis of (E)-1-(4-(4-(3-chloro-5-(pyridin-3-ylmethyl) styryl) phenyl) piperazin-1-yl)ethanone: To a stirred solution of 3-(3-bromo-5-chlorobenzyl) pyridine (100 mg, 0.353 mmol) and 1-(4-(4-vinylphenyl)piperazin-1-yl)ethanone (97 mg, 0.424 mmol) in acetonitrile (10 mL) tri ethyl amine (0.14 mL, 1.059 mmol) was added and the mixture was degassed with argon for 20 minutes. Pd(OAc)₂ (15 mg, 0.070 mmol), PPh₃ (111 mg, 0.424 mmol) were added and again degassed for 20 minutes. The reaction mixture was then refluxed under argon for 16 hours. The reaction mixture was poured into water and extracted with ethyl acetate. The organic phase was dried (Na₂SO₄), filtered, concentrated and the residue was purified by column chromatography on silica eluting with ethyl acetate to afford the title compound as yellow solid (29 mg, 19%). ¹H NMR:(300 MHz, CDCl₃) δ 8.52 (s, 2H), 7.50-7.34 (m, 5H), 7.13 (s, 1H), 7.04-6.98 (m, 2H), 6.91-6.81 (m, 3H), 3.95 (s, 2H), 3.78 (s, 2H), 3.63 (d, J=4.8 Hz, 2H), 3.22 (d, J=5.1 Hz, 4H), 2.14 (s, 3H); ESIMS: m/z=432.0 [(M+H)⁺].

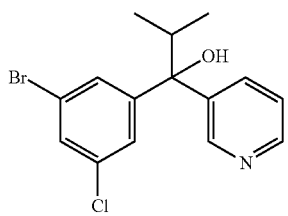

EXAMPLE 61

Synthesis of 1-(3-bromo-5-chlorophenyl)-2-methyl-1-(pyridin-3-yl) propan-1-ol: To a stirred solution of (3-bromo-5-chlorophenyl)(pyridin-3-yl)methanone (500 mg, 1.68 mmol) in tetrahydrofuran (10 mL) was added isopropyl magnesium chloride (2.0 M, 1.68 mL, 3.37 mmol) at 0° C. and stirring continued for 2 hours at the same temperature. The reaction mixture was then warmed to room temperature and was stirred for overnight. The mixture was poured into water and extracted with ethyl acetate. The organic layer was dried (Na₂SO₄), filtered and concentrated and the residue was purified by using column chromatography on silica (100-200 mesh) eluting with 50% ethyl acetate in petroleum ether to afford the title compound as yellow oil (210 mg, 36.5%). ¹H NMR: (400 MHz, CDCl₃) δ 8.74 (d, J=2.0 Hz, 1H), 8.47 (t, J=4.4 Hz, 1H), 7.80-7.77 (m, 1H), 7.53-7.52 (t, J=3.6 Hz, 1H), 7.42 (t, J=3.2 Hz, 1H), 7.35-7.34 (m, 1H), 7.27-7.24 (m, 1H), 4.14-4.09 (m, 1H), 2.86-2.80 (m, 1H), 0.91-0.88 (m, 6H); ESIMS: m/z=339.9 [(M+H)⁺].

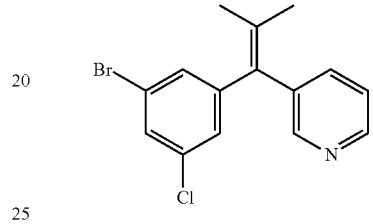

EXAMPLE 62

Synthesis of 3-(1-(3-bromo-5-chlorophenyl)-2-methylprop-1-enyl) pyridine: HBr in acetic acid solution (5 mL) was added to (1-(3-bromo-5-chlorophenyl)-2-methyl-1-(pyridin-3-yl) propan-1-ol (100 mg, 0.293 mmol) at 0° C. and the reaction mixture was then refluxed for overnight. The mixture was poured into water and extracted with ethyl acetate. The organic layer was washed with saturated NaHCO₃ solution, dried (Na₂SO₄), filtered and concentrated to afford the title compound as brown liquid (62 mg, 65%). ¹H NMR: (400 MHz, CDCl₃) δ 8.47 (d, J=5.2 Hz, 1H), 8.40 (s, 1H), 7.38-7.35 (m, 2H), 7.24-7.21 (m, 1H), 7.15-7.14 (t, J=2.8 Hz, 1H), 7.04-7.03 (m, 1H), 1.85-1.79 (m, 6H); ESIMS: m/z=321.9 [(M+H)⁺].

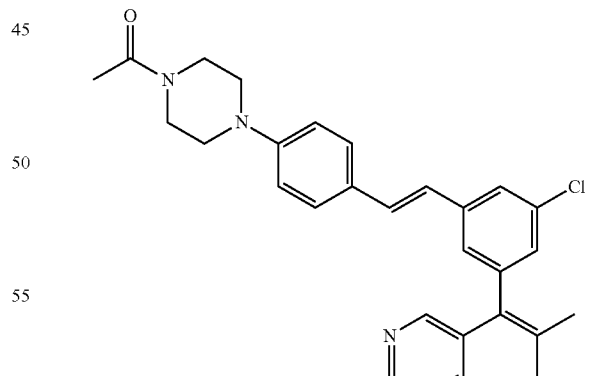

EXAMPLE 63

Synthesis of (E)-1-(4-(4-(3-chloro-5-(2-methyl-1-(pyridin-3-yl)prop-1-enyl)styryl)phenyl)piperazin-1-yl)ethanone: To a stirred solution of 3-(1-(3-bromo-5-chlorophenyl)-2-methylprop-1-enyl) pyridine (92 mg, 0.286 mmol)

and 1-(4-(4-vinylphenyl)piperazin-1-yl)ethanone (79 mg, 0.344 mmol) in acetonitrile (10 mL) triethylamine (0.11 mL, 0.858 mmol) was added and the mixture was degassed with argon for 20 minutes. Pd(OAc)$_2$ (12 mg, 0.057 mmol) and PPh$_3$ (90 mg, 0.34 mmol) were added and again degassed for 20 minutes. The reaction mixture was then refluxed under argon for 16 hours. The mixture was poured into water and extracted with ethyl acetate. The organic layer was dried (Na$_2$SO$_4$), filtered and concentrated and the residue was purified by preparative thin layer chromatography (Solvent system: ethyl acetate) to afford the title compound as brown solid (28 mg, 21%). $^1$H NMR: (300 MHz, CDCl$_3$) δ 8.47 (s, 2H), 7.40 (d, J=8.7 Hz, 3H), 7.34 (s, 2H), 7.19 (s, 1H), 7.07 (s, 1H), 6.97 (s, 1H), 6.91-6.86 (m, 3H), 3.78 (s, 2H), 3.63 (s, 2H), 3.22 (m, 4H), 2.14 (s, 3H), 1.29-1.25 (m, 6H); ESIMS: m/z=472.1 [(M+H)$^+$].

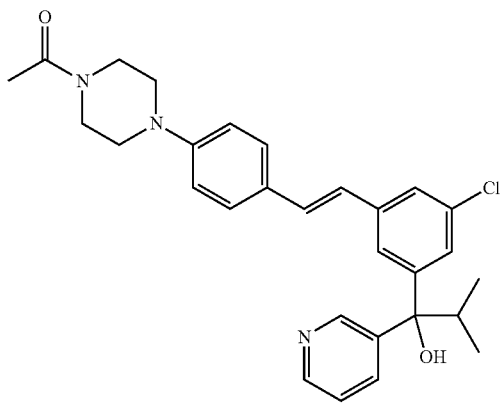 [SMILES: CC(=O)N1CCN(c2ccc(/C=C/c3cc(Cl)cc(C(O)(c4cccnc4)C(C)C)c3)cc2)CC1]

EXAMPLE 63

Synthesis of (E)-1-(4-(4-(3-chloro-5-(1-hydroxy-2-methyl-1-(pyridin-3-yl)propyl)styryl)phenyl)piperazin-1-yl)ethanone: To a stirred solution of (1-(3-bromo-5-chlorophenyl)-2-methyl-1-(pyridin-3-yl) propan-1-ol (100 mg, 0.293 mmol) and 1-(4-(4-vinylphenyl)piperazin-1-yl)ethanone (81 mg, 0.352 mmol) in acetonitrile (10 mL) triethylamine (0.12 mL, 0.879 mmol) was added and the mixture was degassed with argon for 20 minutes. Pd(OAc)$_2$ (13 mg, 0.06 mmol) and PPh$_3$ (92 mg, 0.35 mmol) were added and again degassed for 20 minutes. The reaction mixture was then refluxed under argon for 16 hours. The mixture was poured into water and extracted with ethyl acetate. The organic layer was dried (Na$_2$SO$_4$), filtered, concentrated and the residue was purified by preparative thin layer chromatography (Solvent system: ethyl acetate) to afford the title compound as brown solid (30 mg, 20%). $^1$H NMR: (300MHz, CDCl$_3$) δ 8.78 (s, 1H), 8.46 (d, J=3.9 Hz, 1H), 7.82 (d, J=7.8 Hz, 1H) 7.43-7.40 (m, 3H), 7.33 (s, 2H), 6.99 (d, J=16.5 Hz, 1H), 6.88 (d, J=8.4 Hz, 3H), 6.83 (s, 1H), 4.94 (s, 1H), 3.78 (d, J=6.0 Hz, 2H), 3.63 (d, J=5.4 Hz, 2H), 3.26-3.21 (m, 4H), 2.91-2.86 (m, 1H). 2.14 (s, 1H), 1.29-1.25 (m, 6H); ESIMS: m/z=490.0 [(M+H)$^+$].

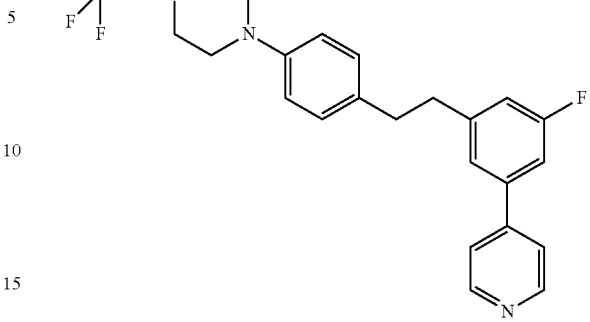

EXAMPLE 64

Synthesis of 1-(4-(3-fluoro-5-(pyridin-4-yl)phenethyl)phenyl)-4-(trifluoromethylsulfonyl)piperazine: 10% Pd-C (20 mg) was added to a solution of (E)-1-(4-(3-fluoro-5-(pyridin-4-yl)styryl)phenyl)-4-(trifluoromethylsulfonyl)piperazine (100 mg, 0.20 mmol) in EtOH (10 mL) and the reaction mixture was then stirred under H$_2$ (20 psi) at room temperature for 16 h. The reaction mixture was filtered through celite and the residue was washed with pentane to afford 1-(4-(3-fluoro-5-(pyridin-4-yl)phenethyl)phenyl)-4-(trifluoromethylsulfonyl)piperazine as off white solid (20 mg, 20%).$^1$H NMR (300 MHz, CDCl$_3$) δ 8.80-8.70 (m, 2H), 7.60-7.40 (m, 2H), 7.17-7.14 (m, 2H), 7.11 (d, J=8.4 Hz, 2H), 6.96-6.93 (m, 1H), 6.88 (d, J=8.4 Hz, 2H), 3.70-3.62 (m, 4H), 3.28-3.20 (m, 4H), 2.96-2.88 (m, 4H); ESIMS: m/z=494.1 [(M+H)$^+$].

The following compounds can be prepared by the procedure of 1-(4-(3-fluoro-5-(pyridin-4-yl)phenethyl)phenyl)-4-(trifluoromethylsulfonyl)piperazine. The skilled practitioner will know how to substitute the appropriate reagents, starting materials and purification methods known to those skilled in the art, in order to prepare the compounds provided herein.

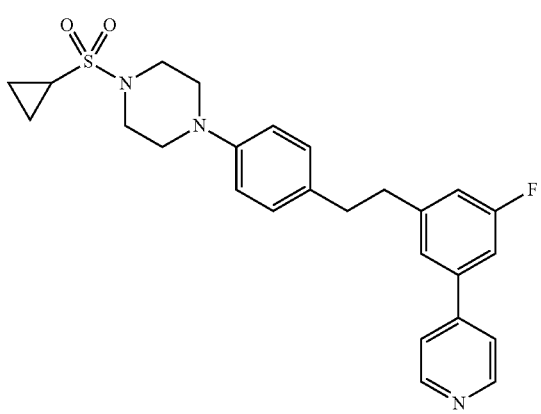 [SMILES: O=S(=O)(C1CC1)N1CCN(c2ccc(CCc3cc(F)cc(-c4ccncc4)c3)cc2)CC1]

EXAMPLE 65

Synthesis of 1-(cyclopropylsulfonyl)-4-(4-(3-fluoro-5-(pyridin-4-yl)phenethyl)phenyl)piperazine: The title compounds were prepared according to the procedure for 1-(4-

(3-fluoro-5-(pyridin-4-yl)phenethyl)phenyl)-4-(trifluoromethylsulfonyl)piperazine, except (E)-1-(cyclopropylsulfonyl)-4-(4-(3-fluoro-5-(pyridin-4-yl)styryl)phenyl)piperazine was substituted for 1-(4-(3-fluoro-5-(pyridin-4-yl)phenethyl)phenyl)-4-(trifluoromethylsulfonyl)piperazine. $^{1}$H NMR (400 MHz, CDCl$_3$) δ 8.70-8.64 (m, 2H), 7.43 (d, J=5.6 Hz, 2H), 7.15-7.14 (m, 2H), 7.10 (d, J=8.8 Hz, 2H), 6.95-6.93 (m, 1H), 6.89 (d, J=8.4 Hz, 2H), 3.47 (t, J=4.4 Hz, 4H), 3.23 (t, J=5.2 Hz, 4H), 2.98-2.88 (m, 4H), 2.32-2.28 (m, 1H), 1.23-1.19 (m, 2H), 1.04-1.00 (m, 2H); ESIMS: m/z=466.2 [(M+H)$^+$].

compounds were prepared according to the procedure for 1-(4-(3-fluoro-5-(pyridin-4-yl)phenethyl)phenyl)-4-(trifluoromethylsulfonyl)piperazine, except (E)-ethyl 2-(4-(4-(3-fluoro-5-(pyridin-4-yl)styryl)phenyl) piperazine-1-carboxamido)acetate was substituted for 1-(4-(3-fluoro-5-(pyridin-4-yl)phenethyl)phenyl)-4-(trifluoromethylsulfonyl)piperazine. $^{1}$H NMR (300 MHz, CDCl$_3$) δ 8.66 (d, J=5.7 Hz, 2H), 7.43 (d, J=6.0 Hz, 2H), 7.15-7.13 (m, 2H), 7.09 (d, J=8.7 Hz, 2H), 6.96-6.92 (m, 1H), 6.88 (d, J=8.2 Hz, 2H), 5.02-4.98 (m, 1H), 4.26-4.19 (m, 2H), 4.04-3.99 (m, 2H), 3.57 (t, J=4.8 Hz, 4H), 3.15 (t, J=5.1 Hz, 4H), 2.98-2.85 (m, 4H), 1.32-1.24 (m, 3H); ESIMS: m/z=491.2 [(M+H)$^+$].

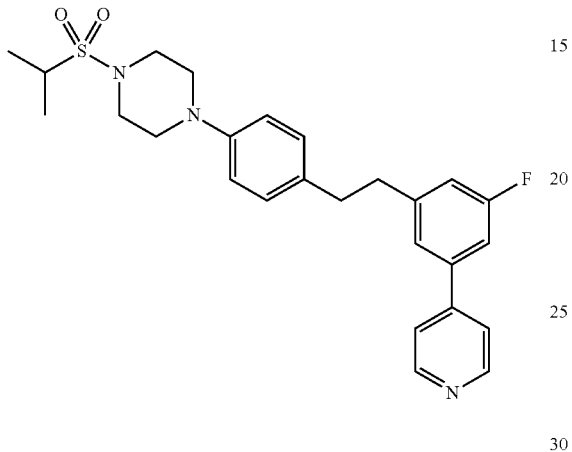

EXAMPLE 66

Synthesis of 1-(4-(3-fluoro-5-(pyridin-4-yl)phenethyl)phenyl)-4-(isopropylsulfonyl)piperazine: The title compounds were prepared according to the procedure for 1-(4-(3-fluoro-5-(pyridin-4-yl)phenethyl)phenyl)-4-(trifluoromethylsulfonyl)piperazine, except (E)-1-(4-(3-fluoro-5-(pyridin-4-yl)styryl)phenyl)-4-(isopropylsulfonyl)piperazine was substituted for 1-(4-(3-fluoro-5-(pyridin-4-yl)phenethyl)phenyl)-4-(trifluoromethylsulfonyl)piperazine. $^{1}$H NMR (400 MHz, CDCl$_3$) δ 8.70-8.62 (m, 2H), 7.43 (d, J=4.8 Hz, 2H), 7.40-7.15 (m, 2H), 7.09 (d, J=8.8 Hz, 2H), 6.95-6.93 (m, 1H), 6.88 (d, J=8.8 Hz, 2H), 3.53-3.49 (m, 4H), 3.24-3.17 (m, 5H), 2.97-2.87 (m, 4H), 1.38-1.37 (m, 6H); ESIMS: m/z=468.1 [(M+H)$^+$].

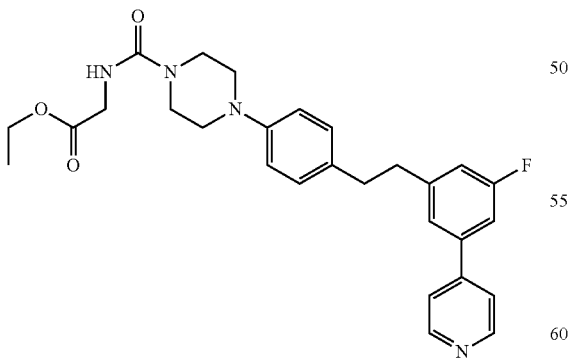

EXAMPLE 67

Synthesis of ethyl 2-(4-(4-(3-fluoro-5-(pyridin-4-yl)phenethyl)phenyl)piperazine-1-carboxamido)acetate: The title

EXAMPLE 68

Synthesis of 1-(ethylsulfonyl)-4-(4-(3-fluoro-5-(pyridin-4-yl)phenethyl)phenyl)piperazine: The title compounds were prepared according to the procedure for 1-(4-(3-fluoro-5-(pyridin-4-yl)phenethyl)phenyl)-4-(trifluoromethylsulfonyl)piperazine, except (E)-1-(ethylsulfonyl)-4-(4-(3-fluoro-5-(pyridin-4-yl)styryl)phenyl)piperazine was substituted for 1-(4-(3-fluoro-5-(pyridin-4-yl)phenethyl)phenyl)-4-(trifluoromethylsulfonyl) piperazine. $^{1}$H NMR (300 MHz, CDCl$_3$) δ 8.70-8.62 (m, 2H), 7.44 (d, J=4.5 Hz, 2H), 7.15-7.13 (m, 2H), 7.10 (d, J=8.4 Hz, 2H), 6.96-6.92 (m, 1H), 6.88 (d, J=8.4 Hz, 2H), 3.45 (t, J=4.8 Hz, 4H), 3.21 (t, J=4.8 Hz, 4H), 3.04-2.89 (m, 6H), 1.40 (t, J=7.2 Hz, 3H); ESIMS: m/z=454.0 [(M+H)$^+$].

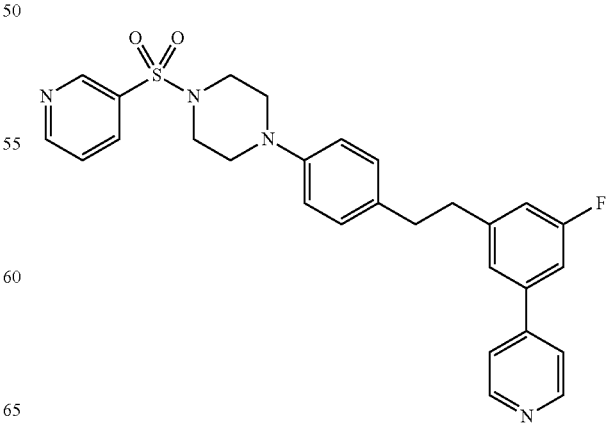

EXAMPLE 69

Synthesis of 1-(4-(3-fluoro-5-(pyridin-4-yl)phenethyl)phenyl)-4-(pyridin-3-ylsulfonyl)piperazine: The title compounds were prepared according to the procedure for 1-(4-(3-fluoro-5-(pyridin-4-yl)phenethyl)phenyl)-4-(trifluoromethylsulfonyl)piperazine, except (E)-1-(4-(3-fluoro-5-(pyridin-4-yl)styryl)phenyl)-4-(pyridin-3-ylsulfonyl)piperazine was substituted for 1-(4-(3-fluoro-5-(pyridin-4-yl)phenethyl)phenyl)-4-(trifluoromethylsulfonyl)piperazine. $^1$H NMR (300 MHz, CDCl$_3$) δ 9.03 (s, 1H), 8.86 (d, J=4.5 Hz, 1H), 8.68-8.62 (m, 2H), 8.10-8.07 (m, 1H), 7.53-7.49 (m, 1H), 7.42 (d, J=3.9 Hz, 2H), 7.18-7.10 (m, 2H), 7.07 (d, J=8.4 Hz, 2H), 6.94-6.91 (m, 1H), 6.82 (d, J=8.1 Hz, 2H), 3.27-3.20 (m, 8H), 2.93-2.84 (m, 4H); ESIMS: m/z=503.2 [(M+H)$^+$].

EXAMPLE 71

Synthesis of 1-(4-(4-(3-fluoro-5-(pyridin-4-yl)phenethyl)phenyl)piperazin-1-yl)ethanone: The title compounds were prepared according to the procedure for 1-(4-(3-fluoro-5-(pyridin-4-yl)phenethyl)phenyl)-4-(trifluoromethylsulfonyl)piperazine, except (E)-1-(4-(4-(3-fluoro-5-(pyridin-4-yl)styryl)phenyl)piperazin-1-yl)ethanone was substituted for 1-(4-(3-fluoro-5-(pyridin-4-yl)phenethyl)phenyl)-4-(trifluoromethylsulfonyl)piperazine. $^1$H NMR (400 MHz, CDCl$_3$) δ 8.66 (d, J=5.6 Hz, 2H), 7.43 (d, J=6.0 Hz, 2H), 7.15-7.13 (m, 2H), 7.09 (d, J=8.0 Hz, 2H), 6.95-6.93 (m, 1H), 6.88 (d, J=8.8 Hz, 2H), 3.77 (t, J=4.8 Hz, 2H), 3.61 (t, J=5.2 Hz, 2H), 3.15-3.10 (m, 4H), 2.97-2.87 (m, 4H), 2.14 (s, 3H); ESIMS: m/z=404.3 [(M+H)$^+$].

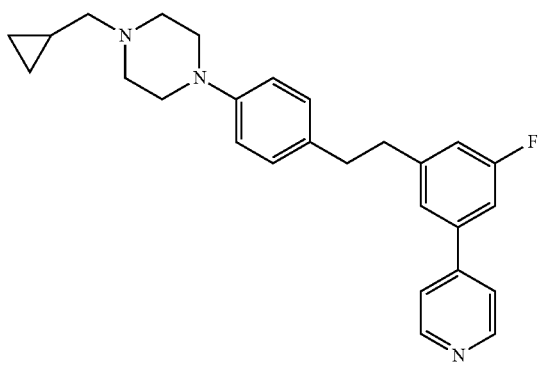 [SMILES: Fc1cc(CCc2ccc(N3CCN(CC4CC4)CC3)cc2)cc(-c2ccncc2)c1]

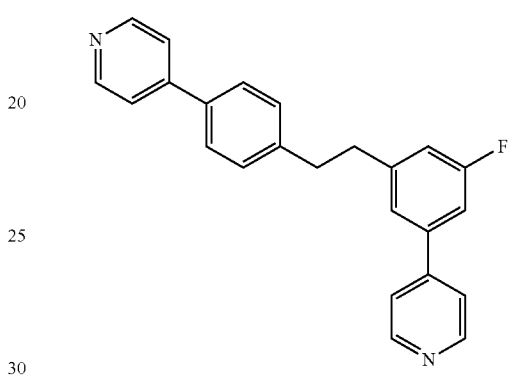

EXAMPLE 70

Synthesis of 1-(cyclopropylmethyl)-4-(4-(3-fluoro-5-(pyridin-4-yl)phenethyl)phenyl)piperazine: The title compounds were prepared according to the procedure for 1-(4-(3-fluoro-5-(pyridin-4-yl)phenethyl)phenyl)-4-(trifluoromethylsulfonyl)piperazine, except (E)-1-(cyclopropylmethyl)-4-(4-(3-fluoro-5-(pyridin-4-yl)styryl)phenyl)piperazine was substituted for 1-(4-(3-fluoro-5-(pyridin-4-yl)phenethyl)phenyl)-4-(trifluoromethylsulfonyl)piperazine. $^1$H NMR (400 MHz, CDCl$_3$) δ 8.66 (d, J=5.6 Hz, 2H), 7.42 (d, J=6.0 Hz, 2H), 7.15-7.13 (m, 2H), 7.07 (d, J=8.4 Hz, 2H), 6.96-6.94 (m, 1H), 6.88 (d, J=8.8 Hz, 2H), 3.26-3.20 (m, 4H), 2.97-2.93 (m, 2H), 2.89-2.87 (m, 2H), 2.78-2.70 (m, 4H), 2.37-2.35 (m, 2H), 0.89-0.88 (m, 1H), 0.56-0.55 (m, 2H), 0.15-0.14 (m, 2H); ESIMS: m/z=416.2 [(M+H)$^+$].

EXAMPLE 72

Synthesis of 4-(3-fluoro-5-(4-(pyridin-4-yl)phenethyl)phenyl)pyridine: The title compounds were prepared according to the procedure for 1-(4-(3-fluoro-5-(pyridin-4-yl)phenethyl)phenyl)-4-(trifluoromethylsulfonyl)piperazine, except (E)-4-(3-fluoro-5-(4-(pyridin-4-yl)styryl)phenyl)pyridine was substituted for 1-(4-(3-fluoro-5-(pyridin-4-yl)phenethyl)phenyl)-4-(trifluoromethylsulfonyl)piperazine. $^1$H NMR (400 MHz, CDCl$_3$) δ 8.65-8.64 (m, 4H), 7.59 (d. J=7.6 Hz, 2H), 7.50 (d, J=6.0 Hz, 2H), 7.42 (d, J=6.0 Hz, 2H), 7.30-7.26 (m, 2H), 7.18-7.16 (m, 2H), 6.99-6.96 (m, 1H), 3.10-3.00 (m, 4H); ESIMS: m/z=355.6 [(M+H)$^+$].

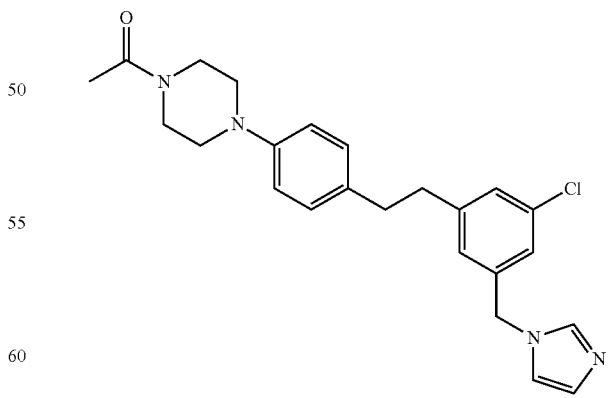

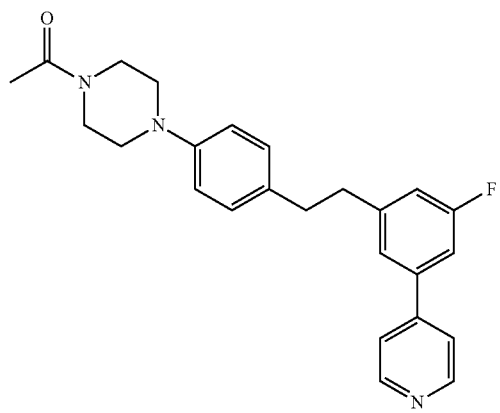 [SMILES: CC(=O)N1CCN(c2ccc(CCc3cc(F)cc(-c4ccncc4)c3)cc2)CC1]

EXAMPLE 73

Synthesis of 1-(4-(4-(3-((1H-imidazol-1-yl)methyl)-5-chlorophenethyl)phenyl)piperazin-1-yl)ethanone: The title compounds were prepared according to the procedure for 1-(4-(3-fluoro-5-(pyridin-4-yl)phenethyl)phenyl)-4-(trifluoromethylsulfonyl)piperazine, except (E)-1-(4-(4-(3-((1H-imidazol-1-yl)methyl)-5-chlorostyryl) phenyl)piperazin-1-yl)ethanone was substituted for 1-(4-(3-fluoro-5-(pyridin-4-yl)phenethyl)phenyl)-4-(trifluoromethyl sulfonyl) piperazine. $^1$H NMR (400 MHz, CDCl$_3$) δ 7.68-7.50 (m, 1H), 7.10 (s, 1H), 7.04-7.00 (m, 3H), 6.94 (s, 1H), 6.84-6.81 (m, 3H), 6.73 (s, 1H), 5.02 (s, 2H), 3.75 (t, J=5.2 Hz, 2H), 3.60 (t, J=4.8 Hz, 2H), 3.14-3.08 (m, 4H), 2.82-2.75 (m, 4H), 2.12 (s, 3H) ; ESIMS: m/z=422.9 [(M+H)$^+$].

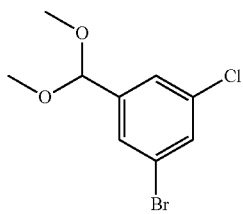

EXAMPLE 74

Synthesis of 1-bromo-3-chloro-5-(dimethoxymethyl)benzene: Trimethylorthoformate (3.6 mL, 34.15 mmol) was added drop wise to a stirred solution of 3-bromo-5-chlorobenzaldehyde (1.5 g, 6.8 mmol) and toluene-4-sulfonic acid. H$_2$O (0.129 g, 0.68 mmol) in methanol (15 mL) and the mixture was refluxed for 12 hours. The reaction mixture was poured into 10% NaHCO$_3$ solution and extracted with ethyl acetate. The organic layer was washed with water, brine and dried (Na$_2$SO$_4$) filtered and concentrated to afford the title compound as pale yellow liquid (1.4 g, 78%); $^1$H NMR: (400 MHz, CDCl$_3$,) δ 7.50-7.46 (m, 2H), 7.39 (s, 1H), 5.35 (s, 1H), 3.32 (s, 6H).

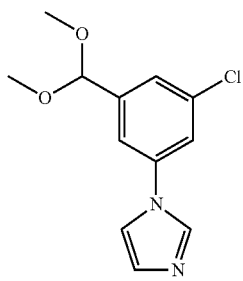 [SMILES: COC(OC)c1cc(Cl)cc(-n2ccnc2)c1]

EXAMPLE 75

Synthesis of 1-(3-chloro-5-(dimethoxymethyl)phenyl)-1H-imidazole: Sodium hydride (60% in paraffin, 180 mg, 7.6 mmol) was added to a stirred solution of imidazole in dry N,N-dimethylformamide (5.0 mL). After stirring at room temperature for 1 hour, 1-bromo-3-chloro-5-(dimethoxymethyl)benzene (1.0 g, 3.8 mmol) was added, followed by Cu powder (68 mg, 1.14 mmol). The reaction mixture was then heated at 150° C. for 36 hours. Reaction mixture was poured into ice-water and filtered. The filtrate was extracted with ethyl acetate, the organic layer was washed with water, followed by brine, dried (Na$_2$SO$_4$) filtered and concentrated and the residue was purified by column chromatography on silica (100-200 mesh) eluting with petroleum ether to afford the title compound as pale yellow liquid (0.3 g, 32%).$^1$H NMR: (300 MHz, CDCl$_3$,) δ 7.89 (s, 1H), 7.45-7.37(m, 3H), 7.31 (s, 1H), 7.26(s, 1H), 5.41 (s, 1H), 3.35(s, 6H). ESIMS: m/z 253.0 [(M+H)$^+$].

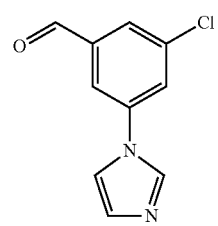 [SMILES: O=Cc1cc(Cl)cc(-n2ccnc2)c1]

EXAMPLE 76

Synthesis of 3-chloro-5-(1H-imidazol-1-yl)benzaldehyde: 4N HCl solution (20 mL) was added to a stirred solution of 1-(3-chloro-5-(dimethoxymethyl)phenyl)-1H-imidazole (0.2 g, 0.79 mmol) in methanol (10 mL) and the reaction mixture was stirred at room temperature for 16 hours. The reaction mixture was poured into 10% NaHCO$_3$ solution and extracted with ethyl acetate. The organic layer was washed with water, brine, dried (Na$_2$SO$_4$) filtered and concentrated to afford the title compound as pale yellow solid (0.15 g, 92%). $^1$H NMR: (300 MHz, CDCl$_3$) δ 0.05 (s, 1H), 8.20-8.00 (m, 1H), 7.84 (d, J=9.3 Hz, 2H), 7.67 (s, 1H), 7.50-7.30 (m, 2H). ESIMS: m/z=207 [(M+H)$^+$].

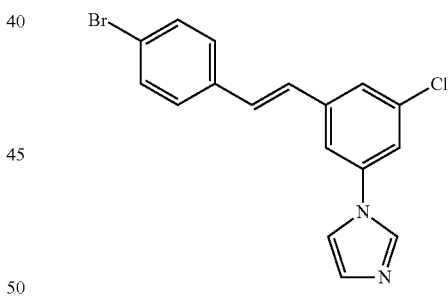

EXAMPLE 77

Synthesis of (E)-1-(3-(4-bromostyryl)-5-chlorophenyl)-1H-imidazole: To a stirred solution of (4-bromobenzyl) triphenylphosphonium bromide (2.5 g, 5.8 mmol) in dry toluene (10 mL) was added Potassium bis(trimethylsilyl) amide (0.11 mL, 11.68 mmol) at 0° C. and stirred for 30 minutes, then 3-chloro-5-(1H-imidazol-1-yl)benzaldehyde (0.3 g, 1.46 mmol) was added and stirred for 30 minutes at 0° C. The reaction mixture poured into ice water and extracted with ethyl acetate. The organic layer was washed with water followed by brine, and dried (Na$_2$SO$_4$). The crude product was recrystallized from ether to afford the title compound as off white sold (0.21 g, 41%). ¹H NMR: (300 MHz, CDCl₃,) δ 7.88 (s, 1H), 7.53-7.49 (m, 3H), 7.40-7.37 (m, 3H), 7.30 (s 2H), 7.26-7.24(m, 1H), 7.14 (d, J=16.2 Hz, 1H), 7.06 (d, J=16.2 Hz 1H). ESIMS: m/z=359 [(M+H)⁺].

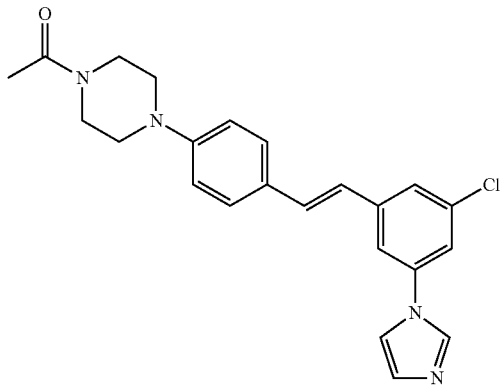 [SMILES: CC(=O)N1CCN(c2ccc(/C=C/c3cc(Cl)cc(-n4ccnc4)c3)cc2)CC1]

EXAMPLE 78

Synthesis of (E)-1-(4-(4-(3-chloro-5-(1H-imidazol-1-yl)styryl)phenyl)piperazin-1-yl)ethanone: To a stirred solution of (E)-1-(3-(4-bromostyryl)-5-chlorophenyl)-1H-imidazole (0.2 g, 0.56 mmol) in dry toluene (5.0 mL) was added 1-acetylpiperazine (0.093 g, 0.73 mmol) followed by cesium carbonate (0.36 g, 1.12 mmol) and the reaction mixture was degassed with argon gas for 10 minutes. 2-Dicyclohexylphosphino-2',4',6'-triisopropylbiphenyl (X-Phos, 0.026 g, 0.056 mmol), palladium acetate (0.012 g, 0.056 mmol) were added and degassed for another 10 minutes. The reaction mixture was then refluxed for 12 hours. The reaction mixture was filtered, concentrated and the residue was purified by column chromatography on silica (100-200 mesh) by gradient elution with 10% ethyl acetate in petroleum ether followed by 2% methanol in ethyl acetate to afford the title compound as pale yellow solid (35 mg, 16%) . ¹H NMR: (300 MHz, CDCl₃,) δ 7.66 (s, 1H), 7.47 (d, J=8.4 Hz 1H), 7.23-7.08 (m, 5H), 6.93(d, J=8.1 Hz 1H), 6.81 (d, J=8.4 Hz 2H), 6.68 (d, J=12 Hz 1H), 6.43 (d, J=12.0 Hz 1H), 3.78 (t, J=5.1 Hz, 2H), 3.63 (t, J=4.5 Hz, 2H), 3.28-3.16 (m, 4H), 2.14 (s, 3H). ESIMS: m/z=407 [(M+H)⁺].

EXAMPLE 79

Synthesis of (E)-1-(4-(3-fluoro-5-(pyridin-4-yl)styryl)phenyl)-4-(methylsulfonyl)piperazine: The title compounds were prepared according to the procedure for (E)-1-(cyclopropylsulfonyl)-4-(4-(3-fluoro-5-(pyridin-4-yl)styryl)phenyl)piperazine, except methanesulfonyl chloride was substituted for cyclopropanesulfonyl chloride. ¹H NMR: (300 MHz, CDCl₃) δ 8.70 (d, J=4.8 Hz, 2H), 7.52-7.45 (m, 5H), 7.27-7.24 (m, 1H), 7.19-7.16 (m, 1H), 7.14 (d, J=16.2 Hz, 1H), 7.01 (d, J=16.5 Hz, 1H), 6.95 (d, J=8.7 Hz, 2H), 3.38-3.34 (m, 8H), 2.83 (s, 3H); ESIMS: m/z=438.2 [(M+H)⁺].

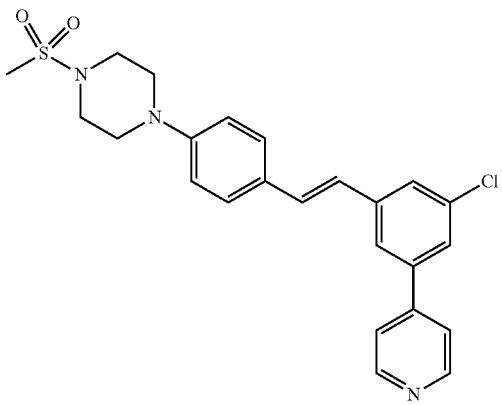 [SMILES: CS(=O)(=O)N1CCN(c2ccc(/C=C/c3cc(Cl)cc(-c4ccncc4)c3)cc2)CC1]

EXAMPLE 80

Synthesis of (E)-1-(4-(3-chloro-5-(pyridin-4-yl)styryl)phenyl)-4-(methylsulfonyl)piperazine: The title compounds were prepared according to the procedure for (E)-1-(cyclopropylsulfonyl)-4-(4-(3-fluoro-5-(pyridin-4-yl)styryl)phenyl)piperazine, except methanesulfonyl chloride was substituted for cyclopropanesulfonyl chloride and (E)-1-(4-(3-chloro-5-(pyridin-4-yl)styryl)phenyl)piperazine was substituted for (E)-1-(4-(3-fluoro-5-(pyridin-4-yl)styryl)phenyl)piperazine. ¹H NMR: (300 MHz, CDCl₃) δ 8.74-8.68 (m, 2H), 7.57-7.45 (m, 6H), 7.15 (d, J=16.5 Hz, 1H), 6.99-6.92 (m, 4H), 3.44-3.32 (m, 8H), 2.83 (s, 3H); ESIMS: m/z=454.2 [(M+H)⁺].

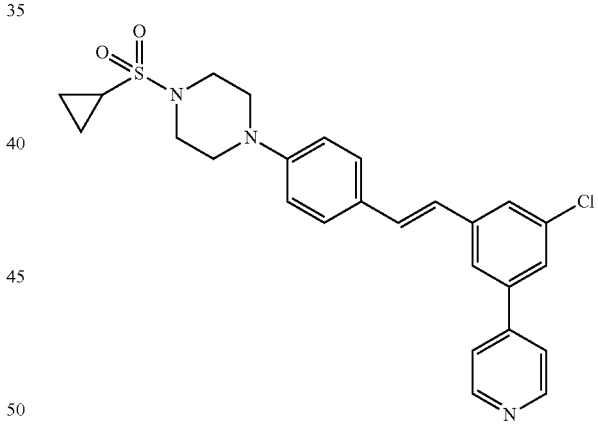

EXAMPLE 81

Synthesis of (E)-1-(4-(3-chloro-5-(pyridin-4-yl)styryl)phenyl)-4-(cyclopropylsulfonyl)piperazine: The title compounds were prepared according to the procedure for (E)-1-(cyclopropylsulfonyl)-4-(4-(3-fluoro-5-(pyridin-4-yl)styryl)phenyl)piperazine, except (E)-1-(4-(3-chloro-5-(pyridin-4-yl)styryl)phenyl)piperazine was substituted for (E)-1-(4-(3-fluoro-5-(pyridin-4-yl)styryl)phenyl)piperazine. ¹H NMR: (400 MHz, CDCl₃) δ 8.70 (d, J=4.4 Hz, 2H), 7.57-7.45 (m, 7H), 7.14 (d, J=16.0 Hz, 1H), 6.98-6.92 (m, 3H), 3.48 (t, J=4.4 Hz, 4H), 3.33 (t, J=5.2 Hz, 4H), 2.31-2.29 (m, 1H), 1.23-1.20 (m, 2H), 1.03-1.01 (m, 2H); ESIMS: m/z=480.2 [(M+H)⁺].

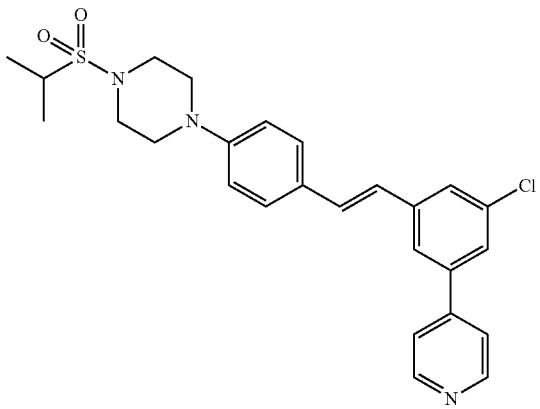 [SMILES: CC(C)S(=O)(=O)N1CCN(c2ccc(/C=C/c3cc(Cl)cc(-c4ccncc4)c3)cc2)CC1]

EXAMPLE 82

Synthesis of (E)-1-(4-(3-chloro-5-(pyridin-4-yl)styryl)phenyl)-4-(isopropylsulfonyl)piperazine: The title compounds were prepared according to the procedure for (E)-1-(cyclopropylsulfonyl)-4-(4-(3-fluoro-5-(pyridin-4-yl)styryl)phenyl)piperazine, except isopropylsulfonyl chloride was substituted for cyclopropanesulfonyl chloride and (E)-1-(4-(3-chloro-5-(pyridin-4-yl)styryl)phenyl)piperazine was substituted for (E)-1-(4-(3-fluoro-5-(pyridin-4-yl)styryl)phenyl)piperazine. $^1$H NMR: (400 MHz, CDCl$_3$); 8.70 (d, J=4.4 Hz, 2H), 7.56-7.44 (m, 7H), 7.14 (d, J=16.4 Hz, 1H), 6.98-6.91 (m, 3H), 3.53 (t, J=4.8 Hz, 4H), 3.28 (t, J=5.6 Hz, 4H), 3.25-3.22 (m, 1H), 1.41-1.37 (m, 6H); ESIMS: m/z=482.2 [(M+H)$^+$].

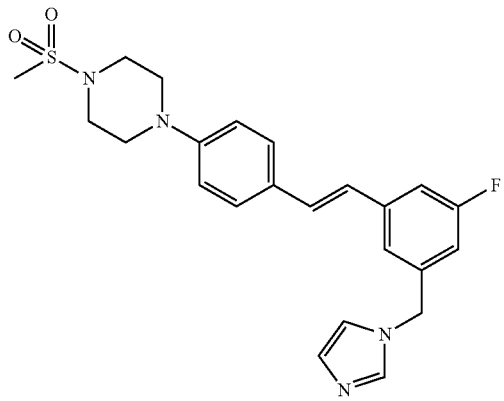 [SMILES: CS(=O)(=O)N1CCN(c2ccc(/C=C/c3cc(F)cc(Cn4ccnc4)c3)cc2)CC1]

EXAMPLE 83

Synthesis of (E)-1-(4-(3-((1H-imidazol-1-yl)methyl)-5-fluorostyryl)phenyl)-4-(methylsulfonyl)piperazine: The title compounds were prepared according to the procedure for (E)-1-(4-(3-((1H-imidazol-1-yl)methyl)-5-chlorostyryl)phenyl)-4-(3-(trifluoromethoxy)phenyl sulfonyl)piperazine, except methanesulfonyl chloride was substituted for 3-(trifluoromethoxy)benzene-1-sulfonyl chloride and (E)-1-(4-(3-((1H-imidazol-1-yl)methyl)-5-fluorostyryl)phenyl)piperazine was substituted for (E)-1-(4-(3-((1H-imidazol-1-yl)methyl)-5-chlorostyryl)phenyl)piperazine HCl. $^1$H NMR: (300 MHz, DMSO-d$_6$) δ 8.31 (s, 1H), 7.49-7.45 (m, 3H), 7.40-7.34 (m, 2H), 7.27-7.21 (m, 2H), 7.06-6.98 (m, 4H), 5.28 (s, 2H), 3.31-3.24 (m, 8H), 2.92 (s, 3H); ESIMS: m/z=441.2 [(M+H)$^+$].

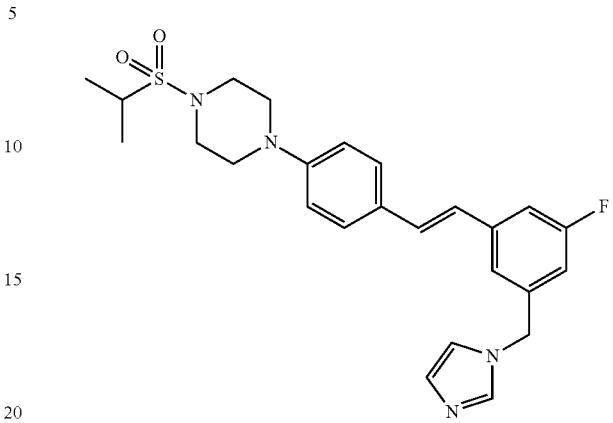

EXAMPLE 84

Synthesis of (E)-1-(4-(3-((1H-imidazol-1-yl)methyl)-5-fluorostyryl)phenyl)-4-(isopropylsulfonyl)piperazine: The title compounds were prepared according to the procedure for (E)-1-(4-(3-((1H-imidazol-1-yl)methyl)-5-chlorostyryl)phenyl)-4-(3-(trifluoromethoxy)phenyl sulfonyl)piperazine, except isopropylsulfonyl chloride was substituted for 3-(trifluoromethoxy)benzene-1-sulfonyl chloride and (E)-1-(4-(3-((1H-imidazol-1-yl)methyl)-5-fluorostyryl)phenyl)piperazine was substituted for (E)-1-(4-(3-((1H-imidazol-1-yl)methyl)-5-chlorostyryl)phenyl)piperazine HCl. $^1$H NMR: (300 MHz, CDCl$_3$) δ 7.61 (s, 1H), 7.43 (d, J=8.7 Hz, 2H), 7.15-7.13 (m, 2H), 7.04-6.98 (m, 2H), 6.93-6.83 (m, 4H), 6.71 (d, J=8.4 Hz, 1H), 5.12 (s, 2H), 3.52 (t, J=4.8 Hz, 4H), 3.27 (t, J=5.1 Hz, 4H), 3.23-3.18 (m, 1H), 1.43-1.33 (m, 6H); ESIMS: m/z=469.3 [(M+H)$^+$].

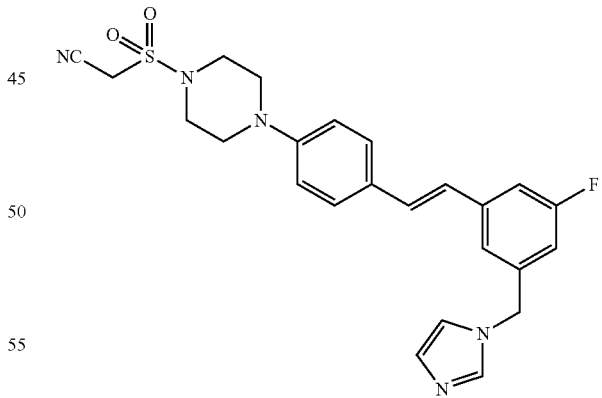

EXAMPLE 85

Synthesis of (E)-2-(4-(4-(3-((1H-imidazol-1-yl)methyl)-5-fluorostyryl)phenyl)piperazin-1-ylsulfonyl)acetonitrile: The title compounds were prepared according to the procedure for (E)-1-(4-(3-((1H-imidazol-1-yl)methyl)-5-chlorostyryl)phenyl)-4-(3-(trifluoromethoxy)phenyl sulfonyl)piperazine, except cyanomethanesulfonyl chloride was substituted for 3-(trifluoromethoxy)benzene-1-sulfonyl chloride and (E)-1-(4-(3-((1H-imidazol-1-yl)methyl)-5-fluorostyryl)phenyl)piperazine was substituted for (E)-1-(4-(3-((1H-imidazol-1-yl)methyl)-5-chlorostyryl)phenyl)piperazine HCl. $^1$H NMR: (400 MHz, CDCl$_3$) δ 7.58 (s, 1H), 7.44 (d, J=9.2 Hz, 2H), 7.15-7.13 (m, 2H), 7.03-6.85 (m, 6H), 6.71 (d, J=8.8 Hz, 1H), 5.12 (s, 2H), 3.98 (s, 2H), 3.66 (t, J=5.2 Hz, 4H), 3.34 (t, J=4.8 Hz, 4H); ESIMS: m/z=466.5 [(M+H)$^+$].

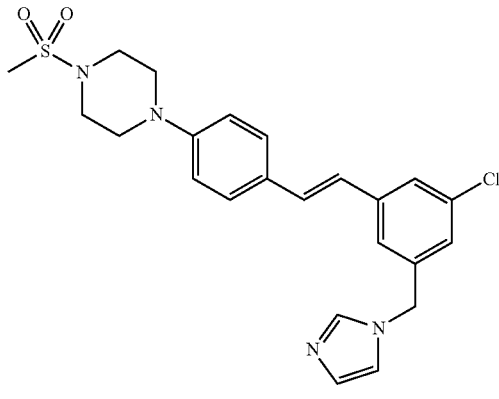 [SMILES: CS(=O)(=O)N1CCN(c2ccc(/C=C/c3cc(Cl)cc(Cn4ccnc4)c3)cc2)CC1]

EXAMPLE 86

Synthesis of (E)-1-(4-(3-((1H-imidazol-1-yl)methyl)-5-chlorostyryl)phenyl)-4-(methylsulfonyl)piperazine: The title compounds were prepared according to the procedure for (E)-1-(4-(3-((1H-imidazol-1-yl)methyl)-5-chlorostyryl)phenyl)-4-(3-(trifluoromethoxy)phenyl sulfonyl)piperazine, except methanesulfonyl chloride was substituted for 3-(trifluoromethoxy)benzene-1-sulfonyl chloride. $^1$H NMR: (400 MHz, CDCl$_3$) δ 7.66 (s, 1H), 7.43-7.41 (m, 3H), 7.16 (s, 1H), 7.06-6.94 (m, 4H), 6.92 (d, J=7.6 Hz, 2H), 6.86 (d, J=16 Hz, 1H), 5.11 (s, 2H), 3.39-3.33 (m, 8H), 2.83 (s, 3H); ESIMS: m/z=457.2 [(M+H)$^+$].

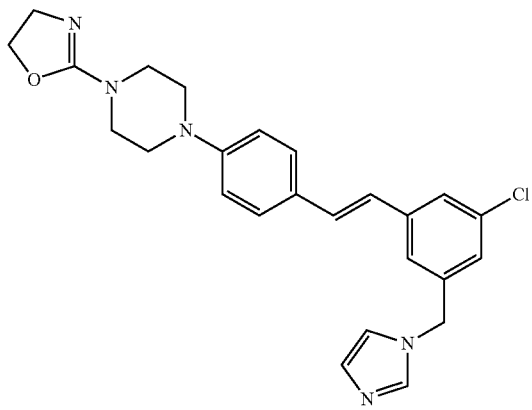 [SMILES: Clc1cc(/C=C/c2ccc(N3CCN(C4=NCCO4)CC3)cc2)cc(Cn2ccnc2)c1]

EXAMPLE 87

Synthesis of (E)-2-(4-(4-(3-((1H-imidazol-1-yl)methyl)-5-chlorostyryl)phenyl)piperazin-1-yl)-4,5-dihydrooxazole: (E)-1-(4-(3-((1H-imidazol-1-yl)methyl)-5-chlorostyryl)phenyl)piperazine (100 mg, 0.26 mmol) was dissolved in methylene chloride (5 mL), 1-chloro-2-isocyanatoethane (33.3 mg, 31.2 mmol) was added, and the reaction was heated to reflux. After 18 hours, the reaction was cooled to room temperature and stripped of solvent. The residue was dissolved in triethyl amine (5 mL) and heated to reflux for 24 hours. The reaction was then cooled, stripped of solvent, and the residue was purified by prep TLC to afford the title compound. $^1$H NMR: (400 MHz, CDCl$_3$) δ 7.60 (s, 1H), 7.41-7.39 (m, 3H), 7.18-7.10 (m, 1H), 7.08-7.03 (m, 2H), 6.99 (d, J=8.4 Hz, 2H), 6.92 (d, J=8.8 Hz, 2H), 6.84 (d, J=16.4 Hz, 1H), 5.10 (s, 2H), 4.35-4.31 (m, 2H), 3.84-3.79 (m, 2H), 3.56-3.54 (m, 4H), 3.25-3.21 (m, 4H); ESIMS: m/z=448.2 [(M+H)$^+$].

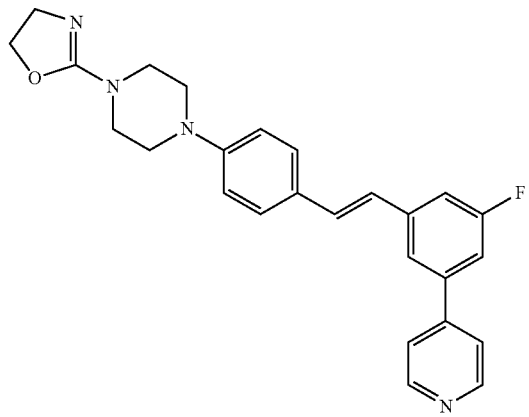 [SMILES: Fc1cc(/C=C/c2ccc(N3CCN(C4=NCCO4)CC3)cc2)cc(-c2ccncc2)c1]

EXAMPLE 88

Synthesis of (E)-2-(4-(4-(3-fluoro-5-(pyridin-4-yl)styryl)phenyl)piperazin-1-yl)-4,5-dihydrooxazole: The title compounds were prepared according to the procedure for (E)-2-(4-(4-(3-((1H-imidazol-1-yl)methyl)-5-chlorostyryl)phenyl)piperazin-1-yl)-4,5-dihydrooxazole except that (E)-1-(4-(3-fluoro-5-(pyridin-4-yl)styryl)phenyl)piperazine was substituted for (E)-1-(4-(3-((1H-imidazol-1-yl)methyl)-5-chlorostyryl)phenyl)piperazine. $^1$H NMR: (400 MHz, CDCl$_3$) δ 8.70 (d, J=6.0 Hz, 2H), 7.52-7.44 (m, 5H), 7.30-7.26 (m, 1H), 7.19-7.14 (m, 1H), 7.09-7.00 (m, 1H), 6.94-6.92 (m, 3H), 4.33 (t, J=8.7 Hz, 2H), 3.82 (t, J=8.7 Hz, 2H), 3.56 (t, J=4.8 Hz, 4H), 3.25 (t, J=5.1 Hz, 4H); ESIMS: m/z=429.0 [(M+H)$^+$].

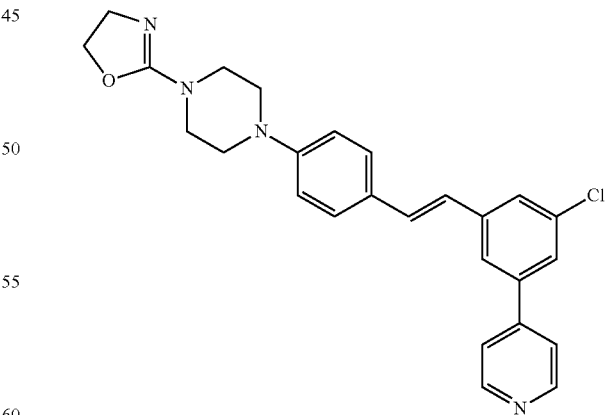

EXAMPLE 89

Synthesis of (E)-2-(4-(4-(3-chloro-5-(pyridin-4-yl)styryl)phenyl)piperazin-1-yl)-4,5-dihydrooxazole: The title compounds were prepared according to the procedure for(E)-2-

(4-(4-(3-((1H-imidazol-1-yl)methyl)-5-chlorostyryl)phenyl)piperazin-1-yl)-4,5-dihydrooxazole except that (E)-1-(4-(3-chloro-5-(pyridin-4-yl)styryl)phenyl)piperazine was substituted for (E)-1-(4-(3-((1H-imidazol-1-yl)methyl)-5-chlorostyryl)phenyl)piperazine. $^1$H NMR: (400 MHz, CDCl$_3$) δ 8.70 (d, J=5.2 Hz, 2H), 7.56-7.50 (m, 4H), 7.46-7.44 (m, 3H), 7.14 (d, J=16.4 Hz, 1H), 6.97-6.92 (m, 3H), 4.34 (t, J=8.8 Hz, 2H), 3.82 (t, J=8.8 Hz, 2H), 3.60-3.55 (m, 4H), 3.25 (t, J=5.44 Hz, 4H); ESIMS: m/z=445.2 [(M+H)$^+$].

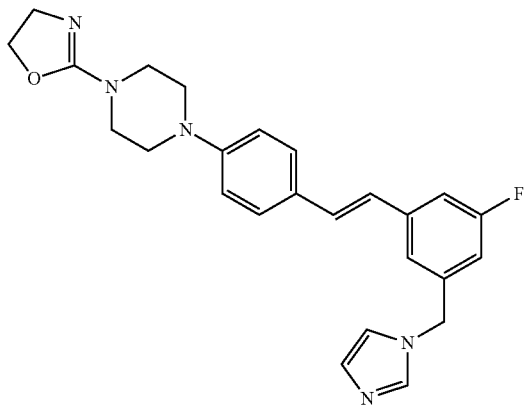 [SMILES: Fc1cc(/C=C/c2ccc(N3CCN(C4=NCCO4)CC3)cc2)cc(Cn2ccnc2)c1]

EXAMPLE 90

Synthesis of (E)-2-(4-(4-(3-((1H-imidazol-1-yl)methyl)-5-fluorostyryl)phenyl)piperazin-1-yl)-4,5-dihydrooxazole: The title compounds were prepared according to the procedure for (E)-2-(4-(4-(3-((1H-imidazol-1-yl)methyl)-5-chlorostyryl)phenyl)piperazin-1-yl)-4,5-dihydrooxazole except that (E)-1-(4-(3-((1H-imidazol-1-yl)methyl)-5-fluorostyryl)phenyl)piperazine was substituted for (E)-1-(4-(3-((1H-imidazol-1-yl)methyl)-5-chlorostyryl)phenyl)piperazine. $^1$H NMR: (300 MHz, CDCl$_3$) δ 7.58 (s, 1H), 7.42 (d, J=7.8 Hz, 2H), 7.16-7.10 (m, 2H), 7.03-6.82 (m, 6H), 6.70-6.67 (m, 1H), 5.11 (s, 2H), 4.33 (t, J=9.0 Hz, 2H), 3.82 (t, J=8.4 Hz, 2H), 3.60-3.50 (m, 4H), 3.28-3.20 (m, 4H); ESIMS: m/z=432.1 [(M+H)$^+$].

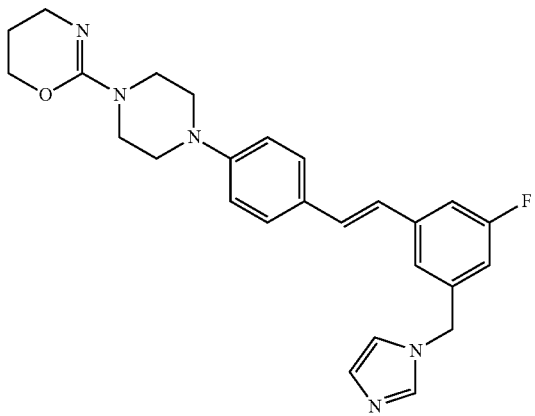 [SMILES: Fc1cc(/C=C/c2ccc(N3CCN(C4=NCCCO4)CC3)cc2)cc(Cn2ccnc2)c1]

EXAMPLE 91

Synthesis of (E)-2-(4-(4-(3-((1H-imidazol-1-yl)methyl)-5-fluorostyryl)phenyl)piperazin-1-yl)-5,6-dihydro-4H-1,3-oxazine: The title compounds were prepared according to the procedure for (E)-2-(4-(4-(3-((1H-imidazol-1-yl)methyl)-5-chlorostyryl)phenyl)piperazin-1-yl)-4,5-dihydrooxazole except that (E)-1-(4-(3-((1H-imidazol-1-yl)methyl)-5-fluorostyryl)phenyl)piperazine was substituted for (E)-1-(4-(3-((1H-imidazol-1-yl)methyl)-5-chlorostyryl)phenyl)piperazine and 1-chloro-3-isocyanatopropane was substituted for 1-chloro-2-isocyanatoethane. $^1$H NMR: (300 MHz, CDCl$_3$) δ 7.58 (s, 1H), 7.43 (d, J=8.7 Hz, 2H), 7.15-7.13 (m, 2H), 7.03-6.98 (m, 2H), 6.93-6.82 (m, 4H), 6.70 (d, J=8.7 Hz, 1H), 5.11 (s, 2H), 3.63 (t, J=6.3 Hz, 2H), 3.54 (t, J=4.5 Hz, 4H), 3.47-3.43 (m, 2H), 3.25 (t, J=5.4 Hz, 4H), 2.08-1.99 (m, 2H); ESIMS: m/z=446.0 [(M+H)$^+$].

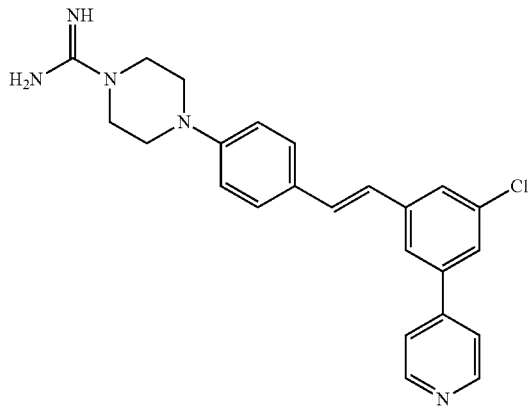 [SMILES: N=C(N)N1CCN(c2ccc(/C=C/c3cc(Cl)cc(-c4ccncc4)c3)cc2)CC1]

EXAMPLE 92

Synthesis of (E)-4-(4-(3-chloro-5-(pyridin-4-yl)styryl)phenyl)piperazine-1-carboximidamide: (E)-1-(4-(3-chloro-5-(pyridin-4-yl)styryl)phenyl)piperazine (100 mg, 0.27 mmol) and triethyl amine (40.4 mg, 56 uL, 0.4 mmol) were dissolved in tetrahydrofuran (5 ml), 1H-pyrazole-1-carboximidamide hydrochloride (46.7 mg, 0.32 mmol) was added, and the reaction was stirred at reflux for 24 hours. The reaction was then cooled to room temperature, the solvents were removed under vacuum, and the residual material was purified by prep TLC to afford the title compound. $^1$H NMR: (300 MHz, DMSO-d$_6$) δ 8.68-8.67 (m, 2H), 7.94 (s, 1H), 7.81-7.79 (m, 2H), 7.73 (d, J=7.8 Hz, 2H), 7.53-7.41 (m, 6H), 7.16 (d, J=16.5 Hz, 1H), 7.03-7.00 (m, 2H), 3.62-3.56 (m, 4H), 3.36-3.30 (m, 4H); ESIMS: m/z=418.2 [(M+H)$^+$].

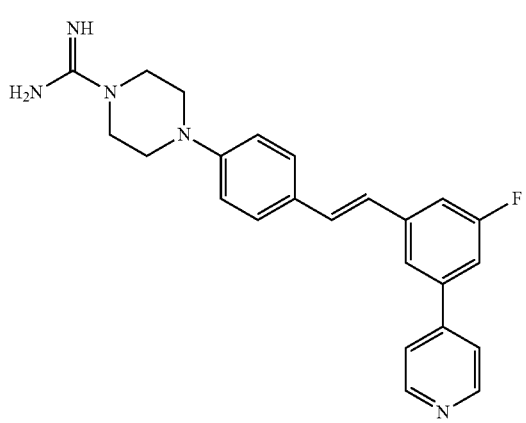 [SMILES: N=C(N)N1CCN(c2ccc(/C=C/c3cc(F)cc(-c4ccncc4)c3)cc2)CC1]

EXAMPLE 93

Synthesis of (E)-4-(4-(3-fluoro-5-(pyridin-4-yl)styryl)phenyl)piperazine-1-carboximidamide: The title compounds were prepared according to the procedure for (E)-4-(4-(3-chloro-5-(pyridin-4-yl)styryl)phenyl)piperazine-1-carboximidamide except that (E)-1-(4-(3-fluoro-5-(pyridin-4-yl)styryl)phenyl)piperazine was substituted for (E)-1-(4-(3-chloro-5-(pyridin-4-yl)styryl)phenyl)piperazine. $^1$H NMR: (300 MHz, DMSO-$d_6$) δ 8.67 (d, J=6.3 Hz, 2H), 7.83-7.78 (m, 3H), 7.53-7.49 (m, 4H), 7.42-7.37 (m, 4H), 7.16-7.12 (m, 1H), 7.02 (d, J=8.7 Hz, 2H), 3.60-3.55 (m, 4H), 3.34-3.29 (m, 4H); ESIMS: m/z 402.2=[(M+H)$^+$].

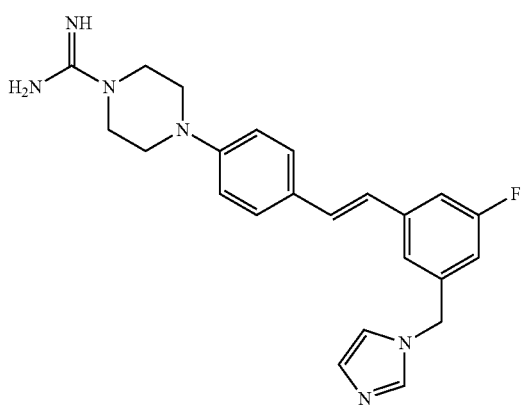 [SMILES: N=C(N)N1CCN(c2ccc(/C=C/c3cc(F)cc(Cn4ccnc4)c3)cc2)CC1]

EXAMPLE 94

Synthesis of (E)-4-(4-(3-((1H-imidazol-1-yl)methyl)-5-fluorostyryl)phenyl)piperazine-1-carboximidamide: The title compounds were prepared according to the procedure for (E)-4-(4-(3-chloro-5-(pyridin-4-yl)styryl)phenyl)piperazine-1-carboximidamide except that (E)-1-(4-(3-((1H-imidazol-1-yl)methyl)-5-fluorostyryl)phenyl)piperazine was substituted for (E)-1-(4-(3-chloro-5-(pyridin-4-yl)styryl)phenyl)piperazine. $^1$H NMR: (300 MHz, DMSO-$d_6$) δ 7.79 (s, 1H), 7.49-7.46 (m, 5H), 7.36-7.33 (m, 1H), 7.27-7.20 (m, 3H), 7.05-6.92 (m, 5H), 5.20 (s, 2H), 3.61-3.55 (m, 4H), 3.34-3.28 (m, 4H); ESIMS: m/z=405.0 [(M+H)$^+$].

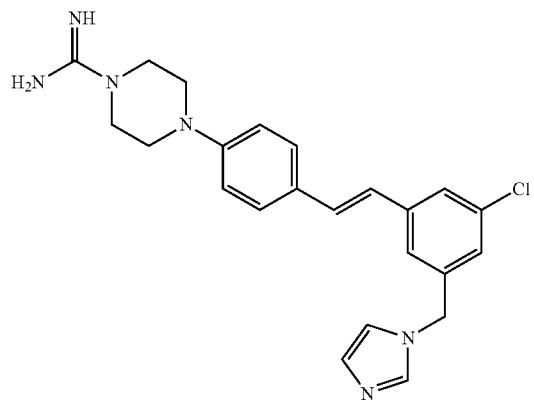 [SMILES: N=C(N)N1CCN(c2ccc(/C=C/c3cc(Cl)cc(Cn4ccnc4)c3)cc2)CC1]

EXAMPLE 95

Synthesis of (E)-4-(4-(3-((1H-imidazol-1-yl)methyl)-5-chlorostyryl)phenyl)piperazine-1-carboximidamide: The title compounds were prepared according to the procedure for (E)-4-(4-(3-chloro-5-(pyridin-4-yl)styryl)phenyl)piperazine-1-carboximidamide except that (E)-1-(4-(3-((1H-imidazol-1-yl)methyl)-5-chlorostyryl)phenyl)piperazine was substituted for (E)-1-(4-(3-chloro-5-(pyridin-4-yl)styryl)phenyl)piperazine. $^1$H NMR: (400 MHz, CDCl$_3$) δ 7.84-7.81 (m, 4H), 7.57 (s, 1H), 7.49-7.44 (m, 3H), 7.27-7.14 (m, 3H), 7.04-6.92 (m, 4H), 5.21 (s, 2H), 3.65-3.58 (m, 4H), 3.35-3.25 (m, 4H); ESIMS; ESIMS: m/z=421.2 [(M+H)$^+$].

EXAMPLE 96

The compounds in the Table 22 below and in FIG. 2 represent the extraction of over 200 compounds which realized the in vitro and in vivo goals. The target goals are defined in FIG. 1. As seen in FIG. 2 and the table below, the in vitro goals are defined by efficacy targets: CYP17, CYP11, and CYP21. The off-target enzymes (where potency should be low) are CYP 19 and CYP3A4. Other parameters are no liver effects also estimated by bile acid synthesis inhibition.

Table 22: Representative examples of compounds of the disclosure and their potencies in Cyp17, Cyp11, and Cyp21 assays.

| Entry | Structure | Cyp17 | Cyp11 | Cyp21 |
|---|---|---|---|---|
| | | IC$_{50}$ (nM) | | |
| 1 | (structure) | 2500 | 1300 | 10000 |

-continued
| Entry | Structure | Cyp17 | Cyp11 IC$_{50}$ (nM) | Cyp21 |
|---|---|---|---|---|
| 2 | 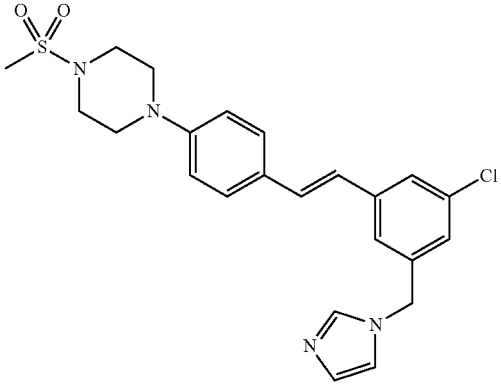 [SMILES: CS(=O)(=O)N1CCN(c2ccc(/C=C/c3cc(Cl)cc(Cn4ccnc4)c3)cc2)CC1] | 180 | 24 | 2200 |
| 3 | 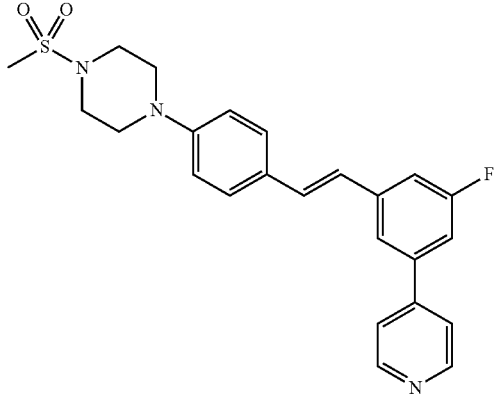 [SMILES: CS(=O)(=O)N1CCN(c2ccc(/C=C/c3cc(F)cc(-c4ccncc4)c3)cc2)CC1] | 5 | 200 | 740 |
| 4 | 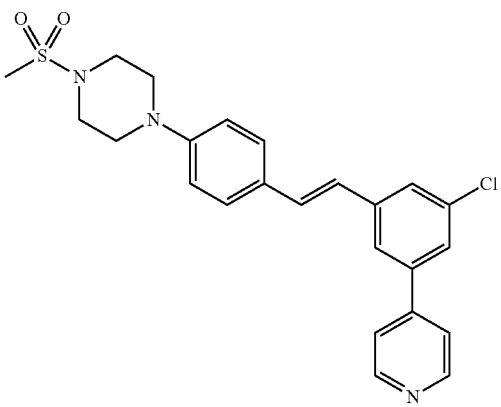 [SMILES: CS(=O)(=O)N1CCN(c2ccc(/C=C/c3cc(Cl)cc(-c4ccncc4)c3)cc2)CC1] | 5 | 450 | 840 |
| 5 | 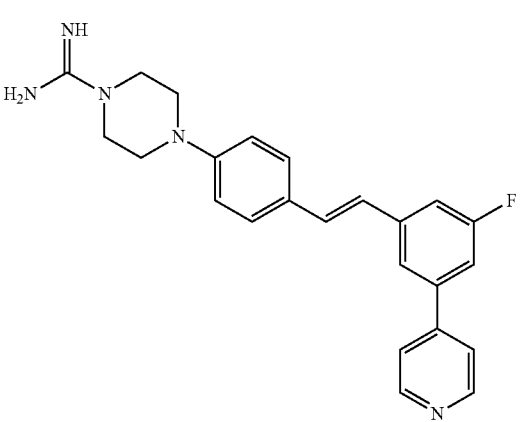 [SMILES: N=C(N)N1CCN(c2ccc(/C=C/c3cc(F)cc(-c4ccncc4)c3)cc2)CC1] | 18 | 3600 | 10000 |

-continued
| Entry | Structure | Cyp17 | Cyp11 | Cyp21 |
|---|---|---|---|---|
| | | | IC$_{50}$ (nM) | |
| 6 | 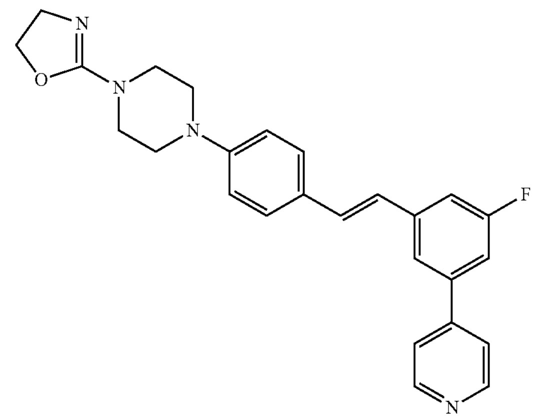 [SMILES: Fc1cc(/C=C/c2ccc(N3CCN(C4=NCCO4)CC3)cc2)cc(-c2ccncc2)c1] | 5 | 1800 | 1200 |
| 7 | 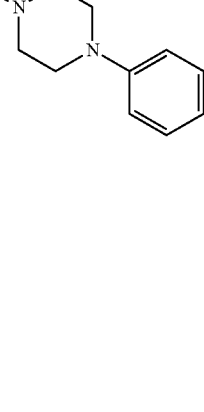 | 5 | 51 | 416 |
| 8 | 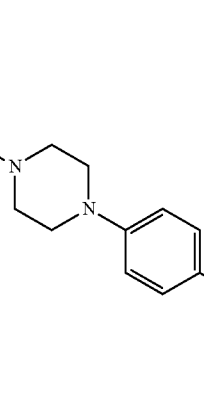 | 5 | 58 | 565 |

-continued

| Entry | Structure | Cyp17 | Cyp11 IC$_{50}$ (nM) | Cyp21 |
|-------|-----------|-------|------|-------|
| 9 | 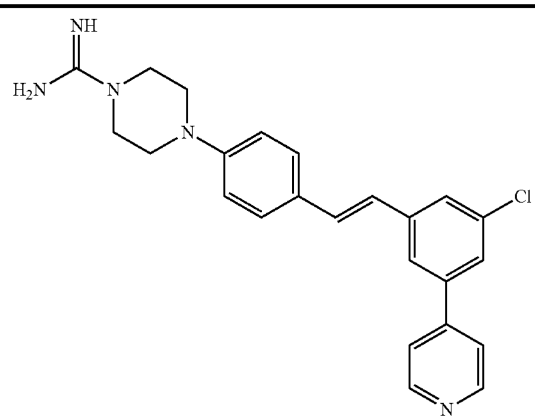 | 0.017 | 10000 | 10000 |
| 10 | 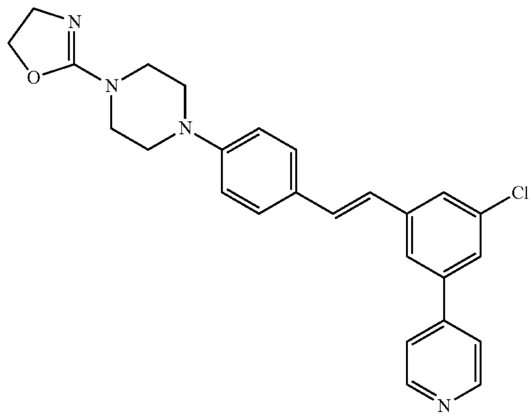 [SMILES: Clc1cc(/C=C/c2ccc(N3CCN(C4=NCCO4)CC3)cc2)cc(-c2ccncc2)c1] | 5 | 3500 | 1200 |
| 11 | 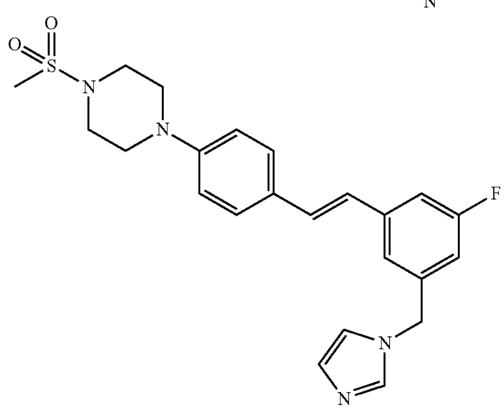 | 58 | 49 | 10000 |
| 12 | 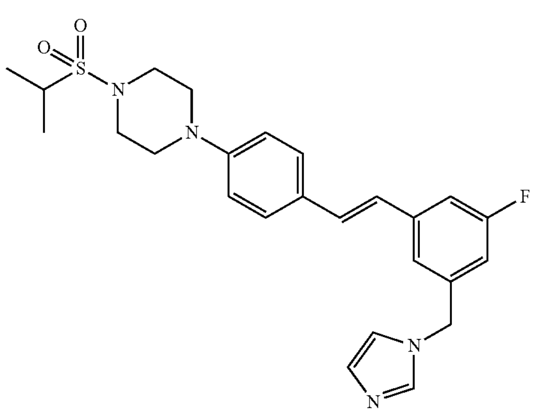 [SMILES: CC(C)S(=O)(=O)N1CCN(c2ccc(/C=C/c3cc(F)cc(Cn4ccnc4)c3)cc2)CC1] | 39 | 5 | 700 |

-continued

| Entry | Structure | Cyp17 | Cyp11 | Cyp21 |
|---|---|---|---|---|
|  |  | IC$_{50}$ (nM) | | |
| 13 | 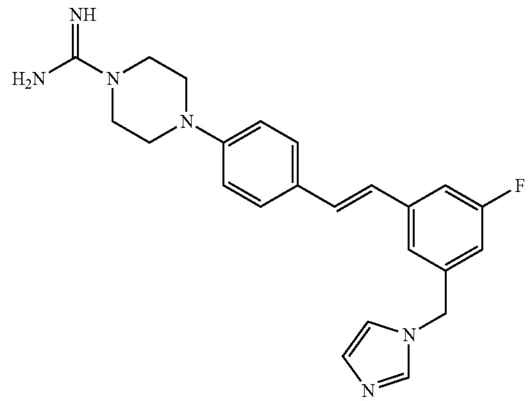 [SMILES: N=C(N)N1CCN(c2ccc(/C=C/c3cc(F)cc(Cn4ccnc4)c3)cc2)CC1] | 1200 | 1400 | 10000 |
| 14 | 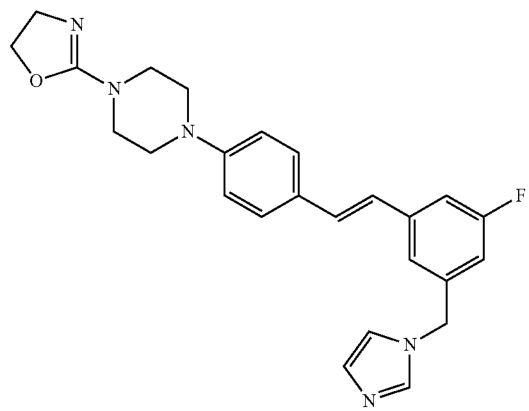 [SMILES: Fc1cc(/C=C/c2ccc(N3CCN(C4=NCCO4)CC3)cc2)cc(Cn2ccnc2)c1] | 117 | 130 | 10000 |
| 15 | 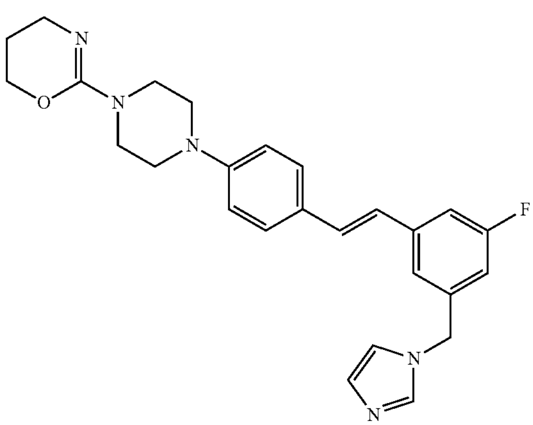 [SMILES: Fc1cc(/C=C/c2ccc(N3CCN(C4=NCCCO4)CC3)cc2)cc(Cn2ccnc2)c1] | 42 | 17 | 1000 |

-continued

| Entry | Structure | Cyp17 | Cyp11 | Cyp21 |
|---|---|---|---|---|
|   |   | IC$_{50}$ (nM) | | |
| 16 | [structure] | 86 | 73 | 10000 |
| 17 | [structure] | 100 | 130 | 3500 |

EXAMPLE 97

Pharmacokinetic studies in the guinea pig were run using 1 mg/kg IV dosing (20% DMA, 40% TEG, 40% water) and 10 mg/kg oral dosing (2% Tween-80, 98% HPMC (1% water)). The oral PK data is summarized in the tables below. COR-510032 and 510068 met the criteria for bioavailability and were tested in the efficacy model (guinea pigs) to check for the lowering of cortisol and testosterone.

510032

510024

| | | |
|---|---|---|
| Dose(mg/kg) | 10 | 10 |
| Cmax(ng/mL) | 1018 | 127 |
| Tmax | 3.00 | 4.00 |
| t1/2 (h) | 6.0 | 3.1 |
| AUC$_{0\_last}$ (ng·h/mL) | 8231 | 1201 |
| AUC$_{0\text{-}inf}$ (ng·h/mL) | 14891 | 2177 |
| AUC$_{Extra}$(%) | 43.93 | 44.85 |

-continued

| | | |
|---|---|---|
| DNAUC(0-inf) | 823.1 | 120.1 |
| MRT$_{0\_last}$ (h) | 5.56 | 5.97 |
| Rsq | 0.91 | 0.94 |
| Bioavailability | 184.21 | 14.34 |

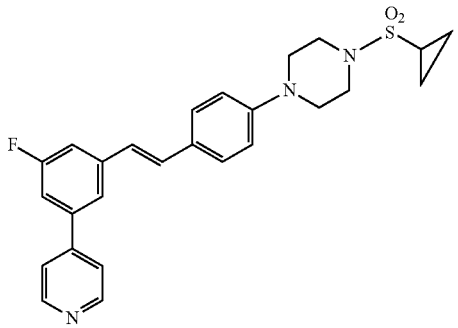

510064

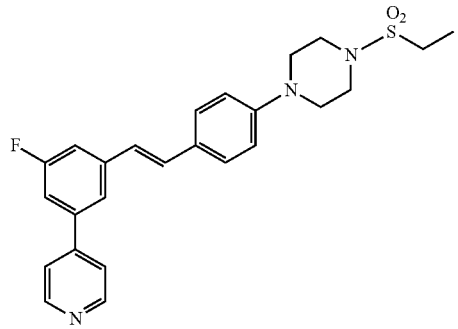

510065

| | | |
|---|---|---|
| Dose(mg/kg) | 10 | 10 |
| Cmax(ng/mL) | 172 | 540 |
| Tmax | 8 | 5.33 |
| t1/2 (h) | NC | 4.8 |
| AUC$_{0\_last}$ (ng·h/mL) | 1601 | 3301 |
| AUC$_{0-inf}$ (ng·h/mL) | NC | 4190 |
| AUC$_{Extra}$(%) | NC | 18.25 |
| DNAUC(0-inf) | 160 | 330.1 |
| MRT$_{0\_last}$ (h) | 7 | 5.54 |
| Rsq | NC | 0.68 |
| Bioavailability | 207 | 22.34 |

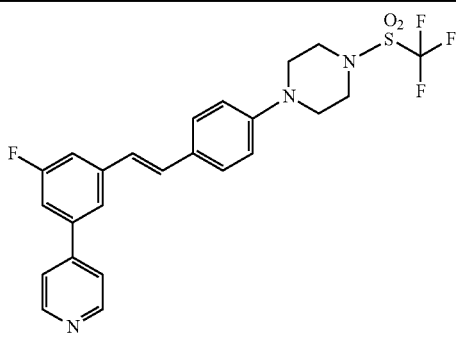

510068

| | |
|---|---|
| Dose(mg/kg) | 10 |
| Cmax(ng/mL) | 271 |
| Tmax | 3.33 |
| t1/2 (h) | 5.3 |
| AUC$_{0\_last}$ (ng·h/mL) | 1646 |
| AUC$_{0-inf}$ (ng·h/mL) | 2453 |
| AUC$_{Extra}$(%) | 25.87 |
| DNAUC(0-inf) | 164.6 |
| MRT$_{0\_last}$ (h) | 5.01 |
| Rsq | 0.81 |
| Bioavailability | 22.08 |

Formulations

Some embodiments of the present invention also relate to compositions or formulations which comprise the cortisol lowering agents according to embodiments described herein. In general, the compositions of embodiments described herein comprise an effective amount of one or more compounds of the disclosure and salts thereof according to embodiments described herein which are effective for providing cortisol lowering; and one or more excipients.

In this document, the term "excipient" and "carrier" are used interchangeably and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means to achieve effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of embodiments described herein have improved cellular potency, pharmacokinetic properties, as well as improved oral bioavailability.

The present embodiments also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitonally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

The compounds of embodiments described herein can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the compounds of embodiments described herein (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical formulations containing the compounds of embodiments described herein and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of embodiments described herein. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

The compounds of embodiments described herein can be formulated for parenteral administration by injection, e.g., by bolus injection or continuous infusion. The compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to embodiments described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of embodiments described herein can also be formulated in rectal compositions such as suppositories or retention enemas, e.g., containing conventional suppository bases such as cocoa butter or other glycerides.

In addition to the formulations described previously, the compounds of embodiments described herein can also be formulated as a depot preparation. Such long acting formulations can be administered by implantation (for example, subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of embodiments described herein, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compounds of embodiments described herein can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to embodiments described herein include from about 0.001 mg to about 1000 mg of one or more compounds of the disclosure according to embodiments described herein and one or more excipients; from about 0.01 mg to about 100 mg of one or more compounds of the disclosure according to embodiments described herein and one or more excipients; from about 100 mg to about 250 mg of one or more compounds of the disclosure according to embodiments described herein and one or more excipients; from about 250 mg to about 500 mg of one or more compounds of the disclosure according to embodiments described herein and one or more excipients; from about 500 mg to about 750 mg of one or more compounds of the disclosure according to embodiments described herein and one or more excipients; from about 750 mg to about 1000 mg of one or more compounds of the disclosure according to embodiments described herein and one or more excipients; and from about 0.1 mg to about 10 mg of one or more compounds of the disclosure according to embodiments described herein; and one or more excipients.

In some embodiments, the compositions according to embodiments described herein are administered orally to a patient once daily.

In some embodiments, the compositions according to embodiments described herein are administered orally to a patient twice daily.

In some embodiments, the compositions according to embodiments described herein are administered orally to a patient three time per day.

In some embodiments, the compositions according to embodiments described herein are administered orally to a patient once weekly.

Procedures

Embodiments of the present invention also include procedures that can be utilized in evaluating and selecting compounds as cortisol lowering agents.

Cyp17 assay protocol: AD293 cells that stably over-express recombinant CYP-17 were seeded in 96 well plates coated with poly D-lysine (15,000 cell per well) and incubated at 37° C. for 24 hours in Dulbecco's Modified Eagle Medium (DMEM) with Fetal Bovine Serum (FBS) that is stripped of hormones by charcoal treatment. The media is then removed, the cells are washed once with Phosphate buffer saline solution, and 50 μL Dulbecco's Modified Eagle Medium (DMEM) with Fetal Bovine Serum (FBS) that is stripped of hormones by charcoal treatment is added. Compounds of the disclosure are then added to the wells in eight concentration spanning 10 μM to 4.5 nM, and the plates are incubated for an additional 60 minutes at 37° C. [21-$^3$H] 17α-hydroxyl-Pregnenolone is then added (50 nCi per well, 31.25 nM) and the plates are incubated for an additional 4 hours at 37° C. The media is then collected, 200 μL of chloroform is added, and the mixture is shaken for 1 hour. The aqueous layer is then separated and analyzed for the presence of $^3$H-acetic acid using a Perkin Elmer Topcount NXT to determine IC50s of the compounds of the disclosure.

Cyp21 assay protocol: AD293 cells that stably over-express recombinant CYP-21 were seeded in 96 well plates coated with poly D-lysine (10,000 cell per well) and incubated at 37° C. for 24 hours in Dulbecco's Modified Eagle Medium (DMEM) with Fetal Bovine Serum (FBS) that is stripped of hormones by charcoal treatment. The media is then removed, the cells are washed once with Phosphate buffer saline solution, and 50 μL Dulbecco's Modified Eagle Medium (DMEM) with Fetal Bovine Serum (FBS) that is stripped of hormones by charcoal treatment is added. Compounds of the disclosure are then added to the wells in eight concentration spanning 10 μM to 4.5 nM, and the plates are incubated for an additional 60 minutes at 37° C. 17α-OH Progesterone is then added (1.0 μM) and the plates are incubated for an additional 45 minutes at 37° C. After incubation, 50 uL of the supernatant (medium) is transferred into a fresh plate and 150 uL of an acetonitrile solution containing 200 ng/ml of Telmisartan is added. The sample is mixed and then placed in a centrifuge at 2000 rpm for 5 minutes. 100 uL of the supernatant is transferred into a fresh 96 well deep well plate, 100 uL of 1:1 methanol: water was added, the solution was mixed and then analyzed by LC/MS for the presence of 11-deoxycortisol using an Agilent 1200 RRLC/ABSCIEX API4000 LC-MS or Shimadzu Prominance/ABSCIEX API4000 LC-MS to determine $IC_{50}$s of the compounds of the disclosure.

Cyp11 assay protocol: AD293 cells that stably over-express recombinant CYP-11 were seeded in 96 well plates coated with poly D-lysine (15,000 cell per well) and incubated at 37° C. for 24 hours in Dulbecco's Modified Eagle Medium (DMEM) with Fetal Bovine Serum (FBS) that is stripped of hormones by charcoal treatment. The media is then removed, the cells are washed once with Phosphate buffer saline solution, and 50 μL Dulbecco's Modified Eagle Medium (DMEM) with Fetal Bovine Serum (FBS) that is stripped of hormones by charcoal treatment is added. Compounds of the disclosure are then added to the wells in eight concentration spanning 10 μM to 4.5 nM, and the plates are incubated for an additional 60 minutes at 37° C. 11-deoxycortisol is then added (2.0 μM) and the plates are incubated for an additional 12 hours at 37° C. After incubation, 50 uL of the supernatant (medium) is transferred into a fresh plate and 150 uL of an acetonitrile solution containing 200 ng/ml of Telmisartan is added. The sample is mixed and then placed in a centrifuge at 2000 rpm for 5 minutes. 100 uL of the supernatant is transferred into a fresh 96 well deep well plate, 100 uL of 1:1 methanol: water was added, the solution was mixed and then analyzed by LC/MS for the presence of cortisol using an Agilent 1200 RRLC/ABSCIEX API4000 LC-MS or Shimadzu Prominance/ABSCIEX API4000 LC-MS to determine $IC_{50}$s of the compounds of the disclosure.

Results for representative compounds according to the present invention are listed in Table 23.

TABLE 23

Representative examples of compounds of the disclosure and their potencies in Cyp17, Cyp11, and Cyp21 assays.

| Entry | Structure | Cyp17 | Cyp11 IC$_{50}$ (nM) | Cyp21 |
|---|---|---|---|---|
| 1 | (4-bromophenyl)-styryl-phenol with imidazole | 1200 | 1400 | 10000 |
| 2 | acetylpiperazinyl-phenyl-styryl-phenol with imidazole | 220 | 4800 | 1950 |
| 3 | acetylpiperazinyl-phenyl-styryl-(chloro)phenyl-CH$_2$-imidazole | 42.0 | 44 | |
| 4 | acetylpiperazinyl-phenyl-styryl-(hydroxy)phenyl-CH$_2$-imidazole | 88.0 | 51 | 2400 |

TABLE 23-continued
Representative examples of compounds of the disclosure and their potencies in Cyp17, Cyp11, and Cyp21 assays.
| Entry | Structure | Cyp17 | Cyp11 IC$_{50}$ (nM) | Cyp21 |
|---|---|---|---|---|
| 5 | 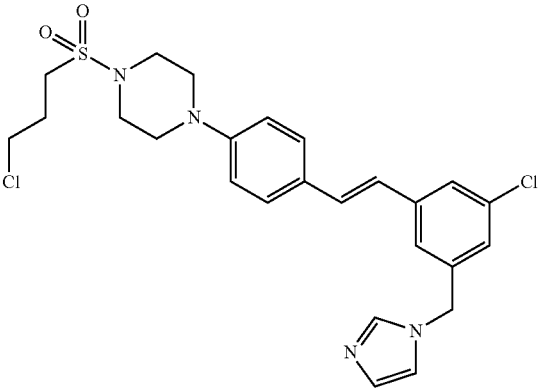 [SMILES: O=S(=O)(CCCCl)N1CCN(c2ccc(/C=C/c3cc(Cl)cc(Cn4ccnc4)c3)cc2)CC1] | 31.0 | 13 | 2870 |
| 6 | 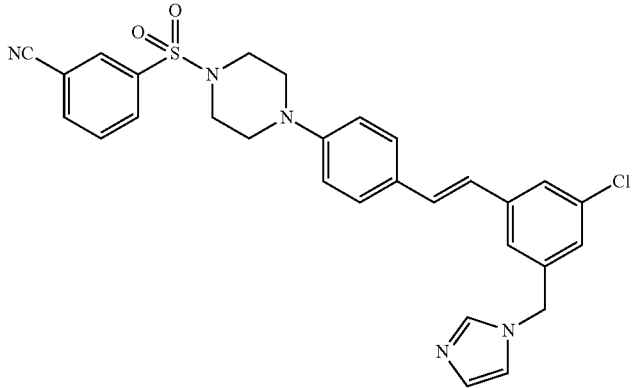 [SMILES: N#Cc1cccc(S(=O)(=O)N2CCN(c3ccc(/C=C/c4cc(Cl)cc(Cn5ccnc5)c4)cc3)CC2)c1] | 21.0 | 4 | 1200 |
| 7 | 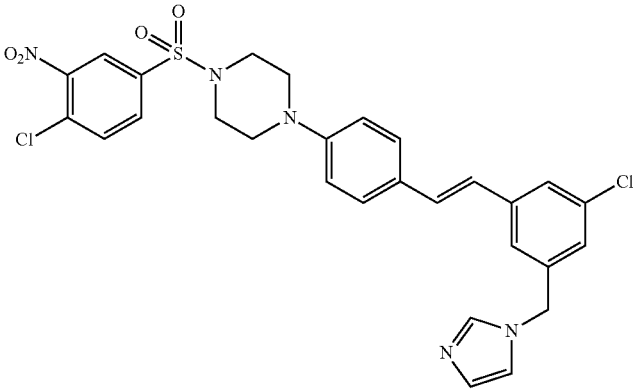 [SMILES: O=[N+]([O-])c1cc(S(=O)(=O)N2CCN(c3ccc(/C=C/c4cc(Cl)cc(Cn5ccnc5)c4)cc3)CC2)ccc1Cl] | 106.0 | 57 | 10000 |

TABLE 23-continued

Representative examples of compounds of the disclosure and their potencies in Cyp17, Cyp11, and Cyp21 assays.

| Entry | Structure | Cyp17 IC$_{50}$ (nM) | Cyp11 IC$_{50}$ (nM) | Cyp21 IC$_{50}$ (nM) |
|---|---|---|---|---|
| 8 | 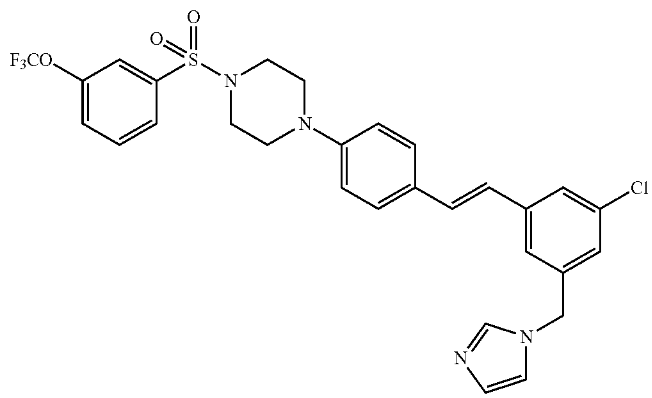 [SMILES: O=S(=O)(c1cccc(OC(F)(F)F)c1)N1CCN(c2ccc(/C=C/c3cc(Cl)cc(Cn4ccnc4)c3)cc2)CC1] | 17.0 | 4 | 520 |
| 9 | 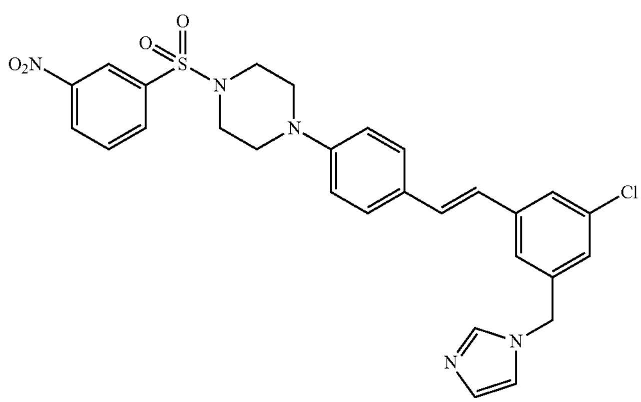 [SMILES: O=[N+]([O-])c1cccc(S(=O)(=O)N2CCN(c3ccc(/C=C/c4cc(Cl)cc(Cn5ccnc5)c4)cc3)CC2)c1] | 9.0 | 4 | 160 |
| 10 | 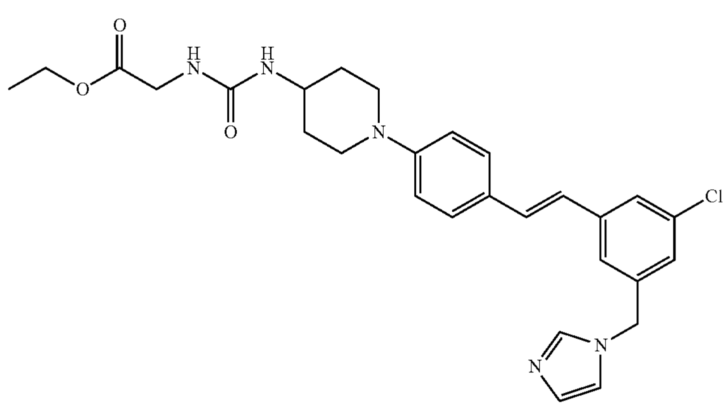 [SMILES: CCOC(=O)CNC(=O)NC1CCN(c2ccc(/C=C/c3cc(Cl)cc(Cn4ccnc4)c3)cc2)CC1] | 3.5 | 73 | 250 |

TABLE 23-continued

Representative examples of compounds of the disclosure and their potencies in Cyp17, Cyp11, and Cyp21 assays.

| Entry | Structure | Cyp17 | Cyp11 IC$_{50}$ (nM) | Cyp21 |
|---|---|---|---|---|
| 11 | 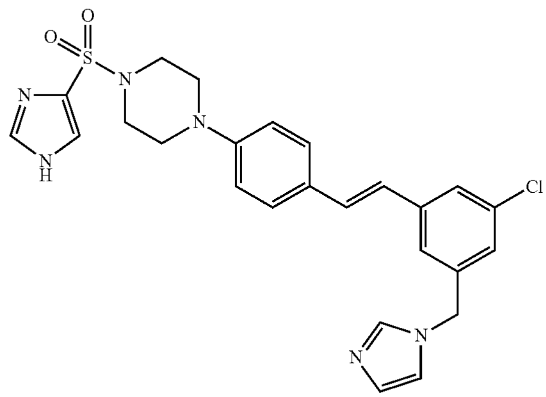 [SMILES: O=S(=O)(c1c[nH]cn1)N1CCN(c2ccc(/C=C/c3cc(Cl)cc(Cn4ccnc4)c3)cc2)CC1] | 6.2 | 7 | 10000 |
| 12 | 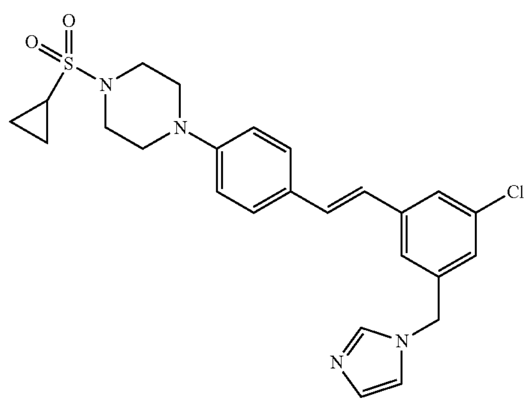 [SMILES: O=S(=O)(C1CC1)N1CCN(c2ccc(/C=C/c3cc(Cl)cc(Cn4ccnc4)c3)cc2)CC1] | 21.0 | 22 | 340 |
| 13 | 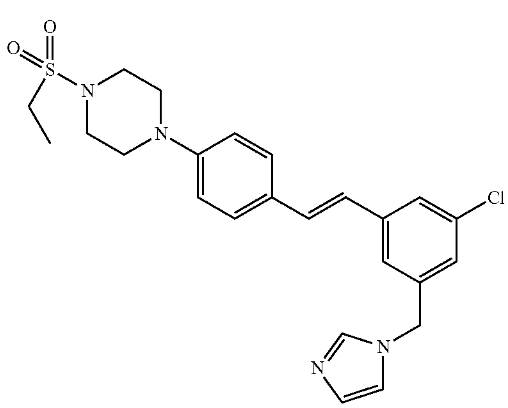 [SMILES: CCS(=O)(=O)N1CCN(c2ccc(/C=C/c3cc(Cl)cc(Cn4ccnc4)c3)cc2)CC1] | 24 | 23 | 540 |

TABLE 23-continued

Representative examples of compounds of the disclosure and their potencies in Cyp17, Cyp11, and Cyp21 assays.

| Entry | Structure | Cyp17 | Cyp11 IC$_{50}$ (nM) | Cyp21 |
|---|---|---|---|---|
| 14 | 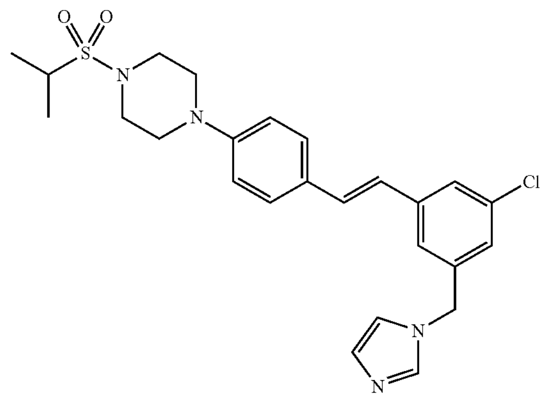 [SMILES: CC(C)S(=O)(=O)N1CCN(c2ccc(/C=C/c3cc(Cl)cc(Cn4ccnc4)c3)cc2)CC1] | 38 | 240 | 85 |
| 15 | 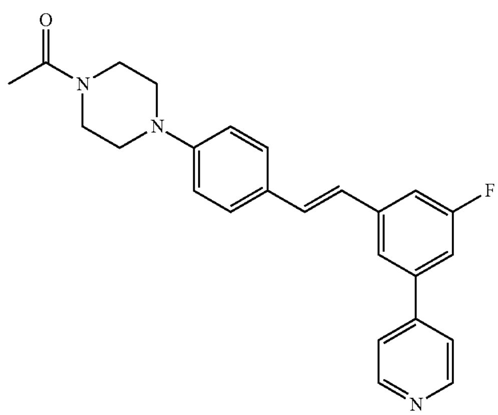 [SMILES: CC(=O)N1CCN(c2ccc(/C=C/c3cc(F)cc(-c4ccncc4)c3)cc2)CC1] | 4.60 | 1200 | 430 |
| 16 | 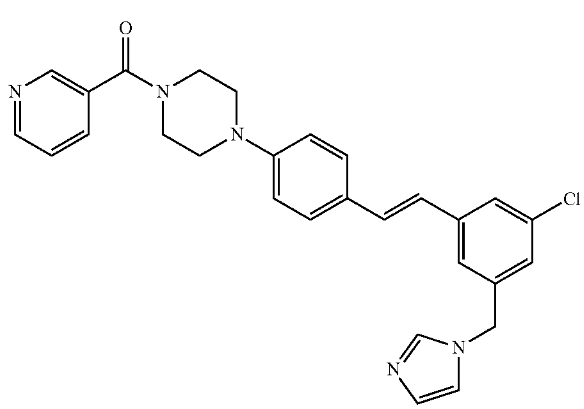 [SMILES: O=C(c1cccnc1)N1CCN(c2ccc(/C=C/c3cc(Cl)cc(Cn4ccnc4)c3)cc2)CC1] | 26 | 4.9 | 10000 |

TABLE 23-continued
Representative examples of compounds of the disclosure and their potencies in Cyp17, Cyp11, and Cyp21 assays.
| Entry | Structure | Cyp17 | Cyp11 IC$_{50}$ (nM) | Cyp21 |
|---|---|---|---|---|
| 17 | 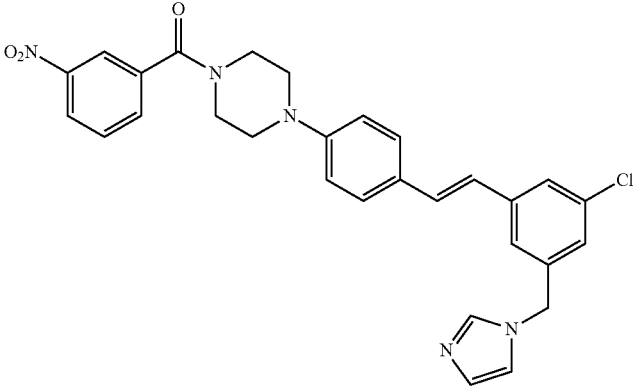 [SMILES: O=C(c1cccc([N+](=O)[O-])c1)N1CCN(c2ccc(/C=C/c3cc(Cl)cc(Cn4ccnc4)c3)cc2)CC1] | 17.0 | 4.0 | 10000 |
| 18 | 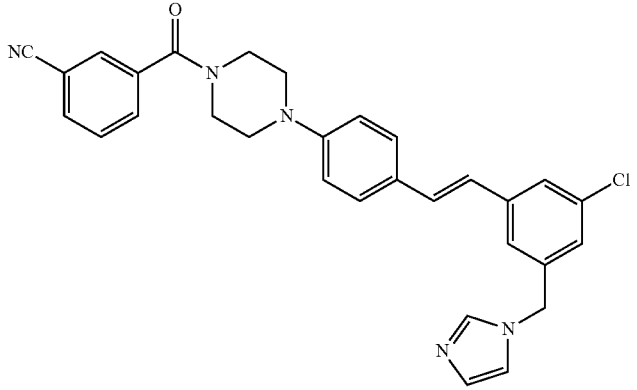 [SMILES: N#Cc1cccc(C(=O)N2CCN(c3ccc(/C=C/c4cc(Cl)cc(Cn5ccnc5)c4)cc3)CC2)c1] | 22.0 | 4.0 | 10000 |
| 19 | 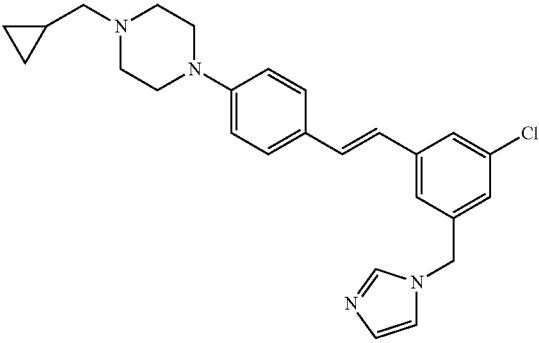 [SMILES: Clc1cc(/C=C/c2ccc(N3CCN(CC4CC4)CC3)cc2)cc(Cn2ccnc2)c1] | 17.0 | 11.0 | 585 |
| 20 | 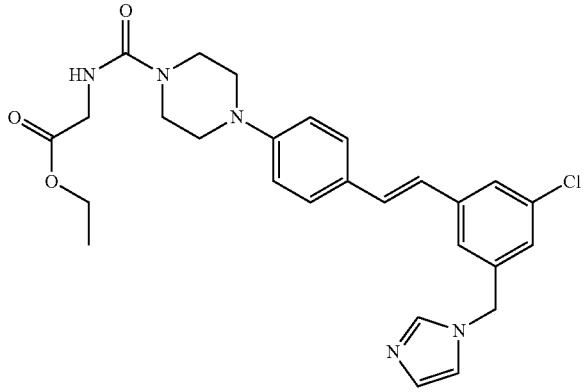 [SMILES: CCOC(=O)CNC(=O)N1CCN(c2ccc(/C=C/c3cc(Cl)cc(Cn4ccnc4)c3)cc2)CC1] | 41.0 | 27.0 | 360 |

TABLE 23-continued

Representative examples of compounds of the disclosure and their potencies in Cyp17, Cyp11, and Cyp21 assays.

| Entry | Structure | Cyp17 | Cyp11 IC$_{50}$ (nM) | Cyp21 |
|---|---|---|---|---|
| 21 | 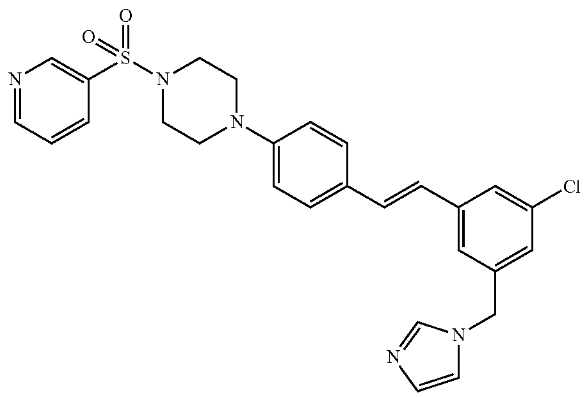 [SMILES: O=S(=O)(c1cccnc1)N1CCN(c2ccc(/C=C/c3cc(Cl)cc(Cn4ccnc4)c3)cc2)CC1] | 17.0 | 4.0 | 1380 |
| 22 | 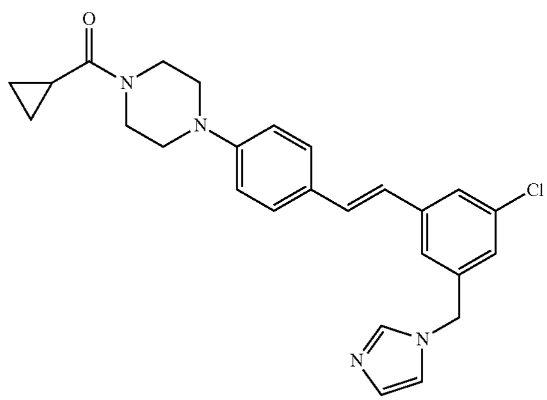 [SMILES: O=C(C1CC1)N1CCN(c2ccc(/C=C/c3cc(Cl)cc(Cn4ccnc4)c3)cc2)CC1] | 48.0 | 19.0 | 1400 |
| 23 | 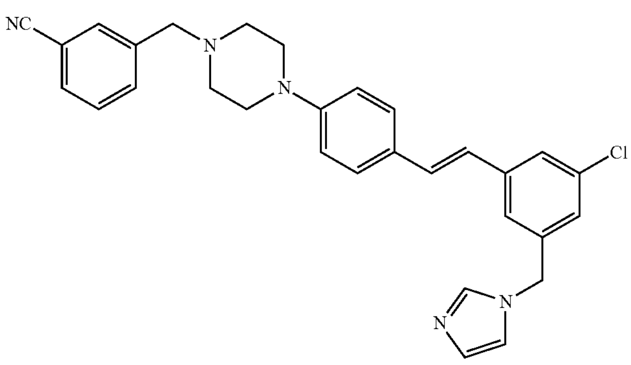 [SMILES: N#Cc1cccc(CN2CCN(c3ccc(/C=C/c4cc(Cl)cc(Cn5ccnc5)c4)cc3)CC2)c1] | 25.0 | 7.0 | 285 |
| 24 | 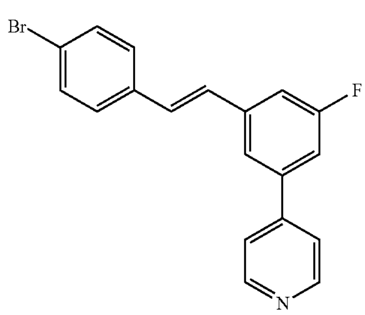 [SMILES: Fc1cc(/C=C/c2ccc(Br)cc2)cc(-c2ccncc2)c1] | 42 | 10000 | 2600 |

TABLE 23-continued

Representative examples of compounds of the disclosure and their potencies in Cyp17, Cyp11, and Cyp21 assays.

| Entry | Structure | Cyp17 | Cyp11 IC$_{50}$ (nM) | Cyp21 |
|---|---|---|---|---|
| 25 | 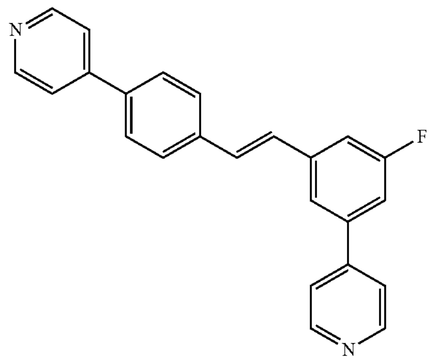 [SMILES: Fc1cc(/C=C/c2ccc(-c3ccncc3)cc2)cc(-c2ccncc2)c1] | 11 | 3700 | 850 |
| 26 | 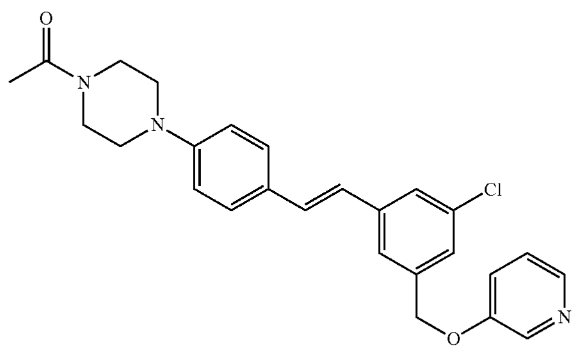 [SMILES: CC(=O)N1CCN(c2ccc(/C=C/c3cc(Cl)cc(COc4cccnc4)c3)cc2)CC1] | 135 | 140 | 10000 |
| 27 | 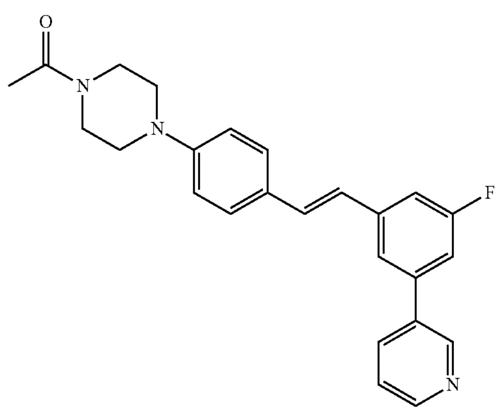 [SMILES: CC(=O)N1CCN(c2ccc(/C=C/c3cc(F)cc(-c4cccnc4)c3)cc2)CC1] | 610 | 10000 | 10000 |
| 28 | 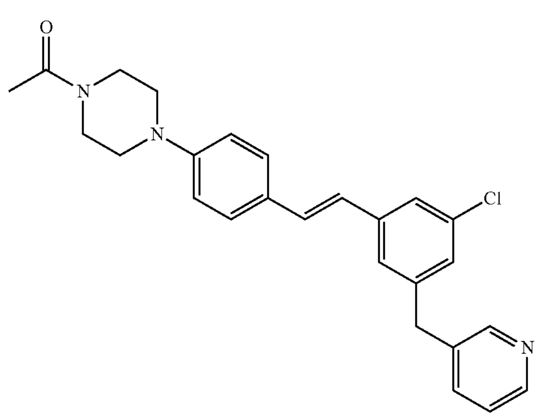 [SMILES: CC(=O)N1CCN(c2ccc(/C=C/c3cc(Cl)cc(Cc4cccnc4)c3)cc2)CC1] | 35 | 180 | 10000 |

TABLE 23-continued
Representative examples of compounds of the disclosure and their potencies in Cyp17, Cyp11, and Cyp21 assays.
| Entry | Structure | Cyp17 | Cyp11 IC$_{50}$ (nM) | Cyp21 |
|---|---|---|---|---|
| 29 | 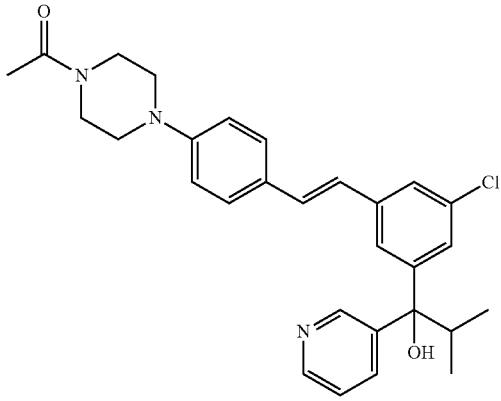 [SMILES: CC(=O)N1CCN(c2ccc(/C=C/c3cc(Cl)cc(C(O)(c4cccnc4)C(C)C)c3)cc2)CC1] | 240 | 370 | 3300 |
| 30 | 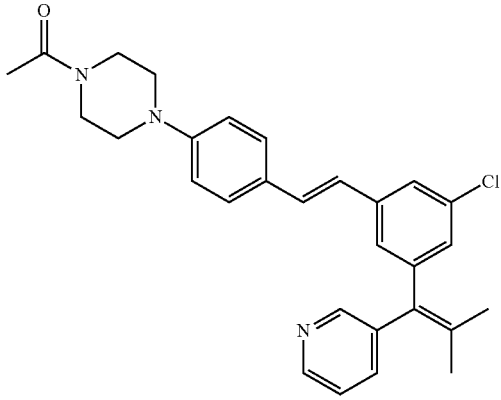 [SMILES: CC(=O)N1CCN(c2ccc(/C=C/c3cc(Cl)cc(C(=C(C)C)c4cccnc4)c3)cc2)CC1] | 210 | 1800 | 2400 |
| 31 | 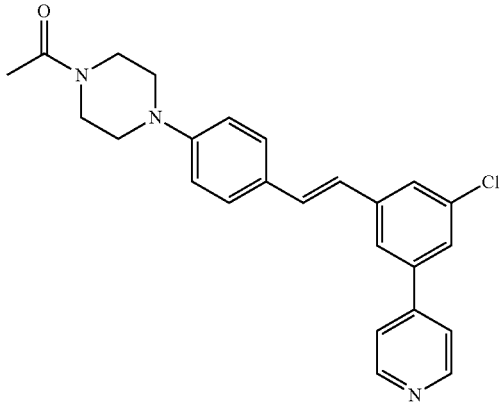 [SMILES: CC(=O)N1CCN(c2ccc(/C=C/c3cc(Cl)cc(-c4ccncc4)c3)cc2)CC1] | 5.00 | 10000 | 1100 |

TABLE 23-continued

Representative examples of compounds of the disclosure and their potencies in Cyp17, Cyp11, and Cyp21 assays.

| Entry | Structure | Cyp17 | Cyp11 IC$_{50}$ (nM) | Cyp21 |
|---|---|---|---|---|
| 32 | 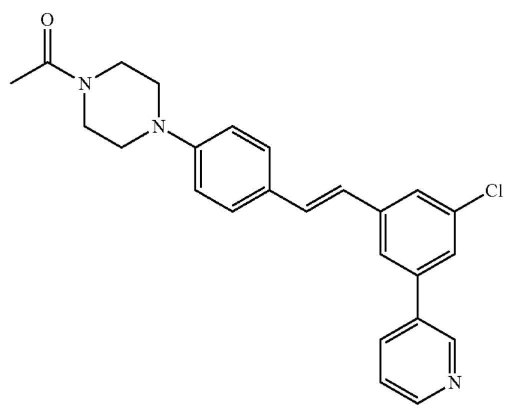 [SMILES: CC(=O)N1CCN(c2ccc(/C=C/c3cc(Cl)cc(-c4cccnc4)c3)cc2)CC1] | 620.00 | 10000 | 10000 |
| 33 | 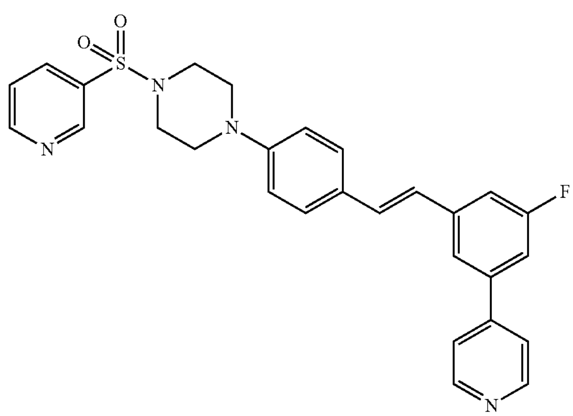 [SMILES: O=S(=O)(c1cccnc1)N1CCN(c2ccc(/C=C/c3cc(F)cc(-c4ccncc4)c3)cc2)CC1] | 7.00 | 220 | 3300 |
| 34 | 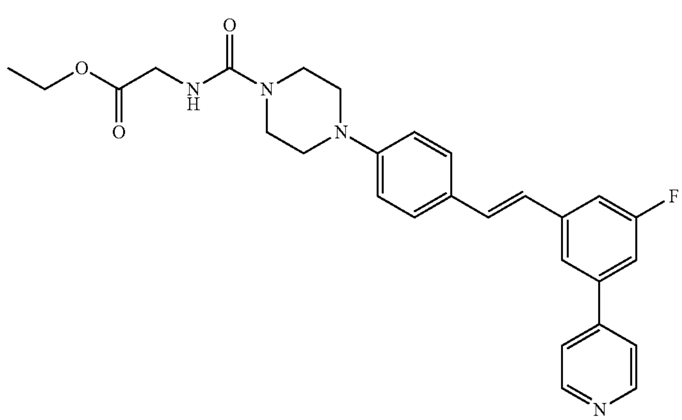 [SMILES: CCOC(=O)CNC(=O)N1CCN(c2ccc(/C=C/c3cc(F)cc(-c4ccncc4)c3)cc2)CC1] | 8.00 | 1300 | 1010 |

TABLE 23-continued

Representative examples of compounds of the disclosure and their potencies in Cyp17, Cyp11, and Cyp21 assays.

| Entry | Structure | Cyp17 | Cyp11 IC$_{50}$ (nM) | Cyp21 |
|---|---|---|---|---|
| 35 | (cyclopropyl-SO$_2$-piperazine-phenyl-CH=CH-(3-fluoro-5-(pyridin-4-yl)phenyl)) | 5 | 140 | 393 |
| 36 | (ethyl-SO$_2$-piperazine-phenyl-CH=CH-(3-fluoro-5-(pyridin-4-yl)phenyl)) | 5 | 200 | 520 |
| 37 | (4-(pyridin-4-yl)phenyl-CH$_2$CH$_2$-(3-fluoro-5-(pyridin-4-yl)phenyl)) | 190 | 10000 | 490 |
| 38 | (cyclopropylmethyl-piperazine-phenyl-CH=CH-(3-fluoro-5-(pyridin-4-yl)phenyl)) | 5 | 54 | 770 |

TABLE 23-continued
Representative examples of compounds of the disclosure and their potencies in Cyp17, Cyp11, and Cyp21 assays.
| Entry | Structure | Cyp17 | Cyp11 IC$_{50}$ (nM) | Cyp21 |
|---|---|---|---|---|
| 39 | 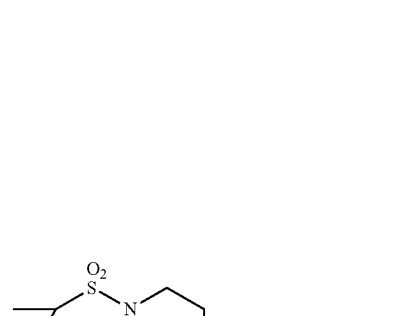 | 5 | 1500 | 316 |
| 40 | 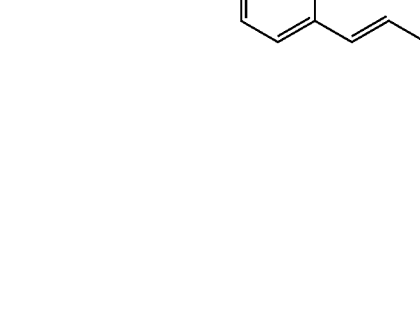 | 1.0 | | 190 |
| 41 | 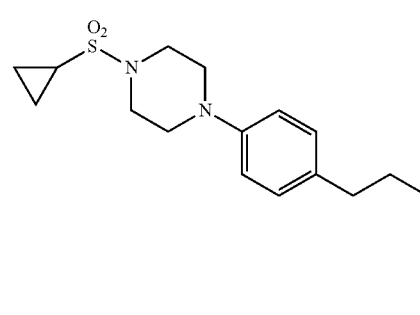 | 3.0 | | 1200 |

TABLE 23-continued

Representative examples of compounds of the disclosure and their potencies in Cyp17, Cyp11, and Cyp21 assays.

| Entry | Structure | Cyp17 | Cyp11 IC$_{50}$ (nM) | Cyp21 |
|---|---|---|---|---|
| 42 | 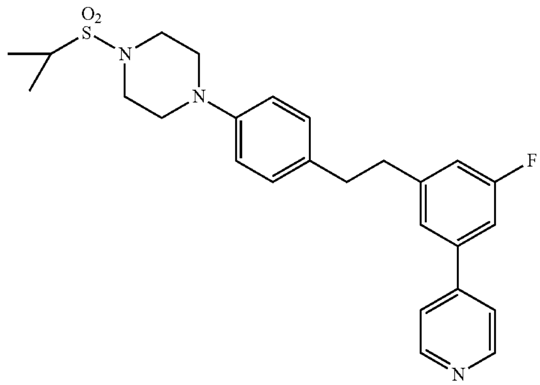 [SMILES: CC(C)S(=O)(=O)N1CCN(c2ccc(CCc3cc(F)cc(-c4ccncc4)c3)cc2)CC1] | 4.0 | | 1000 |
| 43 | 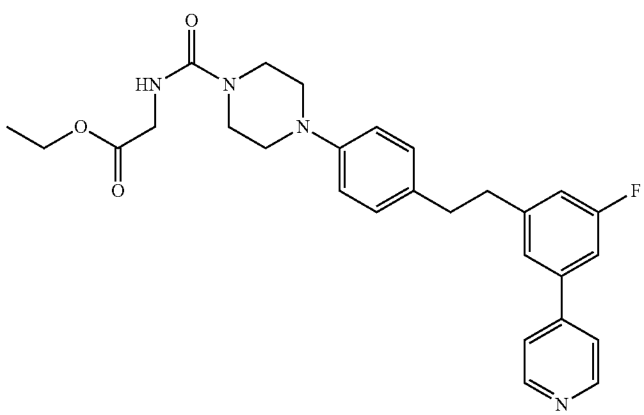 [SMILES: CCOC(=O)CNC(=O)N1CCN(c2ccc(CCc3cc(F)cc(-c4ccncc4)c3)cc2)CC1] | 7.0 | 160 | 10000 |
| 44 | 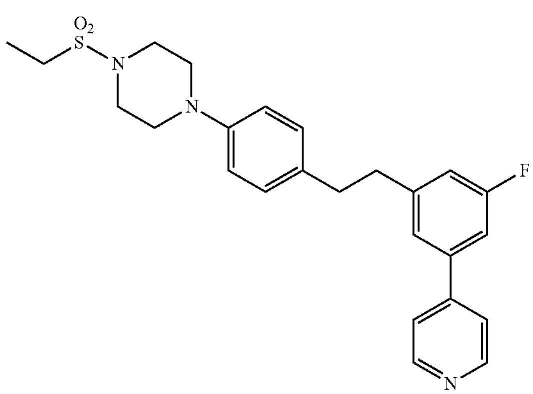 [SMILES: CCS(=O)(=O)N1CCN(c2ccc(CCc3cc(F)cc(-c4ccncc4)c3)cc2)CC1] | 2 | 330 | 1600 |

TABLE 23-continued

Representative examples of compounds of the disclosure and their potencies in Cyp17, Cyp11, and Cyp21 assays.

| Entry | Structure | Cyp17 | Cyp11 IC$_{50}$ (nM) | Cyp21 |
|---|---|---|---|---|
| 45 | 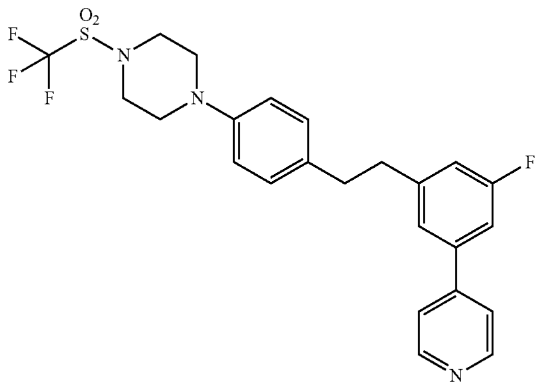 [SMILES: O=S(=O)(N1CCN(c2ccc(CCc3cc(F)cc(-c4ccncc4)c3)cc2)CC1)C(F)(F)F] | 16.5 | 183 | 2800 |
| 46 | 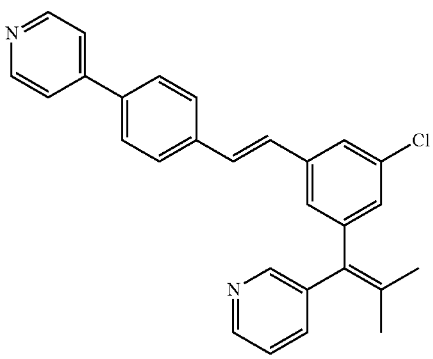 [SMILES: CC(C)=C(c1cccnc1)c1cc(Cl)cc(/C=C/c2ccc(-c3ccncc3)cc2)c1] | | 300 | |
| 47 | 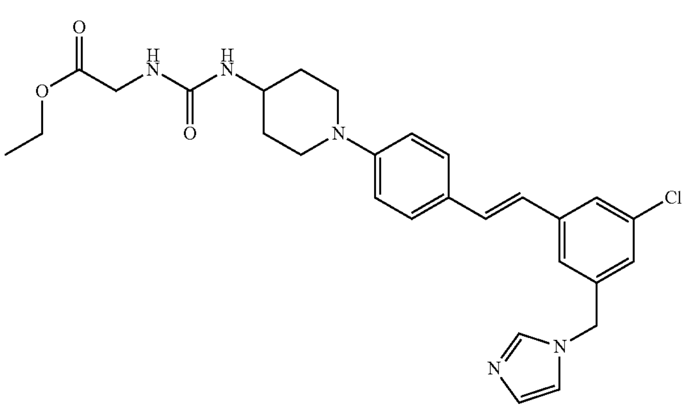 [SMILES: CCOC(=O)CNC(=O)NC1CCN(c2ccc(/C=C/c3cc(Cl)cc(Cn4ccnc4)c3)cc2)CC1] | 3.5 | 250 | 73 |

TABLE 23-continued

Representative examples of compounds of the disclosure and their potencies in Cyp17, Cyp11, and Cyp21 assays.

| Entry | Structure | Cyp17 | Cyp11 IC$_{50}$ (nM) | Cyp21 |
|---|---|---|---|---|
| 48 | 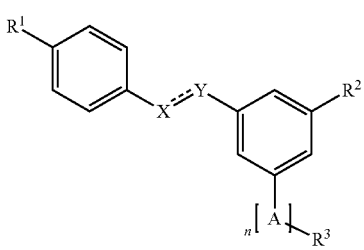 | 21 | 1.4 | 10000 |

What is claimed is:

1. A compound having formula (I):

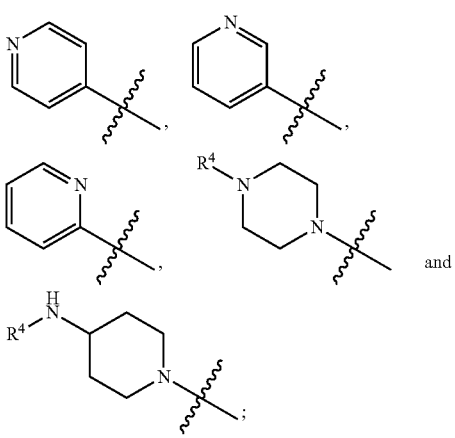

including hydrates, solvates, enantiomers, diastereomers, and pharmaceutically acceptable salts thereof, wherein:

X and Y are each independently CH and connected by a double bond, or X and Y are each independently CH$_2$ and connected by a single bond;

R$^1$ is selected from a group consisting of Br,

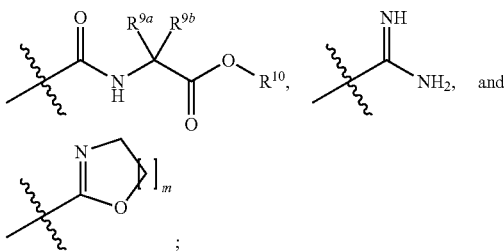

R$^2$ is selected from a group consisting of hydrogen, hydroxyl, fluorine, and chlorine;

R$^3$ is selected from a group consisting of optionally substituted 2-pyridyl, optionally substituted 3-pyridyl, optionally substituted 4-pyridyl, optionally substituted 1-imidazoyl, optionally substituted 2-imidazoyl, optionally substituted 4-imidazoyl, and CH$_2$Oheteroaryl;

R$^4$ is selected from a group consisting of optionally substituted C$_{1-6}$ alkyl, optionally substituted C$_{1-6}$ branched alkyl, optionally substituted C$_{3-7}$ cycloalkyl, optionally substituted phenyl, optionally substituted benzyl, COR$^5$, C(O)OR$^6$, C(O)NR$^{7a}$R$^{7b}$, SO$_2$R$^8$,

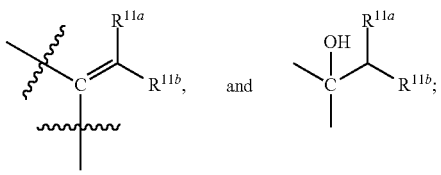

A is selected from a group consisting of CH$_2$, n is 0 or 1;
m is 1 or 2;

R$^5$ is selected from the group consisting of optionally substituted C$_{1-6}$ linear alkyl, optionally substituted C$_{1-6}$ branched alkyl, optionally substituted C$_{3-7}$ cycloalkyl, optionally substituted aryl, and optionally substituted heteroaryl;

R$^6$ is selected from the group consisting of optionally substituted C$_{1-6}$ linear alkyl, optionally substituted C$_{1-6}$ branched alkyl, and optionally substituted C$_{3-7}$ cycloalkyl;

R$^{7a}$ and R$^{7b}$ are each independently selected from a group consisting of hydrogen, optionally substituted C$_{1-6}$ linear alkyl, optionally substituted $C_{1-6}$ branched alkyl, and optionally substituted $C_{3-7}$ cycloalkyl;

$R^8$ is selected from the group consisting of optionally substituted $C_{1-6}$ linear alkyl, optionally substituted $C_{1-6}$ branched alkyl, optionally substituted $C_{3-7}$ cycloalkyl, optionally substituted $C_{1-6}$ haloalkyl, optionally substituted aryl, optionally substituted $C_{3-7}$ heterocyclyl, and optionally substituted heteroaryl;

$R^{9a}$ and $R^{9b}$ are each independently selected from a group consisting of hydrogen, optionally substituted $C_{1-6}$ linear alkyl, optionally substituted $C_{1-6}$ branched alkyl, optionally substituted aryl, optionally substituted benzyl, —$CH_2OR^6$, —$CH_2SR^6$, and $CH_2$heteroaryl;

$R^{10}$ is selected from the group consisting of optionally substituted $C_{1-6}$ linear alkyl, optionally substituted $C_{1-6}$ branched alkyl, and optionally substituted $C_{3-7}$ cycloalkyl; and $R^{11a}$ and $R^{11b}$ are each independently selected from a group consisting of hydrogen and optionally substituted $C_{1-6}$ linear alkyl.

2. A compound selected from the group consisting of:
(E)-1-(4-(4-(3-((1H-imidazol-1-yl)methyl)-5-chlorostyryl)phenyl)piperazin-1-yl)ethanone;
(E)-1-(4-(3-((1H-imidazol-1-yl)methyl)-5-chlorostyryl)phenyl)-4-(3-(trifluoromethoxy)phenylsulfonyl)piperazine;
(E)-1-(4-(3-((1H-imidazol-1-yl)methyl)-5-chlorostyryl)phenyl)-4-(3-chloropropylsulfonyl)piperazine;
(E)-3-(4-(4-(3-((1H-imidazol-1-yl)methyl)-5-chlorostyryl)phenyl)piperazin-1-ylsulfonyl)benzonitrile;
(E)-1-(4-(3-((1H-imidazol-1-yl)methyl)-5-chlorostyryl)phenyl)-4-(4-chloro-3-nitrophenylsulfonyl)piperazine;
(E)-1-(4-(3-((1H-imidazol-1-yl)methyl)-5-chlorostyryl)phenyl)-4-(3-nitrophenylsulfonyl)piperazine;
(E)-1-(4-(4-(3-((1H-imidazol-1-yl)methyl)-5-hydroxystyryl)phenyl)piperazin-1-yl)ethanone;
(E)-1-(4-(3-((1H-imidazol-1-yl)methyl)-5-chlorostyryl)phenyl)-4-(1H-imidazol-4-ylsulfonyl)piperazine;
(E)-1-(4-(3-((1H-imidazol-1-yl)methyl)-5-chlorostyryl)phenyl)-4-(cyclopropylsulfonyl)piperazine;
(E)-1-(4-(3-((1H-imidazol-1-yl)methyl)-5-chlorostyryl)phenyl)-4-(ethylsulfonyl) piperazine;
(E)-1-(4-(3-((1H-imidazol-1-yl)methyl)-5-chlorostyryl)phenyl)-4-(isopropylsulfonyl) piperazine;
(E)-1-(4-(4-(3-fluoro-5-(pyridin-4-yl)styryl)phenyl)piperazin-1-yl)ethanone;
(E)-(4-(4-(3-((1H-imidazol-1-yl)methyl)-5-chlorostyryl)phenyl)piperazin-1-yl)(pyridin-3-yl)methanone;
(E)-(4-(4-(3-((1H-imidazol-1-yl)methyl)-5-chlorostyryl)phenyl)piperazin-1-yl)(3-nitrophenyl)methanone;
(E)-3-(4-(4-(3-((1H-imidazol-1-yl)methyl)-5-chlorostyryl)phenyl)piperazine-1-carbonyl)benzonitrile;
(E)-(4-(4-(3-((1H-imidazol-1-yl)methyl)-5-chlorostyryl)phenyl)piperazin-1-yl)(cyclopropyl)methanone;
(E)-1-(4-(3-((1H-imidazol-1-yl)methyl)-5-chlorostyryl)phenyl)-4-(cyclopropylmethyl)piperazine;
(E)-ethyl 2-(4-(4-(3-((1H-imidazol-1-yl)methyl)-5-chlorostyryl)phenyl)piperazine-1-carboxamido)acetate;
(E)-1-(4-(3((1H-imidazol-1-yl)methyl)-5-chlorostyryl)phenyl)-4-(pyridin-3-ylsulfonyl)piperazine;
(E)-3-((4-(4-(3-((1H-imidazol-1-yl)methyl)-5-chlorostyryl)phenyl)piperazin-1-yl)methyl)benzonitrile;
(E)-1-(4-(4-(3-chloro-5-((pyridin-3-yloxy)methyl)styryl)phenyl)piperazin-1-yl)ethanone;
(E)-4-(3-(4-bromostyryl)-5-fluorophenyl)pyridine;
(E)-4-(3-fluoro-5-(4-(pyridin-4-yl)styryl)phenyl)pyridine;
(E)-1-(4-(4-(3-fluoro-5-(pyridin-3-yl)styryl)phenyl)piperazin-1-yl)ethanone;
(E)-1-(4-(4-(3-chloro-5-(pyridin-3-ylmethyl)styryl)phenyl)piperazin-1-yl)ethanone;
(E)-1-(4-(4-(3-chloro-5-(1-hydroxy-2-methyl-1-(pyridin-3-yl)propyl)styryl)phenyl)piperazin-1-yl)ethanone;
(E)-1-(4-(4-(3-chloro-5-(2-methyl-1-(pyridin-3-yl)prop-1-enyl)styryl)phenyl)piperazin-1-yl)ethanone;
(E)-1-(4-(4-(3-chloro-5-(pyridin-4-yl)styryl)phenyl)piperazin-1-yl)ethanone;
(E)-1-(4-(4-(3-chloro-5-(pyridin-3-yl)styryl)phenyl)piperazin-1-yl)ethanone;
(E)-1-(4-(3-fluoro-5-(pyridin-4-yl)styryl)phenyl)-4-(pyridin-3-ylsulfonyl)piperazine;
(E)-ethyl 2-(4-(4-(3-fluoro-5-(pyridin-4-yl)styryl)phenyl)piperazine-1-carboxamido)acetate;
(E)-1-(cyclopropylsulfonyl)-4-(4-(3-fluoro-5-(pyridin-4-yl)styryl)phenyl)piperazine;
(E)-1-(ethylsulfonyl)-4-(4-(3-fluoro-5-(pyridin-4-yl)styryl)phenyl)piperazine;
(E)-1-(4-(3-fluoro-5-(pyridin-4-yl)styryl)phenyl)-4-(trifluoromethylsulfonyl)piperazine;
1-(cyclopropylmethyl)-4-(4-(3-fluoro-5-(pyridin-4-yl)phenethyl)phenyl)piperazine;
4-(3-fluoro-5-(4-(pyridin-4-yl)phenethyl)phenyl)pyridine;
(E)-1-(3-(4-bromostyryl)-5-chlorophenyl)-1H-imidazole;
(E)-1-(4-(4-(3-chloro-5-(1H-imidazol-1-yl)styryl)phenyl)piperazin-1-yl)ethanone;
(E)-1-(4-(3-fluoro-5-(pyridin-4-yl)styryl)phenyl)-4-(isopropylsulfonyl)piperazine;
1-(cyclopropylsulfonyl)-4-(4-(3-fluoro-5-(pyridin-4-yl)phenethyl)phenyl)piperazine;
1-(4-(3-fluoro-5-(pyridin-4-yl)phenethyl)phenyl)-4-(isopropylsulfonyl)piperazine;
ethyl 2-(4-(4-(3-fluoro-5-(pyridin-4-yl)phenethyl)phenyl)piperazine-1-carboxamido)acetate;
1-(ethylsulfonyl)-4-(4-(3-fluoro-5-(pyridin-4-yl)phenethyl)phenyl)piperazine;
1-(4-(3-fluoro-5-(pyridin-4-yl)phenethyl)phenyl)-4-(trifluoromethylsulfonyl)piperazine;
1-(4-(3-fluoro-5-(pyridin-4-yl)phenethyl)phenyl)-4-(pyridin-3-ylsulfonyl)piperazine;
(E)-1-(cyclopropylmethyl)-4-(4-(3-fluoro-5-(pyridin-4-yl)styryl)phenyl)piperazine;
(E)-tert-butyl 1-(4-(3-((1H-imidazol-1-yl)methyl)-5-chlorostyryl)phenyl)piperidin-4-ylcarbamate;
(E)-1-(4-(3-((1H-imidazol-1-yl)methyl)-5-chlorostyryl)phenyl)piperidin-4-amine;
(E)-ethyl 2-(3-(1-(4-(3-((1H-imidazol-1-yl)methyl)-5-chlorostyryl)phenyl)piperidin-4-yl)ureido)acetate;
(E)-tert-butyl 2-(4-(4-(3-fluoro-5-(pyridin-4-yl)styryl)phenyl)piperazin-1-yl)-2-oxoacetate;
(E)-1-(4-(3-fluoro-5-(pyridin-4-yl)styryl)phenyl)piperazine;
1-(4-(4-(3-fluoro-5-(pyridin-4-yl)phenethyl)phenyl)piperazin-1-yl)ethanone;
1-(4-(4-(3-((1H-imidazol-1-yl)methyl)-5-chlorophenethyl)phenyl)piperazin-1-yl)ethanone;
and pharmaceutically acceptable salts thereof.

3. A method of treating a subject having the disease diabetes mellitus, said method comprising administering to the subject an effective amount of at least one compound according to claim 1 to treat the disease.

4. The method of claim 3, wherein the at least one compound is administered in a composition further comprising at least one excipient.

5. The compound of claim 1 wherein A is $CH_2$ and n is 0 or 1.

6. The compound of claim 1 wherein X and Y are each independently CH and connected by a double bond.

7. The compound of claim 6 wherein A is $CH_2$ and n is 1.

8. The compound of claim 6 wherein n is 0.

9. The compound of claim 8 wherein $R^1$ is

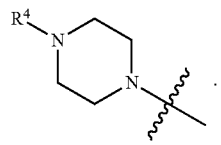

10. The compound of claim 1 wherein X and Y are each independently $CH_2$ and connected by a single bond.

11. The compound of claim 10 wherein A is $CH_2$ and n is 1.

12. The compound of claim 10 wherein n is 0.

13. The compound of claim 12 wherein $R^1$ is

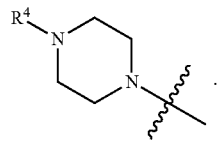

* * * * *